United States Patent
Froidevaux et al.

(10) Patent No.: US 11,608,341 B2
(45) Date of Patent: Mar. 21, 2023

(54) SUBSTITUTED TETRAHYDROPYRAZOLO[3,4-D] PYRIMIDINES AND TETRAHYDROPYRAZOLO[4,3-D] PYRIMIDINES AS C5A RECEPTOR MODULATORS

(71) Applicant: Idorsia Pharmaceuticals Ltd., Allschwil (CH)

(72) Inventors: Sylvie Froidevaux, Allschwil (CH); Francis Hubler, Allschwil (CH); Mark Murphy, Allschwil (CH); Dorte Renneberg, Allschwil (CH); Simon Stamm, Allschwil (CH)

(73) Assignee: Idorsia Pharmaceuticals Ltd., Allschwil (CH)

(*) Notice: Subject to any disclaimer, the term of this patent is extended or adjusted under 35 U.S.C. 154(b) by 0 days.

(21) Appl. No.: 16/961,600

(22) PCT Filed: Jan. 9, 2019

(86) PCT No.: PCT/EP2019/050372
§ 371 (c)(1),
(2) Date: Jul. 10, 2020

(87) PCT Pub. No.: WO2019/137927
PCT Pub. Date: Jul. 18, 2019

(65) Prior Publication Data
US 2020/0369672 A1    Nov. 26, 2020

(30) Foreign Application Priority Data
Jan. 10, 2018    (WO) ................ PCT/EP2018/050598

(51) Int. Cl.
*A61K 31/519* (2006.01)
*C07D 487/04* (2006.01)

(52) U.S. Cl.
CPC ................ *C07D 487/04* (2013.01)

(58) Field of Classification Search
CPC .......................... A61K 31/519; C07D 487/04
USPC ....................................... 514/258.1; 544/253
See application file for complete search history.

(56) References Cited

FOREIGN PATENT DOCUMENTS

| WO | 2006042102 A2 | 4/2006 | |
|----|----|----|----|
| WO | 2006042102 A3 | 2/2007 | |
| WO | 2014134426 A1 | 9/2014 | |
| WO | 2015033299 A1 | 3/2015 | |
| WO | 2015034820 A1 | 3/2015 | |
| WO | 2015044900 A1 | 4/2015 | |
| WO | 2019141803 A1 | 7/2019 | |
| WO | 2019141808 A1 | 7/2019 | |
| WO | WO-2019137927 A1 * | 7/2019 | ........... C07D 487/04 |
| WO | 2021005101 A1 | 1/2021 | |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Zwirner, J., et al. (1999) Mol Immunol 36(13-14): 877-884.
Yan, S., et al. (2014) J Dermatol Sci 76(3): 240-245.
Zha H., et al. (2017) Oncoimmunology 6(10): e1349587.
Written Opinion of the International Searching Authority, International Application No. PCT/EP2019/050372, dated Feb. 8, 2019, 5 pages.
Kirklin, J. K., et al. (1983) J Thorac Cardiovasc Surg 86(6): 845-857.
Kohl, J. and J. E. Gessner (1999) Mol Immunol 36(13-14): 893-903.
Lawley, T. J., et al. (1979) J Immunol 123(3): 1382-1387.
Li, L., et al. (2015) Metabolism 64(5): 597-610.
Liu, L., et al. (2014) J Clin Immunol 34(2): 224-232.
Ma, R., et al. (2013) J Clin Immunol 33(1): 172-178.
Mantovani, S., et al. (2014) J Neuroimmunol 276(1-2): 213-218.
Marc, M. M., et al. (2004) Am J Respir Cell Mol Biol 31(2): 216-219.
Mavroidis, M., et al. (2015) Basic Res Cardiol 110(3): 27.
Mrowietz, U., et al. (2001) Exp Dermatol 10(4): 238-245.
Mueller, M., et al. (2013) Immunobiology 218(9): 1131-1138.
Mulligan, M. S., et al. (1996) J Clin Invest 98(2): 503-512.
N.S. Merle et al. (2015), Front Immunol 6: 257.
Nataf, S., et al. (1999) J Immunol 162(7): 4018-4023.
NCT02222155.
Neuber, K., R. et al. (1991) Immunology 73(1): 83-87.
O'Barr, S. A., et al. (2001) J Immunol 166(6): 4154-4162.
Pandey et al. (2017) Nature 543: 108-112.

(Continued)

*Primary Examiner* — Douglas M Willis
(74) *Attorney, Agent, or Firm* — Jeff B. Vockrodt; Culhane Meadows, PLLC

(57) ABSTRACT

The present invention relates to derivatives of formula (I)

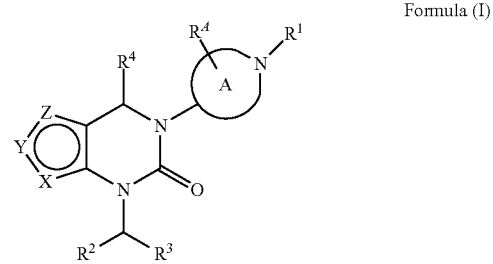

Formula (I)

wherein Ring A, X, Y, Z, $R^4$, $R^1$, $R^2$, $R^3$ and $R^4$ are as described in the description, to their preparation, to pharmaceutically acceptable salts thereof, and to their use as pharmaceuticals, to pharmaceutical compositions containing one or more compounds of formula (I), and especially to their use as C5a receptor modulators.

22 Claims, No Drawings

(56) References Cited

OTHER PUBLICATIONS

Pandey, M. K. (2013) Curr Allergy Asthma Rep 13(6): 596-606.
Pawaria, S., et al. (2014) J Immunol 193(7): 3288-3295.
Porcel, J. M., et al. (1995) Clin Immunol Immunopathol 74(3): 283-288.
Remington, The Science and Practice of Pharmacy, 21st Edition (2005), Part 5, "Pharmaceutical Manufacturing" [published by Lippincott Williams & Wilkins]).
Ricklin, D., et al. (2010), Nat Immunol 11(9): 785-797.
Riley, R. D., et al. (2000) J Thorac Cardiovasc Surg 120(2): 350-358.
Sarma, J. V. and P. A. Ward (2012) Cell Health Cytoskelet 4: 73-82.
Singhrao et al. (1999) Experimental Neurology 159, 362-376.
Smedegard, G., et al. (1989) Am J Pathol 135(3): 489-497.
Song, D., et al. (2015) Am J Reprod Immunol 74(4): 345-356.
Sprott, H., et al. (2000) J Rheumatol 27(2): 402-404.
Staab, E. B., et al. (2014) Int Immunopharmacol 21(2): 293-300.
Stevens, J. H., et al. (1986) J Clin Invest 77(6): 1812-1816.
Strachan, A. J., et al. (2000) J Immunol 164(12): 6560-6565.
Tajbakhsh M. et al., Synthesis, 2011, 3, 490-496.
Tofukuji, M., et al. (1998) J Thorac Cardiovasc Surg 116(6): 1060-1068.
Tsuji, R. F., et al. (2000) J Immunol 165(3): 1588-1598.
Unnewehr, H., et al. (2013) J Immunol 190(8): 4215-4225.
Volanikis, J.; Vasculitis, 2nd Edition (2008), Edited by Ball and Bridges, Oxford University Press, pp. 47-53.
Wakerley, B. R. and N. Yuki (2015) Expert Rev Neurother 15(8): 847-849.
Wang Y., et al., (2016) Cancer Discovery 6(9) 1022-1035.
Wang, X. J., et al. (2007) Neurochem Int 50(1): 39-50.
Web page Innate Pharma—IPH5401, 2018; https://www.innatepharma.com/en/pipeline/iph5401-first-class-anti-c5ar-mab.
Weisman, H. F., T. et al. (1990) Science 249(4965): 146-151.
Werfel, T., et al. (1997) Arch Dermatol Res 289(2): 83-86.
Xiao, H. et al (2014) J Am Soc Nephrol 25(2): 225-231.
Zecher, D., et al. (2014) Arterioscler Thromb Vasc Biol 34(2): 313-320.
Wong EK, Kavanagh D, Transl Res. (2015) 165(2):306-20.
Yuan, G., et al. (2003) Chin Med J (Engl) 116(9): 1408-1412.
Zhang et al., Clin J Am Soc Nephrol (2014) 9: 1876-1882.
Woodruff, T. M., et al. (2003) J Immunol 171(10): 5514-5520.
Woodruff, T. M., et al. (2008) J Immunol 181(12): 8727-8734.
"Handbook of Pharmaceutical Salts. Properties, Selection and Use.", P. Heinrich Stahl, Camille G. Wermuth (Eds.), Wiley-VCH, 2008.
"Pharmaceutical Salts and Co-crystals", Johan Wouters and Luc Quéré (Eds.), RSC Publishing, 2012.
"Protective Groups in Organic Synthesis", T.W. Greene, P.G.M. Wuts, Wiley-Interscience, 1999.
Ager, R. R., et al. (2010) J Neurochem 113(2): 389-401.
Amsterdam, E. A., et al. (1995) Am J Physiol 268(1 Pt 2): H448-457.
Bao, L., et al. (2005) Eur J Immunol 35(8): 2496-2506.
Basta, M. and D. R. Branch (2014) Clin Exp Immunol 178 Suppl 1: 87-88.
Baumann, U., et al. (2000) J Immunol 164(2): 1065-1070.
Bless, N. M., et al. (1999) Am J Physiol 276(1 Pt 1): L57-63.
Bozic, C. R., et al. (1996) Science 273(5282): 1722-1725.
Cao, Q., et al. (2012) Am J Physiol Cell Physiol 302(12): pp. 1731-1740.
Charles J., et al (2013) Semin Nephrol 33(6): 557-564.
Cheng, L., et al. (2013). Invest Ophthalmol Vis Sci 54(13): 8191-8198.
Craddock, P. R., et al. (1977) J Clin Invest 60(1): 260-264.
Craddock, P. R., et al. (1977) N Engl J Med 296(14): 769-774.
Czermak, B. J., et al. (1998) J Leukoc Biol 64(1): 40-48.
Czermak, B. J., et al. (1999) Nat Med 5(7): 788-792.
Dang, L., et al. (2015) Mol Med Rep 11(6): 4183-4189.
Davin, J. C., N. C. van de Kar (2015) Ther Adv Hematol 6(4): 171-185.
De Hoog, V. C., et al. (2014) Cardiovasc Res 103(4): 521-529.
Diani, M., G. Altomare and E. Reali (2015) Autoimmun Rev 14(4): 286-292.
Distelmaier, K., et al. (2009) Thromb Haemost 102(3): 564-572.
Farrar, C. A. and S. H. Sacks (2014) Curr Opin Organ Transplant 19(1): 8-13.
Fiebiger, E., et al. (1998) J Clin Invest 101(1): 243-251.
Fonseca, M. I., et al. (2013) J Neuroinflammation 10: 25.
Gammon, W. R. (1989) Immunol Ser 46: 509-525.
Gasque, P., et al. (1997) Am J Pathol 150(1): 31-41.
Grant, E. P., et al. (2002) J Exp Med 196(11): 1461-1471.
Guo, R. F. and P. A. Ward (2005) Annu Rev Immunol 23: 821-852.
Guo, R. F., et al. (2000) J Clin Invest 106(10): 1271-1280.
Halstead, S. K., et al. (2008) Brain 131 (Pt 5): 1197-1208.
Hammerschmidt, D. E., et al. (1980) Lancet 1(8175): 947-949.
Hartung, H. P., et al. (1987) Neurology 37(6): 1006-1009.
Heideman, M. and T. E. Hugli (1984) J Trauma 24(12): 1038-1043.
Heimbach, L., et al. (2011) J Biol Chem 286(17): 15003-15009.
Hoesel, L. M., et al. (2007) J Immunol 178(12): 7902-7910.
Hopken, U., et al. (1996) Eur J Immunol 26(5): 1103-1109.
Howard, R. J., et al. (1988) Arch Surg 123(12): 1496-1501.
Howell et al. (2011), J. Clin. Invest. 121(4): 1429-1444.
Huang, Y. M., et al. (2015) Arthritis Rheumatol 67(10): 2780-2790.
Huber-Lang, M., et al. (2001) J Immunol 166(2): 1193-1199.
Humayun, S., et al. (2009) J Neuroimmunol 210(1-2): 52-62.
Jacob, A., B. Hack, et al. (2010) J Neuroimmunol 221(1-2): 46-52.
Jain, U., et al. (2013) Br J Pharmacol 168(2): 488-501.
Janeway's "Immunobiology", 8th edition (2012), Kenneth Murphy, Garland Science, p. 48-72.
Johswich, K., et al. (2009) Inflamm Bowel Dis 15(12): 1812-1823.
Jose, P. J., et al. (1990) Ann Rheum Dis 49(10): 747-752.
Kallenberg, C. G. and P. Heeringa (2015) Mol Immunol 68(1): 53-56).
Kaplan, A. P. (2004) J Allergy Clin Immunol 114(3): 465-474.
Karsten, C. M. and J. Kohl (2012) Immunobiology 217(11): 1067-1079.
Akbari et al., "Synthesis of Some New Pyrazolo [3,4-d]pyrimidines and Thiazolo [4,5-d]pyrimidines and Evaluation of Their Antimicrobial Activities," Phosphorus, Sulfur and Silicon, 183: Jun. 2008, 1471-1477.
Zerovnik, et al., "Synthesis of 1,5,6,7-Tetrahydro-4H-pyrazolo[4,3-c] Pyridin-4-ones as Conformationally Constrained Pyrazole Analogues of Histamine," Apr. 21, 2010, 11 pages.

\* cited by examiner

SUBSTITUTED TETRAHYDROPYRAZOLO[3,4-D]PYRIMIDINES AND TETRAHYDROPYRAZOLO[4,3-D]PYRIMIDINES AS C5A RECEPTOR MODULATORS

The present invention relates to novel C5a receptor modulators of formula (I) and their use as pharmaceuticals. The invention also concerns related aspects including processes for the preparation of the compounds, pharmaceutical compositions containing one or more compounds of formula (I), and their use as C5a receptor modulators, especially in the treatment of vasculitic diseases or disorders, inflammatory diseases or disorders involving intravascular microvesicle release, immune complex (IC) diseases or disorders, neurodegenerative diseases or disorders, complement related inflammatory diseases or disorders, bullous diseases or disorders, diseases or disorders related to ischemia and/or ischemic reperfusion injury, inflammatory bowel diseases or disorders, and autoimmune diseases or disorders; as well as in contact sensitivity or an inflammation caused by contact with artificial surfaces; increased leukocyte and platelet activation (and infiltration to tissues thereof); pathologic sequelae associated to an intoxication or an injury such as a trauma, an hemorrhage, a shock, or surgery including transplantation, such sequelae including multiple organ failure (MOF), septic shock, shock due to intoxication, or acute lung inflammatory injury; pathologic sequelae associated with insulin-dependent diabetes mellitus; myocardial infarction or thrombosis; edema or an increased capillary permeability; reduction of coronary endothelial dysfunction induced by cardiopulmonary bypass and/or cardioplegia; or cancer.

BACKGROUND OF THE INVENTION

C5aR1 (CD88) is a seven transmembrane bound G protein coupled receptor (GPCR) belonging to the rhodopsin like family, the gene of which is located on chromosome 19. It couples to pertussis toxin sensitive Gialpha2, Gialpha3 or pertussis toxin insensitive Galpha16 and initiates several downstream signaling pathways. C5aR1 is expressed on a number of immune cell types including monocytes, neutrophils, mast cells, basophils and eosinophils. In addition, it is expressed on many other cell types including hepatocytes, pulmonary and endothelial cells, microglia, neurons and renal glomerular cells. There are a number of ligands described which bind to the C5aR. These include C5a, C5adesArg and C5a+1 kDa. C5a is a central effector molecule of the complement system which itself is a complex enzymatic cascade evolved to crucially complement the immune system against invading pathogens, however, a significant body of evidence shows that inadvertent complement activation leads to many acute inflammatory disorders and autoimmune diseases (Ricklin, D., et al. (2010) "Complement: a key system for immune surveillance and homeostasis." Nat Immunol 11(9): 785-797) and specifically C5a has been shown to be elevated in a number of these inflammatory and autoimmune disorders. The complement system is activated through four pathways: The classical pathway, and the mannose binding lectin (MBL) pathway which is similar to the classical pathway except for the initial recognition and activation steps which recognize pathogens or antibody complexes. The alternative pathway is activated by binding of spontaneously activated complement C3 protein (C3b fragment) to pathogen surface. These three pathways all lead to the eventual formation of C3 convertases, which is the point where the 3 pathways converge (Guo, R. F. and P. A. Ward (2005) Annu Rev Immunol 23: 821-852). Subsequently C3 convertases lead to the formation of the anaphalatoxins C3a and C5a, together with other complement proteins required to produce the membrane attack complex. A fourth pathway, the extrinsic pathway involves plasma proteases (e.g. elastase, thrombin) which act directly on C3 or C5 leading to the subsequent production of C3a and C5a. The anaphylatoxin C5a leads to the recruitment and activation of inflammatory cells of the innate and adaptive system, partly through the enhancement of cell adhesion molecule expression, the release of granule-based enzymes, delayed or enhanced apoptosis, phagocytosis, oxidative burst, histamine secretion and release and chemotaxis. In addition, it elicits the release of other pro inflammatory mediators, such as TNF-a, IL-1, IL-6, IL-8, prostaglandins, and leukotrienes) (N. S. Merle et al. (2015) "Complement System Part II: Role in Immunity." Front Immunol 6: 257), activation of endothelial cells and vascular permeability which may lead to events in which at the end thrombotic microangiopathy can occur. Therefore, C5a represents one of the most potent inflammatory molecules produced during immune responses and because of its fundamental biology it is potentially implicated in a very wide range of pathologies (Janeway's Immunobiology, $8^{th}$ edition (2012), Kenneth Murphy, Garland Science, p. 48-72).

C5a is central to the immune system and as such is important in key aspects of inflammation and tissue injury. In addition, there is considerable experimental evidence in the literature that implicates increased levels of C5a with a number of diseases and disorders, in particular in autoimmune and inflammatory diseases and disorders (Ricklin, D., et al. (2010) Nat Immunol 11(9): 785-797).

There is a large body of evidence about C5a and its receptor C5aR in contributing to vasculitic diseases, which demonstrate that C5a levels are elevated and give rise to leukocyte migration and subsequent inflammation which then leads to the eventual destruction of vessel walls (Charles J., et al (2013) Semin Nephrol 33(6): 557-564; Vasculitis, $2^{nd}$ Edition (2008), Edited by Ball and Bridges, Oxford University Press, pp 47-53; Huang, Y. M., et al. (2015) Arthritis Rheumatol 67(10): 2780-2790; Kallenberg, C. G. and P. Heeringa (2015) Mol Immunol 68(1): 53-56). Inhibition of the C5aR with a C5aR antagonist was effective at ameliorated anti-myeloperoxidase (MPO)-induced NCGN in mice expressing the human C5a receptor (Xiao, H. et al (2014) J Am Soc Nephrol 25(2): 225-231) and was confirmed to be effective in a phase II trial of patients with anti-neutrophil cytoplasmic antibody (ANCA) associated vasculitis (ClinicalTrials.gov Identifier NCT02222155). Therefore, a C5a antagonist may be useful to treat vasculitic diseases such as ANCA associated vasculitis, leukoclastic vasculitis, Wegener's granulomatosis, microscopic polyangiitis, Churg-Strauss syndrome, Henoch-Schönlein purpura, polyateritis nodosa, rapidly progressive glomerulonephritis (RPGN), cryoglobulinaemia, giant cell arteritis (GCA), Behcet's disease and Takayasu's arteritis (TAK).

C5a is generated when human blood makes contact with artificial surfaces, such as in cardiopulmonary bypass and hemodialysis procedures for instance on the artificial surface of the heart-lung machine in association with vascular surgery such as coronary artery bypass grafting or heart valve replacement or on surfaces of a kidney dialysis machine (Howard, R. J., et al. (1988) Arch Surg 123(12): 1496-1501; Kirklin, J. K., et al. (1983) J Thorac Cardiovasc Surg 86(6): 845-857; Craddock, P. R., et al. (1977) J Clin Invest 60(1): 260-264; Craddock, P. R., et al. (1977) N Engl J Med 296(14): 769-774) or in association with contact with other artificial vessels or container surfaces (e.g. ventricular assist devices, artificial heart machines, transfusion tubing, blood storage bags, plasmapheresis, plateletpheresis, and the like). As such C5aR antagonists could prove useful in preventing deleterious consequences of contact sensitivity and/or inflammation caused by contact with artificial surfaces. In addition, it may be useful in treating inflammatory disorders involving intravascular microvesicle release such as for example thrombotic microangiopathy and sickle cell disease (Zecher, D., et al. (2014) Arterioscler Thromb Vasc Biol 34(2): 313-320). A C5aR antagonist could also prove useful in certain hemotological diseases which are associated with activation of coagulation and fibrinolytic systems, disseminated intravascular coagulation (DIC), pernicious anemia, warm and cold autoimmune hemolytic anemia (AIHA), anti-phospholipid syndrome and its associated complications, arterial and venous thrombosis, pregnancy complications such as recurrent miscarriage and fetal death, preeclampsia, placental insufficiency, fetal growth restriction, cervical remodeling and preterm birth, idiopathic thrombocytopenic purpura (ITP), atypical hemolytic uremic syndrome (aHUS), paroxysmal nocturnal hemoglobinuria (PNH) and allergic transfusion reactions. The C5-specific humanized antibody, eculizumab is approved for paroxysmal nocturnal hemoglobinuria and atypical haemolytic uraemic syndrome (aHUS) (Wong E K, Kavanagh D, Transl Res. (2015) 165(2):306-20) and has been shown to be efficacious in renal transplant such as acute antibody-mediated kidney allograft rejection and cold agglutinin disease further supporting a potential role for C5aR antagonists in these diseases.

In myocardial ischemia-reperfusion injury C5a has been described to have an important function. Complement depletion reduced myocardial infarct size in mice (Weisman, H. F., T. et al. (1990) Science 249(4965): 146-151; De Hoog, V. C., et al. (2014) Cardiovasc Res 103(4): 521-529) and treatment with anti-C5a antibodies reduced injury in a rat model of hindlimb ischemia-reperfusion (Bless, N. M., et al. (1999) Am J Physiol 276(1 Pt 1): L57-63). Reperfusion injury during myocardial infarction was also markedly reduced in pigs that were re-treated with a monoclonal anti-C5a IgG (Amsterdam, E. A., et al. (1995) Am J Physiol 268(1 Pt 2): H448-457). A recombinant human C5aR antagonist reduces infarct size in a porcine model of surgical revascularization (Riley, R. D., et al. (2000) J Thorac Cardiovasc Surg 120(2): 350-358) providing evidence for the utility of a C5aR antagonist in these diseases. In addition, diseases related to ischemia/reperfusion injury, such as those resulting from transplants, including solid organ transplant, where C5a has been shown to play an important role (Farrar, C. A. and S. H. Sacks (2014) Curr Opin Organ Transplant 19(1): 8-13), could benefit from a C5aR antagonist as could related syndromes such as ischemic reperfusion injury, ischemic colitis and cardiac ischemia (Mueller, M., et al. (2013) Immunobiology 218(9): 1131-1138).

Furthermore, diseases where complement plays a role such as coronary thrombosis (Distelmaier, K., et al. (2009) Thromb Haemost 102(3): 564-572), vascular occlusion, post-surgical vascular reocclusion, atherosclerosis, traumatic central nervous system injury, arrhythmogenic cardiomyopathy (Mavroidis, M., et al. (2015) Basic Res Cardiol 110(3): 27) and Gaucher disease (Pandey et al. (2017) Nature 543: 108-112) could also benefit from a C5aR antagonist. Thus, C5aR modulators may be used preventatively in a patient at risk for myocardial infarction or thrombosis (i.e. a patient who has one or more recognized risk factors for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

C5a causes increased capillary permeability and edema, leukocyte and platelet activation and infiltration to tissues, as well as bronchoconstriction (Sarma, J. V. and P. A. Ward (2012) Cell Health Cytoskelet 4: 73-82; Czermak, B. J., et al. (1998) J Leukoc Biol 64(1): 40-48). Administration of an anti-C5a monoclonal antibody was shown to reduce cardiopulmonary bypass and cardioplegia-induced coronary endothelial dysfunction (Tofukuji, M., et al. (1998) J Thorac Cardiovasc Surg 116(6): 1060-1068).

C5a and its receptor are also involved in the pathogenesis of acute respiratory distress syndrome (ARDS) (Hammerschmidt, D. E., et al. (1980) Lancet 1(8175): 947-949), Chronic Obstructive Pulmonary Disorder (COPD) (Marc, M. M., et al. (2004) Am J Respir Cell Mol Biol 31(2): 216-219), and multiple organ failure (MOF) (Huber-Lang, M., et al. (2001) "Role of C5a in multiorgan failure during sepsis." J Immunol 166(2): 1193-1199; Heideman, M. and T. E. Hugli (1984) J Trauma 24(12): 1038-1043;). C5a increases monocyte production of two important proinflammatory cytokines TNF-α and IL-I which contribute to pathology in these diseases. C5a has also been shown to play an important role in the development of tissue injury, and particularly pulmonary injury, in animal models of septic shock (Smedegard, G., et al. (1989) Am J Pathol 135(3): 489-497; Unnewehr, H., et al. (2013) J Immunol 190(8): 4215-4225). In sepsis models using rats, pigs and non-human primates, anti-C5a antibodies administered to the animals before treatment with endotoxin or *E. coli* resulted in decreased tissue injury, as well as decreased production of IL-6 (Hopken, U., et al. (1996) Eur J Immunol 26(5): 1103-1109; Stevens, J. H., et al. (1986) J Clin Invest 77(6): 1812-1816). Inhibition of C5a with anti-C5a polyclonal antibodies has been shown to significantly improve survival rates in a caecal ligation/puncture model of sepsis in rats (Czermak, B. J., et al. (1999) Nat Med 5(7): 788-792). In the same sepsis model, anti-C5a antibodies were shown to inhibit apoptosis of thymocytes (Guo, R. F., et al. (2000) J Clin Invest 106(10): 1271-1280). Anti-C5a antibodies were also protective in a cobra venom factor model of lung injury in rats, and in immune complex-induced lung injury (Mulligan, M. S., et al. (1996) J Clin Invest 98(2): 503-512). The importance of C5a in immune complex-mediated lung injury was also shown in mouse (Bozic, C. R., et al. (1996) Science 273(5282): 1722-1725). Therefore, a C5aR antagonist could be of benefit in many inflammatory disorders and related conditions including neutropenia, sepsis, septic shock, stroke, inflammation associated with severe burns (Hoesel, L. M., et al. (2007) J Immunol 178(12): 7902-7910), osteoarthritis (Yuan, G., et al. (2003) Chin Med J (Engl) 116(9): 1408-1412), as well as acute (adult) respiratory distress syndrome (ARDS), chronic pulmonary obstructive disorder (COPD), bronchial asthma (Pandey, M. K. (2013) Curr Allergy Asthma Rep 13(6): 596-606), systemic inflammatory response syndrome (SIRS), tissue graft rejection, hyperacute rejection of transplanted organs, and the like, and multiple organ dysfunction syndrome (MODS). In addition, C5aR antagonists may be beneficial in treating pathologic sequelae associated with insulin-dependent diabetes mellitus such as diabetic kidney disease (Li, L., et al. (2015) Metabolism 64(5): 597-610), diabetic retinopathy (Cheng, L., et al. (2013). Invest Ophthalmol Vis Sci 54(13): 8191-8198), lupus nephropathy (Bao, L., et al. (2005) Eur J Immunol 35(8): 2496-2506), Heyman nephritis, membranous nephritis, and other forms of glomerulonephritis such as C3 glomerulopathy including dense deposit disease (DDD) (Zhang et al., Clin J Am Soc Nephrol (2014) 9: 1876-1882). Furthermore, the compound eculizumab has been shown to have potential utility for the treatment of neuromyelitis optica.

C5aR antagonists substantially reduced ovalbumin (OVA)-induced total cell (60%), neutrophil (66%) and eosinophil (65%) influxes in lavage fluid sampling suggesting that C5aR blockage might represent a novel therapeutic agent for reducing asthmatic outcomes (Staab, E. B., et al. (2014) Int Immunopharmacol 21(2): 293-300).

The complement system and in particular C5a contribute to the development of many bullous diseases among other things through activation of innate cells including mast cells and neutrophils (e.g. bullous pemphigoid, bullous acquisita, pemphigus foliaceus and pemphigus vulgaris). The detachment of epidermal basal keratinocytes from the underlying basement membrane is thought to be caused by autoantibodies to keratinocytes at the cutaneous basement membrane leading to blisters and a high influx of neutrophils in both the upper dermal layers and within the blister cavities. In experimental models a reduction of neutrophils or absence of complement (total or C5-selective) can inhibit formation of sub-epidermal blisters (Heimbach, L, et al. (2011) J Biol Chem 286(17): 15003-15009; Gammon, W. R. (1989) Immunol Ser 46: 509-525). Recent evidence has emerged to suggest that inhibition of C5a may prove beneficial in the treatment of the skin disorder hidradenitis suppurativa where an antibody against human C5a was shown to improve patient outcome in an open label phase II clinical trial. A C5a receptor antagonist may therefore be useful in bullous diseases.

Complement is believed to be important in inflammatory bowel disease (IBD) pathology and the C5aR is found to be expressed in the epithelial cells of the colon. (Cao, Q., et al. (2012) Am J Physiol Cell Physiol 302(12): C1731-1740). In addition, pharmacological inhibition of C5a activity by PMX205 a peptidic C5aR antagonist is efficacious in preventing DSS-induced colitis, providing further evidence that targeting CD88 in patients with IBD irritable bowel syndrome, ulcerative colitis, Crohn's disease, inflammatory bowel disease (IBD) (Johswich, K., et al. (2009) Inflamm Bowel Dis 15(12): 1812-1823) could be of therapeutic benefit (Woodruff, T. M., et al. (2003) J Immunol 171(10): 5514-5520; Jain, U., et al. (2013) Br J Pharmacol 168(2): 488-501).

There is a body of evidence suggesting a role for C5a and its receptor in pathologies of the CNS. C5aR expression is upregulated on reactive astrocytes, microglia, and endothelial cells in an inflamed human central nervous system (O'Barr, S. A., et al. (2001) J Immunol 166(6): 4154-4162; Gasque, P., et al. (1997) Am J Pathol 150(1): 31-41) and C5a has been reported to be involved in the pathogenesis of many neurodegenerative diseases, such as amyotrophic lateral sclerosis (ALS) (Mantovani, S., et al. (2014) J Neuroimmunol 276(1-2): 213-218; Humayun, S., et al. (2009) J Neuroimmunol 210(1-2): 52-62; Woodruff, T. M., et al. (2008) J Immunol 181(12): 8727-8734), Alzheimer disease (Fonseca, M. I., et al. (2013) J Neuroinflammation 10: 25; Ager, R. R., et al. (2010) J Neurochem 113(2): 389-401), Parkinson's disease (Wang, X. J., et al. (2007) Neurochem Int 50(1): 39-50) and Huntington's disease (Singhrao et al. (1999) Experimental Neurology 159, 362-376). Furthermore C5a is found to be elevated in the CSF of Guillain-Barre syndrome patients (Hartung, H. P., et al. (1987) Neurology 37(6): 1006-1009; Wakerley, B. R. and N. Yuki (2015) Expert Rev Neurother 15(8): 847-849) and an anti C5 antibody was found to be effective in reducing neuropathy in the mouse (Halstead, S. K., et al. (2008) Brain 131 (Pt 5): 1197-1208; Basta, M. and D. R. Branch (2014) Clin Exp Immunol 178 Suppl 1: 87-88). Also, inhibition of the C5a receptor alleviates experimental CNS lupus (Zwirner, J., et al. (1999) Mol Immunol 36(13-14): 877-884; Jacob, A., B. Hack, et al. (2010) J Neuroimmunol 221(1-2): 46-52). Therefore, C5aR antagonists provided herein may be to treat ALS, Alzheimer's disease, multiple sclerosis, Guillain-Barre syndrome, Parkinson's disease, Huntington's disease and also cognitive function decline associated with cardiopulmonary bypass surgery and related procedures in addition to central nervous system involvement in diseases such as SLE, Sjögren's syndrome and associated immunological profiles.

In many autoimmune diseases Immunoglobulin G-containing immune complex (IC) depositions are found. These contribute to the pathophysiology of the diseases which frequently manifest in different organs of the body including the kidneys, heart, lungs, liver, blood vessels, the nervous system and the skin. There are numerous such IC diseases and examples are systemic lupus erthyematosus (SLE), cryoglobulinemia, rheumatoid arthritis, Sjögren's syndrome (Lawley, T. J., et al. (1979) J Immunol 123(3): 1382-1387), Goodpasture syndrome (antiglomerular basement antibody disease), and hypersensitivity. Immune complexes are known to induce C5 convertases leading to C5a production which subsequently contributes to these diseases (Karsten, C. M. and J. Kohl (2012) Immunobiology 217(11): 1067-1079). In animal models reproducing the mechanisms of IC activation of complement, C5aR has been shown to play an important role. Studies show that C5aR deficient mice and the use of a peptidic C5aR antagonist result in protection from tissue injury induced by ICs. (Strachan, A. J., et al. (2000) J Immunol 164(12): 6560-6565; Kohl, J. and J. E. Gessner (1999) Mol Immunol 36(13-14): 893-903; Baumann, U., et al. (2000) J Immunol 164(2): 1065-1070). Therefore, inhibitors of C5aR could be useful to treat IC diseases including the autoimmune diseases rheumatoid arthritis (Jose, P. J., et al. (1990) Ann Rheum Dis 49(10): 747-752; Grant, E. P., et al. (2002) J Exp Med 196(11): 1461-1471; Yuan, G., et al. (2003) Chin Med J (Engl) 116(9): 1408-1412)), osteoarthritis, systemic lupus erythematosus (Porcel, J. M., et al. (1995) Clin Immunol Immunopathol 74(3): 283-288; Pawaria, S., et al. (2014) J Immunol 193(7): 3288-3295), lupus nephritis (Bao, L., et al. (2005) Eur J Immunol 35(8): 2496-2506), lupus glomerulonephritis and IgA nephropathy (Liu, L, et al. (2014) J Clin Immunol 34(2): 224-232), Heyman nephritis, membranous nephritis and other forms of glomerulonephritis, vasculitis, dermatomyositis (Fiebiger, E., et al. (1998) J Clin Invest 101(1): 243-251), pemphigus, systemic sclerosis (scleroderma) (Sprott, H., et al. (2000) J Rheumatol 27(2): 402-404), bronchial asthma, autoimmune hemolytic and thrombocytopenic states, Goodpasture's syndrome (and associated glomerulonephritis and pulmonary hemorrhage) (Ma, R., et al. (2013) J Clin Immunol 33(1): 172-178), immunovasculitis, and complement mediated thrombotic microangiopathies including atypical haemolytic uremic syndrome (Song, D., et al. (2015) Am J Reprod Immunol 74(4): 345-356; Davin, J. C., N. C. van de Kar (2015) Ther Adv Hematol 6(4): 171-185), mixed cryoglobulinemia, atopic dermatitis (Neuber, K., R. et al. (1991) Immunology 73(1): 83-87; Dang, L., et al. (2015) Mol Med Rep 11(6): 4183-4189), and chronic urticaria (Kaplan, A. P. (2004) J Allergy Clin Immunol 114(3): 465-474; Yan, S., et al. (2014) J Dermatol Sci 76(3): 240-245). Furthermore, the compound eculizumab has been shown to have potential utility for the treatment of myasthenia gravis, and anti-phospholipid syndrome.

C5a is present in psoriatic plaques and C5aR expression has also been reported in psoriasis where T cells, neutrophils mast cells and dendritic cells are involved in pathogenesis of the disease and are chemotactic to C5a (Diani, M., G. Altomare and E. Reali (2015) Autoimmun Rev 14(4): 286-292). Neutrophil accumulation under the stratum corneum is observed in the highly inflamed areas of psoriatic plaques, and psoriatic lesion (scale) extracts contain highly elevated levels of C5a and exhibit potent chemotactic activity towards neutrophils, an effect that can be inhibited by addition of a C5a antibody. Furthermore, T cells and neutrophils are chemo-attracted by C5a under certain conditions (Nataf, S., et al. (1999) J Immunol 162(7): 4018-4023; Tsuji, R. F., et al. (2000) J Immunol 165(3): 1588-1598; Werfel, T., et al. (1997) Arch Dermatol Res 289(2): 83-86; Mrowietz, U., et al. (2001) Exp Dermatol 10(4): 238-245) meaning C5aR antagonists may be of benefit in treating psoriasis. Furthermore, complement has been implicated in the pathogenesis of glaucoma (Howell et al. (2011), J. Clin. Invest. 121(4): 1429-1444). In addition, there is experimental evidence to suggest a beneficial role of C5aR antagonists in treating cancer with checkpoint blockers. For example, an antibody against the C5aR receptor (IPH5401) has been reported to be efficacious in murine models of cancer (web page Innate Pharma-IPH5401, 2018; https://www.innate-pharma.com/en/pipeline/iph5401-first-class-anti-c5ar-mab; Zah H., et al. (2017) Oncoimmunology 6(10): e1349587; Wang Y., et al., (2016) Cancer Discovery 6(9) 1022-1035).

Thus, C5a and C5aR are believed to be clinically implicated in vasculitic diseases or disorders, inflammatory diseases or disorders involving intravascular microvesicle release, immune complex (IC) diseases or disorders, neurodegenerative diseases or disorders, complement related inflammatory diseases or disorders, bullous diseases or disorders, diseases or disorders related to ischemia and/or ischemic reperfusion injury, inflammatory bowel diseases or disorders, and autoimmune diseases or disorders; as well as in contact sensitivity or an inflammation caused by contact with artificial surfaces; increased leukocyte and platelet activation (and infiltration to tissues thereof); pathologic sequelae associated to an intoxication or an injury such as a trauma, an hemorrhage, a shock, or surgery including transplantation, including multiple organ failure (MOF), septic shock, shock due to intoxication, or acute lung inflammatory injury; pathologic sequelae associated with insulin-dependent diabetes mellitus; myocardial infarction or thrombosis; edema or an increased capillary permeability; reduction of coronary endothelial dysfunction induced by cardiopulmonary bypass and/or cardioplegia, or cancer.

There is therefore a requirement for new small organic molecule modulators of the C5a receptor (C5aR), especially antagonists of the C5aR, that could be useful for inhibiting pathogenic events associated with elevated levels of C5a and/or with C5aR activation.

DETAILED DESCRIPTION OF THE INVENTION

The present invention provides cyclic urea derivatives of formula (I) which are modulators of the C5a receptor, and, thus, may be useful for the prevention or treatment of diseases which respond to the C5a receptor.

1) A first aspect of the invention relates to compounds of the formula (I)

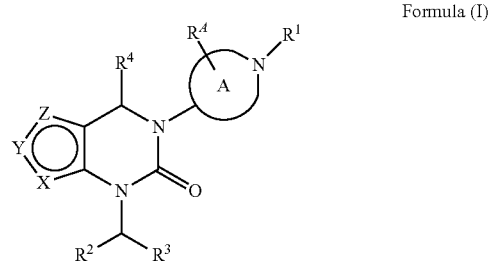

Formula (I)

wherein
Y represents $NR^5$; and X and Z independently represent N or CH (notably Y represents $NR^5$; one of X and Z represents N, and the other of X and Z represents N or CH);
Y represents $CR^6$; one of X and Z represents $NR^7$, O or S, and the other of X and Z represents N; or
Y represents N; one of X and Z represents $NR^8$, and the other of X and Z represents N or CH;
ring A represents a saturated 4- to 7-membered monocyclic carbocyclic ring containing the ring nitrogen atom to which $R^1$ is attached, wherein said ring A is optionally mono-substituted with $R^A$; wherein $R^A$ represents $(C_{1-4})$alkyl (especially methyl) [preferably ring A is substituted with $R^1$ and carries no further substituent (i.e. $R^A$ is absent)];
$R^1$ represents phenyl; 5-membered heteroaryl, or 6-membered heteroaryl wherein said phenyl, 5-membered heteroaryl or 6-membered heteroaryl independently is mono-, di- or tri-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; cyano; or $(C_{3-6})$cycloalkyl;
$R^2$ represents phenyl, 5-membered heteroaryl, or 6-membered heteroaryl; wherein said phenyl, 5-membered heteroaryl, or 6-membered heteroaryl independently is mono-, or di-, or tri-substituted, wherein the substituents are independently selected from
$(C_{1-4})$alkyl;
$(C_{1-4})$alkoxy;
$(C_{1-3})$fluoroalkyl;
$(C_{1-3})$fluoroalkoxy;
halogen;
$(C_3)$cycloalkyl-$X^{21}$—, wherein $X^{21}$ represents a direct bond, —O—, or —$(C_{1-3})$alkylene-O—, and wherein the $(C_{3-6})$cycloalkyl optionally contains one ring oxygen atom; or
$R^{21a}R^{21b}N$—, wherein $R^{21a}$ and $R^{21b}$ independently represent hydrogen or $(C_{1-4})$alkyl;
$R^3$ represents hydrogen or $(C_{1-3})$alkyl (especially hydrogen);
$R^4$ represents hydrogen, or $(C_{1-4})$alkyl (especially hydrogen);
$R^5$ represents
hydrogen;
$(C_{1-4})$alkyl;
$(C_{1-4})$alkyl which is mono-substituted with hydroxy, $(C_{1-4})$alkoxy, cyano, or $R^{N1}R^{N2}N$—, wherein $R^{N1}$ and $R^{N2}$ together with the nitrogen atom form a 4- to 6-membered saturated ring optionally containing one further ring heteroatom selected from O and N;

wherein said ring is optionally mono-substituted with $(C_{1-4})$alkyl, or $(C_{1-4})$alkoxy;

$R^{N1}$ and $R^{N2}$ are independently selected from hydrogen, $(C_{1-4})$alkyl, $(C_{3-6})$cycloalkyl-$(C_{0-4})$alkylene-, or $(C_{1-4})$alkoxy-$(C_{2-4})$alkylene;

$R^{N1}$ represents $(C_{1-4})$alkyl-C(O)—; and $R^{N2}$ represents hydrogen, or $(C_{1-4})$alkyl; or $R^{N1}$ represents phenylsulfonyl-, wherein the phenyl is optionally substituted by one to three substituents independently selected from $(C_{1-4})$alkyl, $(C_{1-4})$alkoxy, halogen, cyano, or nitro; and $R^{N2}$ represents hydrogen, or $(C_{1-4})$alkyl;

$(C_{2-4})$alkyl which is di- or tri-substituted, wherein the substituents are independently selected from hydroxy, $(C_{1-4})$alkoxy, or $R^{N1}R^{N2}N$—, wherein $R^{N1}$ and $R^{N2}$ together with the nitrogen atom form a 4- to 6-membered saturated ring; or $R^{N1}$ and $R^{N2}$ are independently selected from hydrogen, or $(C_{1-4})$alkyl;

$(C_{2-4})$fluoroalkyl;

$(CH_3)_3Si$—$(CH_2)_2$—O—$(C_{1-4})$alkylene-;

$(C_{2-5})$alkynyl;

$(C_{2-5})$alkenyl;

$R^{N3}R^{N4}N$—C(O)—$(C_{0-4})$alkylene-, wherein $R^{N3}$ and $R^{N4}$ independently are hydrogen or $(C_{1-4})$alkyl;

$(C_{1-4})$alkoxy-C(O)—$(C_{0-4})$alkylene-;

$(C_{1-4})$alkoxy-C(O)—$(C_{2-4})$alkylene-, wherein the $(C_{2-4})$ alkylene is mono-substituted by $R^{N5}R^{N6}N$—, wherein $R^{N5}$ and $R^{N6}$ independently are hydrogen or $(C_{1-4})$alkyl $(C_{1-4})$alkoxy-C(O)—$(C_{2-4})$alkylene-, wherein the $(C_{2-4})$ alkylene is substituted by one to three halogen;

$(C_{1-4})$alkoxy-C(O)—NH—$(C_{2-4})$alkylene-, wherein the $(C_{2-4})$alkylene- is optionally substituted by one to three halogen;

$(C_{3-6})$cycloalkyl-$(C_{0-4})$alkylene-, wherein the cycloalkyl is optionally substituted by one or two substituents independently selected from fluoro, $(C_{1-4})$alkyl, nitro, or $(C_{1-4})$alkoxy-C(O)—NH—; or ring$^B$-$X^B$—; wherein $X^B$ is a direct bond, or $(C_{1-4})$alkylene-; and wherein ring$^B$ is a 4- to 6-membered saturated heterocyclyl containing one or two ring heteroatom independently selected from O, S, and NR$^B$, wherein said ring$^B$ is attached to $X^B$ at a ring carbon atom; wherein said ring$^B$ is optionally substituted by one or two substituents independently selected from oxo, hydroxy, fluoro, $(C_{1-4})$alkyl or $(C_{1-4})$alkoxy; and wherein $R^B$ independently represents hydrogen;
$(C_{1-4})$alkyl; $(C_{2-4})$fluoroalkyl;
$(C_{1-4})$alkyl-C(O)—;
$(C_{1-4})$alkoxy-C(O)—;
$(C_{1-4})$alkyl-SO$_2$—;
$R^{N7}R^{N8}N$—SO$_2$— wherein $R^{N7}$ and $R^N$ are independently hydrogen or $(C_{1-4})$alkyl;
$R^{N9}R^{N10}N$—C(O)— wherein $R^{N9}$ and $R^{N10}$ are independently hydrogen or $(C_{1-4})$alkyl;
Ring$^C$-O—C(O)—, and wherein ring$^C$ is $(C_{3-6})$cycloalkyl optionally containing one ring oxygen atom, wherein ring$^C$ is optionally substituted with one $R^C$, wherein $R^C$ is $(C_{1-4})$alkyl or $(C_{1-4})$fluoroalkyl; or
Ring$^D$, wherein ring$^D$ is a 5- to 6-membered heteroaryl containing 1 to 3 heteroatoms independently selected from O, N or S, wherein ring$^D$ is unsubstituted or mono-substituted with $R^D$, wherein $R^D$ is $(C_{1-4})$alkyl or $(C_{1-4})$fluoroalkyl;

$R^6$ represents
hydrogen;
$(C_{1-4})$alkyl;
$(C_{1-4})$fluoroalkyl; or
$(C_{3-6})$cycloalkyl-$(C_{0-4})$alkylene-, wherein the cycloalkyl is optionally substituted by one to three substituents independently selected from halogen or $(C_{1-4})$alkyl;

$R^7$ represents
hydrogen;
$(C_{1-4})$alkyl; or
$(CH_3)_3Si$—$(CH_2)_2$—O—$(C_{1-4})$alkylene-; and $R^8$ represents
hydrogen;
$(C_{1-4})$alkyl;
$(C_{2-4})$fluoroalkyl;
$(C_{3-6})$cycloalkyl-$(C_{0-4})$alkylene-, wherein the cycloalkyl is optionally substituted by one to three substituents independently selected from halogen or $(C_{1-4})$alkyl;
$(C_{1-4})$alkoxy-C(O)—$(C_{1-4})$alkylene-; or
$(CH_3)_3Si$—$(CH_2)_2$—O—$(C_{1-4})$alkylene-.

The compounds of formula (I) may contain one or more further stereogenic or asymmetric centers, such as one or more additional asymmetric carbon atoms. The compounds of formula (I) may thus be present as mixtures of stereoisomers or preferably as pure stereoisomers. Mixtures of stereoisomers may be separated in a manner known to a person skilled in the art.

In case a particular compound (or generic structure) is designated as (R)- or (S)-enantiomer/as having an absolute (R)- or (S)-configuration, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center. In analogy, cis- or trans-designations (or (R*,R*) designations) are to be understood as referring to the respective stereoisomer of the respective relative configuration in enriched form, especially in essentially pure form.

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

In some instances, the compounds of formula (I) may contain tautomeric forms. Such tautomeric forms are encompassed in the scope of the present invention. For example, in case the present compounds may contain heterocyclic aromatic rings containing unsubstituted ring nitrogen atoms having a free valency such as triazolyl, or pyrazolyl, such rings may be present in tautomeric forms. For example, the group pyrazol-3-yl represents the tautomeric forms 1H-pyrazol-3-yl and 2H-pyrazol-3-yl. Likewise, in case any of $R^5$, $R^7$, or $R^8$ represents hydrogen, the corresponding compounds of formula (I) may be present in form of tautomers, e.g. as is the case for the following example compounds: 6-[1-(2-Fluoro-6-methyl-phenyl)-piperidin-4-yl]-4-(2-trifluoromethyl-benzyl)-2,4,6,7-tetrahydro-[1,2,3]triazolo[4,5-d]pyrimidin-5-one; 6-[1-(2-Fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one; 6-[1-(2-Fluoro-6-methyl-phenyl)-piperidin-4-yl]-4-(2-trifluoromethyl-benzyl)-2,4,6,7-tetrahydro-pyrazolo[4,3-d]pyrimidin-5-one; 5-[1-(2-Fluoro-6-methyl-phenyl)-piperidin-4-yl]-7-(2-trifluoromethyl-benzyl)-2,4,5,7-tetrahydro-pyrazolo[3,4-d]pyrimidin-6-one; 6-(2'-Methoxy-4'-methyl-3,4,5,6-tetrahydro-2H-[1,3']bipyridinyl-4-yl)-4-(2-trifluoromethyl-benzyl)-2,4,6,7-tetrahydro-pyrazolo[4,3-d]pyrimidin-5-one; 5-(2'-Methoxy-4'-methyl-3,4,5,6-tetrahydro-2H-[1,3']bipyridinyl-4-yl)-7-(2-trifluoromethyl-benzyl)-2,4,5,7-tetrahydro-pyrazolo[3,4-d]pyrimidin-6-one; 6-[1-(2-Fluoro-6-methyl-phenyl)-piperidin-4-yl]-4-(3-trifluoromethyl-pyridin-2-ylmethyl)-2,4,6,7-tetrahydro-pyrazolo[4,3-d]pyrimidin-5-one; 5-[1-(2-Fluoro-6-methyl-phenyl)-piperidin-4-yl]-7-(3-trifluoromethyl-pyridin-2-ylmethyl)-2,4,5,7-tetrahydro-pyrazolo[3,4-d]pyrimidin-6-one; 4-(2-Cyclopropyl-benzyl)-6-(2'-methoxy-4'-methyl-3,4,5,6-tetrahydro-2H-[1,3'] bipyridinyl-4-yl)-7-methyl-2,4,6,7-tetrahydro-pyrazolo[4,3-d]pyrimidin-5-one; 4-(2-Cyclopropyl-benzyl)-6-[1-(2-fluoro-6-methyl-phenyl)-piperidin-4-yl]-7-methyl-2,4,6,7-tetrahydro-pyrazolo[4,3-d]pyrimidin-5-one; 6-(2'-Methoxy-4'-methyl-3,4,5,6-tetrahydro-2H-[1,3']bipyridinyl-4-yl)-7-methyl-4-(2-trifluoromethyl-benzyl)-2,4,6,7-tetrahydro-pyrazolo[4,3-d]pyrimidin-5-one; 5-[1-(2-Fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one; 5-[1-(2-Difluoromethyl-6-fluoro-phenyl)-piperidin-4-yl]-4-methyl-7-(2-trifluoromethyl-benzyl)-2,4,5,7-tetrahydro-pyrazolo[3,4-d]pyrimidin-6-one; 5-[1-(2-Chloro-6-fluoro-phenyl)-piperidin-4-yl]-4-methyl-7-(2-trifluoromethyl-benzyl)-2,4,5,7-tetrahydro-pyrazolo[3,4-d]pyrimidin-6-one; 5-(4'-Difluoromethyl-2'-methoxy-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one; 7-(2-Cyclopropyl-benzyl)-5-(4'-difluoromethyl-2'-methoxy-3,4,5,6-tetrahydro-2H-[1,3']bipyridinyl-4-yl)-4-methyl-2,4,5,7-tetrahydro-pyrazolo[3,4-d]pyrimidin-6-one; 5-[1-(2-Chloro-6-fluoro-phenyl)-piperidin-4-yl]-7-(2-cyclopropyl-benzyl)-4-methyl-2,4,5,7-tetrahydro-pyrazolo[3,4-d]pyrimidin-6-one. Thus, for example the compound 6-[1-(2-Fluoro-6-methyl-phenyl)-piperidin-4-yl]-4-(2-trifluoromethyl-benzyl)-2,4,6,7-tetrahydro-pyrazolo[4,3-d]pyrimidin-5-one is a tautomeric form of 6-[1-(2-Fluoro-6-methyl-phenyl)-piperidin-4-yl]-4-(2-trifluoromethyl-benzyl)-1,4,6,7-tetrahydro-pyrazolo[4,3-d]pyrimidin-5-one, both names representing the same chemical entity. Likewise, the compound 5-[1-(2-Fluoro-6-methyl-phenyl)-piperidin-4-yl]-7-(2-trifluoromethyl-benzyl)-2,4,5,7-tetrahydro-pyrazolo[3,4-d]pyrimidin-6-one is a tautomeric form of 5-(1-(2-fluoro-6-methylphenyl)piperidin-4-yl)-7-(2-(trifluoromethyl)benzyl)-1,4,5,7-tetrahydro-6H-pyrazolo[3,4-d]pyrimidin-6-one, both names representing the same chemical entity.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life and/or reduced dosage requirements, and/or may lead to a modified metabolism pathway, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

Deuterated groups are denominated as follows: for example the group (1,1,2,2,2-$^2$H$_5$-ethyl) denominates the residue

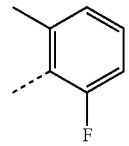

In this patent application, a bond drawn as a dotted line shows the point of attachment of the radical drawn. For example, the radical drawn below

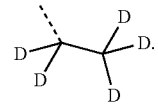

is a 2-fluoro-6-methyl-phenyl group.

Where the plural form is used for compounds, salts, pharmaceutical compositions, diseases and the like, this is intended to mean also a single compound, salt, or the like.

Any reference to compounds of formula (I) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of formula (I), as defined in any one of embodiments 1) to 44), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein. If not explicitly defined otherwise in the respective embodiment or claim, groups defined herein are unsubstituted. Wherever a saturated acyclic or cyclic group contains a heteroatom and/or is attached to a heteroatom that is part of the rest of the molecule and/or is substituted by a substituent that is attached through a heteroatom, such heteroatoms are preferably distant from each other by at least two carbon atoms.

In this application, in case a certain chemical residue is defined as being optionally substituted with a certain number of substituents, this means that said residue is unsubstituted, or substituted with said number of substitutents as explicitly defined.

The term "halogen" means fluorine, chlorine, bromine, or iodine, preferably fluorine or chlorine.

The term "alkyl", used alone or in combination, refers to a saturated straight or branched chain hydrocarbon group containing one to four carbon atoms. The term "$(C_{x-y})$alkyl" (x and y each being an integer), refers to an alkyl group as defined before, containing x to y carbon atoms. For example a $(C_{1-4})$alkyl group contains from one to four carbon atoms. Examples of $(C_{1-4})$alkyl are methyl, ethyl, propyl, isopropyl, butyl, isobutyl, sec.-butyl and tert.-butyl. For avoidance of any doubt, in case a group is referred to as e.g. propyl or butyl, it is meant to be n-propyl, respectively n-butyl. Further, in case a group is referred to as $(C_{0-y})$alkyl group, such group is absent and any free valency of the point of attachment is filled with hydrogen, or it contains 1 up to y carbon atoms as set out before. Examples of $(C_{1-4})$alkyl as used for substituents of $R^1$ are methyl and isopropyl, and in addition ethyl. Examples of $(C_{1-4})$alkyl as used for substituents of $R^2$ are methyl and isopropyl. An example of $(C_{1-4})$alkyl as used for $R^3$ is methyl. An example of $(C_{1-4})$alkyl as used for $R^4$ is methyl. Examples of $(C_{1-4})$alkyl as used for $R^5$ and $R^6$ independently are methyl, ethyl, isopropyl, isobutyl and tert-butyl; especially methyl. An example of $(C_{1-4})$alkyl as used for $R^7$ and $R^8$ is methyl. Examples of $(C_{1-4})$alkyl as used for $R^B$ are methyl, ethyl, isopropyl, and isobutyl.

The term "—$(C_{x-y})$alkylene-", used alone or in combination, refers to bivalently bound alkyl group as defined before containing x to y carbon atoms. Preferably, the points of attachment of a —$(C_{1-y})$alkylene group are in 1,1-diyl, in 1,2-diyl, or in 1,3-diyl arrangement. Preferably, the points of attachment of a —$(C_{2-y})$alkylene group are in 1,2-diyl or in 1,3-diyl arrangement. A —$(C_0)$alkylene- group is absent and refers to a direct bond, thus, the term —$(C_{0-4})$alkylene refers to a direct bond, or —$(C_{1-4})$alkylene. An example of —$(C_{1-4})$alkylene as used for the linker $X^B$ (respectively, for the linker $X^{B1}$ and $X^{B2}$) is methylene.

Alkylene-oxy linker groups —$(C_{1-3})$alkylene-O— as used for example in the substituents $(C_{3-6})$cycloalkyl-$X^{21}$— are to be read from left to right, i.e. they refer to the respective $(C_{3-6})$cycloalkyl-$(C_{1-3})$alkylene-O— groups. An example for $(C_{3-6})$cycloalkyl-$X^{21}$— wherein $X^{21}$ is —$(C_{1-3})$alkylene-O— is cyclopropyl-methoxy. An example for $R^{21a}R^{21b}$N—$(C_{2-3})$alkylene-O— is dimethylamino-ethoxy.

The term "alkynyl", used alone or in combination, refers to a straight or branched hydrocarbon chain containing two to five carbon atoms and one carbon-carbon triple bond. The term "$(C_{x-y})$alkynyl" (x and y each being an integer), refers to an alkynyl group as defined before containing x to y carbon atoms. For example a $(C_{2-5})$alkynyl group contains from two to five carbon atoms. An example of an alkynyl group is 1,1-dimethyl-prop-2-ynyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. Preferred are isopropoxy, ethoxy and methoxy. An example of $(C_{1-4})$alkoxy as used for substituents of $R^1$ is methoxy. Examples of $(C_{1-4})$alkoxy as used for substituents of $R^2$ are methoxy, ethoxy, isopropoxy. Examples of $(C_{1-4})$alkoxy as used for $R^5$ being attached to $(C_{1-4})$alkyl are methoxy and ethoxy.

The term "fluoroalkyl", used alone or in combination, refers to an alkyl group as defined before containing one to four carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl, 2,2,2-trifluoroethyl, 2,2-difluoropropyl, 2,2-difluoro-1-methyl-ethyl, 2-fluoropropyl, 2-fluoro-2-methyl-propyl. Preferred are $(C_1)$fluoroalkyl groups such as trifluoromethyl. Examples of $(C_{1-4})$fluoroalkyl as used for substituents of $R^1$ are trifluoromethyl, and, in addition, difluoromethyl. An example of $(C_{1-4})$fluoroalkyl as used for substituents of $R^2$ is trifluoromethyl. Examples of $(C_{2-4})$fluoroalkyl as used for $R^5$ are 2,2-difluoro-ethyl, 2,2-difluoro-propyl, 2,2-difluoro-1-methyl-ethyl, 2-fluoropropyl, and 2-fluoro-2-methyl-propyl. Examples of $(C_{2-4})$fluoroalkyl as used for $R^7$ are 2-fluoro-2-methyl-propyl and 2,2-difluoro-propyl. Examples of $(C_{2-4})$fluoroalkyl as used for $R^B$ are 2-fluoroethyl, and 2,2-difluoroethyl.

The term "fluoroalkoxy", used alone or in combination, refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$fluoroalkoxy groups such as trifluoromethoxy. An example of $(C_{1-4})$fluoroalkoxy as used for substituents of $R^1$ is trifluoromethoxy. An example of $(C_{1-4})$ fluoroalkoxy as used for substituents of $R^2$ is trifluoromethoxy.

The term "cyano" refers to a group —CN.

The term "cyano-$(C_{1-2})$alkoxy" is to be read from left to right, i.e. it refers to the respective cyano-$(C_{1-2})$alkylene-O— group. An example for cyano-$(C_{1-2})$alkoxy is cyano-methoxy.

The term "cycloalkyl", used alone or in combination, refers to a saturated monocyclic hydrocarbon ring containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms.

Examples of cycloalkyl groups are cyclopropyl, cyclobutyl, cyclopentyl, and cyclohexyl. Preferred are cyclopropyl and cyclobutyl; especially cyclopropyl. An example of $(C_{3-6})$cycloalkyl as used for substituents of $R^1$ is cyclopropyl. An example of $(C_{3-6})$cycloalkyl as used for substituents of $R^2$ is cyclopropyl. Examples of $(C_{3-6})$cycloalkyl as used for $R^5$ being attached to $(C_{0-4})$alkylene- are cyclopropyl, cyclopentyl and cyclohexyl. An example of $(C_{3-6})$cycloalkyl as used for $R^8$ is cyclopropyl.

The term "$(C_{3-6})$cycloalkyl-O—" as used for example in the substituents $(C_{3-6})$cycloalkyl-$X^{21}$— wherein $X^{21}$ is —O— relates to $(C_{3-6})$cycloalkyl as defined above, attached via an —O— linker. Examples of $(C_{3-6})$cycloalkyl-O— as used for substituents of $R^2$ are cyclopropyl-oxy and cyclobutyl-oxy.

The term "cycloalkyl optionally containing one ring oxygen atom", used alone or in combination, refers to a cycloalkyl group as defined before. In addition, one ring carbon atom of said cycloalkyl may be replaced by an oxygen atom.

Examples of such groups are especially cycloalkyl groups such as cyclopropyl, cyclobutyl, cyclopentyl, and cyclohexyl; as well as oxygen containing groups such as oxetanyl, tetrahydrofuranyl, and tetrahydro-2H-pyranyl. Examples of $(C_{3-6})$cycloalkyl-$X^{21}$— groups wherein "the $(C_{3-6})$cycloalkyl optionally contains one ring oxygen atom" as used for substituents of $R^2$ are cyclopropyl, cyclopropyl-oxy, cyclobutyl-oxy, oxetan-3-yl-oxy, cyclopropyl-methoxy, tetrahydropyran-4-yl-oxy, especially oxetan-3-yl-oxy. An example of such group as used for ring is oxetan-3-yl; in particular oxetan-3-yl, 3-methyl-oxetan-3-yl, 3-trifluoromethyl-oxetan-3-yl.

The term "heterocyclyl", used alone or in combination, and if not explicitly defined in a more narrow way, refers to a saturated monocyclic hydrocarbon ring containing one to three (especially one) ring heteroatoms independently selected from nitrogen, sulfur, and oxygen. The term "$(C_{x-y})$heterocyclyl" refers to such a heterocyclyl group containing x to y ring atoms. Heterocyclyl groups are unsubstituted or substituted as explicitly defined; wherein in case a ring nitrogen atom having a free valency is present, such ring nitrogen atom may be substituted as explicitly defined, in addition to further (optional) substituents of such heterocycle. Oxo substituents, if present, are especially attached to a ring carbon atom in alpha position to a ring nitrogen (thus forming together with the nitrogen an amide group, or, in case a ring oxygen is additionally adjacent, a carbamate group, or, in case second ring nitrogen is additionally adjacent, a urea group); or two oxo substituents are substituents of a ring sulfur ring atom (thus forming an —$SO_2$— group).

Heterocyclyl groups as used for the group ring$^B$ are attached to rest of the molecule (i.e. to $X^B$) at a ring carbon atom, comprise one substituted ring nitrogen atom $NR^B$ wherein $R^B$ is as explicitly defined, and are, in addition to $R^B$, optionally substituted as explicitly defined. Examples of heterocyclyl groups as used for the group ring$^B$ are oxetanyl, tetrahydrofuranyl, tetrahydro-2H-pyranyl, azetidinyl, pyrrolidinyl, piperidinyl, and morpholinyl; in particular oxetan-3-yl, azetidin-2-yl, azetidin-3-yl, pyrrolidin-2-yl, pyrrolidin-3-yl, and piperidin-4-yl.

Examples of groups $R^{N1}R^{N2}N$— wherein $R^{N1}$ and $R^{N2}$ together with the nitrogen atom form a 4- to 6-membered saturated ring optionally containing one further ring heteroatom selected from O and N are azetidin-1-yl, pyrrolidin-1-yl, piperidin-1-yl, piperazin-1-yl, and morpholin-4-yl; in particular 3-methoxy-azetidin-1-yl, pyrrolidin-1-yl, piperidin-1-yl, 4-methyl-piperazin-1-yl, and morpholin-4-yl.

Examples of ring A representing "a saturated 4- to 7-membered mono-cyclic carbocyclic ring containing the ring nitrogen atom to which $R^1$ is attached" are azetidin-1,3-diyl, pyrrolidin-1,3-diyl, piperidin-1,4-diyl, piperidin-1,3-yl, and azepan-1,4-diyl; as well as the substituted groups 3-methyl-pyrrolidin-1,3-diyl, and 4-methyl-piperidin-1,4-diyl.

The substituent phenyl as used for $R^1$ independently is mono-, di- or tri-substituted, notably mono-, or di-substituted, especially mono- or di-substituted wherein at least one substituent is attached in ortho position with regard to the point of attachment of the rest of the molecule. Examples are mono-substituted phenyl groups such as 2-methoxy-phenyl; and di-substituted phenyl groups such as 2-chloro-6-methyl-phenyl, 2-fluoro-6-methyl-phenyl, 2,6-dimethyl-phenyl, 2-methoxy-6-methyl-phenyl, 2-fluoro-6-cyano-phenyl, 2-fluoro-6-trifluoromethyl-phenyl, 2-fluoro-6-trifluoromethoxy-phenyl, and, in addition, 2,6-difluorophenyl, 2-chloro-6-fluoro-phenyl, 2-bromo-6-fluoro-phenyl, 2-fluoro-6-ethyl-phenyl, 2-fluoro-6-difluoromethyl-phenyl, and 2-fluoro-6-cyclopropyl-phenyl.

The substituent phenyl as used for $R^2$ is mono-, di- or tri-substituted, notably mono-, or di-substituted, especially mono- or di-substituted wherein at least one substituent is attached in ortho position with regard to the point of attachment of the rest of the molecule. Examples are mono-substituted phenyl group such as 2-chloro-phenyl, 2-cyclopropyl-phenyl, 2-isopropyl-phenyl, 2-ethoxy-phenyl, 2-trifluoromethyl-phenyl, 2-isopropoxy-phenyl, 2-cyclopropoxy-phenyl, 2-(oxetan-3-yloxy)-phenyl, 2-cyclopropylmethoxy-phenyl, 2-trifluoromethoxy-phenyl; di-substituted phenyl groups such as 2-fluoro-6-trifluoromethyl-phenyl and 2-bromo-6-trifluoromethyl-phenyl; and tri-substituted phenyl groups such as 2,4-difluoro-6-isopropoxy-phenyl.

The term "heteroaryl", used alone or in combination, means a 5- to 6-membered monocyclic aromatic ring containing one to a maximum of three heteroatoms, each independently selected from oxygen, nitrogen and sulfur. Examples of such heteroaryl groups are 5-membered heteroaryl such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl; and 6-membered heteroaryl such as pyridinyl, pyrimidinyl, pyridazinyl, and pyrazinyl. The above-mentioned heteroaryl groups are unsubstituted or substituted as explicitly defined. In case 5- or 6-membered heteroaryl group is substituted in ortho-position with regard to the point of attachment of the rest of the molecule, it is understood that such substituent is attached in direct neighbourhood with regard to the point of attachment of the rest of the molecule, i.e. in a relative 1,2-arrangement. Examples of heteroaryl as used for the substituent $R^1$ are notably 6-membered heteroaryl containing one or two nitrogen atoms, or 5-membered heteroaryl containing one or two ring nitrogen atoms and optionally one further heteroatom selected from nitrogen, oxygen or sulfur; in particular 4-chloro-2,5-dimethyl-2H-pyrazol-3-yl, 2,5-dimethyl-4-cyano-pyrazol-3-yl, 3-fluoro-pyridin-2-yl, 3-methoxy-pyridin-2-yl, 2-methoxy-4-methyl-pyridin-3-yl, 2-fluoro-4-methyl-pyridin-3-yl, 2-methyl-4-fluoro-pyridin-3-yl, 2-cyano-4-methyl-pyridin-3-yl, 2,4-dimethoxy-pyridin-3-yl, 4-methoxy-6-methyl-pyrimidin-5-yl, 4,6-dimethoxy-pyrimidin-5-yl, and, in addition, 2-methoxy-4-chloro-pyridin-3-yl, 2-methoxy-4-difluoromethyl-pyridin-3-yl, and 2-methoxy-4-trifluoromethyl-pyridin-3-yl. Examples of heteroaryl as used for the substituent $R^2$ are especially 6-membered heteroaryl containing one or two nitrogen atoms; or 5-membered heteroaryl containing one or two ring nitrogen atoms and one further heteroatom independently selected from nitrogen, oxygen or sulfur; in particular 4-isopropyl-pyrimidin-5-yl, 3-trifluoromethyl-pyrazin-2-yl, 3-trifluoromethyl-pyridin-2-yl, 6-methyl-3-trifluoromethyl-pyridin- 2-yl, 6-deutero-3-trifluoromethyl-pyridin-2-yl, 6-chloro-3-trifluoromethyl-pyridin-2-yl, 6-fluoro-3-trifluoromethyl-pyridin-2-yl, 6-methylamino-3-trifluoromethyl-pyridin-2-yl, 6-methoxy-3-trifluoromethyl-pyridin-2-yl, 6-dimethylamino-3-trifluoromethyl-pyridin-2-yl, 4-trifluoromethyl-pyridin-3-yl, and 4-trifluoromethyl-thiazol-5-yl. Examples of heteroaryl as used for the substituent ring$^D$ are notably 5-membered heteroaryl containing one or two nitrogen atoms and optionally one further heteroatom independently selected from nitrogen, oxygen or sulfur, such as especially oxazolyl, isoxazolyl, oxadiazolyl, thiazolyl, thiadiazolyl; in particular 5-methyl-[1,3,4]-oxadiazol-2-yl, 5-isopropyl-[1,3,4]-oxadiazol-2-yl and 5-trifluoromethyl-[1,3,4]-oxadiazol-2-yl.

Further embodiments of the invention are presented hereinafter:

2) A second embodiment relates to compounds according to embodiment 1), wherein ring A represents a fragment

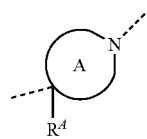

wherein said ring A is selected from azetidin-1,3-diyl, pyrrolidin-1,3-diyl, piperidin-1,4-diyl, piperidin-1,3-yl, and azepan-1,4-diyl (notably ring A is pyrrolidin-1,3-diyl, piperidin-1,4-diyl or azepan-1,4-diyl; especially piperidin-1,4-diyl); and wherein said ring A is substituted with $R^1$ on the ring nitrogen atom (i.e. in respective position 1), and optionally substituted on the ring carbon atom linked to the rest of the molecule (i.e. in position 3 of azetidin-1,3-diyl, pyrrolidin-1,3-diyl and piperidin-1,3-yl, respectively, in position 4 of piperidin-1,4-diyl and azepan-1,4-diyl) with $R^4$, wherein $R^4$ is $(C_{1-4})$alkyl (especially methyl).

In a sub-embodiment, ring A (wherein especially ring A is piperidin-1,4-diyl) is substituted with $R^1$ and carries no further substituent (i.e. $R^4$ in the fragment above is absent and the free valency of the respective ring carbon atom is saturated with hydrogen)].

3) Another embodiment relates to compounds according to embodiments 1) or 2), wherein ring A is substituted with $R^1$ and carries no further substituent

[i.e. ring A represents a fragment

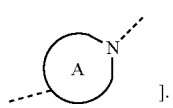

].

4) Another embodiment relates to compounds according to any one of embodiments 1) to 3), wherein Y represents $NR^5$; one of X and Z represents N, and the other of X and Z represents N or CH.

In particular, this embodiment encompasses ring groups wherein
Y represents $NR^5$, X represents N and Z represents CH;
Y represents $NR^5$, X represents CH and Z represents N; or
Y represents $NR^5$, X represents N and Z represents N.

5) Another embodiment relates to compounds according to any one of embodiments 1) to 3), wherein
Y represents $NR^5$, X represents N and Z represents CH.

6) Another embodiment relates to compounds according to any one of embodiments 1) to 3), wherein
Y represents $CR^6$; one of X and Z represents $NR^7$, O or S, and the other of X and Z represents N.

In particular, this embodiment encompasses ring groups wherein
Y represents $CR^6$; X represents O and Z represents N;
Y represents $CR^6$; X represents S and Z represents N; or
Y represents $CR^6$; X represents $NR^7$ and Z represents N; or
Y represents $CR^6$; X represents N and Z represents $NR^7$.

7) Another embodiment relates to compounds according to any one of embodiments 1) to 3), wherein
Y represents CH; X represents $NR^7$ and Z represents N;
Y represents CH; X represents N and Z represents $NR^7$;
Y represents N; X represents $NR^8$ and Z represents CH;
Y represents N; X represents CH and Z represents $NR^8$;
Y represents N; X represents $NR^8$ and Z represents N; or
Y represents N; X represents N and Z represents $NR^8$.

8) Another embodiment relates to compounds according to any one of embodiments 1) to 3), wherein
Y represents CH; X represents N, and Z represents $NR^7$;
Y represents N; X represents CH, and Z represents $NR^8$; or
Y represents N; X represents N and Z represents $NR^8$.

9) Another embodiment relates to compounds according to any one of embodiments 1) to 8), wherein $R^1$ represents
phenyl which is mono-, di- or tri-substituted (notably mono-, or di-substituted, especially mono- or di-substituted wherein at least one substituent is attached in ortho position with regard to the point of attachment of the rest of the molecule), wherein the substituents are independently selected from $(C_{1-4})$alkyl (especially methyl, isopropyl); $(C_{1-4})$alkoxy (especially methoxy); $(C_{1-3})$fluoroalkyl (especially trifluoromethyl, or difluoromethyl); $(C_{1-3})$fluoroalkoxy (especially trifluoromethoxy); halogen (especially fluoro or chloro); cyano; and $(C_{3-6})$cycloalkyl (especially cyclopropyl);
5-membered heteroaryl containing one or two ring nitrogen atoms and optionally one further heteroatom selected from nitrogen, oxygen or sulfur (notably pyrazolyl; especially 2H-pyrazol-3-yl) which is mono-, or di- or tri-substituted (notably di- or tri-substituted), wherein the substituents are independently selected from $(C_{1-4})$alkyl (especially methyl); halogen (especially chloro); cyano; and $(C_{3-6})$cycloalkyl (especially cyclopropyl); or
6-membered heteroaryl containing one or two nitrogen atoms (notably pyridinyl, pyrimidinyl; especially pyridine-2-yl, pyridine-3-yl, pyrimidin-5-yl) which is mono-, or di-substituted (wherein notably at least one substituent is attached in ortho position with regard to the point of attachment of the rest of the molecule; especially such 6-membered heteroaryl is di-substituted in both ortho positions), wherein the substituents are independently selected from $(C_{1-4})$alkyl (especially methyl, isopropyl); $(C_{1-4})$alkoxy (especially methoxy); halogen (especially fluoro); cyano; $(C_{3-6})$cycloalkyl (especially cyclopropyl), and, in addition, $(C_{1-3})$fluoroalkyl (especially trifluoromethyl, difluoromethyl).

10) Another embodiment relates to compounds according to any one of embodiments 1) to 8), wherein $R^1$ represents
phenyl which is mono-, di- or tri-substituted (notably mono-, or di-substituted, especially mono- or di-substituted wherein at least one substituent is attached in ortho position with regard to the point of attachment of the rest of the molecule), wherein the substituents are independently selected from $(C_{1-4})$alkyl (especially methyl, isopropyl); $(C_{1-4})$alkoxy (especially methoxy); $(C_{1-3})$fluoroalkyl (especially trifluoromethyl, or difluoromethyl); $(C_{1-3})$fluoroalkoxy (especially trifluoromethoxy); halogen (especially fluoro or chloro); cyano; and $(C_{3-6})$cycloalkyl (especially cyclopropyl);

pyrazolyl (especially 2H-pyrazol-3-yl) which is mono-, or di- or tri-substituted (notably tri-substituted), wherein the substituents are independently selected from $(C_{1-4})$alkyl (especially methyl); halogen (especially chloro); cyano; and $(C_{3-6})$cycloalkyl (especially cyclopropyl); or pyridinyl, in particular pyridine-2-yl and pyridine-3-yl (especially pyridine-3-yl) which is mono-, or di-substituted (wherein notably at least one substituent is attached in ortho position with regard to the point of attachment of the rest of the molecule; especially such pyridinyl is di-substituted in both ortho positions), wherein the substituents are independently selected from $(C_{1-4})$alkyl (especially methyl, isopropyl); $(C_{1-4})$alkoxy (especially methoxy); halogen (especially fluoro); cyano; $(C_{3-6})$cycloalkyl (especially cyclopropyl); and, in addition, $(C_{1-3})$fluoroalkyl (especially trifluoromethyl, difluoromethyl);

pyrimidinyl, in particular pyrimidin-5-yl, wherein which is mono-, or di-substituted (wherein notably at least one substituent is attached in ortho position with regard to the point of attachment of the rest of the molecule; especially such pyrimidinyl is di-substituted in both ortho positions), wherein the substituents are independently selected from $(C_{1-4})$alkyl (especially methyl, isopropyl); and $(C_{1-4})$alkoxy (especially methoxy).

11) Another embodiment relates to compounds according to any one of embodiments 1) to 8), wherein $R^1$ represents phenyl which is mono-, di- or tri-substituted (notably mono-, or di-substituted, especially mono- or di-substituted wherein at least one substituent is attached in ortho position with regard to the point of attachment of the rest of the molecule), wherein the substituents are independently selected from $(C_{1-4})$alkyl (especially methyl, isopropyl); $(C_{1-4})$alkoxy (especially methoxy); $(C_{1-3})$fluoroalkyl (especially trifluoromethyl, or difluoromethyl); $(C_{1-3})$fluoroalkoxy (especially trifluoromethoxy); halogen (especially fluoro and chloro); and cyano;

pyrazolyl (especially 2H-pyrazol-3-yl) which is mono-, or di- or tri-substituted (notably tri-substituted), wherein the substituents are independently selected from $(C_{1-4})$alkyl (especially methyl); and halogen (especially chloro);

pyridinyl, in particular pyridine-2-yl and pyridine-3-yl (especially pyridine-3-yl) which is mono-, or di-substituted (wherein notably at least one substituent is attached in ortho position with regard to the point of attachment of the rest of the molecule; especially such pyridinyl is di-substituted in both ortho positions), wherein the substituents are independently selected from $(C_{1-4})$alkyl (especially methyl, isopropyl); $(C_{1-4})$alkoxy (especially methoxy); halogen (especially fluoro); and, in addition, $(C_{1-3})$fluoroalkyl (especially trifluoromethyl, difluoromethyl).

12) Another embodiment relates to compounds according to any one of embodiments 1) to 8), wherein $R^1$ represents phenyl which is mono-, di- or tri-substituted (notably mono-, or di-substituted, especially mono- or di-substituted wherein at least one substituent is attached in ortho position with regard to the point of attachment of the rest of the molecule), wherein the substituents are independently selected from $(C_{1-4})$alkyl (especially methyl); $(C_{1-4})$alkoxy (especially methoxy); $(C_{1-3})$fluoroalkyl (especially trifluoromethyl, or difluoromethyl); $(C_{1-3})$fluoroalkoxy (especially trifluoromethoxy); halogen (especially fluoro and chloro); cyano; and, in addition, cyclopropyl;

pyridinyl (notably pyridine-2-yl or pyridine-3-yl; especially pyridine-3-yl) which is mono-, or di-substituted (wherein notably at least one substituent is attached in ortho position with regard to the point of attachment of the rest of the molecule; especially such pyridinyl is di-substituted in both ortho positions), wherein the substituents are independently selected from $(C_{1-4})$alkyl (especially methyl); $(C_{1-4})$alkoxy (especially methoxy); halogen (especially fluoro); and, in addition, $(C_{1-3})$fluoroalkyl (especially trifluoromethyl, difluoromethyl) and cyclopropyl.

13) Another embodiment relates to compounds according to any one of embodiments 1) to 8), wherein $R^1$ represents phenyl which is mono- or di-substituted, wherein at least one substituent is attached in ortho position with regard to the point of attachment of the rest of the molecule (especially di-substituted in both ortho positions), wherein the substituents are independently selected from $(C_{1-4})$alkyl (especially methyl, isopropyl); $(C_{1-4})$alkoxy (especially methoxy); halogen (especially fluoro or chloro); cyano; and, in addition, $(C_{1-3})$fluoroalkyl (especially trifluoromethyl, difluoromethyl) and cyclopropyl; or pyridinyl which is di-substituted, wherein at least one substituent is attached in ortho position with regard to the point of attachment of the rest of the molecule (especially di-substituted in both ortho positions), wherein the substituents are independently selected from $(C_{1-4})$alkyl (especially methyl, isopropyl); $(C_{1-4})$alkoxy (especially methoxy); halogen (especially fluoro); and, in addition, $(C_{1-3})$fluoroalkyl (especially trifluoromethyl, difluoromethyl).

14) Another embodiment relates to compounds according to any one of embodiments 1) to 8), wherein $R^1$ represents phenyl which is mono-, or di-substituted; wherein at least one substituent is attached in ortho position with regard to the point of attachment of the rest of the molecule;

wherein said ortho-substituent is $(C_{1-4})$alkyl (especially methyl); $(C_{1-4})$alkoxy (especially methoxy); halogen (especially fluoro); or $(C_{1-3})$fluoroalkyl (especially difluoromethyl); [especially such substituent is methyl, methoxy, fluoro, or difluoromethyl; in particular methyl, fluoro, or difluoromethyl];

and, if present, the remaining substituent independently is methyl; methoxy; halogen; or cyano; [especially such remaining substituent is methyl, methoxy or fluoro; in particular methyl or fluoro]; wherein especially such remaining substituent is attached in the other ortho position with regard to the point of attachment of the rest of the molecule.

15) Another embodiment relates to compounds according to any one of embodiments 1) to 8), wherein $R^1$ is 2-chloro-6-methyl-phenyl, 2-fluoro-6-methyl-phenyl, 2,6-dimethyl-phenyl, 2-methoxy-6-methyl-phenyl, 2-fluoro-6-cyano-phenyl, 2-fluoro-6-trifluoromethyl-phenyl, 2-fluoro-6-trifluoromethoxy-phenyl, 4-chloro-2,5-dimethyl-2H-pyrazol-3-yl, 2,5-dimethyl-4-cyano-pyrazol-3-yl, 3-fluoro-pyridin-2-yl, 3-methoxy-pyridin-2-yl, 2-methoxy-4-methyl-pyridin-3-yl, 2-fluoro-4-methyl-pyridin-3-yl, 2-methyl-4-fluoro-, 2-cyano-4-methyl-pyridin-3-yl, 2,4-dimethoxypyridin-3-yl, 4-methoxy-6-methyl-pyrimidin-5-yl, or 4,6-dimethoxy-pyrimidin-5-yl, and, in addition, 2,6-difluorophenyl, 2-chloro-6-fluoro-phenyl, 2-bromo-6-fluoro-phenyl, 2-fluoro-6-difluoromethyl-phenyl, 2-fluoro-6-cyclopropyl-phenyl, 2-methoxy-4-chloro-pyridin-3-yl, 2-methoxy-4-difluoromethyl-pyridin-3-yl, or 2-methoxy-4-trifluoromethyl-pyridin-3-yl [especially $R^1$ is 2-chloro-6-methyl-phenyl, 2-fluoro-6-methyl-phenyl, 2,6-dimethyl-phenyl, 2-methoxy-6-methyl-phenyl, 2-fluoro-6-cyano-phenyl, 2-fluoro-6-trifluoromethyl-phenyl, 2-fluoro-6-trifluoromethoxy-phenyl, 2-methoxy-4-methyl-pyridin-3-yl, or 2-cyano-4-methyl-pyridin-3-yl; or $R^1$ is 2,6-difluorophenyl, 2-chloro-6-fluoro-phenyl, 2-bromo-6-fluoro-phenyl, 2-fluoro-6-difluoromethyl-phenyl, 2-fluoro-6-cyclopropyl-phenyl, 2-methoxy-4-chloro-pyridin-3-yl, 2-methoxy-4-difluoromethyl-pyridin-3-yl, or 2-methoxy-4-trifluoromethyl-pyridin-3-yl].

16) Another embodiment relates to compounds according to any one of embodiments 1) to 15), wherein $R^2$ represents phenyl, 5-membered heteroaryl (notably 5-membered heteroaryl containing one or two ring nitrogen atoms and one further heteroatom independently selected from nitrogen, oxygen or sulfur; especially thiazolyl); or 6-membered heteroaryl (notably 6-membered heteroaryl containing one or two nitrogen atoms; especially pyridinyl, pyrimidinyl, pyrazinyl, pyridazinyl); wherein said phenyl, 5-membered heteroaryl, or 6-membered heteroaryl, independently is mono-, or di-, or tri-substituted (notably mono-, or di-substituted, especially mono-, or di-substituted wherein at least one substituent is attached in ortho position with regard to the point of attachment of the rest of the molecule), wherein the substituents are independently selected from $(C_{1-4})$alkyl (especially methyl, isopropyl);
$(C_{1-4})$alkoxy (especially methoxy, ethoxy, isopropoxy);
$(C_{1-3})$fluoroalkyl (especially trifluoromethyl);
$(C_{1-3})$fluoroalkoxy (especially trifluoromethoxy);
halogen (especially bromo, chloro, fluoro);
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl contains one optional ring oxygen atom; [especially such group $(C_{3-6})$cycloalkyl-$X^{21}$— is cyclopropyl, cyclopropyl-oxy, oxetan-3-yl-oxy, cyclopropyl-methoxy]; and
$R^{21a}R^{21b}N$—, wherein $R^{21a}$ and $R^{21b}$ independently represent hydrogen or $(C_{1-4})$alkyl; [especially such group $R^{21a}R^{21b}N$— is dimethylamino, methylamino];
wherein preferably said substituent in ortho position, if present, is $(C_{1-4})$alkyl, $(C_{1-4})$alkoxy, $(C_{1-3})$fluoroalkyl, $(C_{1-3})$fluoroalkoxy, or $(C_{3-6})$cycloalkyl-$X^{21}$— (especially such ortho substituent is trifluoromethyl); and the other substituents, if present, are independently selected from $(C_{1-4})$alkyl, $(C_{1-4})$alkoxy, halogen, and $R^{21a}R^{21b}N$—.

17) Another embodiment relates to compounds according to any one of embodiments 1) to 15), wherein $R^2$ represents phenyl; wherein said phenyl is mono-, or di-, or tri-substituted (notably mono-, or di-substituted, especially mono-, or di-substituted wherein at least one substituent is attached in ortho position with regard to the point of attachment of the rest of the molecule), wherein the substituents are independently selected from
$(C_{1-4})$alkyl (especially methyl, isopropyl);
$(C_{1-4})$alkoxy (especially methoxy, ethoxy, isopropoxy);
$(C_{1-3})$fluoroalkyl (especially trifluoromethyl);
$(C_{1-3})$fluoroalkoxy (especially trifluoromethoxy);
halogen (especially bromo, chloro, fluoro); and
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl contains one optional ring oxygen atom; [especially such group $(C_{3-6})$cycloalkyl-$X^{21}$— is cyclopropyl, cyclopropyl-oxy, oxetan-3-yl-oxy, cyclopropyl-methoxy];
wherein preferably said substituent in ortho position, if present, is $(C_{1-4})$alkyl, $(C_{1-4})$alkoxy, $(C_{1-3})$fluoroalkyl, $(C_{1-3})$fluoroalkoxy, or $(C_{3-6})$cycloalkyl-$X^{21}$— (especially such ortho substituent is trifluoromethyl); and the other substituents, if present, are independently selected from $(C_4)$alkyl, $(C_{1-4})$alkoxy, and halogen; or
5-membered heteroaryl containing one or two ring nitrogen atoms and one further heteroatom independently selected from nitrogen, oxygen or sulfur (notably thiazolyl; especially thiazol-5-yl); wherein said 5-membered heteroaryl is mono-, or di-substituted (especially di-substituted), wherein the substituents are independently selected from
$(C_{1-4})$alkyl (especially methyl, isopropyl);
$(C_{1-3})$fluoroalkyl (especially trifluoromethyl); and
$(C_{3-6})$cycloalkyl (especially cyclopropyl); or
6-membered heteroaryl containing one or two nitrogen atoms (notably pyridinyl, pyrimidinyl, or pyrazinyl; especially pyridin-2-yl, pyridin-3-yl, pyrimid-5-yl or pyrazin-2-yl); wherein said 6-membered heteroaryl independently is mono-, or di-substituted (notably mono-, or di-substituted, especially mono-, or di-substituted wherein at least one substituent is attached in ortho position with regard to the point of attachment of the rest of the molecule), wherein the substituents are independently selected from
$(C_{1-4})$alkyl (especially methyl, isopropyl);
$(C_{1-4})$alkoxy (especially methoxy, ethoxy, isopropoxy);
$(C_{1-3})$fluoroalkyl (especially trifluoromethyl);
halogen (especially chloro, fluoro); and
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl contains one optional ring oxygen atom; [especially such group $(C_{3-6})$cycloalkyl-$X^{21}$— is cyclopropoxy, oxetan-3-yl-oxy, cyclopropyl-methoxy]; $R^{21a}R^{21b}N$—, wherein $R^{21a}$ and $R^{21b}$ independently represent hydrogen or $(C_{1-4})$alkyl; [especially such group $R^{21a}R^{21b}N$— is dimethylamino, methylamino];
wherein preferably said substituent in ortho position, if present, is $(C_{1-3})$fluoroalkyl (especially trifluoromethyl), and the other substituents, if present, are selected from $(C_{1-4})$alkyl, $(C_{1-4})$alkoxy, halogen, and $R^{21a}R^{21b}N$—.

18) Another embodiment relates to compounds according to any one of embodiments 1) to 15), wherein $R^2$ represents phenyl; wherein said phenyl is mono-, or di-substituted (notably mono-substituted, especially mono-substituted in ortho position with regard to the point of attachment of the rest of the molecule), wherein the substituents are independently selected from
$(C_{1-4})$alkyl (especially isopropyl);
$(C_{1-4})$alkoxy (especially, ethoxy, isopropoxy);
$(C_{1-3})$fluoroalkyl (especially trifluoromethyl);
$(C_{1-3})$fluoroalkoxy (especially trifluoromethoxy);
halogen (especially chloro, fluoro); and
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl contains one optional ring oxygen atom; [especially such group $(C_{3-6})$cycloalkyl-$X^{21}$— is cyclopropoxy, oxetan-3-yl-oxy, cyclopropyl-methoxy];

wherein preferably said substituent in ortho position, if present, is $(C_{1-4})$alkyl, $(C_{1-4})$alkoxy, $(C_{1-3})$fluoroalkyl, $(C_{1-3})$fluoroalkoxy, or $(C_{3-6})$cycloalkyl-$X^{21}$— (especially such ortho substituent is trifluoromethyl); or 6-membered heteroaryl containing one or two nitrogen atoms (notably pyridinyl; especially pyridin-2-yl); wherein said 6-membered heteroaryl independently is mono-, or di-substituted (notably mono-, or di-substituted, especially mono-, or di-substituted wherein at least one substituent is attached in ortho position with regard to the point of attachment of the rest of the molecule), wherein the substituents are independently selected from $(C_{1-4})$alkoxy (especially methoxy);
$(C_{1-3})$fluoroalkyl (especially trifluoromethyl);
halogen (especially chloro, fluoro); and
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl contains one optional ring oxygen atom; [especially such group $(C_{3-6})$cycloalkyl-$X^{21}$— is cyclopropoxy, oxetan-3-yl-oxy, cyclopropyl-methoxy];

wherein preferably said substituent in ortho position, if present, is $(C_{1-3})$fluoroalkyl (especially trifluoromethyl); and the other substituent, if present, is selected from $(C_{1-4})$alkyl, $(C_{1-4})$alkoxy, and halogen.

19) Another embodiment relates to compounds according to any one of embodiments 1) to 15), wherein $R^2$ is 2-chlorophenyl, 2-cyclopropyl-phenyl, 2-isopropyl-phenyl, 2-ethoxy-phenyl, 2-trifluoromethyl-phenyl, 2-isopropoxy-phenyl, 2-cyclopropoxy-phenyl, 2-(oxetan-3-yloxy)-phenyl, 2-cyclopropylmethoxy-phenyl, 2-fluoro-6-trifluoromethyl-phenyl, 2-bromo-6-trifluoromethyl-phenyl, 2-trifluoromethoxy-phenyl, 2,4-difluoro-6-isopropoxy-phenyl, 4-isopropyl-pyrimid-5-yl, 3-trifluoromethyl-pyrazin-2-yl, 3-trifluoromethyl-pyridin-2-yl, 6-methyl-3-trifluoromethyl-pyridin-2-yl, 6-chloro-3-trifluoromethyl-pyridin-2-yl, 6-fluoro-3-trifluoromethyl-pyridin-2-yl, 6-methylamino-3-trifluoromethyl-pyridin-2-yl, 6-methoxy-3-trifluoromethyl-pyridin-2-yl, 6-dimethylamino-3-trifluoromethyl-pyridin-2-yl, 4-trifluoromethyl-pyridin-3-yl or 2-methyl-4-trifluoromethyl-thiazol-5-yl [especially 2-chloro-phenyl, 2-cyclopropyl-phenyl, 2-isopropyl-phenyl, 2-ethoxy-phenyl, 2-trifluoromethyl-phenyl, 2-isopropoxy-phenyl, 2-cyclopropoxy-phenyl, 2-(oxetan-3-yloxy)-phenyl, 2-cyclopropylmethoxy-phenyl, 2-fluoro-6-trifluoromethyl-phenyl, 2-trifluoromethoxy-phenyl, 3-trifluoromethyl-pyridin-2-yl, 6-chloro-3-trifluoromethyl-pyridin-2-yl, 6-fluoro-3-trifluoromethyl-pyridin-2-yl, or 6-methoxy-3-trifluoromethyl-pyridin-2-yl; in particular 2-trifluoromethyl-phenyl, 3-trifluoromethyl-pyridin-2-yl, 6-chloro-3-trifluoromethyl-pyridin-2-yl, 6-fluoro-3-trifluoromethyl-pyridin-2-yl].

20) Another embodiment relates to compounds according to any one of embodiments 1) to 19), wherein $R^3$ represents hydrogen, or methyl (especially hydrogen).

21) Another embodiment relates to compounds according to any one of embodiments 1) to 20), wherein $R^4$ represents hydrogen or methyl (especially hydrogen).

22) Another embodiment relates to compounds according to any one of embodiments 1) to 21), wherein $R^5$ represents hydrogen;
$(C_{1-4})$alkyl (especially methyl);
$(C_{1-4})$alkyl which is mono-substituted with $(C_{1-4})$alkoxy (especially methoxy, ethoxy), or cyano;
$(C_{2-4})$alkyl which is mono-substituted with hydroxy or $R^{N1}R^{N2}N$—, wherein $R^{N1}$ and $R^{N2}$ together with the nitrogen atom form a 4- to 6-membered saturated ring optionally containing one further ring heteroatom selected from O and N; wherein said ring is optionally mono-substituted with $(C_{1-4})$alkyl, or $(C_{1-4})$alkoxy;
$R^{N1}$ and $R^{N2}$ are independently selected from hydrogen, $(C_{1-4})$alkyl, $(C_{3-6})$cycloalkyl-$(C_{0-4})$alkylene-, or $(C_{1-4})$alkoxy-$(C_{2-4})$alkylene;
$R^{N1}$ represents $(C_{1-4})$alkyl-C(O)—; and $R^{N2}$ represents hydrogen, or $(C_{1-4})$alkyl; or
$R^{N1}$ represents phenylsulfonyl-, wherein the phenyl is optionally substituted by one to three substituents independently selected from $(C_{1-4})$alkyl, $(C_{1-4})$alkoxy, halogen, cyano, or nitro; and $R^{N2}$ represents hydrogen, or $(C_{1-4})$alkyl;

$(C_{3-4})$alkyl which is di-substituted, wherein the substituents are independently selected from hydroxy, $(C_{1-4})$alkoxy, or $R^{N11}R^{N12}N$—, wherein $R^{N11}$ and $R^{N12}$ are independently selected from hydrogen, or $(C_{1-4})$alkyl;
$(C_{2-4})$fluoroalkyl;
$(C_{2-5})$alkynyl;
$(C_{2-5})$alkenyl;
$R^{N3}R^{N4}N$—C(O)—$(C_{1-4})$alkylene-, wherein $R^{N3}$ and $R^{N4}$ independently are hydrogen or $(C_{1-4})$alkyl;
$(C_{1-4})$alkoxy-C(O)—$(C_{1-4})$alkylene-;
$(C_{1-4})$alkoxy-C(O)—$(C_{2-4})$alkylene-, wherein the $(C_{2-4})$alkylene is mono-substituted by $R^{N5}R^{N6}N$—, wherein $R^{N5}$ and $R^{N6}$ independently are hydrogen or $(C_{1-4})$alkyl
$(C_{1-4})$alkoxy-C(O)—$(C_{2-4})$alkylene-, wherein the $(C_{2-4})$alkylene is substituted by one to three halogen;
$(C_{1-4})$alkoxy-C(O)—NH—$(C_{2-4})$alkylene-, wherein the $(C_{2-4})$alkylene- is optionally substituted by one to three halogen;
$(C_{3-6})$cycloalkyl-$(C_{0-4})$alkylene-, wherein the cycloalkyl is optionally substituted by one or two substituents independently selected from fluoro, methyl, nitro, or $(C_{1-4})$alkoxy-C(O)—NH—; or
ring$^B$-$X^B$—; wherein $X^B$ is a direct bond, or $(C_{1-4})$alkylene- (especially methylene); and wherein ring$^B$ is a 4- to 6-membered saturated heterocyclyl containing one ring heteratom which is O, or $NR^B$, wherein said ring$^B$ is attached to $X^B$ at a ring carbon atom;
wherein said ring$^B$ is optionally substituted by one or two substituents independently selected from oxo, hydroxy, fluoro, $(C_{1-4})$alkyl (especially methyl) or $(C_{1-4})$alkoxy (especially methoxy); and wherein $R^B$ independently represents hydrogen;
$(C_{1-4})$alkyl;
$(C_{2-4})$fluoroalkyl;
$(C_{1-4})$alkyl-C(O)—;
$(C_{1-4})$alkoxy-C(O)—;
$(C_{1-4})$alkyl-SO$_2$—;
$R^{N7}R^{N8}N$—SO$_2$— wherein $R^{N7}$ and $R^{N8}$ are independently hydrogen or $(C_{1-4})$alkyl;
$R^{N9}R^{N10}N$—C(O)— wherein $R^{N9}$ and $R^{N10}$ are independently hydrogen or $(C_{1-4})$alkyl;
Ring$^C$-O—C(O)—, and wherein ring$^C$ is $(C_{3-6})$cycloalkyl optionally containing one ring oxygen atom, wherein ring$^C$ is optionally substituted with one $R^C$, wherein $R^C$ is $(C_{1-4})$alkyl or $(C_{1-4})$fluoroalkyl; or
Ring$^D$, wherein ring$^D$ is a 5- to 6-membered heteroaryl containing 1 to 3 heteroatoms independently selected from O, N or S (especially 5-membered heteroaryl containing one or two nitrogen atoms and optionally one further heteroatom independently selected from nitrogen, oxygen or sulfur), wherein ring$^D$ is unsubstituted or mono-substituted with $R^D$, wherein $R^D$ is $(C_{1-4})$alkyl or $(C_{1-4})$fluoroalkyl.

23) Another embodiment relates to compounds according to any one of embodiments 1) to 21), wherein $R^5$ represents
hydrogen;
$(C_{1-4})$alkyl;
$(C_{1-4})$alkyl which is mono-substituted with $(C_{1-4})$alkoxy (especially methoxy, ethoxy), or cyano;
$(C_{2-4})$alkyl which is mono-substituted with hydroxy or $R^{N1}R^{N2}N$—, wherein
  $R^{N1}$ and $R^{N2}$ together with the nitrogen atom form a 4- to 6-membered saturated ring optionally containing one further ring heteroatom selected from O and N; wherein said ring is optionally mono-substituted with $(C_{1-4})$alkyl, or $(C_{1-4})$alkoxy;
  $R^{N1}$ and $R^{N2}$ are independently selected from hydrogen, $(C_{1-4})$alkyl, $(C_{3-6})$cycloalkyl-$(C_{0-4})$alkylene-, or $(C_{1-4})$alkoxy-$(C_{2-4})$alkylene;
  $R^{N1}$ represents $(C_{1-4})$alkyl-C(O)—; and $R^{N2}$ represents hydrogen, or $(C_{1-4})$alkyl; or
  $R^{N1}$ represents phenylsulfonyl-, wherein the phenyl is optionally substituted by one to three substituents independently selected from $(C_{1-4})$alkyl, $(C_{1-4})$alkoxy, halogen, cyano, or nitro; and $R^{N2}$ represents hydrogen, or $(C_{1-4})$alkyl;
$(C_{3-4})$alkyl which is di-substituted, wherein the substituents are independently selected from hydroxy, $(C_{1-4})$alkoxy, or $R^{N11}R^{N12}N$—, wherein $R^{N11}$ and $R^{N12}$ are independently selected from hydrogen, or $(C_{1-4})$alkyl;
$(C_{2-4})$fluoroalkyl;
$(C_{2-5})$alkenyl;
$(C_{1-4})$alkoxy-C(O)—$(C_{1-4})$alkylene-;
$(C_{3-6})$cycloalkyl-$(C_{0-4})$alkylene-, wherein the cycloalkyl is optionally substituted by one or two substituents independently selected from fluoro, methyl, nitro, or $(C_{1-4})$alkoxy-C(O)—NH—;
ring$^{B1}$-$X^{B1}$—; wherein $X^{B1}$ is a direct bond, or $(C_{1-4})$alkylene- (especially methylene); and wherein ring$^{B1}$ is a 4- to 6-membered saturated heterocyclyl containing one ring heteroatom which is O (especially oxetanyl), wherein said ring$^{B1}$ is attached to $X^{B1}$ at a ring carbon atom; wherein said ring$^B$ is optionally substituted by one substituent selected from hydroxy, fluoro, $(C_{1-4})$alkyl (especially methyl) or $(C_{1-4})$alkoxy (especially methoxy); or
ring$^{B2}$-$X^{B2}$—; wherein $X^{B2}$ is a direct bond, or $(C_{1-4})$alkylene- (especially methylene); and wherein ring$^{B2}$ is a 4- to 6-membered saturated heterocyclyl containing one ring heteroatom which is $NR^B$ (especially azetidinyl, or pyrrolidinyl), wherein said ring$^{B2}$ is attached to $X^{B2}$ at a ring carbon atom; wherein said ring$^{B2}$ is optionally substituted by one oxo substituent, or by one or two fluoro substituents; and wherein $R^B$ independently represents
hydrogen;
$(C_{1-4})$alkyl;
$(C_{2-4})$fluoroalkyl;
$(C_{1-4})$alkyl-C(O)—;
$(C_{1-4})$alkoxy-C(O)—;
$(C_{1-4})$alkyl-SO$_2$—;
$R^{N7}R^{N8}N$—SO$_2$— wherein $R^{N7}$ and $R^{N8}$ are independently hydrogen or $(C_{1-4})$alkyl;
$R^{N9}R^{N10}N$—C(O)— wherein $R^{N9}$ and $R^{N10}$ are independently hydrogen or $(C_{1-4})$alkyl;
Ring$^C$-O—C(O)—, and wherein ring$^C$ is $(C_{3-6})$cycloalkyl optionally containing one ring oxygen atom, wherein ring$^C$ is optionally substituted with one $R^C$, wherein $R^C$ is $(C_{1-4})$alkyl or $(C_{1-4})$fluoroalkyl; or
Ring$^D$, wherein ring$^D$ is a 5- to 6-membered heteroaryl containing 1 to 3 heteroatoms independently selected from O, N or S (especially 5-membered heteroaryl containing one or two nitrogen atoms and optionally one further heteroatom independently selected from nitrogen, oxygen or sulfur), wherein ring$^D$ is unsubstituted or mono-substituted with $R^D$, wherein $R^D$ is $(C_{1-4})$alkyl or $(C_{1-4})$fluoroalkyl.

24) Another embodiment relates to compounds according to any one of embodiments 1) to 21), wherein $R^5$ represents
hydrogen;
$(C_{1-4})$alkyl (especially methyl);
$(C_{1-4})$alkyl which is mono-substituted with $(C_{1-4})$alkoxy (especially methoxy, ethoxy), or cyano;
$(C_{2-4})$alkyl which is mono-substituted with hydroxy;
$(C_{2-4})$fluoroalkyl (especially 2,2-difluoro-propyl);
$(C_{2-5})$alkenyl;
$(C_{1-4})$alkoxy-C(O)—$(C_{1-4})$alkylene-;
$(C_{3-6})$cycloalkyl-$(C_{0-4})$alkylene-, wherein the cycloalkyl is optionally substituted by one or two substituents independently selected from fluoro, and methyl; [especially such $(C_{3-6})$cycloalkyl-$(C_{0-4})$alkylene- is cyclopropyl];
ring$^{B1}$-$X^{B1}$—; wherein $X^{B1}$ is a direct bond or methylene; and wherein ring$^{B1}$ is a 4- to 6-membered saturated heterocyclyl containing one ring heteroatom which is O (especially oxetanyl), wherein said ring$^{B1}$ is attached to $X^{B1}$ at a ring carbon atom; wherein said ring$^{B1}$ is optionally substituted by one substituent selected from hydroxy, fluoro, or $(C_{1-4})$alkyl (especially methyl);
ring$^{B2}$-$X^{B2}$—; wherein $X^{B2}$ is a direct bond, or methylene; and wherein ring$^{B2}$ is a 4- to 6-membered saturated heterocyclyl containing one ring heteroatom which is $NR^B$ (especially azetidinyl, or pyrrolidinyl), wherein said ring$^B$ is attached to $X^{B2}$ at a ring carbon atom; wherein said ring$^{B2}$ is optionally substituted by one oxo substituent, or by two fluoro substituents; and wherein $R^B$ independently represents
hydrogen;
$(C_{2-4})$fluoroalkyl;
$(C_{1-4})$alkoxy-C(O)—;
Ring$^C$-O—C(O)—, and wherein ring$^C$ is $(C_{3-6})$cycloalkyl optionally containing one ring oxygen atom, wherein ring$^C$ is optionally substituted with one methyl; or
Ring$^D$, wherein ring$^D$ is a 5- to 6-membered heteroaryl containing 1 to 3 heteroatoms independently selected from O, N or S (especially oxadiazolyl), wherein ring$^D$ is unsubstituted or mono-substituted with $R^D$, wherein $R^D$ is $(C_{1-4})$alkyl or $(C_{1-4})$fluoroalkyl.
[$R^5$ especially represents $(C_{1-4})$alkyl (especially methyl); $(C_{2-4})$fluoroalkyl (especially 2,2-difluoro-propyl); or $(C_{3-6})$cycloalkyl-$(C_{0-4})$alkylene-, wherein the cycloalkyl is optionally substituted by one or two substituents independently selected from fluoro, and methyl; [especially cyclopropyl]; Examples for such substituents $R^5$ are especially methyl, cyclopropyl and 2,2-difluoropropyl].

25) Another embodiment relates to compounds according to any one of embodiments 1) to 21), wherein $R^5$ represents
$(C_{1-4})$alkyl (especially methyl);
$(C_{1-4})$alkyl which is mono-substituted with $(C_{1-4})$alkoxy (especially methoxy, ethoxy), or cyano;

($C_{2-4}$)alkyl which is mono-substituted with hydroxy or $R^{N1}R^{N2}N$—, wherein $R^{N1}$ and $R^{N2}$ together with the nitrogen atom form a 4- to 6-membered saturated ring optionally containing one further ring heteroatom selected from O and N; wherein said ring is optionally mono-substituted with ($C_{1-4}$)alkyl, or ($C_{1-4}$)alkoxy;

$R^{N1}$ and $R^{N2}$ are independently selected from hydrogen, ($C_{1-4}$)alkyl, ($C_{3-6}$)cycloalkyl-($C_{0-4}$)alkylene-, or ($C_{1-4}$)alkoxy-($C_{2-4}$)alkylene;

$R^{N1}$ represents ($C_{1-4}$)alkyl-C(O)—; and $R^{N2}$ represents hydrogen, or ($C_{1-4}$)alkyl; or $R^{N1}$ represents phenylsulfonyl-, wherein the phenyl is optionally substituted by one to three substituents independently selected from ($C_{1-4}$)alkyl, ($C_{1-4}$)alkoxy, halogen, cyano, or nitro; and $R^{N2}$ represents hydrogen, or ($C_{1-4}$)alkyl;

($C_{3-4}$)alkyl which is di-substituted, wherein the substituents are independently selected from hydroxy, ($C_{1-4}$)alkoxy, or $R^{N11}R^{N12}N$—, wherein $R^{N11}$ and $R^{N12}$ are independently selected from hydrogen, or ($C_{1-4}$)alkyl; or ($C_{3-6}$)cycloalkyl-($C_{0-4}$)alkylene-, wherein the cycloalkyl is optionally substituted by one or two substituents independently selected from fluoro, and methyl [especially such ($C_{3-6}$)cycloalkyl-($C_{0-4}$)alkylene- is cyclopropyl].

[Examples for such substituents are methyl, ethyl, isopropyl, isobutyl, tert-butyl, cyanomethyl, 1-cyanoethyl, 2-cyanopropyl, 1-cyano-1-methyl-ethyl, methoxymethyl, ethoxymethyl, 2-hydroxyethyl, 2-hydroxypropyl, 3-hydroxy-2-methyl-propyl, 2-hydroxy-1,1-dimethyl-ethyl, 2-hydroxy-2-methyl-propyl, 2-(3-methoxy-azetidin-1-yl)-ethyl, 2-pyrrolidin-1-yl-ethyl-, 2-piperidin-1-yl-ethyl-, 2-(4-methyl-piperazin-1-yl)-ethyl-, 2-morpholin-4-yl-ethyl, 2-aminoethyl, 2-amino-propyl, 2-amino-1-methyl-ethyl, 2-methylamino-ethyl, 3-amino-2-methyl-propyl, 2-amino-1,1-dimethyl-ethyl, 2-amino-2-methyl-propyl, 2-cyclopropylamino-ethyl, cyclopropylmethylamino-ethyl, 2-(isopropyl-methyl-amino)ethyl, 2-[(methoxy-ethyl)-methyl-amino]-ethyl, $CH_3C(O)NH-CH_2CH_2$—, 2-(4-chloro-phenyl-sulfonylamino)-2-methyl-prop-1-yl, 2-(2-nitro-phenyl-sulfonylamino)-2-methyl-prop-1-yl, 2,3-dihydroxy-propyl, 2-dimethylamino-3-hydroxy-propyl, 2-hydroxy-3-methoxy-propyl, 3-methoxy-2-hydroxy-propyl, and, in addition, cyclopropyl. Preferred are methyl, ethyl, isopropyl, isobutyl, tert-butyl, cyanomethyl, 1-cyanoethyl, 2-cyanopropyl, methoxymethyl, ethoxymethyl, 2-hydroxyethyl, 2-hydroxypropyl, 3-hydroxy-2-methyl-propyl, 2-hydroxy-1,1-dimethyl-ethyl, 2-hydroxy-2-methyl-propyl, 2,3-dihydroxy-propyl, 3-methoxy-2-hydroxy-propyl, 3-methoxy-2-hydroxy-propyl, 2-(3-methoxy-azetidin-1-yl)-ethyl, 2-pyrrolidin-1-yl-ethyl-, 2-piperidin-1-yl-ethyl-, 2-morpholin-4-yl-ethyl, 2-cyclopropylmethylamino-ethyl, 2-[(2-methoxy-ethyl)-methyl-amino]-ethyl, 2-(4-chloro-phenyl-sulfonylamino)-2-methyl-prop-1-yl, and, in addition, cyclopropyl].

26) Another embodiment relates to compounds according to any one of embodiments 1) to 21), wherein $R^5$ represents ($C_{2-4}$)fluoroalkyl (especially 2,2-difluoro-ethyl, 2,2-difluoro-propyl, 2,2-difluoro-1-methyl-ethyl, 2-fluoropropyl, 2-fluoro-2-methyl-propyl; in particular 2,2-difluoro-propyl).

27) Another embodiment relates to compounds according to any one of embodiments 1) to 21), wherein $R^5$ represents ($C_{2-5}$)alkynyl (especially 1,1-dimethyl-prop-2-ynyl).

28) Another embodiment relates to compounds according to any one of embodiments 1) to 21), wherein $R^5$ represents ($C_{2-4}$)alkenyl (especially isopropenyl, 2-methyl-propenyl, or 2-methyl-allyl).

29) Another embodiment relates to compounds according to any one of embodiments 1) to 21), wherein $R^5$ represents $R^{N3}R^{N4}N-C(O)-(C_{0-4})$alkylene-, wherein $R^{N3}$ and $R^{N4}$ independently are hydrogen or ($C_{1-4}$)alky (especially $(CH_3)_2N-C(O)$—, (isobutyl)(methyl)N—C(O)—, $H_2N-C(O)CH_2$—, $H_2N-C(O)-CH(CH_3)$—, $(CH_3)_2N-C(O)-CH_2$— or $H_2N-C(O)-C(CH_3)_2$—).

30) Another embodiment relates to compounds according to any one of embodiments 1) to 21), wherein $R^5$ represents ($C_{1-4}$)alkoxy-C(O)—($C_{0-4}$)alkylene-; ($C_{1-4}$)alkoxy-C(O)—($C_{2-4}$)alkylene-, wherein the ($C_{2-4}$)alkylene is mono-substituted by $R^{N5}R^{N6}N$—, wherein $R^{N5}$ and $R^{N6}$ independently are hydrogen or ($C_{1-4}$)alkyl (especially $(CH_3)_2CH-O-C(O)$—, $(CH_3)_2CHCH_2-O-C(O)$—, $CH_3-C(O)-CH_2$—, $H_3CO-C(O)-C(CH_3)_2$—, $H_3CO-C(O)-CH(CH_3)CH_2$— and $CH_3-C(O)-CH[N(CH_3)_2]-CH_2$—).

31) Another embodiment relates to compounds according to any one of embodiments 1) to 21), wherein $R^5$ represents ($C_{1-4}$)alkoxy-C(O)—NH—($C_{2-4}$)alkylene-, wherein the ($C_{2-4}$)alkylene- is optionally substituted by one to three halogen (especially fluoro). [Examples for such a substituent are 2-(tert-butoxycarbonylamino)-ethyl, and 2,2,2-trifluoro-(1-(tert-butyloxycarbonyl-amino)-1-(methyl)-ethan-1-yl).

32) Another embodiment relates to compounds according to any one of embodiments 1) to 21), wherein $R^5$ represents ($C_{3-6}$)cycloalkyl-($C_{0-4}$)alkylene-, wherein the cycloalkyl is optionally substituted by one or two substituents independently selected from fluoro, ($C_{1-4}$)alkyl, nitro, or ($C_{1-4}$)alkoxy-C(O)—NH— (especially fluoro, methyl) [examples for ($C_{3-6}$)cycloalkyl-($C_{0-4}$)alkylene- are especially cyclopropyl, cyclopropylmethyl, 1-fluoro-cyclopropyl-methyl, 1-methyl-cyclopropyl-methyl, 2,2-difluoro-cyclopropylmethyl; in particular cyclopropyl].

33) Another embodiment relates to compounds according to any one of embodiments 1) to 21), wherein $R^5$ represents ring$^B$-$X^B$—; wherein $X^B$ is a direct bond, or ($C_{1-4}$)alkylene- (especially methylene); and wherein ring$^B$ is a 4- to 6-membered saturated heterocyclyl containing one or two ring heteratom independently selected from O, S, and $NR^B$, wherein said ring$^B$ is attached to $X^B$ at a ring carbon atom (especially oxetan-3-yl, azetidin-2-yl, azetidin-3-yl, pyrrolidin-2-yl, pyrrolidin-3-yl, piperidin-4-yl);

wherein said ring$^B$ is optionally substituted by one or two substituents selected from oxo, hydroxy, fluoro, ($C_{1-4}$)alkyl (especially methyl, ethyl), or ($C_{1-4}$)alkoxy (especially methoxy); (such that ring$^B$ is especially oxetan-3-yl, 3-fluoro-oxetan-3-yl, 3-methyl-oxetan-3-yl, 3-methoxy-oxetan-3-yl, 3-hydroxy-oxetan-3-yl, azetidin-2-yl, azetidin-3-yl, 2-oxo-azetidin-3-yl, pyrrolidin-2-yl, pyrrolidin-3-yl, 2-oxo-pyrrolidin-3-yl, 4,4-difluoro-pyrrolidin-2-yl, piperidin-4-yl); and wherein $R^B$ independently represents hydrogen;

($C_{1-4}$)alkyl (especially methyl, ethyl, isopropyl, isobutyl);

($C_{2-4}$)fluoroalkyl (especially 2-fluoroethyl, 2,2-difluoroethyl);

($C_{1-4}$)alkyl-C(O)— (especially methylcarbonyl-, isopropylcarbonyl-);

(C$_{1-4}$)alkoxy-C(O)— (especially methoxycarbonyl-, ethoxycarbonyl-, isopropoxycarbonyl-, isobutoxycarbonyl, tert-butoxycarbonyl);

(C$_{1-4}$)alkyl-SO$_2$— (especially methylsulfonyl);

R$^{N7}$R$^{N8}$N—SO$_2$— wherein R$^{N7}$ and R$^{N8}$ are independently hydrogen or (C$_{1-4}$)alkyl (especially methyl);

R$^{N9}$R$^{N10}$N—C(O)— wherein R$^{N9}$ and R$^{N10}$ are independently hydrogen or (C$_{1-4}$)alkyl (especially methyl);

Ring$^C$-O—C(O)—, and wherein ring$^C$ is (C$_{3-6}$)cycloalkyl optionally containing one ring oxygen atom (especially oxetan-3-yl), wherein ring$^C$ is optionally substituted with one R$^C$, wherein R$^C$ is (C$_{1-4}$)alkyl or (C$_{1-4}$)fluoroalkyl (especially methyl, or trifluoromethyl); or Ring$^D$, wherein ring$^D$ is a 5- to 6-membered heteroaryl containing 1 to 3 heteroatoms independently selected from O, N or S (especially [1,3,4]oxadiazol-2-yl), wherein ring$^D$ is unsubstituted or mono-substituted with R$^D$, wherein R$^D$ is (C$_{1-4}$)alkyl or (C$_{1-4}$)fluoroalkyl (especially methyl, isopropyl, or trifluoromethyl).

[Examples for such groups ring$^B$-X$^B$— according to embodiment 33) are 3-hydroxy-oxetan-3-yl, 3-fluoro-oxetan-3-yl, 3-methyl-oxetan-3-yl, 2-oxo-azetidin-3-yl, 1-ethyl-azetidin-3-yl, 1-(2-fluoro-ethyl)-azetidin-3-yl, 1-(2,2-difluoro-ethyl)azetidin-3-yl, 1-isopropyl-azetidin-3-yl, 1-methylcarbonyl-azetidin-3-yl, 1-methylaminocarbonyl-azetidin-3-yl, 1-isobutyl-azetidin-3-yl, 1-methylsulfonyl-azetidin-3-yl, methoxycarbonyl-azetidin-3-yl, 1-dimethylaminocarbonyl-azetidin-3-yl, 1-1-ethoxyarbonyl-azetidin-3-yl, 1-isopropoxycarbonyl-azetidin-3-yl, 1-isobutoxycarbonyl-azetidin-3-yl, 1-isopropylcarbonyl-azetidin-3-yl, 1-tert-butoxycarbonyl-azetidin-3-yl, 1-dimethylaminosulfonyl-azetidin-3-yl, 1-(5-methyl-[1,3,4]oxadiazo-2-yl)-azetidin-3-yl, 1-(5-isopropyl-[1,3,4]oxadiazol-2-yl)-azetidin-3-yl, 1-(5-trifluoromethyl-[1,3,4]-oxadiazol-2-yl)-azetidin-3-yl, 1-(oxetan-3-yl-oxycarbonyl)-azetidin-3-yl, 1-(3-methyl-oxetan-3-oxycarbonyl)-azetidin-3-yl, 1-(3-trifluoromethyl-oxetan-3-yl-oxycarbonyl)-azetidin-3-yl, azetidin-2-yl-methyl-, 1-methylcarbonyl-azetidin-2-ylmethyl, 1-methoxycarbonyl-azetidin-2-ylmethyl, 1-ethoxyarbonyl-azetidin-3-ylmethyl, 1-isopropoxycarbonyl-azetidin-3-ylmethyl-, 1-tert-butoxycarbonyl-azetidin-2-ylmethyl, 1-methyl-2-oxo-pyrrolidin-3-yl, 1-methylcarbonyl-pyrrolidin-3-yl, 1-isopropyl-2-oxo-pyrrolidin-3-yl, 1-tert-butoxycarbonyl-pyrrolidin3-yl, pyrrolidin-2-yl-methyl-, 4,4-difluoro-pyrrolidin-2yl-methyl-, 1-methylcarbonyl-pyrrolidin-2-yl-methyl-, 1-tert-butoxycarbonyl-pyrrolidin-2-ylmethyl-, and 1-tert-butoxycarbonyl-4,4-di-fluoro-pyrrolidin-2-yl-methyl-. Preferred examples are 1-(2,2-difluoro-ethyl)azetidin-3-yl, 4,4-difluoro-azetidin-2-yl-methyl, 1-methoxycarbonyl-azetidin-2-ylmethyl, 1-isobutoxycarbonyl-azetidin-3-yl, 1-tert-butoxycarbonyl-azetidin-3-yl, 1-isopropoxycarbonyl-azetidin-2-yl-methyl, 1-tert-butoxycarbonyl-azetidin-2-ylmethyl, 1-tert-butoxycarbonyl-4,4-difluoro-azetidin-2-ylmethyl, 1-isopropoxycarbonyl-azetidin-3-yl, 1-ethoxycarbonyl-azetidin-2-yl-methyl, 1-ethoxycarbonyl-azetidin-3-yl, 2-oxo-azetidin-3-yl, oxetan-3-yl, 3-methyl-oxetan-3-yl-methyl, 3-hydroxy-oxetan-3-ylmethyl, 3-fluoro-oxetan-3-yl-methyl, 3-trifluoromethyl-oxetan-3-yl-methyl, 1-tert-butoxycarbonyl-pyrrolidin-3-yl, 4,4-difluoro-pyrrolidin-2-ylmethyl, 1-(5-trifluoromethyl-[1,3,4]oxadiazol-2-yl)-azetidin-3-yl, 1-(5-isopropyl-[1,3,4]oxadiazol-2-yl)-azetidin-3-yl, 1-(3-trifluoromethyl-oxetan-3-yl-oxycarbonyl)-azetidin-3-yl, 1-(3-methyl-oxetan-3-oxycarbonyl)-azetidin-3-yl, and 1-(oxetan-3-yl-oxycarbonyl)-azetidin-3-yl.]

34) Another embodiment relates to compounds according to any one of embodiments 1) to 21), wherein R$^5$ represents hydrogen.

35) Another embodiment relates to compounds according to any one of embodiments 1) to 21), wherein R$^5$ represents (C$_{1-4}$)alkyl (in particular methyl).

36) Another embodiment relates to compounds according to any one of embodiments 1) to 35), wherein R$^6$ represents hydrogen; (C$_{1-4}$)alkyl; or (C$_{1-4}$)fluoroalkyl (especially R$^6$ represents hydrogen or methyl).

37) Another embodiment relates to compounds according to any one of embodiments 1) to 36), wherein R$^7$ represents hydrogen, (C$_{1-4}$)alkyl (especially methyl), or (CH$_3$)$_3$Si—CH$_2$CH$_2$OCH$_2$—.

38) Another embodiment relates to compounds according to any one of embodiments 1) to 37), wherein R$^8$ represents hydrogen;

(C$_{1-4}$)alkyl (especially methyl);

(C$_{2-4}$)fluoroalkyl (especially 2-fluoro-2-methyl-propyl, 2,2-difluoro-propyl);

(C$_{3-6}$)cycloalkyl or (C$_{3-6}$)cycloalkyl-methyl-, wherein the cycloalkyl is unsubstituted or mono-substituted with methyl (especially cyclopropyl, cyclopropylmethyl, 1-methyl-cyclopropyl-methyl-);

(C$_{1-4}$)alkoxy-C(O)-methylene- (especially methoxycarbonylmethyl-); or

CH$_3$)$_3$Si—CH$_2$CH$_2$OCH$_2$—.

39) The invention, thus, especially relates to compounds of the formula (I) as defined in embodiment 1), and to such compounds further limited by the characteristics of any one of embodiments 2) to 38), under consideration of their respective dependencies; to pharmaceutically acceptable salts thereof; and to the use of such compounds as medicaments especially for use in the prevention/prophylaxis or treatment of diseases and disorders related to pathogenic events associated with elevated levels of C5a and/or with C5aR activation.

For avoidance of any doubt, especially the following embodiments relating to the compounds of formula (I) are thus possible and intended and herewith specifically disclosed in individualized form:

1, 2+1, 4+1, 4+2+1, 5+1, 5+2+1, 9+1, 9+2+1, 9+4+1, 9+4+2+1, 9+5+1, 9+5+2+1, 13+1, 13+2+1, 13+4+1, 13+4+2+1, 13+5+1, 13+5+2+1, 14+1, 14+2+1, 14+4+1, 14+4+2+1, 14+5+1, 14+5+2+1, 15+1, 15+2+1, 15+4+1, 15+4+2+1, 15+5+1, 15+5+2+1, 16+1, 16+2+1, 16+4+1, 16+4+2+1, 16+5+1, 16+5+2+1, 16+9+1, 16+9+2+1, 16+9+4+1, 16+9+4+2+1, 16+9+5+1, 16+9+5+2+1, 16+13+1, 16+13+2+1, 16+13+4+1, 16+13+4+2+1, 16+13+5+1, 16+13+5+2+1, 16+14+1, 16+14+2+1, 16+14+4+1, 16+14+4+2+1, 16+14+5+1, 16+14+5+2+1, 16+15+1, 16+15+2+1, 16+15+4+1, 16+15+4+2+1, 16+15+5+1, 16+15+5+2+1, 18+1, 18+2+1, 18+4+1, 18+4+2+1, 18+5+1, 18+5+2+1, 18+9+1, 18+9+2+1, 18+9+4+1, 18+9+4+2+1, 18+9+5+1, 18+9+5+2+1, 18+13+1, 18+13+2+1, 18+13+4+1, 18+13+4+2+1, 18+13+5+1, 18+13+5+2+1, 18+14+1, 18+14+2+1, 18+14+4+1, 18+14+4+2+1, 18+14+5+1, 18+14+5+2+1, 18+15+1, 18+15+2+1, 18+15+4+1, 18+15+4+2+1, 18+15+5+1, 18+15+5+2+1, 19+1, 19+2+1, 19+4+1, 19+4+2+1, 19+5+1, 19+5+2+1, 19+9+1, 19+9+2+1, 19+9+4+1, 19+9+4+2+1, 19+9+5+1, 19+9+5+2+1, 19+13+1, 19+13+2+1, 19+13+4+1, 19+13+4+2+1, 19+13+5+1, 19+13+5+2+1, 19+14+1,

19+14+2+1, 19+14+4+1, 19+14+4+2+1, 19+14+5+1, 19+14+5+2+1, 19+15+1, 19+15+2+1, 19+15+4+1, 19+15+4+2+1, 19+15+5+1, 19+15+5+2+1, 23+1, 23+2+1, 23+4+1, 23+4+2+1, 23+5+1, 23+5+2+1, 23+9+1, 23+9+2+1, 23+9+4+1, 23+9+4+2+1, 23+9+5+1, 23+9+5+2+1, 23+13+1, 23+13+2+1, 23+13+4+1, 23+13+4+2+1, 23+13+5+1, 23+13+5+2+1, 23+14+1, 23+14+2+1, 23+14+4+1, 23+14+4+2+1, 23+14+5+1, 23+14+5+2+1, 23+15+1, 23+15+2+1, 23+15+4+1, 23+15+4+2+1, 23+15+5+1, 23+15+5+2+1, 23+16+1, 23+16+2+1, 23+16+4+1, 23+16+4+2+1, 23+16+5+1, 23+16+5+2+1, 23+16+9+1, 23+16+9+2+1, 23+16+9+4+1, 23+16+9+4+2+1, 23+16+9+5+1, 23+16+9+5+2+1, 23+16+13+1, 23+16+13+2+1, 23+16+13+4+1, 23+16+13+4+2+1, 23+16+13+5+1, 23+16+13+5+2+1, 23+16+14+1, 23+16+14+2+1, 23+16+14+4+1, 23+16+14+4+2+1, 23+16+14+5+1, 23+16+14+5+2+1, 23+16+15+1, 23+16+15+2+1, 23+16+15+4+1, 23+16+15+4+2+1, 23+16+15+5+1, 23+16+15+5+2+1, 23+18+1, 23+18+2+1, 23+18+4+1, 23+18+4+2+1, 23+18+5+1, 23+18+5+2+1, 23+18+9+1, 23+18+9+2+1, 23+18+9+4+1, 23+18+9+4+2+1, 23+18+9+5+1, 23+18+9+5+2+1, 23+18+13+1, 23+18+13+2+1, 23+18+13+4+1, 23+18+13+4+2+1, 23+18+13+5+1, 23+18+13+5+2+1, 23+18+14+1, 23+18+14+2+1, 23+18+14+4+1, 23+18+14+4+2+1, 23+18+14+5+1, 23+18+14+5+2+1, 23+18+15+1, 23+18+15+2+1, 23+18+15+4+1, 23+18+15+4+2+1, 23+18+15+5+1, 23+18+15+5+2+1, 23+19+1, 23+19+2+1, 23+19+4+1, 23+19+4+2+1, 23+19+5+1, 23+19+5+2+1, 23+19+9+1, 23+19+9+2+1, 23+19+9+4+1, 23+19+9+4+2+1, 23+19+9+5+1, 23+19+9+5+2+1, 23+19+13+1, 23+19+13+2+1, 23+19+13+4+1, 23+19+13+4+2+1, 23+19+13+5+1, 23+19+13+5+2+1, 23+19+14+1, 23+19+14+2+1, 23+19+14+4+1, 23+19+14+4+2+1, 23+19+14+5+1, 23+19+14+5+2+1, 23+19+15+1, 23+19+15+2+1, 23+19+15+4+1, 23+19+15+4+2+1, 23+19+15+5+1, 23+19+15+5+2+1, 24+1, 24+2+1, 24+4+1, 24+4+2+1, 24+5+1, 24+5+2+1, 24+9+1, 24+9+2+1, 24+9+4+1, 24+9+4+2+1, 24+9+5+1, 24+9+5+2+1, 24+13+1, 24+13+2+1, 24+13+4+1, 24+13+4+2+1, 24+13+5+1, 24+13+5+2+1, 24+14+1, 24+14+2+1, 24+14+4+1, 24+14+4+2+1, 24+14+5+1, 24+14+5+2+1, 24+15+1, 24+15+2+1, 24+15+4+1, 24+15+4+2+1, 24+15+5+1, 24+15+5+2+1, 24+16+1, 24+16+2+1, 24+16+4+1, 24+16+4+2+1, 24+16+5+1, 24+16+5+2+1, 24+16+9+1, 24+16+9+2+1, 24+16+9+4+1, 24+16+9+4+2+1, 24+16+9+5+1, 24+16+9+5+2+1, 24+16+13+1, 24+16+13+2+1, 24+16+13+4+1, 24+16+13+4+2+1, 24+16+13+5+1, 24+16+13+5+2+1, 24+16+14+1, 24+16+14+2+1, 24+16+14+4+1, 24+16+14+4+2+1, 24+16+14+5+1, 24+16+14+5+2+1, 24+16+15+1, 24+16+15+2+1, 24+16+15+4+1, 24+16+15+4+2+1, 24+16+15+5+1, 24+16+15+5+2+1, 24+18+1, 24+18+2+1, 24+18+4+1, 24+18+4+2+1, 24+18+5+1, 24+18+5+2+1, 24+18+9+1, 24+18+9+2+1, 24+18+9+4+1, 24+18+9+4+2+1, 24+18+9+5+1, 24+18+9+5+2+1, 24+18+13+1, 24+18+13+2+1, 24+18+13+4+1, 24+18+13+4+2+1, 24+18+13+5+1, 24+18+13+5+2+1, 24+18+14+1, 24+18+14+2+1, 24+18+14+4+1, 24+18+14+4+2+1, 24+18+14+5+1, 24+18+14+5+2+1, 24+18+15+1, 24+18+15+2+1, 24+18+15+4+1, 24+18+15+4+2+1, 24+18+15+5+1, 24+18+15+5+2+1, 24+19+1, 24+19+2+1, 24+19+4+1, 24+19+4+2+1, 24+19+5+1, 24+19+5+2+1, 24+19+9+1, 24+19+9+2+1, 24+19+9+4+1, 24+19+9+4+2+1, 24+19+9+5+1, 24+19+9+5+2+1, 24+19+13+1, 24+19+13+2+1, 24+19+13+4+1, 24+19+13+4+2+1, 24+19+13+5+1, 24+19+13+5+2+1, 24+19+14+1, 24+19+14+2+1, 24+19+14+4+1, 24+19+14+4+2+1, 24+19+14+5+1, 24+19+14+5+2+1, 24+19+15+1, 24+19+15+2+1, 24+19+15+4+1, 24+19+15+4+2+1, 24+19+15+5+1, 24+19+15+5+2+1, 26+1, 26+2+1, 26+4+1, 26+4+2+1, 26+5+1, 26+5+2+1, 26+9+1, 26+9+2+1, 26+9+4+1, 26+9+4+2+1, 26+9+5+1, 26+9+5+2+1, 26+13+1, 26+13+2+1, 26+13+4+1, 26+13+4+2+1, 26+13+5+1, 26+13+5+2+1, 26+14+1, 26+14+2+1, 26+14+4+1, 26+14+4+2+1, 26+14+5+1, 26+14+5+2+1, 26+15+1, 26+15+2+1, 26+15+4+1, 26+15+4+2+1, 26+15+5+1, 26+15+5+2+1, 26+16+1, 26+16+2+1, 26+16+4+1, 26+16+4+2+1, 26+16+5+1, 26+16+5+2+1, 26+16+9+1, 26+16+9+2+1, 26+16+9+4+1, 26+16+9+4+2+1, 26+16+9+5+1, 26+16+9+5+2+1, 26+16+13+1, 26+16+13+2+1, 26+16+13+4+1, 26+16+13+4+2+1, 26+16+13+5+1, 26+16+13+5+2+1, 26+16+14+1, 26+16+14+2+1, 26+16+14+4+1, 26+16+14+4+2+1, 26+16+14+5+1, 26+16+14+5+2+1, 26+16+15+1, 26+16+15+2+1, 26+16+15+4+1, 26+16+15+4+2+1, 26+16+15+5+1, 26+16+15+5+2+1, 26+18+1, 26+18+2+1, 26+18+4+1, 26+18+4+2+1, 26+18+5+1, 26+18+5+2+1, 26+18+9+1, 26+18+9+2+1, 26+18+9+4+1, 26+18+9+4+2+1, 26+18+9+5+1, 26+18+9+5+2+1, 26+18+13+1, 26+18+13+2+1, 26+18+13+4+1, 26+18+13+4+2+1, 26+18+13+5+1, 26+18+13+5+2+1, 26+18+14+1, 26+18+14+2+1, 26+18+14+4+1, 26+18+14+4+2+1, 26+18+14+5+1, 26+18+14+5+2+1, 26+18+15+1, 26+18+15+2+1, 26+18+15+4+1, 26+18+15+4+2+1, 26+18+15+5+1, 26+18+15+5+2+1, 26+19+1, 26+19+2+1, 26+19+4+1, 26+19+4+2+1, 26+19+5+1, 26+19+5+2+1, 26+19+9+1, 26+19+9+2+1, 26+19+9+4+1, 26+19+9+4+2+1, 26+19+9+5+1, 26+19+9+5+2+1, 26+19+13+1, 26+19+13+2+1, 26+19+13+4+1, 26+19+13+4+2+1, 26+19+13+5+1, 26+19+13+5+2+1, 26+19+14+1, 26+19+14+2+1, 26+19+14+4+1, 26+19+14+4+2+1, 26+19+14+5+1, 26+19+14+5+2+1, 26+19+15+1, 26+19+15+2+1, 26+19+15+4+1, 26+19+15+4+2+1, 26+19+15+5+1, 26+19+15+5+2+1.

In the list above the numbers refer to the embodiments according to their numbering provided hereinabove whereas "+" indicates the dependency from another embodiment. The different individualized embodiments are separated by commas. In other words, "26+18+14+1" for example refers to embodiment 26) depending on embodiment 18), depending on embodiment 14), depending on embodiment 1), i.e. embodiment "26+18+14+1" corresponds to the compounds of formula (I) according to embodiment 1) further limited by all the features of the embodiments 14), 18), and 26).

40) A second aspect of the invention relates to compounds of the formula (I) according to embodiment 1), which are also compounds of the formula (II)

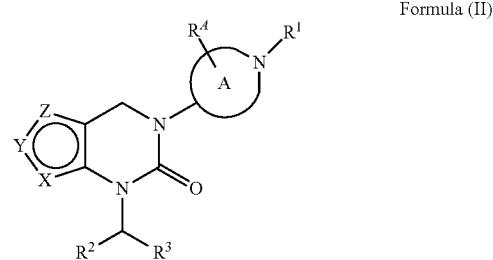

Formula (II)

wherein
Y represents NR$^5$; and X and Z independently represent N or CH (notably Y represents NR$^5$; one of X and Z represents N, and the other of X and Z represents N or CH);
Y represents CR$^6$; one of X and Z represents NR$^7$, O or S, and the other of X and Z represents N; or
Y represents N; one of X and Z represents NR$^8$, and the other of X and Z represents N or CH;

ring A represents a saturated 4- to 7-membered monocyclic carbocyclic ring containing the ring nitrogen atom to which $R^1$ is attached, wherein said ring A is optionally mono-substituted with $R^A$; wherein $R^A$ represents $(C_{1-4})$alkyl (especially methyl) [preferably ring A is substituted with $R^1$ and carries no further substituent (i.e. $R^A$ is absent)];

$R^1$ represents phenyl; 5-membered heteroaryl, or 6-membered heteroaryl wherein said phenyl, 5-membered heteroaryl or 6-membered heteroaryl independently is mono-, di- or tri-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; cyano; or $(C_{3-6})$cycloalkyl;

$R^2$ represents phenyl, 5-membered heteroaryl, or 6-membered heteroaryl; wherein said phenyl, 5-membered heteroaryl, or 6-membered heteroaryl independently is mono-, or di-, or tri-substituted, wherein the substituents are independently selected from $(C_{1-4})$alkyl;
$(C_{1-4})$alkoxy;
$(C_{1-3})$fluoroalkyl;
$(C_{1-3})$fluoroalkoxy;
halogen;
$(C_3)$cycloalkyl-$X^{21}$—, wherein $X^{21}$ represents a direct bond, —O—, or —$(C_{1-3})$alkylene-O—, and wherein the $(C_{3-6})$cycloalkyl optionally contains one ring oxygen atom; or
$R^{21a}R^{21b}N$—, wherein $R^{21a}$ and $R^{21b}$ independently represent hydrogen or $(C_{1-4})$alkyl;

$R^3$ represents hydrogen or $(C_{1-3})$alkyl (especially hydrogen);

$R^5$ represents
hydrogen;
$(C_{1-4})$alkyl;
$(C_{1-4})$alkyl which is mono-substituted with hydroxy, $(C_{1-4})$alkoxy, cyano, or $R^{N1}R^{N2}N$—, wherein
  $R^{N1}$ and $R^{N2}$ together with the nitrogen atom form a 4- to 6-membered saturated ring optionally containing one further ring heteroatom selected from O and N; wherein said ring is optionally mono-substituted with $(C_{1-4})$alkyl, or $(C_{1-4})$alkoxy;
  $R^{N1}$ and $R^{N2}$ are independently selected from hydrogen, $(C_{1-4})$alkyl, $(C_{3-6})$cycloalkyl-$(C_{0-4})$alkylene-, or $(C_{1-4})$alkoxy-$(C_{2-4})$alkylene;
  $R^{N1}$ represents $(C_{1-4})$alkyl-C(O)—; and $R^{N2}$ represents hydrogen, or $(C_{1-4})$alkyl; or
  $R^{N1}$ represents phenylsulfonyl-, wherein the phenyl is optionally substituted by one to three substituents independently selected from $(C_{1-4})$alkyl, $(C_{1-4})$alkoxy, halogen, cyano, or nitro; and $R^{N2}$ represents hydrogen, or $(C_{1-4})$alkyl;
$(C_{2-4})$alkyl which is di- or tri-substituted, wherein the substituents are independently selected from hydroxy, $(C_{1-4})$alkoxy, or $R^{N1}R^{N2}N$—, wherein
  $R^{N1}$ and $R^{N2}$ together with the nitrogen atom form a 4- to 6-membered saturated ring; or
  $R^{N1}$ and $R^{N2}$ are independently selected from hydrogen, or $(C_{1-4})$alkyl;
$(C_{2-4})$fluoroalkyl;
$(CH_3)_3Si$—$(CH_2)_2$—O—$(C_{1-4})$alkylene-;
$(C_{2-5})$alkynyl;
$(C_{2-5})$alkenyl;
$R^{N3}R^{N4}N$—C(O)—$(C_{0-4})$alkylene-, wherein $R^{N3}$ and $R^{N4}$ independently are hydrogen or $(C_{1-4})$alkyl;
$(C_{1-4})$alkoxy-C(O)—$(C_{0-4})$alkylene-;
$(C_{1-4})$alkoxy-C(O)—$(C_{2-4})$alkylene-, wherein the $(C_{2-4})$alkylene is mono-substituted by $R^{N5}R^{N6}N$—, wherein $R^{N5}$ and $R^{N6}$ independently are hydrogen or $(C_{1-4})$alkyl
$(C_{1-4})$alkoxy-C(O)—$(C_{2-4})$alkylene-, wherein the $(C_{2-4})$alkylene is substituted by one to three halogen;
$(C_{1-4})$alkoxy-C(O)—NH—$(C_{2-4})$alkylene-, wherein the $(C_{2-4})$alkylene- is optionally substituted by one to three halogen;
$(C_{3-6})$cycloalkyl-$(C_{0-4})$alkylene-, wherein the cycloalkyl is optionally substituted by one or two substituents independently selected from fluoro, $(C_{1-4})$alkyl, nitro, or $(C_{1-4})$alkoxy-C(O)—NH—; or
ring$^B$-$X^B$—; wherein $X^B$ is a direct bond, or $(C_{1-4})$alkylene-; and wherein ring$^B$ is a 4- to 6-membered saturated heterocyclyl containing one or two ring heteroatom independently selected from O, S, and $NR^B$, wherein said ring$^B$ is attached to $X^B$ at a ring carbon atom;
wherein said ring$^B$ is optionally substituted by one or two substituents independently selected from oxo, hydroxy, fluoro, $(C_{1-4})$alkyl or $(C_{1-4})$alkoxy; and wherein
$R^B$ independently represents
hydrogen;
$(C_{1-4})$alkyl;
$(C_{2-4})$fluoroalkyl;
$(C_{1-4})$alkyl-C(O)—;
$(C_{1-4})$alkoxy-C(O)—;
$(C_{1-4})$alkyl-$SO_2$—;
$R^{N7}R^{N8}N$—$SO_2$— wherein $R^{N7}$ and $R^{N8}$ are independently hydrogen or $(C_{1-4})$alkyl;
$R^{N9}R^{N10}N$—C(O)— wherein $R^{N9}$ and $R^{N10}$ are independently hydrogen or $(C_{1-4})$alkyl;
Ring$^C$-O—C(O)—, and wherein ring$^C$ is $(C_{3-6})$cycloalkyl optionally containing one ring oxygen atom, wherein ring$^C$ is optionally substituted with one $R^C$, wherein $R^C$ is $(C_{1-4})$alkyl or $(C_{1-4})$fluoroalkyl; or
Ring$^D$, wherein ring$^D$ is a 5- to 6-membered heteroaryl containing 1 to 3 heteroatoms independently selected from O, N or S, wherein ring$^D$ is unsubstituted or mono-substituted with $R^D$, wherein $R^D$ is $(C_{1-4})$alkyl or $(C_{1-4})$fluoroalkyl;

$R^6$ represents
hydrogen;
$(C_{1-4})$alkyl;
$(C_{1-4})$fluoroalkyl; or
$(C_{3-6})$cycloalkyl-$(C_{0-4})$alkylene-, wherein the cycloalkyl is optionally substituted by one to three substituents independently selected from halogen or $(C_{1-4})$alkyl;

$R^7$ represents
hydrogen;
$(C_{1-4})$alkyl; or
$(CH_3)_3Si$—$(CH_2)_2$—O—$(C_{1-4})$alkylene-; and $R^8$ represents
hydrogen;
$(C_{1-4})$alkyl;
$(C_{2-4})$fluoroalkyl;
$(C_{3-6})$cycloalkyl-$(C_{0-4})$alkylene-, wherein the cycloalkyl is optionally substituted by one to three substituents independently selected from halogen or $(C_{1-4})$alkyl;
$(C_{1-4})$alkoxy-C(O)—$(C_{1-4})$alkylene-; or
$(CH_3)_3Si$—$(CH_2)_2$—O—$(C_{1-4})$alkylene-;
wherein the characteristics disclosed in embodiments 2) to 38), especially as specifically listed in embodiment 39), are intended to apply mutatis mutandis also to the compounds of formula (II) according to embodiment 40).

41) Another embodiment relates to compounds of formula (II) according to embodiment 40), wherein Y represents $NR^5$; and X and Z independently represent N or CH (notably Y represents $NR^5$; one of X and Z represents N, and the other of X and Z represents N or CH);

ring A represents an unsubstituted saturated 4- to 7-membered mono-cyclic carbocyclic ring containing the ring nitrogen atom to which $R^1$ is attached [for avoidance of doubt, said ring A is substituted with $R^1$ and carries no further substituent (i.e. $R^A$ is absent)] [notably ring A represents pyrrolidin-1-3-diyl, or piperidin-1,4-diyl; especially piperidin-1,4-diyl];

$R^1$ represents phenyl, or 6-membered heteroaryl wherein said phenyl, or 6-membered heteroaryl independently is mono-, di- or tri-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; cyano; or $(C_{3-6})$cycloalkyl; [notably $R^1$ represents phenyl or pyridinyl, which phenyl or pyridinyl independently is mono- or di-substituted wherein the substituents are independently selected from $(C_{1-4})$alkyl (especially methyl); $(C_{1-4})$alkoxy (especially methoxy); $(C_{1-3})$fluoroalkyl (especially trifluoromethyl, or difluoromethyl); $(C_{1-3})$fluoroalkoxy (especially trifluoromethoxy); halogen (especially fluoro or chloro); cyano; or $(C_{3-6})$cycloalkyl (especially cyclopropyl)];

$R^2$ represents phenyl, or pyridinyl; wherein said phenyl or pyridinyl independently is mono-, or di-, or tri-substituted, wherein the substituents are independently selected from
$(C_{1-4})$alkyl;
$(C_{1-4})$alkoxy;
$(C_{1-3})$fluoroalkyl;
$(C_{1-3})$fluoroalkoxy;
halogen; or
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl optionally contains one ring oxygen atom;

[notably $R^2$ represents phenyl or pyridinyl, wherein said phenyl or pyridinyl independently is mono- or di-substituted wherein the substituents are independently selected from $(C_{1-4})$alkyl; $(C_{1-4})$alkoxy; $(C_{1-3})$fluoroalkyl (especially trifluormethyl); $(C_{1-3})$fluoroalkoxy; halogen; $(C_{3-6})$cycloalkyl; $(C_{3-6})$cycloalkyl-O—; and $(C_{3-6})$cycloalkyl-$CH_2$—O—; in particular $R^2$ represents phenyl, which is mono-substituted with trifluoromethyl];

$R^3$ represents hydrogen;
$R^5$ represents
hydrogen;
$(C_{1-4})$alkyl;
$(C_{1-4})$alkyl which is mono-substituted with hydroxy, $(C_{1-4})$alkoxy, cyano;
$(C_{2-4})$fluoroalkyl;
$(CH_3)_3Si$—$(CH_2)_2$—O—$(C_{1-4})$alkylene-;
$(C_{2-5})$alkenyl;
$(C_{1-4})$alkoxy-C(O)—$(C_{0-4})$alkylene-;
$(C_{3-6})$cycloalkyl-$(C_{0-4})$alkylene-, wherein the cycloalkyl is optionally substituted by one or two substituents independently selected from fluoro, $(C_{1-4})$alkyl, nitro, or $(C_{1-4})$alkoxy-C(O)—NH—.
ring$^B$-$X^B$—; wherein $X^B$ is a direct bond, or $(C_{1-4})$alkylene-; and wherein ring$^B$ is a 4-membered saturated heterocyclyl containing one ring heteratom selected from O and $NR^B$, wherein said ring$^B$ is attached to $X^B$ at a ring carbon atom;

wherein said ring$^B$ is optionally substituted by one substituent selected from fluoro, $(C_{1-4})$alkyl; and wherein $R^B$ independently represents
$(C_{1-4})$alkoxy-C(O)—;
Ring$^D$, wherein ring$^D$ is a 5- to 6-membered heteroaryl containing 1 to 3 heteroatoms independently selected from O, N or S, wherein ring$^D$ is unsubstituted or mono-substituted with $R^D$, wherein $R^D$ is $(C_{1-4})$alkyl or $(C_{1-4})$fluoroalkyl;
[notably $R^5$ represents $(C_{1-4})$alkyl (especially methyl); $(C_{2-4})$fluoroalkyl (especially 2,2-difluoro-propyl), or $(C_{3-6})$cycloalkyl (especially cyclopropyl)].

42) A third aspect of the invention relates to compounds of the formula (I) according to embodiment 1), which are also compounds of the formula (III)

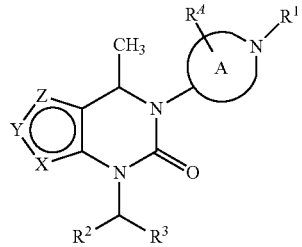

Formula (III)

wherein
Y represents $NR^5$; and X and Z independently represent N or CH (notably Y represents $NR^5$; one of X and Z represents N, and the other of X and Z represents N or CH);
Y represents $CR^6$; one of X and Z represents $NR^7$, O or S, and the other of X and Z represents N; or
Y represents N; one of X and Z represents $NR^8$, and the other of X and Z represents N or CH;
ring A represents a saturated 4- to 7-membered mono-cyclic carbocyclic ring containing the ring nitrogen atom to which $R^1$ is attached, wherein said ring A is optionally mono-substituted with $R^A$; wherein $R^A$ represents $(C_{1-4})$alkyl (especially methyl) [preferably ring A is substituted with $R^1$ and carries no further substituent (i.e. $R^A$ is absent)];
$R^1$ represents phenyl; 5-membered heteroaryl, or 6-membered heteroaryl wherein said phenyl, 5-membered heteroaryl or 6-membered heteroaryl independently is mono-, di- or tri-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; cyano; or $(C_{3-6})$cycloalkyl;
$R^2$ represents phenyl, 5-membered heteroaryl, or 6-membered heteroaryl; wherein said phenyl, 5-membered heteroaryl, or 6-membered heteroaryl independently is mono-, or di-, or tri-substituted, wherein the substituents are independently selected from
$(C_{1-4})$alkyl;
$(C_{1-4})$alkoxy;
$(C_{1-3})$fluoroalkyl;
$(C_{1-3})$fluoroalkoxy;
halogen;
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl optionally contains one ring oxygen atom; or
$R^{21a}R^{21b}N$—, wherein $R^{21a}$ and $R^{21b}$ independently represent hydrogen or $(C_{1-4})$alkyl;

$R^3$ represents hydrogen or $(C_{1-3})$alkyl (especially hydrogen);

$R^5$ represents hydrogen;

$(C_{1-4})$alkyl;

$(C_{1-4})$alkyl which is mono-substituted with hydroxy, $(C_{1-4})$alkoxy, cyano, or $R^{N1}R^{N2}N$—, wherein $R^{N1}$ and $R^{N2}$ together with the nitrogen atom form a 4- to 6-membered saturated ring optionally containing one further ring heteroatom selected from O and N; wherein said ring is optionally mono-substituted with $(C_{1-4})$alkyl, or $(C_{1-4})$alkoxy;

$R^{N1}$ and $R^{N2}$ are independently selected from hydrogen, $(C_{1-4})$alkyl, $(C_{3-6})$cycloalkyl-$(C_{0-4})$alkylene-, or $(C_{1-4})$alkoxy-$(C_{2-4})$alkylene;

$R^{N1}$ represents $(C_{1-4})$alkyl-C(O)—; and $R^{N2}$ represents hydrogen, or $(C_{1-4})$alkyl; or $R^{N1}$ represents phenylsulfonyl-, wherein the phenyl is optionally substituted by one to three substituents independently selected from $(C_{1-4})$alkyl, $(C_{1-4})$alkoxy, halogen, cyano, or nitro; and $R^{N2}$ represents hydrogen, or $(C_{1-4})$alkyl;

$(C_{2-4})$alkyl which is di- or tri-substituted, wherein the substituents are independently selected from hydroxy, $(C_{1-4})$alkoxy, or $R^{N1}R^{N2}N$—, wherein $R^{N1}$ and $R^{N2}$ together with the nitrogen atom form a 4- to 6-membered saturated ring; or $R^{N1}$ and $R^{N2}$ are independently selected from hydrogen, or $(C_{1-4})$alkyl;

$(C_{2-4})$fluoroalkyl;

$(CH_3)_3Si$—$(CH_2)_2$—O—$(C_{1-4})$alkylene-;

$(C_{2-5})$alkynyl;

$(C_{2-5})$alkenyl;

$R^{N3}R^{N4}N$—C(O)—$(C_{0-4})$alkylene-, wherein $R^{N3}$ and $R^{N4}$ independently are hydrogen or $(C_{1-4})$alkyl;

$(C_{1-4})$alkoxy-C(O)—$(C_{0-4})$alkylene-;

$(C_{1-4})$alkoxy-C(O)—$(C_{2-4})$alkylene-, wherein the $(C_{2-4})$alkylene is mono-substituted by $R^{N5}R^{N6}N$—, wherein $R^{N5}$ and $R^{N6}$ independently are hydrogen or $(C_{1-4})$alkyl $(C_{1-4})$alkoxy-C(O)—$(C_{2-4})$alkylene-, wherein the $(C_{2-4})$alkylene is substituted by one to three halogen;

$(C_{1-4})$alkoxy-C(O)—NH—$(C_{2-4})$alkylene-, wherein the $(C_{2-4})$alkylene- is optionally substituted by one to three halogen;

$(C_{3-6})$cycloalkyl-$(C_{0-4})$alkylene-, wherein the cycloalkyl is optionally substituted by one or two substituents independently selected from fluoro, $(C_4)$alkyl, nitro, or $(C_{1-4})$alkoxy-C(O)—NH—; or ring$^B$-$X^B$—; wherein $X^B$ is a direct bond, or $(C_{1-4})$alkylene-; and wherein ring$^B$ is a 4- to 6-membered saturated heterocyclyl containing one or two ring heteroatom independently selected from O, S, and NR$^B$, wherein said ring$^B$ is attached to $X^B$ at a ring carbon atom;

wherein said ring$^B$ is optionally substituted by one or two substituents independently selected from oxo, hydroxy, fluoro, $(C_{1-4})$alkyl or $(C_{1-4})$alkoxy; and wherein R$^B$ independently represents hydrogen;

$(C_{1-4})$alkyl;

$(C_{2-4})$fluoroalkyl;

$(C_{1-4})$alkyl-C(O)—;

$(C_{1-4})$alkoxy-C(O)—;

$(C_{1-4})$alkyl-$SO_2$—;

$R^{N7}R^{N8}N$—$SO_2$— wherein $R^{N7}$ and $R^{N8}$ are independently hydrogen or $(C_{1-4})$alkyl;

$R^{N9}R^{N1}N$—C(O)— wherein $R^{N9}$ and $R^{N10}$ are independently hydrogen or $(C_{1-4})$alkyl;

Ring$^C$-O—C(O)—, and wherein ring$^C$ is $(C_{3-6})$cycloalkyl optionally containing one ring oxygen atom, wherein ring$^C$ is optionally substituted with one R$^C$, wherein R$^C$ is $(C_{1-4})$alkyl or $(C_{1-4})$fluoroalkyl; or Ring$^D$, wherein ring$^D$ is a 5- to 6-membered heteroaryl containing 1 to 3 heteroatoms independently selected from O, N or S, wherein ring$^D$ is unsubstituted or mono-substituted with R$^D$, wherein R$^D$ is $(C_{1-4})$alkyl or $(C_{1-4})$fluoroalkyl;

$R^6$ represents hydrogen;

$(C_{1-4})$alkyl;

$(C_{1-4})$fluoroalkyl; or $(C_{3-6})$cycloalkyl-$(C_{0-4})$alkylene-, wherein the cycloalkyl is optionally substituted by one to three substituents independently selected from halogen or $(C_{1-4})$alkyl;

$R^7$ represents hydrogen;

$(C_{1-4})$alkyl; or $(CH_3)_3Si$—$(CH_2)_2$—O—$(C_{1-4})$alkylene-; and $R^8$ represents hydrogen;

$(C_{1-4})$alkyl;

$(C_{2-4})$fluoroalkyl;

$(C_{3-6})$cycloalkyl-$(C_{0-4})$alkylene-, wherein the cycloalkyl is optionally substituted by one to three substituents independently selected from halogen or $(C_{1-4})$alkyl;

$(C_{1-4})$alkoxy-C(O)—$(C_{1-4})$alkylene-; or $(CH_3)_3Si$—$(CH_2)_2$—O—$(C_1)$alkylene-;

wherein the characteristics disclosed in embodiments 2) to 38) above are intended to apply mutatis mutandis also to the compounds of formula (III) according to embodiment 42); wherein especially the following embodiments are thus possible and intended and herewith specially disclosed in individualized form:

42+2, 42+4+2, 42+4, 42+5+2, 42+5, 42+9+2, 42+9+4+2, 42+9+4, 42+9+5+2, 42+9+5, 42+9, 42+12+2, 42+12+4+2, 42+12+4, 42+12+5+2, 42+12+5, 42+12, 42+13+2, 42+13+4+2, 42+13+4, 42+13+5+2, 42+13+5, 42+13, 42+15+2, 42+15+4+2, 42+15+4, 42+15+5+2, 42+15+5, 42+15, 42+16+2, 42+16+4+2, 42+16+4, 42+16+5+2, 42+16+5, 42+16, 42+19+2, 42+19+4+2, 42+19+4, 42+19+5+2, 42+19+5, 42+19, 42+24+2, 42+24+4+2, 42+24+4, 42+24+5+2, 42+24+5, 42+24+9+2, 42+24+9+4+2, 42+24+9+4, 42+24+9+5+2, 42+24+9+5, 42+24+9, 42+24+12+2, 42+24+12+4+2, 42+24+12+4, 42+24+12+5+2, 42+24+12+5, 42+24+12, 42+24+13+2, 42+24+13+4+2, 42+24+13+4, 42+24+13+5+2, 42+24+13+5, 42+24+13, 42+24+15+2, 42+24+15+4+2, 42+24+15+4, 42+24+15+5+2, 42+24+15+5, 42+24+15, 42+24+16+2, 42+24+16+4+2, 42+24+16+4, 42+24+16+5+2, 42+24+16+5, 42+24+16, 42+24+19+2, 42+24+19+4+2, 42+24+19+4, 42+24+19+5+2, 42+24+19+5, 42+24+19, 42+24;

In the list above, the numbers refer to the embodiments according to their numbering provided hereinabove whereas "+" indicates the dependency from another embodiment. The different individualized embodiments are separated by commas. In other words, "42+24+5" for example refers to embodiment 42) depending on embodiment 24), depending on embodiment 5), i.e. embodiment "42+24+5" corresponds to the compounds of embodiment 42) further limited by the features of the embodiments 5) and 24).

43) Another embodiment relates to compounds of formula (III) according to embodiment 42), wherein Y represents $NR^5$; and X and Z independently represent N or CH (notably Y represents $NR^5$; one of X and Z represents N, and the other of X and Z represents N or CH);

ring A represents an unsubstituted saturated 4- to 7-membered mono-cyclic carbocyclic ring containing the ring nitrogen atom to which $R^1$ is attached [for avoidance of doubt, said ring A is substituted with $R^1$ and carries no further substituent (i.e. $R^A$ is absent)] [notably ring A represents pyrrolidin-1-3-diyl, or piperidin-1,4-diyl; especially piperidin-1,4-diyl];

$R^1$ represents phenyl, or 6-membered heteroaryl wherein said phenyl, or 6-membered heteroaryl independently is mono-, di- or tri-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; cyano; or $(C_{3-6})$cycloalkyl; [notably $R^1$ represents phenyl or pyridinyl, which phenyl or pyridinyl independently is mono- or di-substituted wherein the substituents are independently selected from $(C_{1-4})$alkyl (especially methyl); $(C_{1-4})$alkoxy (especially methoxy); $(C_{1-3})$fluoroalkyl (especially trifluoromethyl, or difluoromethyl); $(C_{1-3})$fluoroalkoxy (especially trifluoromethoxy); halogen (especially fluoro or chloro); cyano; or $(C_{3-6})$cycloalkyl (especially cyclopropyl)];

$R^2$ represents phenyl, or pyridinyl; wherein said phenyl or pyridinyl independently is mono-, or di-, or tri-substituted, wherein the substituents are independently selected from
$(C_{1-4})$alkyl;
$(C_{1-4})$alkoxy;
$(C_{1-3})$fluoroalkyl;
$(C_{1-3})$fluoroalkoxy;
halogen; or
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl optionally contains one ring oxygen atom;
[notably $R^2$ represents phenyl or pyridinyl, wherein said phenyl or pyridinyl independently is mono- or di-substituted wherein the substituents are independently selected from $(C_{1-4})$alkyl; $(C_{1-4})$alkoxy; $(C_{1-3})$fluoroalkyl (especially trifluorormethyl); $(C_{1-3})$fluoroalkoxy; halogen; $(C_{3-6})$cycloalkyl; $(C_{3-6})$cycloalkyl-O—; and $(C_{3-6})$cycloalkyl-$CH_2$—O—; in particular $R^2$ represents phenyl, which is mono-substituted with trifluoromethyl];

$R^3$ represents hydrogen;
$R^5$ represents
hydrogen;
$(C_{1-4})$alkyl;
$(C_{1-4})$alkyl which is mono-substituted with hydroxy, $(C_{1-4})$alkoxy, cyano;
$(C_{2-4})$fluoroalkyl;
$(CH_3)_3Si$—$(CH_2)_2$—O—$(C_{1-4})$alkylene-;
$(C_{2-5})$alkenyl;
$(C_{1-4})$alkoxy-C(O)—$(C_{0-4})$alkylene-;
$(C_{3-6})$cycloalkyl-$(C_{0-4})$alkylene-, wherein the cycloalkyl is optionally substituted by one or two substituents independently selected from fluoro, $(C_{1-4})$alkyl, nitro, or $(C_{1-4})$alkoxy-C(O)—NH—.
ring$^B$-$X^B$—; wherein $X^B$ is a direct bond, or $(C_{1-4})$alkylene-; and wherein ring$^B$ is a 4-membered saturated heterocyclyl containing one ring heteroatom selected from O and $NR^B$, wherein said ring$^B$ is attached to $X^B$ at a ring carbon atom;

wherein said ring$^B$ is optionally substituted by one substituent selected from fluoro, $(C_{1-4})$alkyl; and wherein $R^B$ independently represents
$(C_{1-4})$alkoxy-C(O)—;
Ring$^D$, wherein ring$^D$ is a 5- to 6-membered heteroaryl containing 1 to 3 heteroatoms independently selected from O, N or S, wherein ring$^D$ is unsubstituted or mono-substituted with $R^D$, wherein $R^D$ is $(C_{1-4})$alkyl or $(C_{1-4})$fluoroalkyl;
[notably $R^5$ represents $(C_{1-4})$alkyl (especially methyl); $(C_{2-4})$fluoroalkyl (especially 2,2-difluoro-propyl), or $(C_{3-6})$cycloalkyl (especially cyclopropyl)].

44) A further aspect of the invention relates to compounds of the formula (III) according to embodiment 42) or 43), which are also compounds of the formula (IV); wherein the absolute configuration is as depicted in formula (IV):

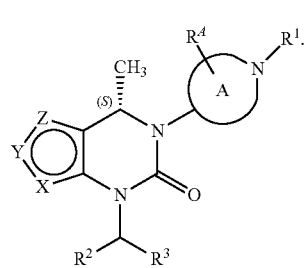

Formula (IV)

Embodiment 44) further relates to the compounds of formula (I) according to any one of embodiments 1) to 39), wherein, in case $R^4$ is different from hydrogen, the absolute configuration is, mutatis mutandis, as depicted in formula (IV).

45) Another embodiment relates to compounds according to embodiment 1) which are selected from the following compounds:

6-[1-(2-Fluoro-6-methyl-phenyl)-piperidin-4-yl]-4-(2-trifluoromethyl-benzyl)-2,4,6,7-tetrahydro-pyrazolo[4,3-d]pyrimidin-5-one;

6-[1-(2-Fluoro-6-methyl-phenyl)-piperidin-4-yl]-2-methyl-4-(2-trifluoromethyl-benzyl)-2,4,6,7-tetrahydro-pyrazolo[4,3-d]pyrimidin-5-one;

6-[1-(2-Fluoro-6-methyl-phenyl)-piperidin-4-yl]-2-methyl-4-(4-trifluoromethyl-pyridin-3-ylmethyl)-2,4,6,7-tetrahydro-pyrazolo[4,3-d]pyrimidin-5-one;

6-[1-(2-Fluoro-6-methyl-phenyl)-piperidin-4-yl]-2-methyl-4-(3-trifluoromethyl-pyridin-2-ylmethyl)-2,4,6,7-tetrahydro-pyrazolo[4,3-d]pyrimidin-5-one;

[6-[1-(2-Fluoro-6-methyl-phenyl)-piperidin-4-yl]-5-oxo-4-(2-trifluoromethyl-benzyl)-4,5,6,7-tetrahydro-pyrazolo[4,3-d]pyrimidin-2-yl]-acetic acid methyl ester;

2-Cyclopropyl-6-[1-(2-fluoro-6-methyl-phenyl)-piperidin-4-yl]-4-(2-trifluoromethyl-benzyl)-2,4,6,7-tetrahydro-pyrazolo[4,3-d]pyrimidin-5-one;

6-[1-(2-Fluoro-6-methyl-phenyl)-piperidin-4-yl]-2-(2-fluoro-2-methyl-propyl)-4-(2-trifluoromethyl-benzyl)-2,4,6,7-tetrahydro-pyrazolo[4,3-d]pyrimidin-5-one;

2-Cyclopropylmethyl-6-[1-(2-fluoro-6-methyl-phenyl)-piperidin-4-yl]-4-(2-trifluoromethyl-benzyl)-2,4,6,7-tetrahydro-pyrazolo[4,3-d]pyrimidin-5-one;

6-[1-(2-Fluoro-6-methyl-phenyl)-piperidin-4-yl]-2-(1-methyl-cyclopropylmethyl)-4-(2-trifluoromethyl-benzyl)-2,4,6,7-tetrahydro-pyrazolo[4,3-d]pyrimidin-5-one;

2-Ethyl-6-[1-(2-fluoro-6-methyl-phenyl)-piperidin-4-yl]-4-(2-trifluoromethyl-benzyl)-2,4,6,7-tetrahydro-pyrazolo[4,3-d]pyrimidin-5-one;

2-tert-Butyl-6-[1-(2-fluoro-6-methyl-phenyl)-piperidin-4-yl]-4-(2-trifluoromethyl-benzyl)-2,4,6,7-tetrahydro-pyrazolo[4,3-d]pyrimidin-5-one;

2-(1-Fluoro-cyclopropylmethyl)-6-[1-(2-fluoro-6-methyl-phenyl)-piperidin-4-yl]-4-(2-trifluoromethyl-benzyl)-2,4,6,7-tetrahydro-pyrazolo[4,3-d]pyrimidin-5-one;

6-[1-(2-Fluoro-6-methyl-phenyl)-piperidin-4-yl]-2-isopropyl-4-(2-trifluoromethyl-benzyl)-2,4,6,7-tetrahydro-pyrazolo[4,3-d]pyrimidin-5-one;

6-[1-(2-Fluoro-6-methyl-phenyl)-piperidin-4-yl]-2-isopropenyl-4-(2-trifluoromethyl-benzyl)-2,4,6,7-tetrahydro-pyrazolo[4,3-d]pyrimidin-5-one;

6-[1-(2-Fluoro-6-methyl-phenyl)-piperidin-4-yl]-4-(2-trifluoromethyl-benzyl)-2-(2-trimethylsilanyl-ethoxymethyl)-2,4,6,7 tetrahydro-pyrazolo[4,3-d]pyrimidin-5-one;

2-(2,2-Difluoro-propyl)-6-[1-(2-fluoro-6-methyl-phenyl)-piperidin-4-yl]-4-(2-trifluoromethyl-benzyl)-2,4,6,7-tetrahydro-pyrazolo[4,3-d]pyrimidin-5-one;

6-[1-(2-Fluoro-6-methyl-phenyl)-piperidin-4-yl]-4-(3-trifluoromethyl-pyridin-2-ylmethyl)-2-(2-trimethylsilanyl-ethoxymethyl)-2,4,6,7-tetrahydro-pyrazolo[4,3-d]pyrimidin-5-one;

6-[1-(2-Fluoro-6-methyl-phenyl)-piperidin-4-yl]-4-(3-trifluoromethyl-pyridin-2-ylmethyl)-2,4,6,7-tetrahydro-pyrazolo[4,3-d]pyrimidin-5-one;

2-(2,2-Difluoro-propyl)-6-[1-(2-fluoro-6-methyl-phenyl)-piperidin-4-yl]-4-(3-trifluoromethyl-pyridin-2-ylmethyl)-2,4,6,7-tetrahydro-pyrazolo[4,3-d]pyrimidin-5-one;

2-(1-Fluoro-cyclopropylmethyl)-6-[1-(2-fluoro-6-methyl-phenyl)-piperidin-4-yl]-4-(3-trifluoromethyl-pyridin-2-ylmethyl)-2,4,6,7-tetrahydro-pyrazolo[4,3-d]pyrimidin-5-one;

2-Cyclopropyl-6-[1-(2-fluoro-6-methyl-phenyl)-piperidin-4-yl]-4-(3-trifluoromethyl-pyridin-2-ylmethyl)-2,4,6,7-tetrahydro-pyrazolo[4,3-d]pyrimidin-5-one;

6-(2'-Methoxy-4'-methyl-3,4,5,6-tetrahydro-2H-[1,3']bipyridinyl-4-yl)-4-(2-trifluoromethyl-benzyl)-2,4,6,7-tetrahydro-pyrazolo[4,3-d]pyrimidin-5-one;

2-(2,2-Difluoro-propyl)-6-(2'-methoxy-4'-methyl-3,4,5,6-tetrahydro-2H-[1,3']bipyridinyl-4-yl)-4-(2-trifluoromethyl-benzyl)-2,4,6,7-tetrahydro-pyrazolo[4,3-d]pyrimidin-5-one;

2-(1-Fluoro-cyclopropylmethyl)-6-(2'-methoxy-4'-methyl-3,4,5,6-tetrahydro-2H-[1,3']bipyridinyl-4-yl)-4-(2-trifluoromethyl-benzyl)-2,4,6,7-tetrahydro-pyrazolo[4,3-d]pyrimidin-5-one;

2-Cyclopropyl-6-(2'-methoxy-4'-methyl-3,4,5,6-tetrahydro-2H-[1,3']bipyridinyl-4-yl)-4-(2-trifluoromethyl-benzyl)-2,4,6,7-tetrahydro-pyrazolo[4,3-d]pyrimidin-5-one;

6-(2'-Methoxy-4'-methyl-3,4,5,6-tetrahydro-2H-[1,3']bipyridinyl-4-yl)-2-methyl-4-(2-trifluoromethyl-benzyl)-2,4,6,7-tetrahydro-pyrazolo[4,3-d]pyrimidin-5-one;

4-(2-Cyclopropyl-benzyl)-6-[1-(2-fluoro-6-methyl-phenyl)-piperidin-4-yl]-2-methyl-2,4,6,7-tetrahydro-pyrazolo[4,3-d]pyrimidin-5-one;

6-[1-(2-Fluoro-6-methyl-phenyl)-piperidin-4-yl]-4-(2-isopropyl-benzyl)-2-methyl-2,4,6,7-tetrahydro-pyrazolo[4,3-d]pyrimidin-5-one;

5-[1-(2-Fluoro-6-methyl-phenyl)-piperidin-4-yl]-7-(2-trifluoromethyl-benzyl)-2-(2-trimethylsilanyl-ethoxymethyl)-2,4,5,7-tetrahydro-pyrazolo[3,4-d]pyrimidin-6-one;

5-[1-(2-Fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-Ethoxymethyl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-methyl-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-[2H3]methyl-7-(2-trifluoromethyl-benzyl)-2,4,5,7-tetrahydro-pyrazolo[3,4-d]pyrimidin-6-one;

[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-acetic acid methyl ester;

5-[1-(2-Fluoro-6-methyl-phenyl)-piperidin-4-yl]-2-(2-hydroxy-ethyl)-7-(2-trifluoromethyl-benzyl)-2,4,5,7-tetrahydro-pyrazolo[3,4-d]pyrimidin-6-one;

7-(2-Cyclopropoxy-benzyl)-5-[1-(2-fluoro-6-methyl-phenyl)-piperidin-4-yl]-2-methyl-2,4,5,7-tetrahydro-pyrazolo[3,4-d]pyrimidin-6-one;

5-[1-(2-Fluoro-6-methyl-phenyl)-piperidin-4-yl]-2-methyl-7-(3-trifluoromethyl-pyridin-2-ylmethyl)-2,4,5,7-tetrahydro-pyrazolo[3,4-d]pyrimidin-6-one;

5-(1-(2-fluoro-6-methylphenyl)piperidin-4-yl)-2-methyl-7-(3-trifluoromethyl-[6-2H]pyridine-2-yl-methyl)-2,4,5,7-tetrahydro-6H-pyrazolo[3,4-d]pyrimidin-6-one;

[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-acetonitrile;

5-[1-(2-Fluoro-6-methyl-phenyl)-piperidin-4-yl]-2-(2-hydroxy-2-methyl-propyl)-7-(2-trifluoromethyl-benzyl)-2,4,5,7-tetrahydro-pyrazolo[3,4-d]pyrimidin-6-one;

2-(2-Amino-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-2-methyl-propionic acid methyl ester;

2-(2,2-Diethoxy-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-acetamide;

2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-N,N-dimethyl-acetamide;

3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-2-methyl-propionic acid methyl ester;

5-[1-(2-Fluoro-6-methyl-phenyl)-piperidin-4-yl]-2-(2-hydroxy-1,1-dimethyl-ethyl)-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-(2-hydroxy-propyl)-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-[2-(3-methoxy-azetidin-1-yl)-ethyl]-7-(2-trifluoromethyl-benzyl)-2,4,5,7-tetrahydro-pyrazolo[3,4-d]pyrimidin-6-one;

7-(6-Chloro-3-trifluoromethyl-pyridin-2-ylmethyl)-5-[1-(2-fluoro-6-methyl-phenyl)-piperidin-4-yl]-2-methyl-2,4,5,7-tetrahydro-pyrazolo[3,4-d]pyrimidin-6-one;

5-[1-(2-Fluoro-6-methyl-phenyl)-piperidin-4-yl]-7-(6-fluoro-3-trifluoromethyl-pyridin-2-ylmethyl)-2-methyl-2,4,5,7-tetrahydro-pyrazolo[3,4-d]pyrimidin-6-one;

5-[1-(2-Fluoro-6-methyl-phenyl)-piperidin-4-yl]-2-methyl-7-(6-methyl-3-trifluoromethyl-pyridin-2-ylmethyl)-2,4,5,7-tetrahydro-pyrazolo[3,4-d]pyrimidin-6-one;

5-[1-(2-Fluoro-6-methyl-phenyl)-piperidin-4-yl]-7-(6-methoxy-3-trifluoromethyl-pyridin-2-ylmethyl)-2-methyl-2,4,5,7-tetrahydro-pyrazolo[3,4-d]pyrimidin-6-one;

5-[1-(2-Fluoro-6-methyl-phenyl)-piperidin-4-yl]-2-(3-hydroxy-2-methyl-propyl)-7-(2-trifluoromethyl-benzyl)-2,4,5,7-tetrahydro-pyrazolo[3,4-d]pyrimidin-6-one;

2-(2,3-Dihydroxy-propyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-((R)-2-hydroxy-3-methoxy-propyl)-7-(2-trifluoromethyl-benzyl)-2,4,5,7-tetrahydro-pyrazolo[3,4-d]pyrimidin-6-one;

2-Chloro-3-[5-[1-(2-fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-propionic acid methyl ester;

3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-2-methyl-propionitrile;

2-(3-Amino-2-methyl-propyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-((S)-2-hydroxy-3-methoxy-propyl)-7-(2-trifluoromethyl-benzyl)-2,4,5,7-tetrahydro-pyrazolo[3,4-d]pyrimidin-6-one;

5-[1-(2,6-Dimethyl-phenyl)-piperidin-4-yl]-2-methyl-7-(2-trifluoromethyl-benzyl)-2,4,5,7-tetrahydro-pyrazolo[3,4-d]pyrimidin-6-one;

5-[1-(2-Methoxy-6-methyl-phenyl)-piperidin-4-yl]-2-methyl-7-(2-trifluoromethyl-benzyl)-2,4,5,7-tetrahydro-pyrazolo[3,4-d]pyrimidin-6-one;

3-Fluoro-2-{4-[2-methyl-6-oxo-7-(2-trifluoromethyl-benzyl)-2,4,6,7-tetrahydro-pyrazolo[3,4-d]pyrimidin-5-yl]-piperidin-1-yl}-benzonitrile;

7-(6-Dimethylamino-3-trifluoromethyl-pyridin-2-ylmethyl)-5-[1-(2-fluoro-6-methyl-phenyl)-piperidin-4-yl]-2-methyl-2,4,5,7-tetrahydro-pyrazolo[3,4-d]pyrimidin-6-one;

5-[1-(2-Fluoro-6-methyl-phenyl)-piperidin-4-yl]-2-methyl-7-(6-methylamino-3-trifluoromethyl-pyridin-2-ylmethyl)-2,4,5,7-tetrahydro-pyrazolo[3,4-d]pyrimidin-6-one;

5-(2'-Fluoro-4'-methyl-3,4,5,6-tetrahydro-2H-[1,3']bipyridinyl-4-yl)-2-methyl-7-(2-trifluoromethyl-benzyl)-2,4,5,7-tetrahydro-pyrazolo[3,4-d]pyrimidin-6-one;

2-Dimethylamino-3-[5-[1-(2-fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-propionic acid methyl ester;

5-(2'-Methoxy-4'-methyl-3,4,5,6-tetrahydro-2H-[1,3']bipyridinyl-4-yl)-2-methyl-7-(2-trifluoromethyl-benzyl)-2,4,5,7-tetrahydro-pyrazolo[3,4-d]pyrimidin-6-one;

2-(2-Dimethylamino-3-hydroxy-propyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-(2-methylamino-ethyl)-7-(2-trifluoromethyl-benzyl)-2,4,5,7-tetrahydro-pyrazolo[3,4-d]pyrimidin-6-one;

2-(2-Dimethylamino-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-7-(2-fluoro-6-trifluoromethyl-benzyl)-2-methyl-2,4,5,7-tetrahydro-pyrazolo[3,4-d]pyrimidin-6-one;

5-[1-(2-Fluoro-6-methyl-phenyl)-piperidin-4-yl]-2-(2-pyrrolidin-1-yl-ethyl)-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-(2-piperidin-1-yl-ethyl)-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-(2-morpholin-4-yl-ethyl)-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-[2-(4-methyl-piperazin-1-yl)-ethyl]-7-(2-trifluoromethyl-benzyl)-2,4,5,7-tetrahydro-pyrazolo[3,4-d]pyrimidin-6-one;

N-{2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-ethyl}-acetamide;

{2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-ethyl}-carbamic acid tert-butyl ester;

2-Methyl-5-(3'-methyl-3,4,5,6-tetrahydro-2H-[1,2']bipyridinyl-4-yl)-7-(2-trifluoromethyl-benzyl)-2,4,5,7-tetrahydro-pyrazolo[3,4-d]pyrimidin-6-one;

2-(2-Cyclopropylamino-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-[2-(isopropyl-methyl-amino)-ethyl]-7-(2-trifluoromethyl-benzyl)-2,4,5,7-tetrahydro-pyrazolo[3,4-d]pyrimidin-6-one;

2-[2-(Cyclopropyl-methyl-amino)-ethyl]-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-{2-[(2-methoxy-ethyl)-methyl-amino]-ethyl}-7-(2-trifluoromethyl-benzyl)-2,4,5,7-tetrahydro-pyrazolo[3,4-d]pyrimidin-6-one;

2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-propionamide;

5-[1-(2-Fluoro-6-methyl-phenyl)-piperidin-4-yl]-2-oxetan-3-yl-7-(2-trifluoromethyl-benzyl)-2,4,5,7-tetrahydro-pyrazolo[3,4-d]pyrimidin-6-one;

2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-propionitrile;

5-[1-(2-Fluoro-6-methyl-phenyl)-piperidin-4-yl]-2-(2-nitro-cyclohexyl)-7-(2-trifluoromethyl-benzyl)-2,4,5,7-tetrahydro-pyrazolo[3,4-d]pyrimidin-6-one;

{2,2,2-Trifluoro-1-[5-[1-(2-fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-1-methyl-ethyl}-carbamic acid tert-butyl ester;

2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-isobutyramide;

4'-Methyl-4-[2-methyl-6-oxo-7-(2-trifluoromethyl-benzyl)-2,4,6,7-tetrahydro-pyrazolo[3,4-d]pyrimidin-5-yl]-3,4,5,6-tetrahydro-2H-[1,3']bipyridinyl-2'-carbonitrile;

5-(4'-Fluoro-2'-methyl-3,4,5,6-tetrahydro-2H-[1,3']bipyridinyl-4-yl)-2-methyl-7-(2-trifluoromethyl-benzyl)-2,4,5,7-tetrahydro-pyrazolo[3,4-d]pyrimidin-6-one;

2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-2-methyl-propionitrile;

2-(2-Amino-1,1-dimethyl-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid tert-butyl ester;

3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-pyrrolidine-1-carboxylic acid tert-butyl ester;

5-(2',4'-Dimethoxy-3,4,5,6-tetrahydro-2H-[1,3']bipyridinyl-4-yl)-2-methyl-7-(2-trifluoromethyl-benzyl)-2,4,5,7-tetrahydro-pyrazolo[3,4-d]pyrimidin-6-one;

2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-pyrrolidine-1-carboxylic acid tert-butyl ester;

{2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-cyclopentyl}-carbamic acid tert-butyl ester;

4-Chloro-N-{2-[5-[1-(2-fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-1,1-dimethyl-ethyl}-benzenesulfonamide;

5-[1-(2-Fluoro-6-methyl-phenyl)-piperidin-4-yl]-2-(1-isobutyl-azetidin-3-yl)-7-(2-trifluoromethyl-benzyl)-2,4,5,7-tetrahydro-pyrazolo[3,4-d]pyrimidin-6-one;

2-[1-(2,2-Difluoro-ethyl)-azetidin-3-yl]-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-[1-(2-Fluoro-ethyl)-azetidin-3-yl]-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

(R)-4,4-Difluoro-2-[5-[1-(2-fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-pyrrolidine-1-carboxylic acid tert-butyl ester;

(S)-4,4-Difluoro-2-[5-[1-(2-fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-pyrrolidine-1-carboxylic acid tert-butyl ester;

N-{2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-1,1-dimethyl-ethyl}-2-nitro-benzenesulfonamide;

2-((R)-4,4-Difluoro-pyrrolidin-2-ylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-((S)-4,4-Difluoro-pyrrolidin-2-ylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-(1-Acetyl-pyrrolidin-3-yl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-(1-Acetyl-azetidin-2-ylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-(1-Acetyl-pyrrolidin-2-ylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid methyl ester;

(S)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid tert-butyl ester;

(S)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid methyl ester;

(S)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid ethyl ester;

(S)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid isopropyl ester;

3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid ethyl ester;

3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid isopropyl ester;

(R)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid tert-butyl ester;

5-[1-(2-Fluoro-6-methyl-phenyl)-piperidin-4-yl]-2-(1-isobutyryl-azetidin-3-yl)-7-(2-trifluoromethyl-benzyl)-2,4,5,7-tetrahydro-pyrazolo[3,4-d]pyrimidin-6-one;

3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid isobutyl ester;

(R)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid methyl ester;

(R)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid ethyl ester;

(R)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid isopropyl ester;

5-[1-(2-Fluoro-6-methyl-phenyl)-piperidin-4-yl]-2-(1-methanesulfonyl-azetidin-3-yl)-7-(2-trifluoromethyl-benzyl)-2,4,5,7-tetrahydro-pyrazolo[3,4-d]pyrimidin-6-one;

3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-sulfonic acid dimethylamide;

5-(2'-Methoxy-4'-methyl-3,4,5,6-tetrahydro-2H-[1,3']bipyridinyl-4-yl)-2-methyl-7-(3-trifluoromethyl-pyridin-2-ylmethyl)-2,4,5,7-tetrahydro-pyrazolo[3,4-d]pyrimidin-6-one;

3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid oxetan-3-yl ester;

3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid 3-trifluoromethyl-oxetan-3-yl ester;

3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid 3-methyl-oxetan-3-yl ester;

5-[1-(2-Fluoro-6-methyl-phenyl)-piperidin-4-yl]-2-[1-(5-methyl-[1,3,4]oxadiazol-2-yl)-azetidin-3-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-[1-(5-isopropyl-[1,3,4]oxadiazol-2-yl)-azetidin-3-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-7-(2-trifluoromethyl-benzyl)-2-[1-(5-trifluoromethyl-[1,3,4]oxadiazol-2-yl)-azetidin-3-yl]-2,4,5,7-tetrahydro-pyrazolo[3,4-d]pyrimidin-6-one;

5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidine-2-carboxylic acid isopropyl ester;

5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidine-2-carboxylic acid dimethylamide;

5-[1-(2-Fluoro-6-methyl-phenyl)-piperidin-4-yl]-2-(2-methyl-propenyl)-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-(2-methyl-allyl)-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-isobutyl-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-[2-([$^2$H$_3$]methyl)[1,1,2,3,3,3-$^2$H$_6$]propyl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-(2-oxo-azetidin-3-yl)-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-(1-methyl-cyclopropylmethyl)-7-(2-trifluoromethyl-benzyl)-2,4,5,7-tetrahydro-pyrazolo[3,4-d]pyrimidin-6-one;

2-(2,2-Difluoro-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-(1,1-Dimethyl-prop-2-ynyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-isopropyl-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-([1,1,1,2,3,3,3-$^2$H$_7$]propan-2-yl)-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-([1,1,1,3,3,3-$^2$H$_6$]propan-2-yl)-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-(3-fluoro-oxetan-3-ylmethyl)-7-(2-trifluoromethyl-benzyl)-2,4,5,7-tetrahydro-pyrazolo[3,4-d]pyrimidin-6-one;

2-Cyclopropylmethyl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-(3-methyl-oxetan-3-ylmethyl)-7-(2-trifluoromethyl-benzyl)-2,4,5,7-tetrahydro-pyrazolo[3,4-d]pyrimidin-6-one;

2-(1-Fluoro-cyclopropylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-(2-fluoro-2-methyl-propyl)-7-(2-trifluoromethyl-benzyl)-2,4,5,7-tetrahydro-pyrazolo[3,4-d]pyrimidin-6-one;

2-Ethyl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-[1,1,2,2,2-$^2$H$_5$]Ethyl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-(3-hydroxy-oxetan-3-ylmethyl)-7-(2-trifluoromethyl-benzyl)-2,4,5,7-tetrahydro-pyrazolo[3,4-d]pyrimidin-6-one;

2-(2,2-Difluoro-propyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-tert-Butyl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-Cyclopropyl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-((S)-2-fluoro-propyl)-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-((R)-2-fluoro-propyl)-7-(2-trifluoromethyl-benzyl)-2,4,5,7-tetrahydro-pyrazolo[3,4-d]pyrimidin-6-one;

2-((S)-2,2-Difluoro-1-methyl-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-((R)-2,2-Difluoro-1-methyl-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-((R)-2,2-Difluoro-cyclopropylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

2-((S)-2,2-Difluoro-cyclopropylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-7-(3-trifluoromethyl-pyridin-2-ylmethyl)-2,4,5,7-tetrahydro-pyrazolo[3,4d]pyrimidin-6-one;

2-(2,2-Difluoro-propyl)-5-[1-(2-fluoro-6-methyl-phenyl)-piperidin-4-yl]-7-(3-trifluoromethyl-pyridin-2-ylmethyl)-2,4,5,7-tetrahydro-pyrazolo[3,4-d]pyrimidin-6-one;

5-(2'-Methoxy-4'-methyl-3,4,5,6-tetrahydro-2H-[1,3']bipyridinyl-4-yl)-7-(2-trifluoromethyl-benzyl)-2-(2-trimethylsilanyl-ethoxymethyl)-2,4,5,7-tetrahydro-pyrazolo[3,4-d]pyrimidin-6-one;

5-(2'-Methoxy-4'-methyl-3,4,5,6-tetrahydro-2H-[1,3']bipyridinyl-4-yl)-7-(2-trifluoromethyl-benzyl)-2,4,5,7-tetrahydro-pyrazolo[3,4-d]pyrimidin-6-one;

2-(1-Fluoro-cyclopropylmethyl)-5-[1-(2-fluoro-6-methyl-phenyl)-piperidin-4-yl]-7-(3-trifluoromethyl-pyridin-2-ylmethyl)-2,4,5,7-tetrahydro-pyrazolo[3,4-d]pyrimidin-6-one;

2-(1-Fluoro-cyclopropylmethyl)-5-(2'-methoxy-4'-methyl-3,4,5,6-tetrahydro-2H-[1,3']bipyridinyl-4-yl)-7-(2-trifluoromethyl-benzyl)-2,4,5,7-tetrahydro-pyrazolo[3,4-d]pyrimidin-6-one;

2-(2,2-Difluoro-propyl)-5-(2'-methoxy-4'-methyl-3,4,5,6-tetrahydro-2H-[1,3']bipyridinyl-4-yl)-7-(2-trifluoromethyl-benzyl)-2,4,5,7-tetrahydro-pyrazolo[3,4-d]pyrimidin-6-one;

2-Cyclopropyl-5-[1-(2-fluoro-6-methyl-phenyl)-piperidin-4-yl]-7-(3-trifluoromethyl-pyridin-2-ylmethyl)-2,4,5,7-tetrahydro-pyrazolo[3,4-d]pyrimidin-6-one;

2-Cyclopropyl-5-(2'-methoxy-4'-methyl-3,4,5,6-tetrahydro-2H-[1,3']bipyridinyl-4-yl)-7-(2-trifluoromethyl-benzyl)-2,4,5,7-tetrahydro-pyrazolo[3,4-d]pyrimidin-6-one;

7-(2-Bromo-6-trifluoromethyl-benzyl)-2-cyclopropyl-5-[1-(2-fluoro-6-methyl-phenyl)-piperidin-4-yl]-2,4,5,7-tetrahydro-pyrazolo[3,4-d]pyrimidin-6-one;

7-(2-Bromo-6-trifluoromethyl-benzyl)-2-(2,2-difluoro-propyl)-5-[1-(2-fluoro-6-methyl-phenyl)-piperidin-4-yl]-2,4,5,7-tetrahydro-pyrazolo[3,4-d]pyrimidin-6-one;

5-[1-(2-Fluoro-6-methyl-phenyl)-4-methyl-piperidin-4-yl]-2-methyl-7-(2-trifluoromethyl-benzyl)-2,4,5,7-tetrahydro-pyrazolo[3,4-d]pyrimidin-6-one;

5-[(S)-1-(2-Fluoro-6-methyl-phenyl)-azepan-4-yl]-2-methyl-7-(2-trifluoromethyl-benzyl)-2,4,5,7-tetrahydro-pyrazolo[3,4-d]pyrimidin-6-one;

5-[(R)-1-(2-Fluoro-6-methyl-phenyl)-azepan-4-yl]-2-methyl-7-(2-trifluoromethyl-benzyl)-2,4,5,7-tetrahydro-pyrazolo[3,4-d]pyrimidin-6-one;

2-Methoxymethyl-5-(2'-methoxy-4'-methyl-3,4,5,6-tetrahydro-2H-[1,3']bipyridinyl-4-yl)-7-(2-trifluoromethyl-benzyl)-2,4,5,7-tetrahydro-pyrazolo[3,4-d]pyrimidin-6-one;

7-(2-Cyclopropyl-benzyl)-5-[1-(2-fluoro-6-methyl-phenyl)-piperidin-4-yl]-2-methyl-2,4,5,7-tetrahydro-pyrazolo[3,4-d]pyrimidin-6-one;

5-[1-(2-Fluoro-6-methyl-phenyl)-piperidin-4-yl]-7-(2-isopropyl-benzyl)-2-methyl-2,4,5,7-tetrahydro-pyrazolo[3,4-d]pyrimidin-6-one;

5-[1-(2-Fluoro-6-methyl-phenyl)-piperidin-4-yl]-2-methyl-7-(2-trifluoromethoxy-benzyl)-2,4,5,7-tetrahydro-pyrazolo[3,4-d]pyrimidin-6-one;

7-(2-Chloro-benzyl)-5-[1-(2-fluoro-6-methyl-phenyl)-piperidin-4-yl]-2-methyl-2,4,5,7-tetrahydro-pyrazolo[3,4-d]pyrimidin-6-one;

5-[1-(4-Chloro-2,5-dimethyl-2H-pyrazol-3-yl)-piperidin-4-yl]-2-methyl-7-(2-trifluoromethyl-benzyl)-2,4,5,7-tetrahydro-pyrazolo[3,4-d]pyrimidin-6-one;

5-[1-(2-Fluoro-6-trifluoromethyl-phenyl)-piperidin-4-yl]-2-methyl-7-(2-trifluoromethyl-benzyl)-2,4,5,7-tetrahydro-pyrazolo[3,4-d]pyrimidin-6-one;

5-[1-(2-Fluoro-6-trifluoromethoxy-phenyl)-piperidin-4-yl]-2-methyl-7-(2-trifluoromethyl-benzyl)-2,4,5,7-tetrahydro-pyrazolo[3,4-d]pyrimidin-6-one;

5-[1-(2-Chloro-6-methyl-phenyl)-piperidin-4-yl]-2-methyl-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-2-methyl-7-[(R)-1-(2-trifluoromethyl-phenyl)-ethyl]-2,4,5,7-tetrahydro-pyrazolo[3,4-d]pyrimidin-6-one;

5-[1-(2-Fluoro-6-methyl-phenyl)-piperidin-4-yl]-2-methyl-7-[(S)-1-(2-trifluoromethyl-phenyl)-ethyl]-2,4,5,7-tetrahydro-pyrazolo[3,4-d]pyrimidin-6-one;

7-(2-Cyclopropylmethoxy-benzyl)-5-[1-(2-fluoro-6-methyl-phenyl)-piperidin-4-yl]-2-methyl-2,4,5,7-tetrahydro-pyrazolo[3,4-d]pyrimidin-6-one;

5-[1-(2-Fluoro-6-methyl-phenyl)-piperidin-4-yl]-7-(4-isopropyl-pyrimidin-5-ylmethyl)-2-methyl-2,4,5,7-tetrahydro-pyrazolo[3,4-d]pyrimidin-6-one;

5-[1-(2-Fluoro-6-methyl-phenyl)-piperidin-4-yl]-2-methyl-7-[2-(oxetan-3-yloxy)-benzyl]-2,4,5,7-tetrahydro-pyrazolo[3,4d]pyrimidin-6-one;

5-[1-(2-Fluoro-6-methyl-phenyl)-piperidin-4-yl]-7-(2-isopropoxy-benzyl)-2-methyl-2,4,5,7-tetrahydro-pyrazolo[3,4-d]pyrimidin-6-one;

7-(2-Ethoxy-benzyl)-5-[1-(2-fluoro-6-methyl-phenyl)-piperidin-4-yl]-2-methyl-2,4,5,7-tetrahydro-pyrazolo[3,4-d]pyrimidin-6-one;

5-[1-(2-Isopropyl-phenyl)-piperidin-4-yl]-2-methyl-7-(2-trifluoromethyl-benzyl)-2,4,5,7-tetrahydro-pyrazolo[3,4-d]pyrimidin-6-one;

5-[1-(2-Cyclopropyl-phenyl)-piperidin-4-yl]-2-methyl-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-7-(4-isopropoxy-pyridazin-3-ylmethyl)-2-methyl-2,4,5,7-tetrahydro-pyrazolo[3,4-d]pyrimidin-6-one;

5-[1-(2-Fluoro-6-methyl-phenyl)-pyrrolidin-3-yl]-2-methyl-7-(2-trifluoromethyl-benzyl)-2,4,5,7-tetrahydro-pyrazolo[3,4-d]pyrimidin-6-one;

5-[(R)-1-(2-Fluoro-6-methyl-phenyl)-pyrrolidin-3-yl]-2-methyl-7-(2-trifluoromethyl-benzyl)-2,4,5,7-tetrahydro-pyrazolo[3,4-d]pyrimidin-6-one;

5-[(R)-1-(2,6-Dimethyl-phenyl)-pyrrolidin-3-yl]-2-methyl-7-(2-trifluoromethyl-benzyl)-2,4,5,7-tetrahydro-pyrazolo[3,4-d]pyrimidin-6-one;

5-[(S)-1-(2,6-Dimethyl-phenyl)-pyrrolidin-3-yl]-2-methyl-7-(2-trifluoromethyl-benzyl)-2,4,5,7-tetrahydro-pyrazolo[3,4-d]pyrimidin-6-one;

5-[(R)-1-(2-Fluoro-6-methyl-phenyl)-3-methyl-pyrrolidin-3-yl]-2-methyl-7-(2-trifluoromethyl-benzyl)-2,4,5,7-tetrahydro-pyrazolo[3,4-d]pyrimidin-6-one;

5-[(S)-1-(2-Fluoro-6-methyl-phenyl)-3-methyl-pyrrolidin-3-yl]-2-methyl-7-(2-trifluoromethyl-benzyl)-2,4,5,7-tetrahydro-pyrazolo[3,4-d]pyrimidin-6-one;

5-[(R)-1-(2-Fluoro-6-methyl-phenyl)-piperidin-3-yl]-2-methyl-7-(2-trifluoromethyl-benzyl)-2,4,5,7-tetrahydro-pyrazolo[3,4-d]pyrimidin-6-one;

5-[1-(2-Fluoro-6-methyl-phenyl)-azetidin-3-yl]-2-methyl-7-(2-trifluoromethyl-benzyl)-2,4,5,7-tetrahydro-pyrazolo[3,4-d]pyrimidin-6-one;

6-[1-(2-Fluoro-6-methyl-phenyl)-piperidin-4-yl]-4-(2-trifluoromethyl-benzyl)-2,4,6,7-tetrahydro-[1,2,3]triazolo[4,5-d]pyrimidin-5-one;

6-[1-(2-Fluoro-6-methyl-phenyl)-piperidin-4-yl]-2-methyl-4-(2-trifluoromethyl-benzyl)-2,4,6,7-tetrahydro-[1,2,3]triazolo[4,5-d]pyrimidin-5-one;

6-[1-(2-Fluoro-6-methyl-phenyl)-piperidin-4-yl]-2-methyl-4-(3-trifluoromethyl-pyridin-2-ylmethyl)-2,4,6,7-tetrahydro-[1,2,3]triazolo[4,5-d]pyrimidin-5-one;

6-(2'-Methoxy-4'-methyl-3,4,5,6-tetrahydro-2H-[1,3']bipyridinyl-4-yl)-2-methyl-4-(2-trifluoromethyl-benzyl)-2,4,6,7-tetrahydro-[1,2,3]triazolo[4,5-d]pyrimidin-5-one; and 6-(2'-Methoxy-4'-methyl-3,4,5,6-tetrahydro-2H-[1,3']bipyridinyl-4-yl)-2-methyl-4-(3-trifluoromethyl-pyridin-2-ylmethyl)-2,4,6,7-tetrahydro-[1,2,3]triazolo[4,5-d]pyrimidin-5-one.

46) In addition to the compounds listed in embodiment 45), further compounds according to embodiment 1) are selected from the following compounds:

(S)-6-[1-(2-Fluoro-6-methyl-phenyl)-piperidin-4-yl]-2,7-dimethyl-4-(2-trifluoromethyl-benzyl)-2,4,6,7-tetrahydro-pyrazolo[4,3-d]pyrimidin-5-one;

(R)-5-[1-(2-Fluoro-6-methyl-phenyl)-piperidin-4-yl]-2,4-dimethyl-7-(2-trifluoromethyl-benzyl)-2,4,5,7-tetrahydro-pyrazolo[3,4-d]pyrimidin-6-one;
(S)-5-[1-(2-Fluoro-6-methyl-phenyl)-piperidin-4-yl]-2,4-dimethyl-7-(2-trifluoromethyl-benzyl)-2,4,5,7-tetrahydro-pyrazolo[3,4-d]pyrimidin-6-one;
(R)-2-(2,2-Difluoro-propyl)-6-[1-(2-fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one;
(S)-2-(2,2-Difluoro-propyl)-6-[1-(2-fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one;
(S)-6-[1-(2-Fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one;
(R)-2-Cyclopropyl-6-[1-(2-fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one;
(S)-2-Cyclopropyl-6-[1-(2-fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one.

47) In addition to the compounds listed in embodiments 45) and 46), further compounds according to embodiment 1) are selected from the following compounds:
1-Cyclopropylmethyl-5-[1-(2-fluoro-6-methyl-phenyl)-piperidin-4-yl]-7-(2-trifluoromethyl-benzyl)-1,4,5,7-tetrahydro-pyrazolo[3,4-d]pyrimidin-6-one;
1-Cyclopropyl-6-[1-(2-fluoro-6-methyl-phenyl)-piperidin-4-yl]-4-(3-trifluoromethyl-pyridin-2-ylmethyl)-1,4,6,7-tetrahydro-pyrazolo[4,3-d]pyrimidin-5-one;
1-Cyclopropylmethyl-6-[1-(2-fluoro-6-methyl-phenyl)-piperidin-4-yl]-4-(2-trifluoromethyl-benzyl)-1,4,6,7-tetrahydro-pyrazolo[4,3-d]pyrimidin-5-one;
6-[1-(2-Fluoro-6-methyl-phenyl)-piperidin-4-yl]-1-(1-methyl-cyclopropylmethyl)-4-(2-trifluoromethyl-benzyl)-1,4,6,7-tetrahydro-pyrazolo[4,3-d]pyrimidin-5-one;
6-[1-(2-Fluoro-6-methyl-phenyl)-piperidin-4-yl]-1-(2-fluoro-2-methyl-propyl)-4-(2-trifluoromethyl-benzyl)-1,4,6,7-tetrahydro-pyrazolo[4,3-d]pyrimidin-5-one;
1-(2,2-Difluoro-propyl)-6-[1-(2-fluoro-6-methyl-phenyl)-piperidin-4-yl]-4-(3-trifluoromethyl-pyridin-2-ylmethyl)-1,4,6,7-tetrahydro-pyrazolo[4,3-d]pyrimidin-5-one;
(S)-1-(2,2-Difluoro-propyl)-6-[1-(2-fluoro-6-methyl-phenyl)-piperidin-4-yl]-7-methyl-4-(2-trifluoromethyl-benzyl)-1,4,6,7-tetrahydro-pyrazolo[4,3-d]pyrimidin-5-one;
6-[1-(2-Fluoro-6-methyl-phenyl)-piperidin-4-yl]-4-(2-trifluoromethyl-benzyl)-1-(2-trimethylsilanyl-ethoxymethyl)-1,4,6,7-tetrahydro-pyrazolo[4,3-d]pyrimidin-5-one;
6-(2'-Methoxy-4'-methyl-3,4,5,6-tetrahydro-2H-[1,3']bipyridinyl-4-yl)-4-(2-trifluoromethyl-benzyl)-1-(2-trimethylsilanyl-ethoxymethyl)-1,4,6,7-tetrahydro-pyrazolo[4,3-d]pyrimidin-5-one;
6-[1-(2-Fluoro-6-methyl-phenyl)-piperidin-4-yl]-4-(3-trifluoromethyl-pyridin-2-ylmethyl)-1-(2-trimethylsilanyl-ethoxymethyl)-1,4,6,7-tetrahydro-pyrazolo[4,3-d]pyrimidin-5-one; and
6-[1-(2-Fluoro-6-methyl-phenyl)-piperidin-4-yl]-7-methyl-4-(2-trifluoromethyl-benzyl)-1-(2-trimethylsilanyl-ethoxymethyl)-1,4,6,7-tetrahydro-pyrazolo[4,3-d]pyrimidin-5-one.

48) In addition to the compounds listed in embodiments 45) to 47), further compounds according to embodiment 1) are selected from the following compounds:
1-[1-(2-Fluoro-6-methyl-phenyl)-piperidin-4-yl]-7-methyl-3-(2-trifluoromethyl-benzyl)-1,3,6,7-tetrahydro-purin-2-one;
1-[1-(2-Fluoro-6-methyl-phenyl)-piperidin-4-yl]-3-(2-trifluoromethyl-benzyl)-7-(2-trimethylsilanyl-ethoxymethyl)-1,3,6,7-tetrahydro-purin-2-one;
6-[1-(2-Fluoro-6-methyl-phenyl)-piperidin-4-yl]-2-methyl-4-(2-trifluoromethyl-benzyl)-6,7-dihydro-4H-oxazolo[5,4-d]pyrimidin-5-one; and
6-[1-(2-Fluoro-6-methyl-phenyl)-piperidin-4-yl]-2-methyl-4-(2-trifluoromethyl-benzyl)-6,7-dihydro-4H-thiazolo[5,4-d]pyrimidin-5-one.

49) In addition to the compounds listed in embodiments 45) to 48), further compounds according to embodiment 1) are selected from the following compounds:
6-[1-(2-Fluoro-6-trifluoromethoxy-phenyl)-piperidin-4-yl]-2-methyl-4-(2-trifluoromethyl-benzyl)-2,4,6,7-tetrahydro-pyrazolo[4,3-d]pyrimidin-5-one;
6-[1-(2-Fluoro-6-trifluoromethyl-phenyl)-piperidin-4-yl]-2-methyl-4-(2-trifluoromethyl-benzyl)-2,4,6,7-tetrahydro-pyrazolo[4,3-d]pyrimidin-5-one;
5-[1-(2-Chloro-6-fluoro-phenyl)-piperidin-4-yl]-2-methyl-7-(2-trifluoromethyl-benzyl)-2,4,5,7-tetrahydro-pyrazolo[3,4-d]pyrimidin-6-one;
5-[1-(2,6-Difluoro-phenyl)-piperidin-4-yl]-2-methyl-7-(2-trifluoromethyl-benzyl)-2,4,5,7-tetrahydro-pyrazolo[3,4-d]pyrimidin-6-one;
7-(2-Cyclopropyl-benzyl)-5-[1-(2-fluoro-6-trifluoromethyl-phenyl)-piperidin-4-yl]-2-methyl-2,4,5,7-tetrahydro-pyrazolo[3,4-d]pyrimidin-6-one;
7-(2-Cyclopropyl-benzyl)-5-[1-(2-fluoro-6-trifluoromethoxy-phenyl)-piperidin-4-yl]-2-methyl-2,4,5,7-tetrahydro-pyrazolo[3,4-d]pyrimidin-6-one;
2-{4-[7-(2-Cyclopropyl-benzyl)-2-methyl-6-oxo-2,4,6,7-tetrahydro-pyrazolo[3,4-d]pyrimidin-5-yl]-piperidin-1-yl}3-fluoro-benzonitrile;
7-(2-Cyclopropyl-benzyl)-5-(2'-methoxy-4'-methyl-3,4,5,6-tetrahydro-2H-[1,3']bipyridinyl-4-yl)-2-methyl-2,4,5,7-tetrahydro-pyrazolo[3,4-d]pyrimidin-6-one;
5-[1-(2-Chloro-6-fluoro-phenyl)-piperidin-4-yl]-7-(2-cyclopropyl-benzyl)-2-methyl-2,4,5,7-tetrahydro-pyrazolo[3,4-d]pyrimidin-6-one;
7-(2-Cyclopropyl-benzyl)-5-[1-(2,6-difluoro-phenyl)-piperidin-4-yl]-2-methyl-2,4,5,7-tetrahydro-pyrazolo[3,4-d]pyrimidin-6-one;
5-(2'-Methoxy-4'-methyl-3,4,5,6-tetrahydro-2H-[1,3']bipyridinyl-4-yl)-2-methyl-7-[(R)-1-(2-trifluoromethyl-phenyl)-ethyl]-2,4,5,7-tetrahydro-pyrazolo[3,4-d]pyrimidin-6-one;
5-(2'-Methoxy-4'-methyl-3,4,5,6-tetrahydro-2H-[1,3']bipyridinyl-4-yl)-2-methyl-7-[(S)-1-(2-trifluoromethyl-phenyl)-ethyl]-2,4,5,7-tetrahydro-pyrazolo[3,4-d]pyrimidin-6-one;
3-Fluoro-2-(4-{2-methyl-6-oxo-7-[(R)-1-(2-trifluoromethyl-phenyl)-ethyl]-2,4,6,7-tetrahydro-pyrazolo[3,4-d]pyrimidin-5-yl}-piperidin-1-yl)-benzonitrile;
3-Fluoro-2-(4-{2-methyl-6-oxo-7-[(S)-1-(2-trifluoromethyl-phenyl)-ethyl]-2,4,6,7-tetrahydro-pyrazolo[3,4-d]pyrimidin-5-yl}-piperidin-1-yl)-benzonitrile;
5-[1-(2,6-Difluoro-phenyl)-piperidin-4-yl]-2-methyl-7-[(S)-1-(2-trifluoromethyl-phenyl)-ethyl]-2,4,5,7-tetrahydro-pyrazolo[3,4-d]pyrimidin-6-one;
5-[1-(2-Difluoromethyl-6-fluoro-phenyl)-piperidin-4-yl]-2-methyl-7-(2-trifluoromethyl-benzyl)-2,4,5,7-tetrahydro-pyrazolo[3,4-d]pyrimidin-6-one;
6-[1-(2-Difluoromethyl-6-fluoro-phenyl)-piperidin-4-yl]-2-methyl-4-(2-trifluoromethyl-benzyl)-2,4,6,7-tetrahydro-pyrazolo[4,3-d]pyrimidin-5-one;

6-[1-(2-Chloro-6-fluoro-phenyl)-piperidin-4-yl]-2-methyl-4-(2-trifluoromethyl-benzyl)-2,4,6,7-tetrahydro-pyrazolo[4,3-d]pyrimidin-5-one;

5-[1-(2-Cyclopropyl-6-fluoro-phenyl)-piperidin-4-yl]-2-methyl-7-(2-trifluoromethyl-benzyl)-2,4,5,7-tetrahydro-pyrazolo[3,4-d]pyrimidin-6-one;

6-[1-(2-Cyclopropyl-6-fluoro-phenyl)-piperidin-4-yl]-2-methyl-4-(2-trifluoromethyl-benzyl)-2,4,6,7-tetrahydro-pyrazolo[4,3-d]pyrimidin-5-one;

7-(2-Cyclopropyl-benzyl)-5-[1-(2-cyclopropyl-6-fluoro-phenyl)-piperidin-4-yl]-2-methyl-2,4,5,7-tetrahydro-pyrazolo[3,4-d]pyrimidin-6-one;

7-(2-Cyclopropyl-benzyl)-5-[1-(2-difluoromethyl-6-fluoro-phenyl)-piperidin-4-yl]-2-methyl-2,4,5,7-tetrahydro-pyrazolo[3,4-d]pyrimidin-6-one.

50) In addition to the compounds listed in embodiments 45) to 49), further compounds according to embodiment 1) are selected from the following compounds:

4-(2-Cyclopropyl-benzyl)-6-[1-(2-fluoro-6-methyl-phenyl)-piperidin-4-yl]-7-methyl-2-(tetrahydro-pyran-2-yl)-2,4,6,7-tetrahydro-pyrazolo[4,3-d]pyrimidin-5-one;

4-(2-Cyclopropyl-benzyl)-6-(2'-methoxy-4'-methyl-3,4,5,6-tetrahydro-2H-[1,3']bipyridinyl-4-yl)-7-methyl-2-(tetrahydro-pyran-2-yl)-2,4,6,7-tetrahydro-pyrazolo[4,3-d]pyrimidin-5-one;

(S)-4-(2-Cyclopropyl-benzyl)-6-(2'-methoxy-4'-methyl-3,4,5,6-tetrahydro-2H-[1,3']bipyridinyl-4-yl)-7-methyl-2,4,6,7-tetrahydro-pyrazolo[4,3-d]pyrimidin-5-one;

(S)-4-(2-Cyclopropyl-benzyl)-6-[1-(2-fluoro-6-methyl-phenyl)-piperidin-4-yl]-7-methyl-2,4,6,7-tetrahydro-pyrazolo[4,3-d]pyrimidin-5-one;

(R)-4-(2-Cyclopropyl-benzyl)-2-(2,2-difluoro-propyl)-6-[1-(2-fluoro-6-methyl-phenyl)-piperidin-4-yl]-7-methyl-2,4,6,7-tetrahydro-pyrazolo[4,3-d]pyrimidin-5-one;

(S)-4-(2-Cyclopropyl-benzyl)-2-(2,2-difluoro-propyl)-6-[1-(2-fluoro-6-methyl-phenyl)-piperidin-4-yl]-7-methyl-2,4,6,7-tetrahydro-pyrazolo[4,3-d]pyrimidin-5-one;

(R)-2-Cyclopropyl-4-(2-cyclopropyl-benzyl)-6-[1-(2-fluoro-6-methyl-phenyl)-piperidin-4-yl]-7-methyl-2,4,6,7-tetrahydro-pyrazolo[4,3-d]pyrimidin-5-one;

(S)-2-Cyclopropyl-4-(2-cyclopropyl-benzyl)-6-[1-(2-fluoro-6-methyl-phenyl)-piperidin-4-yl]-7-methyl-2,4,6,7-tetrahydro-pyrazolo[4,3-d]pyrimidin-5-one;

(S)-2-Cyclopropyl-4-(2-cyclopropyl-benzyl)-6-(2'-methoxy-4'-methyl-3,4,5,6-tetrahydro-2H-[1,3']bipyridinyl-4-yl)-7-methyl-2,4,6,7-tetrahydro-pyrazolo[4,3-d]pyrimidin-5-one;

(R)-2-Cyclopropyl-4-(2-cyclopropyl-benzyl)-6-(2'-methoxy-4'-methyl-3,4,5,6-tetrahydro-2H-[1,3']bipyridinyl-4-yl)-7-methyl-2,4,6,7-tetrahydro-pyrazolo[4,3-d]pyrimidin-5-one;

6-[1-(2-Fluoro-6-methyl-phenyl)-piperidin-4-yl]-7-methyl-2-(tetrahydro-pyran-2-yl)-4-(2-trifluoromethyl-benzyl)-2,4,6,7-tetrahydro-pyrazolo[4,3-d]pyrimidin-5-one;

(R)-6-(2'-Methoxy-4'-methyl-3,4,5,6-tetrahydro-2H-[1,3']bipyridinyl-4-yl)-7-methyl-4-(2-trifluoromethyl-benzyl)-2,4,6,7-tetrahydro-pyrazolo[4,3-d]pyrimidin-5-one;

(R)-2-Cyclopropyl-6-(2'-methoxy-4'-methyl-3,4,5,6-tetrahydro-2H-[1,3']bipyridinyl-4-yl)-7-methyl-4-(2-trifluoromethyl-benzyl)-2,4,6,7-tetrahydro-pyrazolo[4,3-d]pyrimidin-5-one;

(S)-2-Cyclopropyl-6-(2'-methoxy-4'-methyl-3,4,5,6-tetrahydro-2H-[1,3']bipyridinyl-4-yl)-7-methyl-4-(2-trifluoromethyl-benzyl)-2,4,6,7-tetrahydro-pyrazolo[4,3-d]pyrimidin-5-one;

(R)-6-(2'-Methoxy-4'-methyl-3,4,5,6-tetrahydro-2H-[1,3']bipyridinyl-4-yl)-2,7-dimethyl-4-(2-trifluoromethyl-benzyl)-2,4,6,7-tetrahydro-pyrazolo[4,3-d]pyrimidin-5-one;

(R)-2-(2,2-Difluoro-propyl)-5-[1-(2-fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one;

(S)-2-(2,2-Difluoro-propyl)-5-[1-(2-fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one;

(R)-2-Cyclopropyl-5-[1-(2-fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one;

(S)-2-Cyclopropyl-5-[1-(2-fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one;

(R)-2-Cyclopropyl-5-[1-(2-difluoromethyl-6-fluoro-phenyl)-piperidin-4-yl]-4-methyl-7-(2-trifluoromethyl-benzyl)-2,4,5,7-tetrahydro-pyrazolo[3,4-d]pyrimidin-6-one;

(S)-2-Cyclopropyl-5-[1-(2-difluoromethyl-6-fluoro-phenyl)-piperidin-4-yl]-4-methyl-7-(2-trifluoromethyl-benzyl)-2,4,5,7-tetrahydro-pyrazolo[3,4-d]pyrimidin-6-one;

5-[1-(2-Fluoro-6-methyl-phenyl)-piperidin-4-yl]-4-methyl-2-(tetrahydro-pyran-2-yl)-7-(2-trifluoromethyl-benzyl)-2,4,5,7-tetrahydro-pyrazolo[3,4-d]pyrimidin-6-one;

(R)-5-[1-(2-Difluoromethyl-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one;

(S)-5-[1-(2-Difluoromethyl-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one;

(S)-5-[1-(2-Fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one;

(R)-7-(2-Cyclopropyl-benzyl)-5-[1-(2-fluoro-6-methyl-phenyl)-piperidin-4-yl]-2,4-dimethyl-2,4,5,7-tetrahydro-pyrazolo[3,4-d]pyrimidin-6-one;

(S)-7-(2-Cyclopropyl-benzyl)-5-[1-(2-fluoro-6-methyl-phenyl)-piperidin-4-yl]-2,4-dimethyl-2,4,5,7-tetrahydro-pyrazolo[3,4-d]pyrimidin-6-one;

(R)-5-[1-(2-Chloro-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one;

(S)-5-[1-(2-Chloro-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one;

(R)-5-[1-(2-Chloro-6-fluoro-phenyl)-piperidin-4-yl]-7-(2-cyclopropyl-benzyl)-2,4-dimethyl-2,4,5,7-tetrahydro-pyrazolo[3,4-d]pyrimidin-6-one;

(S)-5-[1-(2-Chloro-6-fluoro-phenyl)-piperidin-4-yl]-7-(2-cyclopropyl-benzyl)-2,4-dimethyl-2,4,5,7-tetrahydro-pyrazolo[3,4-d]pyrimidin-6-one;

(S)-7-(2-Cyclopropyl-benzyl)-5-[1-(2-difluoromethyl-6-fluoro-phenyl)-piperidin-4-yl]-2,4-dimethyl-2,4,5,7-tetrahydro-pyrazolo[3,4-d]pyrimidin-6-one;

(R)-7-(2-Cyclopropyl-benzyl)-5-[1-(2-difluoromethyl-6-fluoro-phenyl)-piperidin-4-yl]-2,4-dimethyl-2,4,5,7-tetrahydro-pyrazolo[3,4-d]pyrimidin-6-one;

(R)-7-(2-Cyclopropyl-benzyl)-5-[1-(2-cyclopropyl-6-fluoro-phenyl)-piperidin-4-yl]-2,4-dimethyl-2,4,5,7-tetrahydro-pyrazolo[3,4-d]pyrimidin-6-one;

(S)-7-(2-Cyclopropyl-benzyl)-5-[1-(2-cyclopropyl-6-fluoro-phenyl)-piperidin-4-yl]-2,4-dimethyl-2,4,5,7-tetrahydro-pyrazolo[3,4-d]pyrimidin-6-one;

(R)-6-[1-(2-Chloro-6-fluoro-phenyl)-piperidin-4-yl]-2-cyclopropyl-7-methyl-4-(2-trifluoromethyl-benzyl)-2,4,6,7-tetrahydro-pyrazolo[4,3-d]pyrimidin-5-one;

(S)-6-[1-(2-Chloro-6-fluoro-phenyl)-piperidin-4-yl]-2-cyclopropyl-7-methyl-4-(2-trifluoromethyl-benzyl)-2,4,6,7-tetrahydro-pyrazolo[4,3-d]pyrimidin-5-one;
(R)-2-Cyclopropyl-6-[1-(2-difluoromethyl-6-fluoro-phenyl)-piperidin-4-yl]-7-methyl-4-(2-trifluoromethyl-benzyl)-2,4,6,7-tetrahydro-pyrazolo[4,3-d]pyrimidin-5-one;
(S)-2-Cyclopropyl-6-[1-(2-difluoromethyl-6-fluoro-phenyl)-piperidin-4-yl]-7-methyl-4-(2-trifluoromethyl-benzyl)-2,4,6,7-tetrahydro-pyrazolo[4,3-d]pyrimidin-5-one;
(R)-5-(2'-Methoxy-4'-methyl-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one;
(S)-5-(2'-Methoxy-4'-methyl-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one;
(R)-5-[1-(2-Cyclopropyl-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one;
(S)-5-[1-(2-Cyclopropyl-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one;
(R)-5-[1-(2-Chloro-6-fluoro-phenyl)-piperidin-4-yl]-2-cyclopropyl-4-methyl-7-(2-trifluoromethyl-benzyl)-2,4,5,7-tetrahydro-pyrazolo[3,4-d]pyrimidin-6-one;
(S)-5-[1-(2-Chloro-6-fluoro-phenyl)-piperidin-4-yl]-2-cyclopropyl-4-methyl-7-(2-trifluoromethyl-benzyl)-2,4,5,7-tetrahydro-pyrazolo[3,4-d]pyrimidin-6-one;
(R)-5-[1-(2-Chloro-6-fluoro-phenyl)-piperidin-4-yl]-2-cyclopropyl-7-(2-cyclopropyl-benzyl)-4-methyl-2,4,5,7-tetrahydro-pyrazolo[3,4-d]pyrimidin-6-one;
(S)-5-[1-(2-Chloro-6-fluoro-phenyl)-piperidin-4-yl]-2-cyclopropyl-7-(2-cyclopropyl-benzyl)-4-methyl-2,4,5,7-tetrahydro-pyrazolo[3,4-d]pyrimidin-6-one;
(R)-2-Cyclopropyl-7-(2-cyclopropyl-benzyl)-5-[1-(2-fluoro-6-methyl-phenyl)-piperidin-4-yl]-4-methyl-2,4,5,7-tetrahydro-pyrazolo[3,4-d]pyrimidin-6-one;
(S)-2-Cyclopropyl-7-(2-cyclopropyl-benzyl)-5-[1-(2-fluoro-6-methyl-phenyl)-piperidin-4-yl]-4-methyl-2,4,5,7-tetrahydro-pyrazolo[3,4-d]pyrimidin-6-one;
5-[1-(2-Difluoromethyl-6-fluoro-phenyl)-piperidin-4-yl]-4-methyl-2-(tetrahydro-pyran-2-yl)-7-(2-trifluoromethyl-benzyl)-2,4,5,7-tetrahydro-pyrazolo[3,4-d]pyrimidin-6-one;
5-[1-(2-Chloro-6-fluoro-phenyl)-piperidin-4-yl]-4-methyl-2-(tetrahydro-pyran-2-yl)-7-(2-trifluoromethyl-benzyl)-2,4,5,7-tetrahydro-pyrazolo[3,4-d]pyrimidin-6-one;
5-(4'-Difluoromethyl-2'-methoxy-3,4,5,6-tetrahydro-2H-[1,3']bipyridinyl-4-yl)-4-methyl-2-(tetrahydro-pyran-2-yl)-7-(2-trifluoromethyl-benzyl)-2,4,5,7-tetrahydro-pyrazolo[3,4-d]pyrimidin-6-one;
(R)-2-Cyclopropyl-5-(2'-methoxy-4'-methyl-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one;
(S)-2-Cyclopropyl-5-(2'-methoxy-4'-methyl-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one;
(R)-5-(4'-Difluoromethyl-2'-methoxy-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one;
(S)-5-(4'-Difluoromethyl-2'-methoxy-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one;
(R)-5-[1-(2-Difluoromethyl-6-fluoro-phenyl)-piperidin-4-yl]-4-methyl-7-(2-trifluoromethyl-benzyl)-2,4,5,7-tetrahydro-pyrazolo[3,4-d]pyrimidin-6-one;
(S)-5-[1-(2-Difluoromethyl-6-fluoro-phenyl)-piperidin-4-yl]-4-methyl-7-(2-trifluoromethyl-benzyl)-2,4,5,7-tetrahydro-pyrazolo[3,4-d]pyrimidin-6-one;
(R)-5-[1-(2-Chloro-6-fluoro-phenyl)-piperidin-4-yl]-4-methyl-7-(2-trifluoromethyl-benzyl)-2,4,5,7-tetrahydro-pyrazolo[3,4-d]pyrimidin-6-one;
(S)-5-[1-(2-Chloro-6-fluoro-phenyl)-piperidin-4-yl]-4-methyl-7-(2-trifluoromethyl-benzyl)-2,4,5,7-tetrahydro-pyrazolo[3,4-d]pyrimidin-6-one;
(R)-5-(4'-Difluoromethyl-2'-methoxy-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one;
(S)-5-(4'-Difluoromethyl-2'-methoxy-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one;
(R)-5-[1-(2-Fluoro-6-methyl-phenyl)-piperidin-4-yl]-2,4-dimethyl-7-(3-trifluoromethyl-pyridin-2-ylmethyl)-2,4,5,7-tetrahydro-pyrazolo[3,4-d]pyrimidin-6-one;
(S)-5-[1-(2-Fluoro-6-methyl-phenyl)-piperidin-4-yl]-2,4-dimethyl-7-(3-trifluoromethyl-pyridin-2-ylmethyl)-2,4,5,7-tetrahydro-pyrazolo[3,4-d]pyrimidin-6-one;
(R)-5-(2'-Methoxy-4'-methyl-3,4,5,6-tetrahydro-2H-[1,3']bipyridinyl-4-yl)-2,4-dimethyl-7-(3-trifluoromethyl-pyridin-2-ylmethyl)-2,4,5,7-tetrahydro-pyrazolo[3,4-d]pyrimidin-6-one;
(S)-5-(2'-Methoxy-4'-methyl-3,4,5,6-tetrahydro-2H-[1,3']bipyridinyl-4-yl)-2,4-dimethyl-7-(3-trifluoromethyl-pyridin-2-ylmethyl)-2,4,5,7-tetrahydro-pyrazolo[3,4-d]pyrimidin-6-one;
(R)-2-Cyclopropyl-5-(4'-difluoromethyl-2'-methoxy-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one;
(S)-2-Cyclopropyl-5-(4'-difluoromethyl-2'-methoxy-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one;
(R)-5-[1-(2-Bromo-6-fluoro-phenyl)-piperidin-4-yl]-2-cyclopropyl-4-methyl-7-(2-trifluoromethyl-benzyl)-2,4,5,7-tetrahydro-pyrazolo[3,4-d]pyrimidin-6-one;
(S)-5-[1-(2-Bromo-6-fluoro-phenyl)-piperidin-4-yl]-2-cyclopropyl-4-methyl-7-(2-trifluoromethyl-benzyl)-2,4,5,7-tetrahydro-pyrazolo[3,4-d]pyrimidin-6-one;
(R)-5-(2'-Methoxy-4'-trifluoromethyl-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one;
(S)-5-(2'-Methoxy-4'-trifluoromethyl-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one;
7-(2-Cyclopropyl-benzyl)-5-(4'-difluoromethyl-2'-methoxy-3,4,5,6-tetrahydro-2H-[1,3']bipyridinyl-4-yl)-4-methyl-2-(tetrahydro-pyran-2-yl)-2,4,5,7-tetrahydro-pyrazolo[3,4-d]pyrimidin-6-one;
5-[1-(2-Chloro-6-fluoro-phenyl)-piperidin-4-yl]-7-(2-cyclopropyl-benzyl)-4-methyl-2-(tetrahydro-pyran-2-yl)-2,4,5,7-tetrahydro-pyrazolo[3,4-d]pyrimidin-6-one;
(R)-7-(2-Cyclopropyl-benzyl)-5-(4'-difluoromethyl-2'-methoxy-3,4,5,6-tetrahydro-2H-[1,3']bipyridinyl-4-yl)-2,4-dimethyl-2,4,5,7-tetrahydro-pyrazolo[3,4-d]pyrimidin-6-one;

(S)-7-(2-Cyclopropyl-benzyl)-5-(4'-difluoromethyl-2'-methoxy-3,4,5,6-tetrahydro-2H-[1,3']bipyridinyl-4-yl)-2,4-dimethyl-2,4,5,7-tetrahydro-pyrazolo[3,4-d]pyrimidin-6-one;

(R)-7-(2-Cyclopropyl-benzyl)-5-(2'-methoxy-4'-methyl-3,4,5,6-tetrahydro-2H-[1,3']bipyridinyl-4-yl)-2,4-dimethyl-2,4,5,7-tetrahydro-pyrazolo[3,4-d]pyrimidin-6-one;

(S)-7-(2-Cyclopropyl-benzyl)-5-(2'-methoxy-4'-methyl-3,4,5,6-tetrahydro-2H-[1,3']bipyridinyl-4-yl)-2,4-dimethyl-2,4,5,7-tetrahydro-pyrazolo[3,4-d]pyrimidin-6-one;

(R)-7-(2-Cyclopropyl-benzyl)-5-(4'-difluoromethyl-2'-methoxy-3,4,5,6-tetrahydro-2H-[1,3']bipyridinyl-4-yl)-4-methyl-2,4,5,7-tetrahydro-pyrazolo[3,4-d]pyrimidin-6-one;

(S)-7-(2-Cyclopropyl-benzyl)-5-(4'-difluoromethyl-2'-methoxy-3,4,5,6-tetrahydro-2H-[1,3']bipyridinyl-4-yl)-4-methyl-2,4,5,7-tetrahydro-pyrazolo[3,4-d]pyrimidin-6-one;

(R)-5-[1-(2-Chloro-6-fluoro-phenyl)-piperidin-4-yl]-7-(2-cyclopropyl-benzyl)-4-methyl-2,4,5,7-tetrahydro-pyrazolo[3,4-d]pyrimidin-6-one;

(S)-5-[1-(2-Chloro-6-fluoro-phenyl)-piperidin-4-yl]-7-(2-cyclopropyl-benzyl)-4-methyl-2,4,5,7-tetrahydro-pyrazolo[3,4-d]pyrimidin-6-one;

(R)-7-(2-Cyclopropyl-benzyl)-5-(2'-methoxy-4'-trifluoromethyl-3,4,5,6-tetrahydro-2H-[1,3']bipyridinyl-4-yl)-2,4-dimethyl-2,4,5,7-tetrahydro-pyrazolo[3,4-d]pyrimidin-6-one;

(S)-7-(2-Cyclopropyl-benzyl)-5-(2'-methoxy-4'-trifluoromethyl-3,4,5,6-tetrahydro-2H-[1,3']bipyridinyl-4-yl)-2,4-dimethyl-2,4,5,7-tetrahydro-pyrazolo[3,4-d]pyrimidin-6-one;

(R)-5-(4'-Chloro-2'-methoxy-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one;

(S)-5-(4'-Chloro-2'-methoxy-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one;

(R)-5-(4'-Chloro-2'-methoxy-3,4,5,6-tetrahydro-2H-[1,3']bipyridinyl-4-yl)-7-(2-cyclopropyl-benzyl)-2,4-dimethyl-2,4,5,7-tetrahydro-pyrazolo[3,4-d]pyrimidin-6-one;

(S)-5-(4'-Chloro-2'-methoxy-3,4,5,6-tetrahydro-2H-[1,3']bipyridinyl-4-yl)-7-(2-cyclopropyl-benzyl)-2,4-dimethyl-2,4,5,7-tetrahydro-pyrazolo[3,4-d]pyrimidin-6-one;

(R)-2-Cyclopropyl-7-(2-cyclopropyl-benzyl)-5-(2'-methoxy-4'-methyl-3,4,5,6-tetrahydro-2H-[1,3']bipyridinyl-4-yl)-4-methyl-2,4,5,7-tetrahydro-pyrazolo[3,4-d]pyrimidin-6-one;

(S)-2-Cyclopropyl-7-(2-cyclopropyl-benzyl)-5-(2'-methoxy-4'-methyl-3,4,5,6-tetrahydro-2H-[1,3']bipyridinyl-4-yl)-4-methyl-2,4,5,7-tetrahydro-pyrazolo[3,4-d]pyrimidin-6-one;

(R)-2-Cyclopropyl-7-(2-cyclopropyl-benzyl)-5-(4'-difluoromethyl-2'-methoxy-3,4,5,6-tetrahydro-2H-[1,3']bipyridinyl-4-yl)-4-methyl-2,4,5,7-tetrahydro-pyrazolo[3,4-d]pyrimidin-6-one;

(S)-2-Cyclopropyl-7-(2-cyclopropyl-benzyl)-5-(4'-difluoromethyl-2'-methoxy-3,4,5,6-tetrahydro-2H-[1,3']bipyridinyl-4-yl)-4-methyl-2,4,5,7-tetrahydro-pyrazolo[3,4-d]pyrimidin-6-one;

(R)-5-[1-(2-Bromo-6-fluoro-phenyl)-piperidin-4-yl]-7-(2-cyclopropyl-benzyl)-2,4-dimethyl-2,4,5,7-tetrahydro-pyrazolo[3,4-d]pyrimidin-6-one;

(S)-5-[1-(2-Bromo-6-fluoro-phenyl)-piperidin-4-yl]-7-(2-cyclopropyl-benzyl)-2,4-dimethyl-2,4,5,7-tetrahydro-pyrazolo[3,4-d]pyrimidin-6-one.

The compounds of formula (I) according to embodiments 1) to 50) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or (II), or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) as defined in any one of embodiments 1) to 50).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

For avoidance of any doubt, if compounds are described as useful for the prevention or treatment of certain diseases, such compounds are likewise suitable for use in the preparation of a medicament for the prevention or treatment of said diseases.

The compounds of formula (I) as defined in any one of embodiments 1) to 50) are useful for the prevention/prophylaxis or treatment of diseases and disorders related to pathogenic events associated with elevated levels of C5a and/or with C5aR activation.

Such diseases and disorders related to pathogenic events associated with elevated levels of C5a and/or with C5aR activation are especially:
vasculitic diseases or disorders,
inflammatory diseases or disorders involving intravascular microvesicle release,
immune complex (IC) diseases or disorders,
neurodegenerative diseases or disorders,
complement related inflammatory diseases or disorders,
bullous diseases or disorders, diseases or disorders related to ischemia and/or ischemic reperfusion injury, inflammatory bowel diseases or disorders, autoimmune diseases or disorders, or, in addition to the above listed, cancer.

In addition to the above-listed diseases and disorders, further diseases and disorders related to pathogenic events associated with elevated levels of C5a and/or with C5aR activation are:

further inflammatory diseases or disorders associated with elevated levels of C5a and/or with C5aR activation such as especially neutropenia, sepsis, septic shock, stroke, inflammation associated with severe burns, osteoarthritis, acute (adult) respiratory distress syndrome (ARDS), chronic pulmonary obstructive disorder (COPD), asthma (especially bronchial asthma), systemic inflammatory response syndrome (SIRS), tissue graft rejection, hyperacute rejection of transplanted organs, multiple organ dysfunction syndrome (MODS), diabetic retinopathy, neuromyelitis optica, and glomerulonephritis including Heyman nephritis/membranous glomerulonephritis, Berger's disease (IgA nephropathy), and other forms of glomerulonephritis such as $C_3$ glomerulopathy including dense deposit disease;

as well as hemotological diseases which are associated with activation of coagulation and fibrinolytic systems, disseminated intravascular coagulation (DIC), pernicious anemia, warm and cold autoimmune hemolytic anemia (AIHA), anti-phospholipid syndrome and its associated complications, arterial or venous thrombosis, pregnancy complications such as recurrent miscarriage and fetal death, preeclampsia, placental insufficiency, fetal growth restriction, cervical remodeling and preterm birth, idiopathic thrombocytopenic purpura (ITP), atypical hemolytic uremic syndrome (aHUS), paroxysmal nocturnal hemoglobinuria (PNH), allergic transfusion reactions, acute antibody-mediated kidney allograft rejection, cold agglutinin disease and glaucoma.

The present compounds may in addition be useful for the prevention or treatment of deleterious consequences of contact sensitivity and inflammation caused by contact with artificial surfaces;

the prevention or treatment of increased leukocyte and platelet activation (and infiltration to tissues thereof);

the prevention or treatment of pathologic sequelae (such as especially prevention or treatment of the development of tissue injury, especially of pulmonary tissue injury) associated to an intoxication or an injury such as a trauma, an hemorrhage, a shock, or surgery including transplantation, including multiple organ failure (MOF), septic shock, shock due to intoxication (such as shock due to snake venom), or acute lung inflammatory injury;

the prevention or treatment of pathologic sequelae associated with insulin-dependent diabetes mellitus;

the prevention of/the reduction of the risk of myocardial infarction or thrombosis; prevention or treatment of edema or increased capillary permeability;

the prevention of/the reduction of coronary endothelial dysfunction induced by cardiopulmonary bypass and/or cardioplegia.

Vasculitic diseases or disorders include especially vasculitis, ANCA associated vasculitis and glomerulonephritis (GN, especially rapidly progressive GN) associated with ANCA associated vasculitis, leukoclastic vasculitis, granulomatosis with polyangiitis (GPA, also referred to as Wegener's granulomatosis), microscopic polyangiitis, Churg-Strauss syndrome, Henoch-Schönlein purpura, polyateritis nodosa, cryoglobulinaemia, giant cell arteritis (GCA), Behcet's disease, and Takayasu's arteritis (TAK).

Inflammatory diseases or disorders involving intravascular microvesicle release include especially thrombotic microangiopathy, and sickle cell disease.

Immune complex (IC) diseases or disorders include especially cryoglobulinemia, Sjögren's syndrome (and associated immunological profiles), Goodpasture syndrome (anti-glomerular basement antibody disease) and glomerulonephritis (GN, especially rapidly progressive GN) or pulmonary hemorrhage associated with Goodpasture syndrome, and hypersensitivity;

Neurodegenerative diseases and disorders include especially amyotrophic lateral sclerosis (ALS), Alzheimer's disease, Parkinson's disease, Huntington's disease, Guillain-Barre syndrome, neuropathy, and cognitive function decline associated with cardiopulmonary bypass surgery and related procedures.

Complement related inflammatory diseases or disorders include especially coronary thrombosis, vascular occlusion, post-surgical vascular reocclusion, atherosclerosis, traumatic central nervous system injury, arrhythmogenic cardiomyopathy, bronchoconstriction, acute respiratory distress syndrome (ARDS), Chronic Obstructive Pulmonary Disorder (COPD), complement mediated thrombotic microangiopathies including atypical haemolytic uremic syndrome, and Gaucher disease.

Bullous diseases or disorders include especially bullous pemphigoid, bullous acquisita, pemphigus foliaceus, pemphigus vulgaris, sub-epidermal blisters, and hidradenitis suppurativa.

Diseases or disorders related to ischemia and/or ischemic reperfusion injury include especially ischemic reperfusion injury (including myocardial ischemia-reperfusion injury, and ischemic/reperfusion injury resulting from transplantation, including solid organ transplant), ischemic colitis, and cardiac ischemia.

Inflammatory bowel diseases or disorders include especially irritable bowel syndrome, ulcerative colitis, Crohn's disease, and inflammatory bowel disease (IBD).

Autoimmune diseases or disorders include especially rheumatoid arthritis, osteoarthritis, systemic lupus erythematosus (SLE) and glomerulonephritis (GN, especially rapidly progressive GN) associated with lupus erythematosus (lupus nephritis), central nervous system (CNS) lupus, dermatomyositis, pemphigus, systemic sclerosis (scleroderma), autoimmune hemolytic and thrombocytopenic states, immunovasculitis, mixed cryoglobulinemia, atopic dermatitis, chronic urticaria, psoriasis, myasthenia gravis, and anti-phospholipid syndrome.

Further inflammatory diseases or disorders associated with elevated levels of C5a and/or with C5aR activation include especially neutropenia, sepsis, septic shock, stroke, inflammation associated with severe burns, osteoarthritis, acute (adult) respiratory distress syndrome (ARDS), chronic pulmonary obstructive disorder (COPD), asthma, especially bronchial asthma, systemic inflammatory response syndrome (SIRS), tissue graft rejection, hyperacute rejection of transplanted organs, multiple organ dysfunction syndrome (MODS), diabetic retinopathy, neuromyelitis optica, and glomerulonephritis including Heyman nephritis/membranous glomerulonephritis, Berger's disease (IgA nephropathy), and other forms of glomerulonephritis such as C3 glomerulopathy including dense deposit disease.

The term "cancer" notably refers to skin cancer including melanoma including metastatic melanoma; lung cancer including non-small cell lung cancer; bladder cancer including urinary bladder cancer, urothelial cell carcinoma; renal carcinomas including renal cell carcinoma, metastatic renal cell carcinoma, metastatic renal clear cell carcinoma; gastrointestinal cancers including colorectal cancer, metastatic colorectal cancer, familial adenomatous polyposis (FAP), oesophageal cancer, gastric cancer, gallbladder cancer, cholangiocarcinoma, hepatocellular carcinoma, and pancreatic cancer such as pancreatic adenocarcinoma or pancreatic ductal carcinoma; endometrial cancer; ovarian cancer; cervical cancer; neuroblastoma; prostate cancer including castrate-resistant prostate cancer; brain tumors including brain metastases, malignant gliomas, glioblastoma multiforme, medulloblastoma, meningiomas; breast cancer including triple negative breast carcinoma; oral tumors; nasopharyngeal tumors; thoracic cancer; head and neck cancer; leukemias including acute myeloid leukemia, adult T-cell leukemia; carcinomas; adenocarcinomas; thyroid carcinoma including papillary thyroid carcinoma; choriocarcinoma; Ewing's sarcoma; osteosarcoma; rhabdomyosarcoma; Kaposi's sarcoma; lymphoma including Burkitt's lymphoma, Hodgkin's lymphoma, MALT lymphoma; multiple myelomas; or virally induced tumors.

When used for the prevention/prophylaxis or treatment of a cancer, such use includes use of the present compounds as single therapeutic agents and their use in combination with one or more chemotherapy agents and/or radiotherapy and/or targeted therapy (especially in combination with targeted therapy).

The terms "radiotherapy" or "radiation therapy" or "radiation oncology", refer to the medical use of ionizing radiation in the prevention/prophylaxis (adjuvant therapy) and/or treatment of cancer; including external and internal radiotherapy.

The term "targeted therapy" refers to the prevention/prophylaxis (adjuvant therapy) and/or treatment of cancer with one or more anti-neoplastic agents such as small molecules or antibodies which act on specific types of cancer cells or stromal cells. Some targeted therapies block the action of certain enzymes, proteins, or other molecules involved in the growth and spread of cancer cells. Other types of targeted therapies help the immune system kill cancer cells (immunotherapies); or inhibit angiogenesis, the growth and formation of new blood vessels in the tumor; or deliver toxic substances directly to cancer cells and kill them. An example of a targeted therapy which is in particular suitable to be combined with the compounds of the present invention is immunotherapy, especially immunotherapy targeting the progammed cell death receptor 1 (PD-1 receptor) or its ligand PD-L1.

When used in combination with the present compounds, the term "targeted therapy" especially refers to agents such as:

a) Epidermal growth factor receptor (EGFR) inhibitors or blocking antibodies (for example Gefitinib, Erlotinib, Afatinib, Icotinib, Lapatinib, Panitumumab, Zalutumumab, Nimotuzumab, Matuzumab and Cetuximab);

b) RAS/RAF/MEK pathway inhibitors (for example Vemurafenib, Sorafenib, Dabrafenib, GDC-0879, PLX-4720, LGX818, RG7304, Trametinib (GSK1120212), Cobimetinib (GDC-0973/XL518), Binimetinib (MEK162, ARRY-162), Selumetinib (AZD6244));

c) Aromatase inhibitors (for example Exemestane, Letrozole, Anastrozole, Vorozole, Formestane, Fadrozole);

d) Angiogenesis inhibitors, especially VEGF signalling inhibitors such as Bevacuzimab (Avastin), Ramucirumab, Sorafenib or Axitinib;

e) Immune Checkpoint inhibitors (for example: anti-PD1 antibodies such as Pembrolizumab (Lambrolizumab, MK-3475), Nivolumab, Pidilizumab (CT-011), AMP-514/MED10680, PDR001, SHR-1210; REGN2810, BGBA317; fusion proteins targeting PD-1 such as AMP-224; small molecule anti-PD1 agents such as for example compounds disclosed in WO2015/033299, WO2015/044900 and WO2015/034820; anti-PD1L antibodies, such as BMS-936559, atezolizumab (MPDL3280A, RG7446), MEDI4736, avelumab (MSB0010718C), durvalumab (MEDI4736); anti-PDL2 antibodies, such as AMP224; anti-CTLA-4 antibodies, such as ipilimumab, tremilmumab; anti-Lymphocyte-activation gene 3 (LAG-3) antibodies, such as BMS-986016, IMP701, MK-4280, ImmuFact IMP321; anti T cell immunoglobulin mucin-3 (TIM-3) antibodies, such as MBG453; anti-CD137/4-1BB antibodies, such as BMS-663513/urelumab, PF-05082566; anti T cell immunoreceptor with Ig and ITIM domains (TIGIT) antibodies, such as RG6058 (anti-TIGIT, MTIG7192A);

f) Vaccination approaches (for example dendritic cell vaccination, peptide or protein vaccination (for example with gp100 peptide or MAGE-A3 peptide);

g) Re-introduction of patient derived or allogenic (nonself) cancer cells genetically modified to secrete immunomodulatory factors such as granulocyte monocyte colony stimulating factor (GMCSF) gene-transfected tumor cell vaccine (GVAX) or Fms-related tyrosine kinase 3 (Flt-3) ligand gene-transfected tumor cell vaccine (FVAX), or Toll like receptor enhanced GM-CSF tumor based vaccine (TEGVAX);

h) T-cell based adoptive immunotherapies, including chimeric antigen receptor (CAR) engineered T-cells (for example CTL019);

i) Cytokine or immunocytokine based therapy (for example Interferon alpha, interferon beta, interferon gamma, interleukin 2, interleukin 15);

j) Toll-like receptor (TLR) agonists (for example resiquimod, imiquimod, glucopyranosyl lipid A, CpG oligodesoxynucleotides);

k) Thalidomide analogues (for example Lenalidomide, Pomalidomide);

l) Indoleamin-2,3-Dioxgenase (IDO) and/or Tryptophane-2,3-Dioxygenase (TDO) inhibitors (for example RG6078/NLG919/GDC-0919; Indoximod/1MT (1-methyltryptophan), INCB024360/Epacadostat, PF-06840003 (EOS200271), F001287);

m) Activators of T-cell co-stimulatory receptors (for example anti-OX40/CD134 (Tumor necrosis factor receptor superfamily, member 4, such as RG7888 (MOXR0916), 9B12; MED16469, GSK3174998, MED10562), anti OX40-Ligand/CD252; anti-glucocorticoid-induced TNFR family related gene (GITR) (such as TRX518, MED11873, MK-4166, BMS-986156), anti-CD40 (TNF receptor superfamily member 5) antibodies (such as Dacetuzumab (SGN-40), HCD122, CP-870,893, RG7876, ADC-1013, APX005M, SEA-CD40); anti-CD40-Ligand antibodies (such as BG9588); anti-CD27 antibodies such as Varlilumab);

n) Molecules binding a tumor specific antigen as well as a T-cell surface marker such as bispecific antibodies (for example RG7802 targeting CEA and CD3) or antibody fragments, antibody mimetic proteins such as designed ankyrin repeat proteins (DARPINS), bispecific T-cell engager (BITE, for example AMG103, AMG330);

o) Antibodies or small molecular weight inhibitors targeting colony-stimulating factor-1 receptor (CSF-1R) (for example Emactuzumab (RG7155), Cabiralizumab (FPA-008), PLX3397);

p) Agents targeting immune cell check points on natural killer cells such as antibodies against Killer-cell immunoglobulin-like receptors (KIR) for example Lirilumab (IPH2102/BMS-986015);

q) Agents targeting the Adenosine receptors or the ectonucleases CD39 and CD73 that convert ATP to Adenosine, such as MED19447 (anti-CD73 antibody), PBF-509; CPI-444 (Adenosine A2a receptor antagonist).

When used in combination with the present compounds, immune checkpoint inhibitors, and especially those targeting the PD-1 receptor or its ligand PD-L1, are preferred.

The invention further relates to a method of modulating (especially downregulating) the consequences of the complement activation (especially by activating innate cells) in a subject in need thereof [especially in a subject having a disease or disorder related to pathogenic events associated with elevated levels of C5a and/or with C5aR activation; in particular in a subject having a vasculitic disease or disorder, an inflammatory disease or disorder involving intravascular microvesicle release, an immune complex (IC) disease or disorder, a neurodegenerative disease or disorder, a complement related inflammatory disease or disorder, a bullous disease or disorder, a disease or disorder related to ischemia and/or ischemic reperfusion injury, an inflammatory bowel disease or disorder, or an autoimmune disease or disorder; or in a subject having a contact sensitivity or an inflammation caused by contact with artificial surfaces; an increased leukocyte and platelet activation (and infiltration to tissues thereof); a pathologic sequelae associated to an intoxication or an injury such as a trauma, an hemorrhage, a shock, or surgery including transplantation, including multiple organ failure (MOF), septic shock, shock due to intoxication (such as shock due to snake venom), or acute lung inflammatory injury; a pathologic sequelae associated with insulin-dependent diabetes mellitus; a myocardial infarction or thrombosis; an edema or an increased capillary permeability; or a reduction of coronary endothelial dysfunction induced by cardiopulmonary bypass and/or cardioplegia], comprising administering to said subject a pharmaceutically active amount of a compound of formula (I) as defined in any one of embodiments 1) to 50). For avoidance of doubt, the term "modulating the complement activation" is to be understood as downregulating/reducing the amplification of the immune response and downregulating/reducing the activation of the cell-killing membrane attack complex, especially by activating innate cells.

Preparation of Compounds of Formula (I)

A further aspect of the invention is a process for the preparation of compounds of Formula (I) as defined in any one of embodiments 1) to 50). Compounds of Formula (I) can be prepared from commercially available or well known starting materials according to the methods described in the experimental part, by analogous methods; or according to the general sequence of reactions outlined below, wherein $R^1$, $R^A$, $R^2$, $R^3$, $R^4$, X, Y and Z are as defined for Formula (I). Other abbreviations used herein are explicitly defined or are as defined in the experimental section. In some instances, the generic groups $R^1$, $R^A$, $R^2$, $R^3$, $R^4$, X, Y and Z might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. The compounds obtained may also be converted into salts, especially pharmaceutically acceptable salts thereof in a manner known per se.

Compounds of structure Ia which are compounds of Formula (I) wherein $R^4$ represents hydrogen, can be prepared according to the synthetic routes given in scheme A1 below (wherein ring A may in addition be optionally substituted with $R^A$ as explicitly defined).

Compounds of structure A-1 can be prepared by reductive amination of suitable aldehydes of structure BB-4 with suitable amines of structure BB-7 using standard conditions such as treatment with $NaBH(OAc)_3$ in the optional presence of AcOH and a suitable solvent such as DCM, MeOH, THF or a mixture thereof at temperatures around RT. Alternatively, $NaBH_4$ can be used as reducing agent in the presence of TFE as solvent according to Synthesis, 2011, 3, 490-496. Optionally, a two-step procedure can be applied (i) condensation of a suitable aldehyde of structure BB-4 with amines of structure BB-7 in the presence of a suitable solvent such as MeOH at temperatures around 60° C. and (ii) subsequent reduction of the intermediate imine by treatment with $NaBH_4$ at temperatures between 0° C. and RT (Scheme A1, step a).

Diamino compounds of structure A-2 can be prepared by reduction of the nitro group in compounds of structure A-1 using standard conditions such as catalytic hydrogenation with a suitable catalyst such as Pd/C in a suitable solvent such as EtOAc or EtOH or a mixture thereof (Scheme A1, step b).

Alternatively, diamino compounds of structure A-2 can be prepared by reductive alkylation of a suitable amine of structure BB-5 with ketones of structure BB-8 using standard conditions such as treatment with $NaBH(OAc)_3$ in the optional presence of AcOH and a suitable solvent such as DCM, MeOH, THF or a mixture thereof at temperatures around RT. Treatment of a suitable amine of structure BB-5 with tosylate of structure BB-33 in the presence of a suitable solvent such as MeCN at temperatures around 110° C. under microwave irradiation can be an alternative procedure to provide diamino compounds of structure A-2 (Scheme A1, step c).

An alternative preparation of compounds of structure A-2 may be a reductive amination of a suitable aldehyde of structure BB-6 (or BB-20, respectively) with amines of structure BB-7 using standard conditions such as treatment with $NaBH(OAc)_3$ in the optional presence of AcOH (or with $NaBH_4$, respectively) and in the presence of a suitable solvent such as DCM, MeOH, THF or a mixture thereof (or TFE, respectively) at temperatures around RT (or around 35° C., respectively) (Scheme A1, step d (or step g, respectively)).

Scheme A1

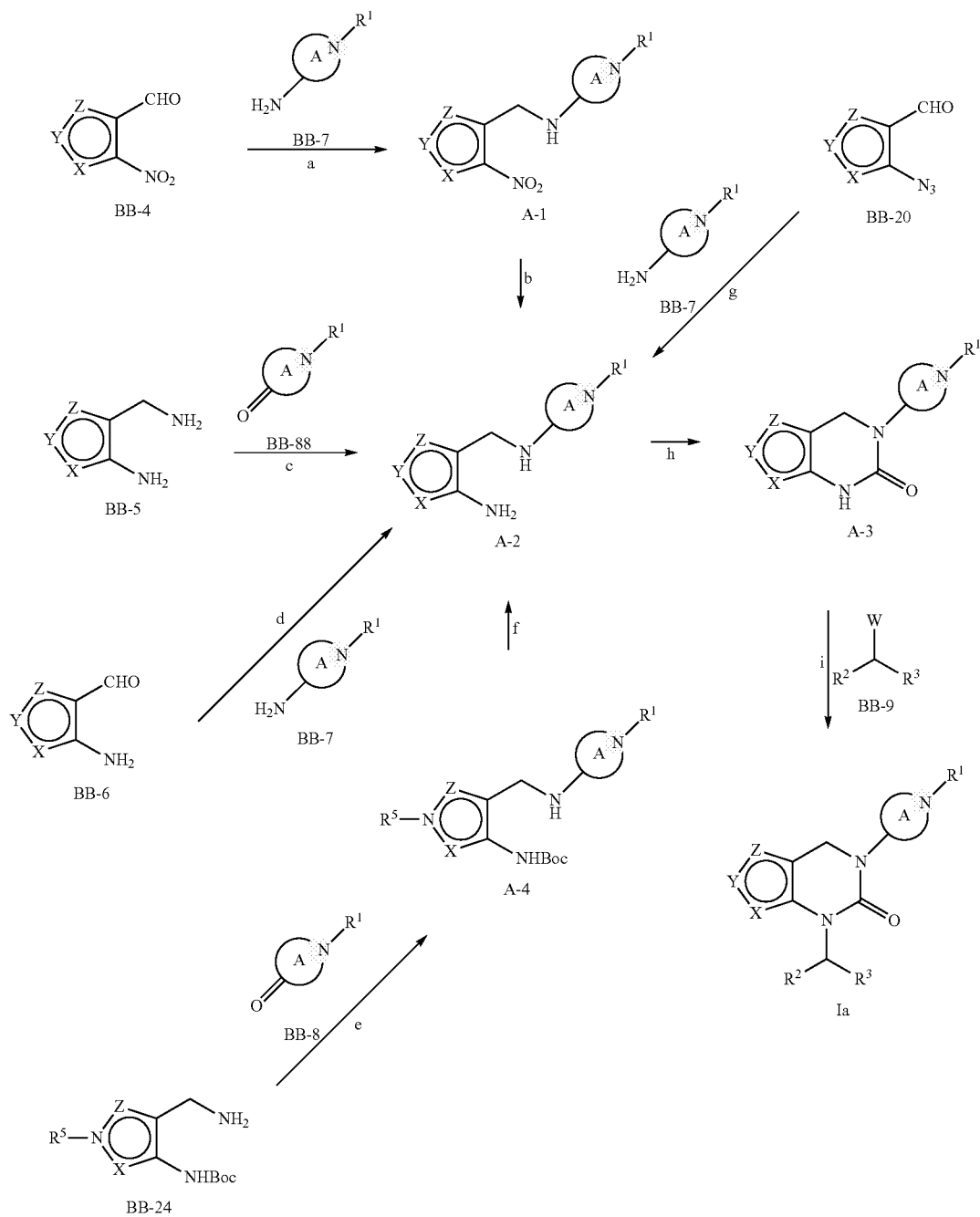

Compounds of structure A-2 may alternatively be prepared by cleavage of the Boc protecting group in suitable compounds of structure A-4 (e.g. wherein $R^5$ represents $(C_{1-4})$alkyl, $(C_{2-3})$fluoroalkyl, or $(C_{3-6})$cycloalkyl-$(C_{0-4})$alkylene, or the like) using a suitable acid such as HCl or TFA in the presence of a suitable solvent such as dioxane, MeOH or DCM at temperatures around RT (Scheme A1, step f).

The reductive alkylation of the amine of structure BB-24 with ketones of structure BB-8 using standard conditions such as treatment with NaBH(OAc)$_3$ in the optional presence of AcOH and a suitable solvent such as DCM, MeOH, THF or a mixture thereof at temperatures around RT can provide compounds of structure A-4 (Scheme A1, step e).

Cyclic ureas of structure A-3 can be prepared by cyclisation of diamines of structure A-2 by treatment with a suitable carbonyl transfer agent such as CDI in the presence of a suitable aprotic solvent such as MeCN or THF at temperatures between RT and 80° C. (Scheme A1, step h).

Alkylation of the nitrogen atom having a free valency in compounds of structure A-3 with a suitable halide of structure BB-9 wherein W represents chlorine or bromine, in the presence of a suitable base such as NaH or K$_2$CO$_3$ and in solvents such as THF, DMF or a mixture of both at temperatures between 0° C. and 50° C. may afford compounds of structure Ia.

Alternatively, alkylation of the nitrogen atom having a free valency in compounds of structure A-3 can be achieved using Mitsunobu conditions by treatment with a suitable alcohol of structure BB-9 wherein W represents hydroxy and for instance a (cyanomethylene)trialkylphosphorane reagent in the presence of a suitable solvent such as toluene at temperatures around 110° C. (Scheme A1, step i).

Compounds of structure Ib, Ic, Id, Ie, If and Ig can be prepared from suitable precursors of structure Ia according to the synthetic routes given in scheme A2 below, wherein said compounds of structure Ia may carry suitable protecting groups or functional groups as indicated.

Compounds of structure Ib wherein at least two of X, Y or Z represent N can be prepared from the corresponding N-SEM derivatives of compounds of structure Ia by cleavage of the SEM protecting group using for instance a suitable acid such as TFA in the presence of a suitable solvent such as DCM at temperatures around RT. An additional treatment with ethylenediamine in the presence of THE as solvent at temperatures around 60° C. might be necessary to achieve complete cleavage of the SEM protecting group (Scheme A2, step a). Subsequently to the TFA procedure, an additional treatment with an acid such as HCl in the presence of a suitable alcohol such as MeOH or EtOH at temperatures around 70° C. can afford the respective alkoxymethyl derivatives of structure Ic (Scheme A2, step g).

Alternatively, compounds of structure Ib wherein at least two of X, Y or Z represent N can be prepared from the corresponding Bn-protected derivatives by cleavage of the Bn protecting group in compounds of structure Ia by catalytic hydrogenation using a suitable catalyst such as Pd/C in the presence of a suitable solvent such as EtOH or MeOH and under a hydrogen atmosphere at temperatures around RT. Catalytic transfer hydrogenation conditions using for instance ammonium formate can be an alternative procedure (Scheme A2, step a).

Alternatively, compounds of structure Ib wherein at least two of X, Y or Z represent N can be prepared from the corresponding THP-protected derivatives by cleavage of the THP protecting group in compounds of structure Ia by treatment with a suitable acid such as TFA in the presence of a suitable solvent such as DCM at temperatures around RT (Scheme A2, step a).

Compounds of structure Ic (or Id or Ie, respectively) wherein $R^5$ (or $R^8$, respectively) represents methyl can be prepared by treatment with a methylating reagent such as MeI in the presence of a suitable base such as DBU and a suitable solvent such as DMF at temperatures around RT. Treatment with MeI in the presence of $Ag_2CO_3$ as base and heating in a suitable solvent such as toluene at temperatures around 85° C. can be an alternative procedure (Scheme A2, step b, c or d).

Scheme A2

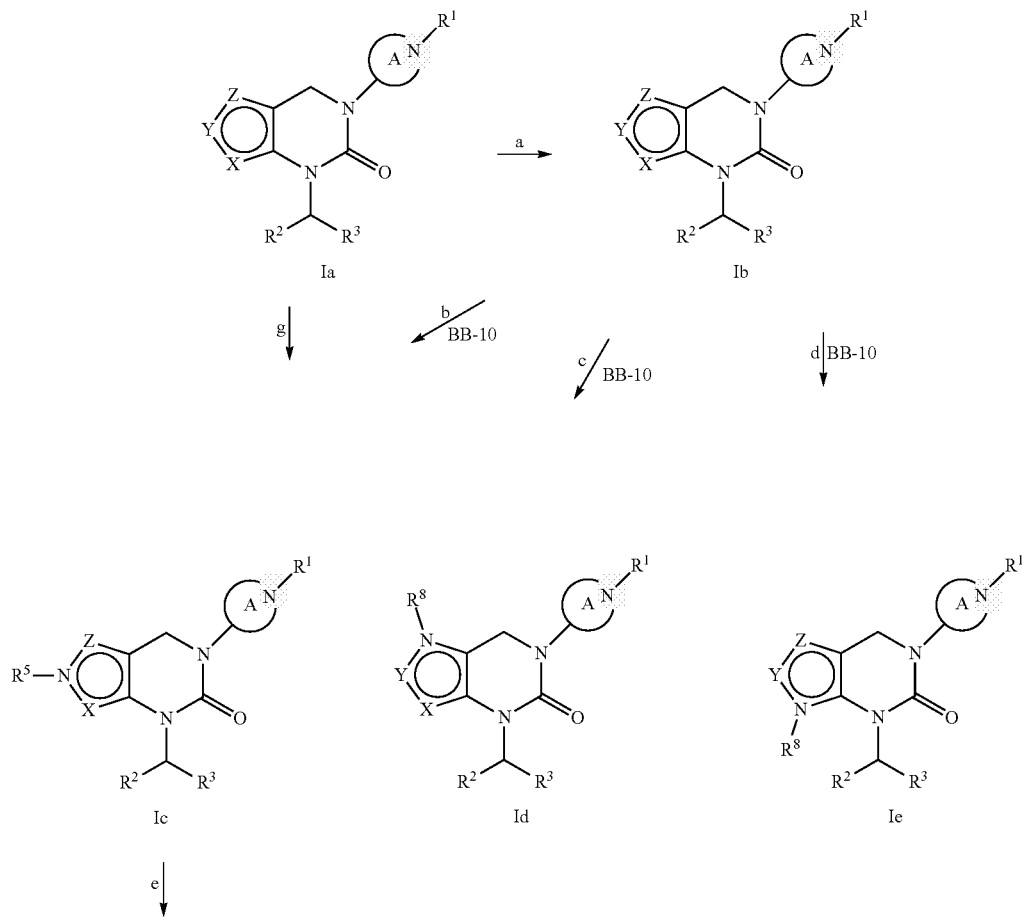

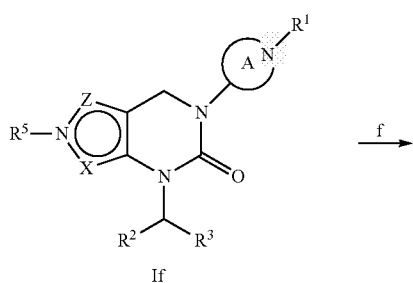
If

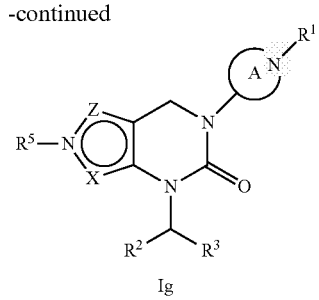
Ig

In compounds of structure Ib, a free NH group corresponding to X, Y or Z can be alkylated by treatment with a suitable halide, aziridine, epoxide or tosylate of structure BB-10 in the presence of a suitable base such as NaH, $K_2CO_3$ or $Cs_2CO_3$ and in solvents such as THF, DMF or DMA or a mixture thereof at temperatures between 0° C. and 150° C. under possible microwave irradiation can afford the corresponding compounds of structure Ic (Scheme A2, step b, c or d).

Alternatively, Mitsunobu conditions can be used by treatment with a suitable alcohol of structure BB-10 and for instance with a (cyanomethylene)trialkylphosphorane reagent in the presence of a suitable solvent such as toluene at temperatures around 110° C. (Scheme A2, step b, c or d).

Conditions for a 1,4-nucleophilic addition can alternatively be applied by treatment with a suitable ethyl or methyl 2-alkenoate or 2-nitroalkene of structure BB-10 in the presence of a suitable base such as CsF, TEA or $K_2CO_3$ and a suitable solvent such as THF or DMF at temperatures between 0° C. and 60° C. (Scheme A2, step b, c or d).

Alternatively, alkoxycarbonylation (or alkylcarbamylation, respectively) can be performed by treatment with a suitable alkylchloroformate (or alkylisocyanate, respectively) of structure BB-10 in the presence of a suitable base such as TEA or DIPEA and a suitable solvent such as DCM or DMF at temperatures between 0° C. and RT. Di-alkylcarbamylation can be achieved by treatment with a suitable carbonyl transfer reagent such as CDI and a suitable amine of structure BB-10 in the presence of a suitable base such as TEA or DIPEA and a suitable solvent such as THF or DCM at temperatures around RT (Scheme A2, step b, c or d).

Alternatively, Chan-Lam conditions can be applied by treatment with a suitable boronic acid or boronic ester of structure BB-10 in the presence of a suitable copper catalyst such as $Cu(OAc)_2$ and a suitable ligand such as 2,2'-bipyridyl, in the presence of a suitable base such as $Na_2CO_3$ and heating in a suitable solvent such as toluene or trifluoromethylbenzene at temperatures between 70° C. and 90° C. (Scheme A2, step b, c or d).

Where suitable for the remaining substituents or functional groups in the molecule, compounds of structure If can be prepared from compounds of structure Ic (and subsequently compounds of structure Ig from compounds of structure If) by conventional functional group transformation, e.g. within the substituent $R^5$, as described below (Scheme A2, step e; subsequently step f):

Carboxylic ester functions can be reduced by treatment with a suitable reducing reagent such as $CaBH_4$ (formed in situ from $NaBH_4$ and $CaCl_2$) in the presence of a suitable solvent such as EtOH at temperatures between −10° C. and RT to give the corresponding primary alcohol.

Nitrile functions can be reduced by treatment with a suitable reducing reagent such as $CoBH_4$ (formed in situ from $NaBH_4$ and $COCl_2$) in the presence of a suitable solvent such as MeOH at temperatures between 0° C. and RT; or by using a suitable catalyst such as Raney nickel in the presence of a suitable base such as ammonia and a suitable solvent such as MeOH at temperatures between 0° C. and RT to give the corresponding primary amine.

Carboxylic ester functions can be hydrolysed by treatment with a suitable base such as LiOH, NaOH or KOH in the presence of water and a suitable solvent such as THF, MeOH or EtOH or a mixture thereof at temperatures between RT and 50° C. The resulting carboxylic acid can subsequently be coupled with a suitable amine by treatment with suitable activating reagents such as the combination EDC.HCl and HOBt in the presence a suitable base such as DIPEA and stirring in a suitable solvent such as DCM or DMF or a mixture thereof at temperatures around RT.

Acetal protected aldehydes can be deprotected by acidic treatment with aq. HCl in the presence of a suitable solvent such as THF at temperatures between RT and 70° C. Resulting aldehydes can subsequently react with a suitable Grignard reagent such as alkyl magnesium bromides in the presence of a suitable solvent such as THF at temperatures between 0° C. and RT. Alternatively, reductive amination with suitable amines using conditions such as treatment with $NaBH(OAc)_3$ in the presence of AcOH (or $NaBH_4$ respectively) and in the presence of a suitable solvent such as DCM, MeOH, THF or a mixture thereof (or TFE respectively) at temperatures between RT and 40° C. can afford corresponding secondary or tertiary amines.

A chlorine substituent can be substituted with suitable amines in the presence of a suitable solvent such as DMF at temperatures around 70° C.

A primary amide can be dehydrated by treatment with a suitable dehydrating reagent such as Burgess reagent in the presence of a suitable solvent such as DCM at temperatures around RT to give the corresponding nitrile.

A tertiary alcohol can be dehydrated by treatment with a suitable dehydrating reagent such as $POCl_3$ in the presence of a suitable solvent such as pyridine and heating at temperatures around 50° C. to give the corresponding alkene.

A Boc protected amine can be deprotected by treatment with a suitable acid such as HCl or TFA in the presence of a suitable solvent such as dioxane, MeOH or DCM at temperatures around RT to release the corresponding free amine.

A trityl protected lactam can be deprotected by treatment with a suitable acid such as TFA in the presence of a suitable solvent such as H₂O at temperatures around 0° C. to release the corresponding free actam.

A 2-nitrobenzensulfonyl protected amine can be deprotected by treatment with a suitable solid-supported thiol such as QuadraPure® MPA in the presence of a suitable base such as Cs₂CO₃ and heating in a suitable solvent such as THE under microwave irradiation at temperatures around 130° C. to give the corresponding free amine.

A carbon-carbon double bond can be reduced by catalytic hydrogenation using a suitable catalyst such as Pd/C in the presence of a suitable solvent such as EtOAc, MeOH or a mixture thereof at temperatures around RT to give the corresponding saturated bond.

A primary or secondary amine can be acylated (or alkylsulfonylated or dialkylsulfamylated, respectively) by treatment with a suitable acyl chloride (or alkylsulfonyl chloride or di-alkylsulfamyl chlorides, respectively) in the presence of a suitable base such as TEA or DIPEA and a suitable solvent such as DCM or DMF at temperatures between 0° C. at RT. Alternatively, it can be alkoxycarbonylated by treatment with a suitable chloroformate or dialkyldicarbonate reagent (or pentafluorophenylcarbonate reagent, respectively) in the presence of a suitable base such as TEA or DIPEA and a suitable solvent such as DCM (or DMF, respectively) at temperatures between 0° C. at RT (or between RT and 110° C., respectively). Alternatively, it can be dialkylcarbamylated by treatment with a suitable carbonyl transfer reagent such as CDI and a suitable amine in the presence of a suitable base such as TEA or DIPEA and a suitable solvent such as THE or DCM at temperatures around RT. Alternatively, it can be alkylated by reductive alkylation with aldehydes using standard conditions such as treatment with NaBH(OAc)₃ in the presence of AcOH and in the presence of a suitable solvent such as DCM, MeOH, THE or a mixture thereof at temperatures between RT and 40° C. Alternatively, alkylation can be achieved by treatment with a suitable halide in the presence of a suitable base such as DIPEA, a catalytic amount of KI and heating in a suitable solvent such as DMF under possible microwave irradiation at temperature between 110° C. and 150° C. Alternatively, a primary or secondary amine can be engaged in an aromatic nuleophilic substitution with a suitable (hetero)aromatic halide in the presence of a suitable base such as DIPEA or K₂CO₃ and stirring in a suitable solvent such as DMSO at temperatures between RT and 110° C. Alternatively, aromatic nucleophilic substitution can be achieved by activation of a suitable (hetero)aromatic alcohol of structure with PyBOP in the presence of a suitable base such as DIPEA in solvents such as DMF at temperatures around RT.

An alcohol can be transformed to a primary amine following the two-step procedure: (i) Mitsunobu conditions to form a phthalimide intermediate by treatment with phthalimide and e.g. a (cyanomethylene)trialkylphosphorane reagent and heating in a suitable solvent such as toluene at temperatures around 110° C. and (ii) cleavage of the phthalimide by treatment with hydrazine hydrate in the presence of a suitable solvent such as EtOH at temperature around 80° C. to release the corresponding primary amine.

Compounds of structure Ia and Ih can further be prepared according to the synthetic routes given in scheme B below.

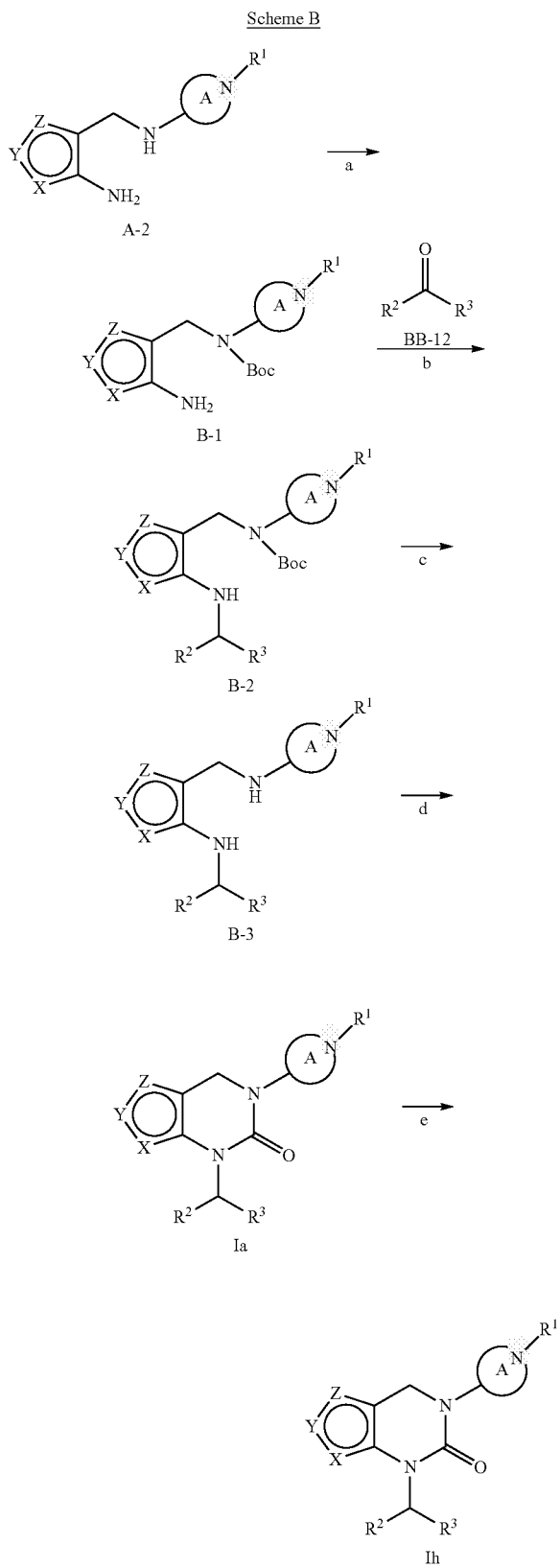

Compounds of structure B-1 wherein none of X, Y and Z represents NH and $R^1$ does not represents Boc can be prepared by treatment of amines of structure A-2 wherein none of X, Y and Z represents NH and $R^1$ does not represents Boc with Boc-anhydride in the presence of a suitable base such as TEA or DIPEA in a suitable solvent such as DCM or THF at temperatures between 0° C. and RT (Scheme B, step a).

Reductive alkylation of amines of structure B-1 with aldehydes or ketones of structure BB-12 using standard conditions such as treatment with $NaBH(OAc)_3$ in the presence of AcOH (or $NaBH_4$, respectively) and in the presence of a suitable solvent such as DCM, MeOH, THF or a mixture thereof (or TFE, respectively) at temperatures between RT and 40° C. can afford compounds of structure B-2 (Scheme B, step b).

Cleavage of the Boc protecting group in compounds of structure B-2 wherein $R^1$ does not represents Boc can be performed by treatment with a suitable acid such as HCl or TFA in the presence of a suitable solvent such as dioxane, MeOH or DCM at temperatures around RT to afford diamines of structure B-3 (Scheme B, step c).

Cyclic ureas of structure Ia can be prepared by cyclisation of compound of structure B-3 by treatment with a suitable carbonyl transfer agent such as CDI, DSC or phosgene in the presence of a suitable aprotic solvent such as MeCN at temperatures around 80° C. (Scheme B, step d).

Catalytic deuteration of (hetero)aryl groups which are substituted by one bromine or chlorine atom with a suitable catalyst such as Pd/C in the presence of a suitable solvent such as EtOAc, $CD_3OD$ or a mixture thereof under a deuterium atmosphere at temperatures around RT may afford the corresponding mono-deuterated (hetero)aryl groups (Scheme B, step e).

Heteroaryl groups which are substituted by one fluorine atom in ortho position to a ring nitrogen atom can be prepared by aromatic nucleophilic substitution of CsF on the corresponding chloro heteroaryl group in the presence of a suitable solvent such as DMSO under possible microwave irradiation at temperatures around 100° C. (Scheme B, step e).

Alkylated (hetero)aryl groups be prepared by Suzuki cross coupling of a suitable aromatic chloride with a ($C_1$-$C_4$)-alkyl boronic acid or boroxine in the presence of a suitable palladium catalyst such as $Pd(dppf)Cl_2 \cdot CH_2Cl_2$ or PEPPSI-IPr, in the presence of a suitable base such as $K_2CO_3$ and heating in a suitable solvent such as dioxane at temperatures around 100° C. (Scheme B, step e).

Aromatic nucleophilic substitution of sodium alkoxides (or suitable amines) on suitable (hetero)aryl groups, e.g. heteroaryl groups which are substituted by one chlorine atom in ortho position of a nitrogen, in the presence of the corresponding alcohol as solvent (or in the presence of a suitable solvent such as MeOH, respectively) at temperatures around 80° C. (or at temperatures between 80° C. and 150° C. under microwave irradiation, respectively) may afford e.g. the compounds of structure Ih wherein $R^2$ represents a mono-, di- or tri-substituted 5- or 6-membered heteroaryl which is substituted by one ($C_{1-4}$)alkoxy substituent (or $R^{21a}R^{21b}N$—) (Scheme B, step e).

Alkylation of a free aromatic hydroxy group, e.g. in compounds of structure Ia wherein $R^2$ represents a phenyl or 5- or 6-membered heteroaryl which is substituted by one hydroxy group, with a suitable alkyl halide, cycloalkyl halide ($C_{3-6}$)cycloalkyl-($C_{0-3}$)alkyl halide wherein the ($C_{3-6}$)cycloalkyl optionally contains one ring oxygen, in the presence of a suitable base such as NaH or $K_2CO_3$ and in solvents such as THF, DMF or a mixture thereof at temperatures between 0° C. and 150° C. and under possible microwave irradiation may alternatively afford the corresponding compounds of structure Ih. Alternatively, Mitsunobu conditions can be used by treatment for instance with a (cyanomethylene)trialkylphosphorane reagent in the presence of a suitable solvent such as toluene at temperatures around 110° C. (Scheme B, step e).

Compounds of structure Ia and Ii and Ij can be prepared according to the synthetic route given in scheme C below.

Compounds of structure C-1 can be prepared by reductive amination of suitable aldehydes of structure BB-14 (or ketones of structure BB-13, respectively) with suitable amines of structure BB-15 (or diamines of structure BB-5, respectively) using standard conditions as set out before. Alternatively, $NaBH_4$ can be used as reducing agent in the presence of TFE as solvent at temperatures around 40° C. according to Synthesis, 2011, 3, 490-496 (Scheme C, step b (or step a, respectively).

Alternatively, compounds of structure C-1 can be prepared by a two step procedure (i) reductive amination of suitable aldehydes of structure BB-4 with suitable amines of structure BB-15 using standard conditions as set out before and (ii) subsequent reduction of the nitro group in intermediates of structure C-4 using standard conditions such as catalytic hydrogenation with a suitable catalyst such as Pd/C in a suitable solvent such as EtOAc or EtOH or a mixture thereof (Scheme C, steps g and h).

Cyclic ureas of structure C-2 can be prepared by cyclisation of compound of structure C-1 by treatment with a suitable carbonyl transfer agent such as CDI in the presence of a suitable aprotic solvent such as MeCN at temperatures around RT (Scheme C, step c).

Alkylation of the nitrogen atom having a free valency in compounds of structure C-2 with a suitable halide of structure BB-9 wherein W represents chlorine or bromine; or using Mitsunobu conditions as set out before (Scheme C, step d).

Cleavage of the Boc protecting group in compounds of structure Ii can be as set out before to afford amines of structure C-3 (Scheme C, step e).

Scheme C

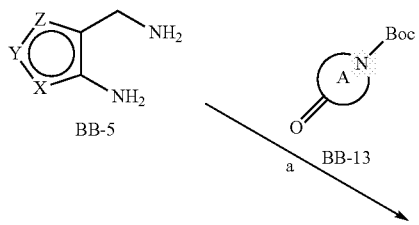

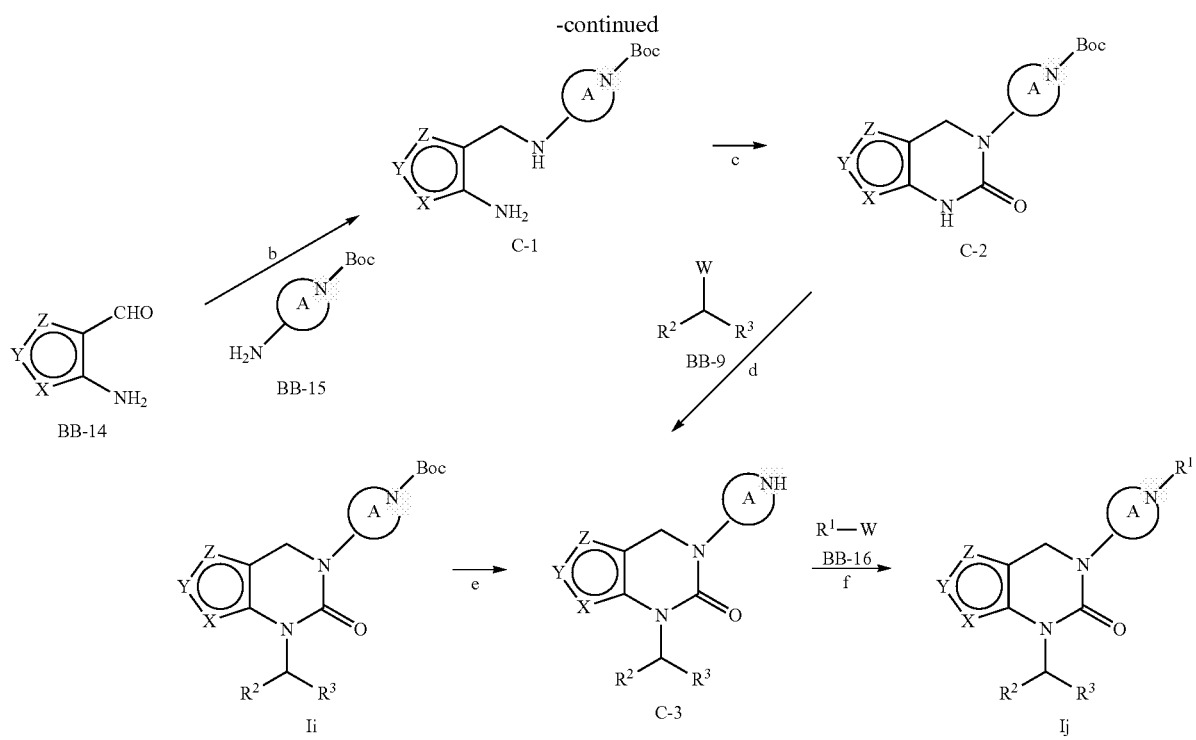

Compounds of structure Ij can be prepared by Buchwald-Hartwig cross coupling of halides of structure BB-16 wherein W represents iodine, bromine or chloride with amines of structure C-3 in the presence of a suitable palladium catalyst such as Pd$_2$(dba)$_3$ and a suitable ligand such as BINAP, in the presence of a suitable base such as sodium tert-butoxide and heating in a suitable solvent such as toluene at temperatures between 100° C. and 110° C. (Scheme C, step f).

Aromatic nucleophilic substitution of amines of structure C-3 on suitable activated halogenides of structure BB-16 wherein W represents chlorine or fluorine in the presence of a suitable base such as K$_2$CO$_3$ or CsF and heating in a suitable solvent such as DMSO under possible microwave irradiation at temperatures between 100° C. and 130° C. may alternatively afford compounds of structure Ij (Scheme C, step f).

Compounds of structure Ij can alternatively be prepared following a three-step procedure: (i) aromatic nucleophilic substitution of amines of structure C-3 on activated halides of structure BB-16 wherein W represents fluorine or chlorine which is substituted for instance by one formyl group in ortho position of the halogen atom W in the presence of a suitable base such as CsF or K$_2$CO$_3$ and heating in a suitable solvent such as DMSO under microwave irradiation at temperatures between 60° C. and 150° C. and (ii) subsequent decarbonylation by treatment with a suitable acid such as toluene-4-sulfonic acid and in the presence of a suitable solvent such as MeOH under possible microwave irradiation at temperatures around 120° C. and (iii) subsequent chlorination by treatment with a chlorinating reagent such as NCS in the presence of a suitable solvent such as THF at temperatures around RT (Scheme C, step f).

Alternatively, compounds of structure Ia can be prepared according to scheme D below.

Scheme D

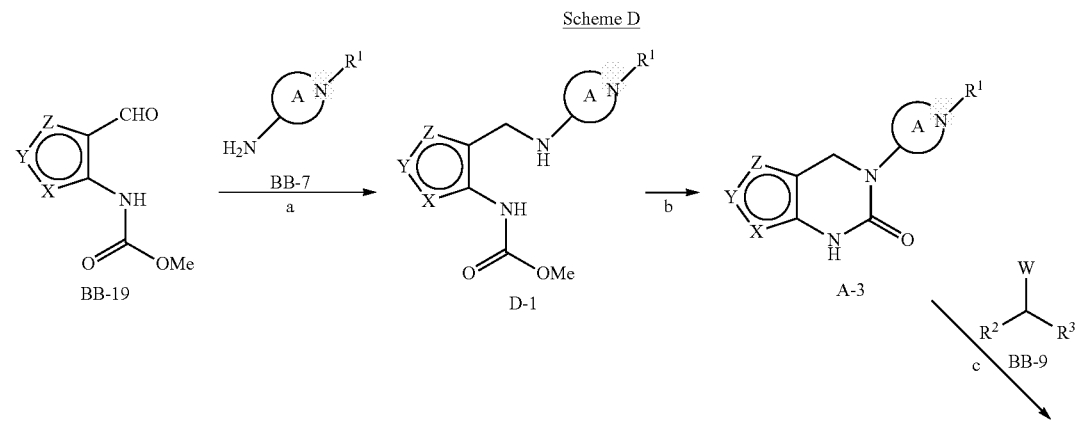

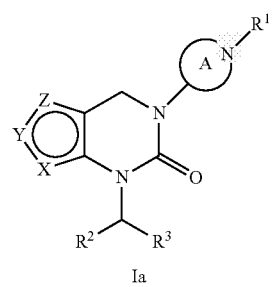

Compounds of structure D-1 can be prepared by reductive amination of suitable aldehydes of structure BB-19 with suitable amines of structure BB-7 using standard conditions as set out before (Scheme D, step a).

Heating compounds of structure D-1 in a suitable solvent such as DMF under microwave irradiation at temperatures around 120° C. can alternatively afford compounds of structure A-3 (Scheme D, step b).

Alkylation of the nitrogen atom having a free valency in compounds of structure A-3 (Scheme D, step c) is described in Scheme A1 (step i).

Alternatively, compounds of structure Ia which are compounds of Formula (I) wherein $R^4$ represents $C_{1-4}$-alkyl can be prepared according to scheme E below.

Compounds of structure E-1 (or E-2, respectively) can be prepared by reductive amination of suitable ketones of structure BB-26 (or BB-27, respectively) with suitable amines of structure BB-7 using standard conditions as set out before. Alternatively, a two-step procedure can be applied (i) condensation of suitable ketones of structure BB-26 wherein $R^4$ represents $(C_{1-4})$alkyl with amines of structure BB-7 in the presence of titanium (IV) isopropoxide at temperatures around RT and (ii) subsequent reduction of the intermediate by treatment with $NaBH_4$ in the presence of a suitable solvent such as EtOH, THF or a mixture thereof at temperatures between −15° C. and RT (Scheme E, step a (or step e, respectively)).

The following sequence of reactions to provide compounds of structure Ia (Scheme E, steps b, c and d) is similar to the one already described in Scheme A1 (steps b, h and i).

Compounds of structure E-4 (or E-7, respectively) can be prepared following a two-step procedure (i) condensation of suitable aldehydes or ketones of structure BB-12 with amines of structure BB-28 (or BB-34, respectively) in the presence of AcOH and a suitable solvent such as THF or MeOH at temperatures between RT and 60° C. and (ii) subsequent reduction of the intermediate imine by treatment with $NaBH_4$ at temperatures between 0° C. and RT (Scheme E, step f (or step j, respectively)).

Scheme E

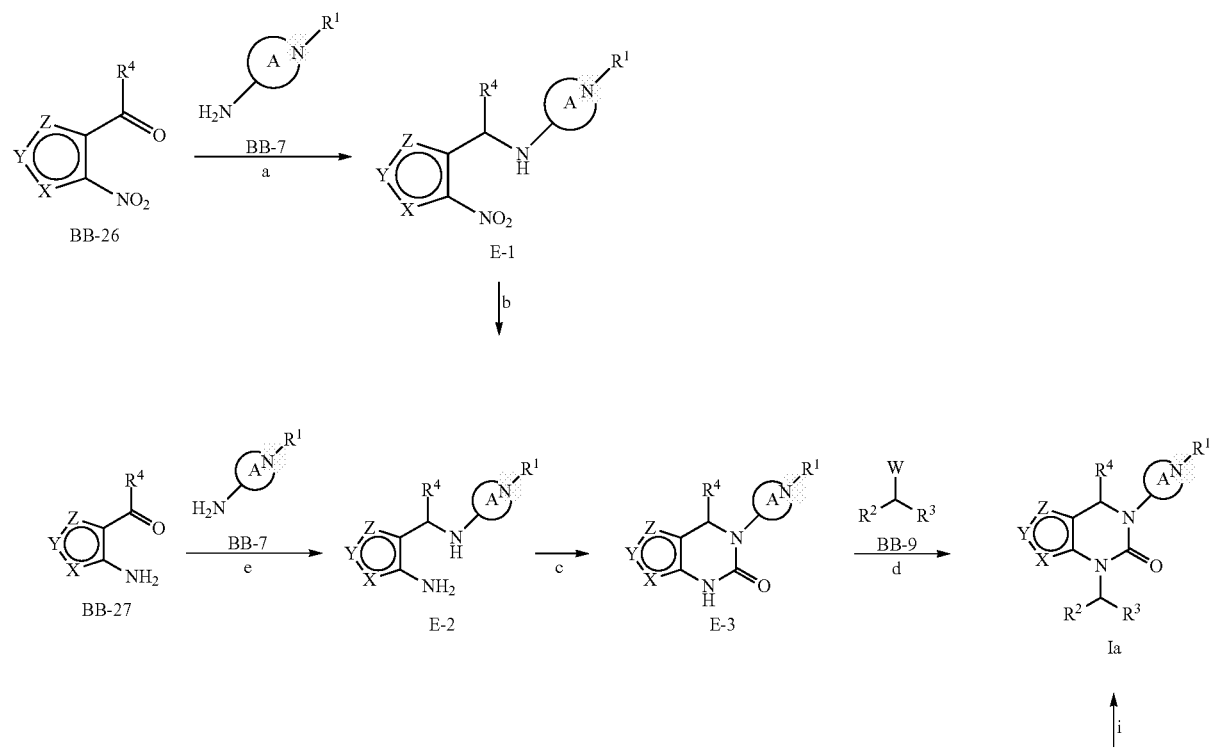

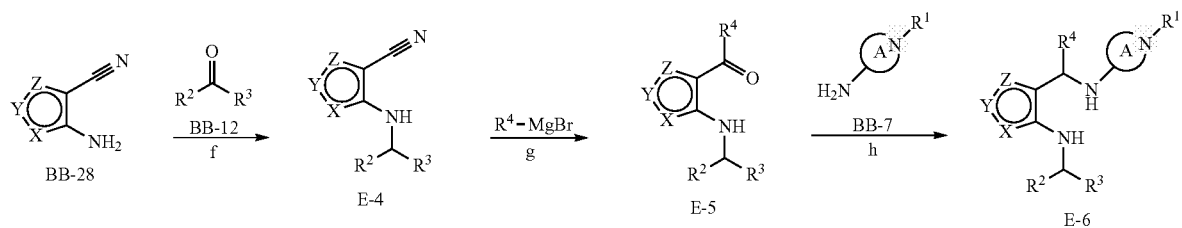

Addition of a suitable Grignard reagent of structure R⁴—MgBr, e.g. wherein R⁴ represents (C₁₋₄)alkyl, on nitriles of structure E-4 in the presence of a suitable aprotic solvent such as THF at temperatures between 0° C. and RT followed by acidic hydrolysis may afford the corresponding ketones of structure E-5 (Scheme E, step g).

Alternatively, compounds of structure E-5 can be prepared by Heck cross coupling of halides of structure E-7 (or E-8, respectively) with butyl vinyl ether or ethyl 1-propenyl ether in the presence of a suitable palladium catalyst such as Pd(OAc)₂ in combination with 1,3-bis(diphenylphosphino) propane or 2-(di-tert-butylphosphino)biphenyl as ligand, in the presence of a suitable base such as K₂CO₃ and heating in a suitable solvent such as a mixture of DMF and H₂O or MeCN at temperatures around 100° C. The consecutive treatment with an acid such as HCl can release the ketone (Scheme E, step m (or step n, respectively).

Compounds of structure E-6 can be prepared following a two-step procedure (i) condensation of suitable ketones of structure E-5 (or E-10, respectively), e.g. wherein R⁴ represents (C₁₋₄)alkyl, with amines of structure BB-7 in the presence of titanium (IV) isopropoxide at temperatures around RT and (ii) subsequent reduction of the intermediate by treatment with NaBH₄ as set out before (Scheme E, step h (or step q, respectively)).

Cyclisation of compounds of structure E-6 by treatment with a suitable carbonyl transfer agent such as DSC or CDT in the possible presence of a suitable base such as TEA and in a suitable aprotic solvent such as DCM or MeCN at temperatures between RT and 80° C. may alternatively afford compounds of structure Ia (Scheme E, step i).

Compounds of structure E-8 wherein Y represents N-THP can be prepared by treatment of compounds of structure E-7 wherein Y represents NH with 3,4-dihydro-2H-pyran in the presence of a catalytic amount of TsOH and a suitable solvent such as DCM at temperatures around 40° C. (Scheme E, step k).

The THP protecting group in compounds of structure E-5 wherein Y represents N-THP can be cleaved by treatment with a suitable acid such as TFA in the presence of a suitable solvent such as DCM at temperatures around RT to release compounds of structure E-9 wherein Y represents NH (Scheme E, step o).

Chan-Lam conditions can be applied to compounds of structure E-9 wherein Y represents NH by treatment with a suitable boronic acid or boronic ester of structure BB-10 in the presence of a suitable copper catalyst such as Cu(OAc)₂ and a suitable ligand such as 2,2'-bipyridyl, in the presence of a suitable base such as Na₂CO₃ and heating in a suitable solvent such as toluene at temperatures between 70° C. and 90° C. (Scheme E, step p).

If not commercially available, aldehydes of structure BB-4 can be prepared according to scheme F below.

Esters of structure BB-1 wherein $R^e$ represents methyl (or ethyl, respectively) can be prepared by esterification of carboxylic acids of structure A by treatment with a strong acid such as H₂SO₄ or HCl (which can be formed in situ from AcCl and MeOH (or EtOH, respectively)) and heating in a suitable alcohol such as MeOH (or EtOH, respectively) at temperatures around 80° C. (Scheme F, step a).

Protection of building blocks of structure BB-1 e.g. by treatment with SEM-Cl in the presence of a suitable base such as TEA or DIPEA and the presence of a suitable solvent such as DCM at temperatures between 0° C. and RT may afford the corresponding compounds of structure BB-2 wherein one of X, Y or Z represents N-SEM (Scheme F, step b).

Scheme F

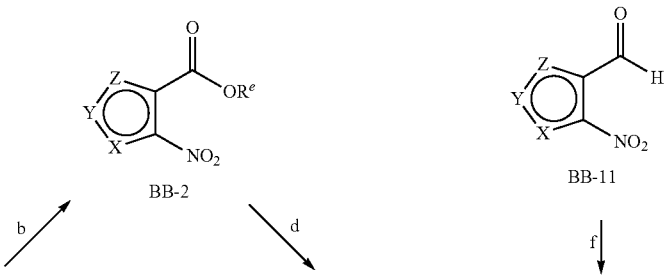

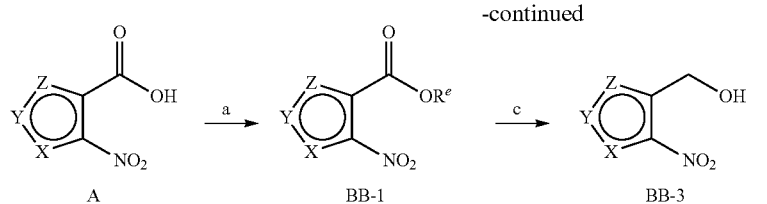
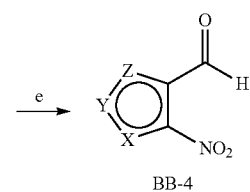

Reduction of carboxylic esters of structure BB-1 or BB-2 can be achieved for instance by treatment with a suitable reducing reagent such as NaBH$_4$ or CaBH$_4$ (formed in situ from NaBH$_4$ and CaCl$_2$) in the presence of a suitable solvent such as MeOH, EtOH or THF or a mixture thereof at temperatures between 0° C. and RT to give alcohols of structure BB-3 (Scheme F, step c and d).

Oxidation of primary alcohols of structure BB-3 by treatment with a suitable oxidizing reagent such as MnO$_2$ in the presence of a suitable solvent such as DCM at temperatures between RT and 45° C. can afford aldehydes of structure BB-4 (Scheme F, step e).

Alternatively, aldehydes of structure BB-4 can be prepared by protection of building blocks of structure BB-11 wherein one of X, Y or Z represents NH with a suitable protecting group. The treatment for instance with SEM-Cl under standard conditions provides building blocks of structure BB-4 wherein one of X, Y or Z represents N-SEM (Scheme F, step f).

If not commercially available, aldehydes of structure BB-19 can be prepared according to scheme G below.

Carbamates of structure BB-17 can be prepared by treatment of suitable amines of structure B (in case none of X, Y and Z represents NH) with methylchloroformate in the presence of a suitable base such as TEA or DIPEA, catalytic amounts of DMAP and in a suitable solvent such as MeCN, DCM or DMF at temperatures between 0° C. and RT (Scheme G, step a).

Reduction of the ester function in building blocks of structure BB-17 can be achieved for instance by treatment with a suitable reducing reagent as set out before to give alcohols of structure BB-18 (Scheme G, step b).

Oxidation of primary alcohols of structure BB-18 by treatment with a suitable oxidizing reagent such as MnO$_2$ as set out before can afford aldehydes of structure BB-19 (Scheme G, step c).

If not commercially available, aldehydes of structure BB-20 can be prepared according to scheme H below.

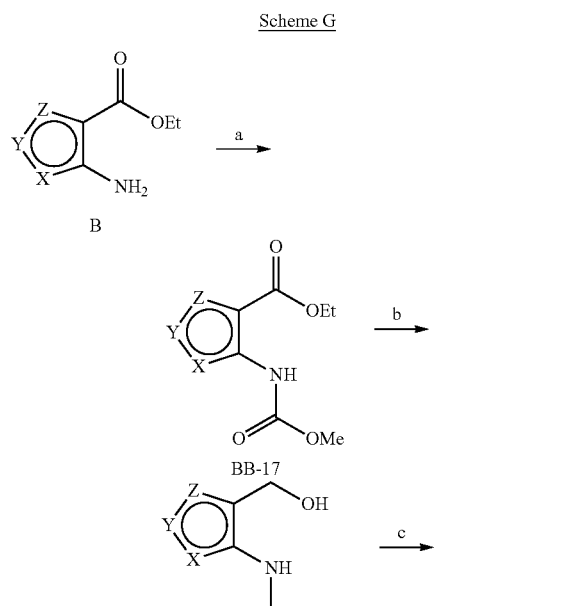

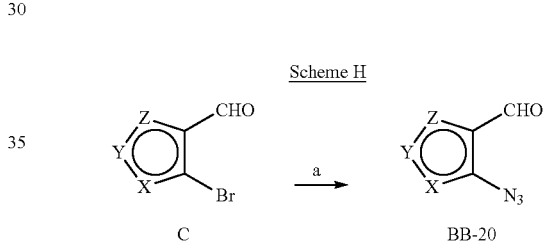

Aromatic nucleophilic substitution of sodium azide on suitable activated bromides of structure C in the presence of a suitable solvent such as DMSO at temperatures around RT can provide aldehydes of structure BB-20 (Scheme H, step a).

If not commercially available, amines of structure BB-24 can be prepared according to scheme I below.

Building blocks of structure BB-21 can be prepared by treatment of amines of structure D wherein one of X, Y or Z represents NH and the two others represent N with Boc$_2$O in the presence of a suitable base such as TEA or DIPEA in a suitable solvent such as THF or DCM at temperatures between 0° C. and RT (Scheme I, step a). Alkylation of building blocks of structure BB-21 wherein one of X, Y or Z represents NH and the two others represent N with suitable halides of structure R$^5$—W wherein W represents chlorine, bromine or iodine using conditions set out before may afford building blocks of structure BB-22 (Scheme I, step b). Dehydration of primary amides of structure BB-22 by treatment for instance with Burgess reagent in a suitable solvent such as DCM at temperatures around RT can provide nitriles of structure BB-23 (Scheme I, step c). Reduction of nitriles of structure BB-23 using standard Raney nickel conditions can afford amines of structure BB-24 (Scheme I, step d).

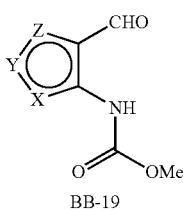

Scheme I

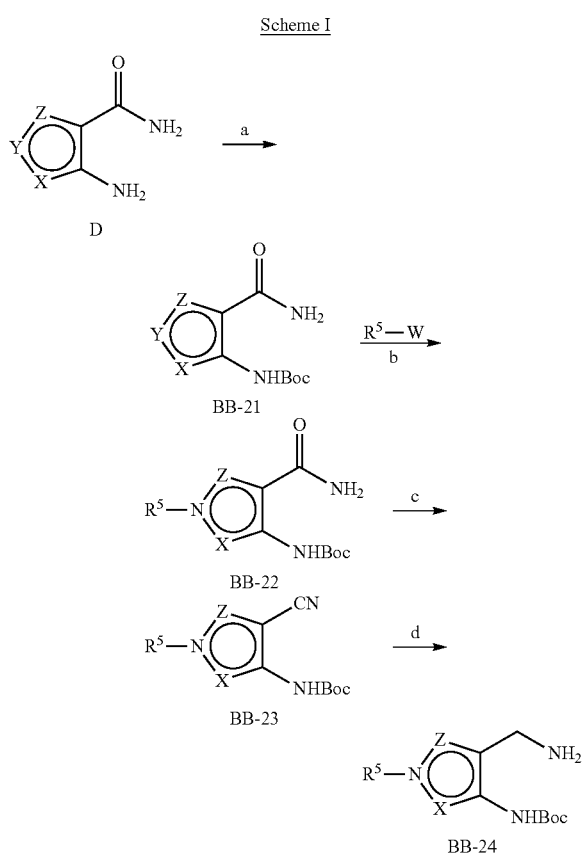

If not commercially available, amines of structure BB-7 and ketones of structure BB-8 can be prepared according to the synthetic routes given in scheme J below.

Scheme J

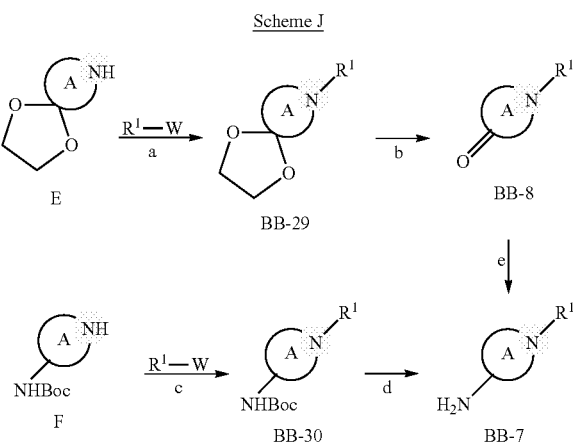

Building blocks of structure BB-29 can be prepared by standard Buchwald-Hartwig cross coupling of halides of structure R¹—W wherein W represents iodine, bromine or chloride with amines of structure E (Scheme J, step a). Alternatively, building blocks of structure BB-29 wherein can be prepared by standard aromatic nucleophilic substitution of amines of structure E on activated halides of structure R¹—W wherein W represents fluorine or chloride (Scheme J, step a). Cleavage of the ketal protecting group in building blocks of structure BB-29 by acidic hydrolysis in the presence of a suitable acid such as aq. HCl and heating in a suitable solvent such as THF at temperatures around 70° C. may afford ketones of structure BB-8 (Scheme J, step b). Building blocks of structure BB-30 can be prepared by standard aromatic nucleophilic substitution of amines of structure F on activated halides of structure R¹—W wherein W represents fluorine or chlorine (Scheme J, step c).

Alternatively, building blocks of structure BB-30 wherein R¹ represents a mono-, di- or tri-substituted phenyl which is substituted by one methyl group at the ortho position to the connecting nitrogen can be prepared following a four-step procedure: (i) aromatic nucleophilic substitution of amines of structure F on halides of structure R¹—W wherein W represents fluorine or chlorine and R¹ represents a suitable mono-, or di-substituted phenyl which is substituted by one formyl group at the ortho position of the halogen atom W in the presence of a suitable base such as $K_2CO_3$ and heating in a suitable solvent such as DMSO at temperatures between 100° C. and 120° C. and (ii) subsequent reduction of the benzaldehyde derivative by treatment with a suitable reducing reagent such as $NaBH_4$ in the presence of a suitable solvent such as MeOH at temperatures between 0° C. and RT and (iii) subsequent acetylation of the resulting benzyl alcohol by treatment with acetyl chloride in the presence of a suitable base such as TEA and in a suitable solvent such as DCM at temperatures between 0° C. and RT and (iv) final catalytic hydrogenation of the resulting benzyl ester with a suitable catalyst such as Pd/C in the presence of a suitable solvent such as EtOAc, MeOH or a mixture thereof at temperatures around RT (Scheme J, step c).

Alternatively, building blocks of structure BB-30 wherein R¹ represents a mono- or di-substituted phenyl or pyridine which is substituted by one difluoromethyl group at the ortho position to the connecting nitrogen can be prepared following a two-step procedure: (i) aromatic nucleophilic substitution of amines of structure F on halides of structure R¹—W wherein W represents fluorine or chlorine and R¹ represents a suitable mono-, or di-substituted phenyl or pyridine which is substituted by one formyl group at the ortho position of the halogen atom W as set out before and (ii) subsequent difluorination of the benzaldehyde derivative by treatment with a suitable fluorinating reagent such as bis(2-methoxyethyl)aminosulfur trifluoride in the presence of a suitable solvent such as DCM at temperatures around RT (Scheme J, step c). An alternative sequence of reactions can provide compounds of structure BB-30 wherein R¹ represents a mono- or di-substituted phenyl which is substituted by one halogen atom at the ortho position to the connecting nitrogen. A three-step procedure is followed (i) aromatic nucleophilic substitution of amines of structure F on halides of structure R¹—W wherein W represents fluorine or chlorine and R¹ represents a suitable mono-, or di-substituted phenyl which is substituted by one nitro group at the ortho position of the halogen atom W as set out before and (ii) subsequent reduction of the nitro group to an amino group as set out before and (iii) subsequent Sandmeyer rxn to introduce a halogen atom using standard conditions. An additional Suzuki or Kumada cross coupling reaction can be used to introduce an $(C_4)$alkyl or $(C_{3-6})$cycloalkyl group at the place of the halogen atom (Scheme J, step c).

Cleavage of the Boc protecting group in building blocks of structure BB-30 can be performed to afford amines of structure BB-7 (Scheme J, step d).

Transformation of ketones of structure BB-8 to amines of structure BB-7 can be achieved by reductive amination with for instance aq. ammonia under catalytic hydrogenation conditions using a suitable catalyst such as Pd/C in the presence of a suitable solvent such as dioxane at temperatures around RT (Scheme J, step e).

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 µm) column, a Daicel ChiraCel OD-H (5-10 µm) column, or a Daicel ChiralPak IA (10 µm), IC (5 µm) or AD-H (5 µm) column. Typical conditions of chiral HPLC are as disclosed in the experimental part below.

The following examples are provided to illustrate the invention. These examples are illustrative only and should not be construed as limiting the invention in any way.

EXPERIMENTAL PART

I. Chemistry

All temperatures are stated in ° C. Commercially available starting materials were used as received without further purification.

Characterization of Compounds

Compounds described in the invention are characterized by LC-MS data (retention time $t_R$ is given in min) and/or NMR using the conditions described below.

Analytical LC-MS:

LC-MS (Method I):

Waters Acquity UPLC i-Class system with Waters i-Class BSM binary pump, Thermo MSQ Plus MS detector and Waters Acquity PDA detector.

Eluents (acidic conditions): A: $H_2O$+0.04% TFA; B: MeCN; gradient: 5% B→95% B; runtime: 1.2 min; flow: 0.8 mL/min; detection: UV/Vis+MS Column Agilent Zorbax RRHD SB-aq, 2.1×50 mm, 1.8 µm LC-MS (Method II):

Dionex Ultimate 3000 system with Dionex HPG-3200RS binary pump, Thermo MSQ Plus MS detector and Dionex DAD-3000RS PDA detector.

Eluents (acidic conditions): A: $H_2O$+0.04% TFA; B: MeCN; gradient: 5% B→95% B; runtime: 1.5 min; flow: 4.5 mL/min; detection: UV/Vis+MS Column Agilent Zorbax SB-aq, 4.6×50 mm, 3.5 µm LC-MS (Method III):

Dionex Ultimate 3000 system with Dionex HPG-3200SD binary pump, Thermo MSQ Plus MS detector and Dionex DAD-3000RS PDA detector.

Eluents (basic conditions): A: $H_2O$+13 mmol/L $NH_4OH$; B: MeCN; gradient: 5% B→95% B; runtime: 1.9 min; flow: 1.6 mL/min; detection: UV/Vis+MS Column Waters BEH $C_{18}$, 3.0×50 mm, 2.5 µm LC-MS (Method IV):

Waters Acquity UPLC i-Class system with Waters i-Class BSM binary pump, Thermo MSQ Plus MS detector and Waters Acquity PDA detector.

Eluents (basic conditions): A: $H_2O$+13 mmol/L $NH_4OH$; B: MeCN; gradient: 5% B→95% B; runtime: 1.9 min; flow: 0.8 mL/min; detection: UV/Vis+MS Column Waters BEH $C_{18}$, 2.1×50 mm, 2.5 µm NMR Spectroscopy:

Bruker Avance HD spectrometer equipped with a 500 MHz Ultrashield™ Magnet and a 5 mm DCH cryoprobe or Bruker Avance II spectrometer equipped with a 400 MHz Ultrashield™ Magnet and a BBO 5 mm probehead. Chemical shifts (S) are reported in parts per million (ppm) relative to proton resonances resulting from incomplete deuteration of the NMR solvent, e.g. for dimethylsulfoxide δ(H) 2.49 ppm, for chloroform δ(H) 7.24 ppm. The abbreviations s, d, t, q and m refer to singlet, doublet, triplet, quartet, multiplet, respectively and br to broad. Coupling constants J are reported in Hz.

Purification of Compounds

The compounds were purified by either column chromatography on silica-gel and/or prep. LC-MS using the conditions described below.

Column Chromatography

Column chromatography (CC) was performed using pre-packed cartridges (SNAP Ultra™, SNAP KP-SIL™, SNAP KP-NH™, Isolute™ Silica II or Isolute™ $NH_2$) from Biotage.

Preparative LC-MS:

Gilson 333/334 Prep-Scale HPLC pump equipped with Gilson LH215 autosampler, Dionex SRD-3200 degasser, Dionex ISO-3100A make-up pump, Dionex DAD-3000 DAD detector and Thermo MSQ Plus Single Quadrupole MS detector. Flow: 75 mL/min. Detection: UV/Vis and/or MS.

Additional information for the purification is summarized in the table below with following definitions:

XBridge: column Waters XBridge C18, 10 µm, 30×75 mm

Zorbax: column Agilent Zorbax SB-aq, 5 µm, 30×75 mm

Atlantis: column Waters Atlantis T3, 10 µm, 30×75 mm

Acidic: eluant: A=$H_2O$ with 0.5% HCOOH, B=MeCN

Basic: eluant: A=$H_2O$ with 0.125% $NH_4OH$, B=MeCN

Very lipophilic gradient: 50% B→95% B over 4 min then 95% B over 2 min

Lipophilic gradient: 30% B→95% B over 4 min then 95% B over 2 min

Normal gradient: 20% B→95% B over 4 min then 95% B over 2 min

Polar gradient: 10% B→95% B over 4 min then 95% B over 2 min

Very polar gradient: 5% B→50% B over 3 min then 50% B→95% B over 1 min and finally 95% B over 2 min

|  | XBridge | Zorbax | Atlantis | |
|---|---|---|---|---|
|  | acidic | basic | acidic | basic |
| Very lipophilic gradient | Method 10 | Method 8 | Method 9 | Method 6 |
| Lipophilic gradient | Method 4 | Method 5 | Method 2 |  |
| Normal gradient | Method 3 | Method 1 | Method 11 |  |
| Polar gradient |  | Method 7 |  |  |
| Very polar gradient |  | Method 12 |  |  |

Abbreviations (as Used Hereinbefore or Hereinafter)

Ac acetyl
AcOH acetic acid
AIBN azobisisobutyronitrile
aq. aqueous
BINAP racemic 2,2'-bis(diphenylphosphino)-1,1'-binaphthyl
Bn benzyl
Boc tert.-butyloxycarbonyl
Cbz benzyloxycarbonyl
CC column chromatography
CDI carbonyl diimidazole
CDT 1,1'-carbonyl-di-(1,2,4-triazole)
CPhos 2-dicyclohexylphosphino-2',6'-bis(N,N-dimethylamino)biphenyl DBU 1,8-diazabicyclo[5.4.0]undec-7-ene
DCM dichloromethane
dioxane 1,4-dioxane
DIPEA diisopropylethylamine
DMA dimethylacetamide
DMF dimethylformamide
DMSO dimethylsulfoxide
Dppf 1,1'-bis(diphenylphosphino)ferrocene
DSC N,N'-disuccinimidyl carbonate
EDC.HCl N-(3-dimethylaminopropyl)-N'-ethylcarbodiimidehydrochloride
eq equivalent(s)
Et ethyl
EtOAc ethyl acetate
EtOH ethanol
Et$_2$O diethylether
g gram(s)
h hour(s)
Hept heptane
HOBt 1-hydroxybenzotriazole
HPLC high performance liquid chromatography
io ionisation
LC-MS liquid chromatography—mass spectrometry
MeCN acetonitrile
MeOH methanol
mg milligram(s)
min minute(s)
mL milliliter(s)
mmol millimole(s)
MS mass spectroscopy NaBH(OAc)$_3$ sodium triacetoxyborohydride
NBS N-bromosuccinimide
NCS N-chlorosuccinimide
NMR nuclear magnetic resonance spectroscopy
OAc acetate
org. organic
ON overnight
PEPPSI-IPr [1,3-bis(2,6-diisopropylphenyl)imidazol-2-ylidene](3-chloropyridyl)palladium(II) dichloride Pd$_2$(dba)$_3$ tris(dibenzylideneacetone)dipalladium(0)
prep. preparative
QuadraPure® MPA mercaptophenyl amino functionalized polystyrene beads
rac racemic
RT room temperature
rxn reaction
sat. saturated
SEM 2-(trimethylsilyl)ethoxymethyl
soln. solution
TEA triethylamine
TFA trifluoroacetic acid
TFE trifluoroethanol
THF tetrahydrofuran
THP tetrahydro-2H-pyranyl
Ts p-toluenesulfonyl
t$_R$ retention time When not commercially available, the building blocks are prepared according to the procedures described below.

Synthesis of Building Blocks BB-1

To a soln. of carboxylic acid A (1 eq) in anh. MeOH (4 mL/mmol) was added AcCl (3 eq) and the rxn mixture was stirred for 2.5 h at 80° C. (see Table 1). MeOH was evaporated off and the residue was partitioned between a sat. aq. soln. of NaHCO$_3$ and EtOAc. The org. phase was washed with a 10% aq. soln. of Na$_2$CO$_3$ and with brine, dried over MgSO$_4$ and concentrated in vacuo.

TABLE 1

| BB-1 | Name | Acid reactant A | t$_R$ [min] (LC/MS method) | MS-data m/z [M + H]$^+$ | $^1$H NMR (500 MHz, DMSO-d6) δ: |
|---|---|---|---|---|---|
| BB-1-1 | 4-Nitro-2H-pyrazole-3-carboxylic acid methyl ester | | commercially available | | |
| BB-1-2 | 5-Nitro-1H-pyrazole-4-carboxylic acid methyl ester or 3-Nitro-1H-pyrazole-4-carboxylic acid methyl ester | 3-Nitro-1H-pyrazole-4-carboxylic acid | 0.55 (I) | no io | 14.34 (s, 1 H), 8.60 (s, 1 H), 3.79 (s, 3 H) |
| BB-1-3 | 1-Methyl-4-nitro-1H-pyrazole-3-carboxylic acid methyl ester | | commercially available | | |

Synthesis of Building Blocks BB-2

To a suspension of BB-1 (1 eq) and SEM-Cl (1.3 eq) in DCM (3.5 mL/mmol) was added dropwise DIPEA (1.5 eq) at 0° C. The rxn mixture was stirred at 0° C. for a given time (see Table 2) and quenched with a sat. aq. soln. of NaHCO$_3$. It was extracted with DCM, the org. phase was washed with a sat. aq. soln. of NaHCO$_3$, dried over MgSO$_4$ and concentrated in vacuo. The crude was purified by CC using Hept/EtOAc.

TABLE 2

| BB-2 | Name | Reactant BB-1 | time [h] | t$_R$ [min] (LC/MS method) | MS-data m/z [M + H]$^+$ | $^1$H NMR (500 MHz, DMSO-d6) δ: |
|---|---|---|---|---|---|---|
| BB-2-1A | 4-Nitro-2-(2-trimethylsilanyl- | BB-1-1 | 0.25 | 1.06 (I) | no io | 8.48 (s, 1 H), 5.61 (s, 2 H), 3.98 (s, 3 H), 3.56 |

TABLE 2-continued

| BB-2 | Name | Reactant BB-1 | time [h] | $t_R$ [min] (LC/MS method) | MS-data m/z $[M + H]^+$ | $^1$H NMR (500 MHz, DMSO-d6) δ: |
|---|---|---|---|---|---|---|
| | ethoxymethyl)-2H-pyrazole-3-carboxylic acid methyl ester | | | | | (m, 2 H), 0.84 (m, 2 H), −0.04 (m, 9 H) |
| BB-2-1B | 4-Nitro-1-(2-trimethylsilanyl-ethoxymethyl)-1H-pyrazole-3-carboxylic acid methyl ester | | | 1.02 (I) | 302.27 | 9.19 (s, 1 H), 5.52 (s, 2 H), 3.91 (s, 3 H), 3.61 (m, 2 H), 0.87 (m, 2 H), −0.03 (s, 9 H) |
| BB-2-2A | 5-Nitro-1-(2-trimethylsilanyl-ethoxymethyl)-1H-pyrazole-4-carboxylic acid methyl ester | BB-1-2 | 0.5 | 1.03 (I) | no io | 8.19 (s, 1 H), 5.69 (s, 2 H), 3.82 (s, 3 H), 3.57 (m, 2 H), 0.82 (m, 2 H), −0.06 (m, 9 H) |
| BB-2-2B | 3-Nitro-1-(2-trimethylsilanyl-ethoxymethyl)-1H-pyrazole-4-carboxylic acid methyl ester | | | 1.00 (I) | 302.15 | 8.80 (s, 1 H), 5.54 (s, 2 H), 3.81 (s, 3 H), 3.61 (m, 2 H), 0.87 (m, 2 H), −0.03 (s, 9 H) |

Synthesis of Building Blocks BB-3

To a soln. of methyl ester BB-1 or BB-2 (1 eq) in a mixture of THF (6.3 mL/mmol) and MeOH (0.8 mL/mmol) was added portionwise NaBH$_4$ (4 to 8 eq) at 0° C. The rxn mixture was stirred at 0° C. for a given time (see Table 3), poured into an aq. sat. soln. of NH$_4$Cl and extracted with EtOAc. The org. phase was washed with brine, dried over MgSO$_4$ and concentrated in vacuo. The crude was purified by CC using Hept/EtOAc.

Synthesis of Building Blocks BB-4

Method A (Oxidation)

To a soln. of alcohol BB-3 (1 eq) in anh. DCM (10 mL/mmol) was added portionwise MnO$_2$ (9 to 10 eq) at RT and the rxn mixture was stirred at a given temperature for a given time (see Table 4). It was filtered over a pad of celite and the filtrate was concentrated in vacuo.

TABLE 3

| BB-3 | Name | Reactant BB-1 or BB-2 | time [h] | $t_R$ [min] (LC/MS method) | MS-data m/z $[M + H]^+$ | $^1$H NMR (500 MHz, DMSO-d6) δ: |
|---|---|---|---|---|---|---|
| BB-3-1A | [4-Nitro-2-(2-trimethylsilanyl-ethoxymethyl)-2H-pyrazol-3-yl]-methanol | BB-2-1A | 2.5 | 0.92 (I) | 273.91 | |
| BB-3-1B | [4-Nitro-1-(2-trimethylsilanyl-ethoxymethyl)-1H-pyrazol-3-yl]-methanol | BB-2-1B | 2.5 | 0.87 (I) | 273.97 | |
| BB-3-2 | [3-Nitro-1-(2-trimethylsilanyl-ethoxymethyl)-1H-pyrazol-4-yl]-methanol | BB-2-2B | 3.5 | 0.89 (I) | no io | 8.06 (s, 1 H), 5.51 (s, 2 H), 5.39 (t, J = 5.4 Hz, 1 H), 4.66 (dd, J = 5.4 Hz, 2 H), 3.59 (m, 2 H), 0.87 (m, 2 H), −0.03-0.01 (m, 9 H) |
| BB-3-3 | (1-Methyl-4-nitro-1H-pyrazol-3-yl)-methanol | BB-1-3 | 0.5 | 0.37 (II) | no io | 8.80 (s, 1 H), 5.22 (t, J = 5.9 Hz, 1 H), 4.66 (d, J = 5.8 Hz, 2 H), 3.88 (s, 3 H) |

Method B (SEM Protection)

To a soln. of BB-11 (1 eq) in anh. DMF (9 mL/mmol) was added portionwise NaH (1.1 eq, as a 60% dispersion in mineral oil) at 0° C. The rxn mixture was stirred for 10 min at 0° C. and SEM-Cl (1.4 eq) was added dropwise. It was allowed to reach RT, stirred for a given time (see Table 4) at RT and partitioned between EtOAc and water. The org. phase was washed with brine, dried over MgSO$_4$ and concentrated in vacuo. The crude was purified by CC using Hept/EtOAc.

Step B: Nitrile Reduction (see Table 6)

Nitrile BB-5A (1 eq) was dissolved in a 7M soln. of NH$_3$ in MeOH (7 mL/mmol). The flask was evacuated three times and refilled with nitrogen. Raney nickel (0.1 eq) was added at 0° C. and the temperature was allowed to reach RT. The flask was evacuated and refilled three times with hydrogen. The suspension was stirred under a hydrogen atmosphere for 11 h and filtered over a pad of Celite. The cake was washed with EtOAc and MeOH and the filtrate was concentrated in vacuo.

TABLE 4

| BB-4 | Name | Reactant BB-3 or BB-11 | Method T [° C.] time [h] | $t_R$ [min] (LC/MS method) | MS-data m/z [M + H]$^+$ | $^1$H NMR (500 MHz, DMSO-d6) δ: |
|---|---|---|---|---|---|---|
| BB-4-1A | 4-Nitro-2-(2-trimethylsilanyl-ethoxymethyl)-2H-pyrazole-3-carbaldehyde | BB-3-1A | A 45 18 | 1.04 (I) | no io | 10.28 (s, 1 H), 8.52 (s, 1 H), 5.74 (s, 2 H), 3.60 (m, 2 H), 0.85 (m, 2 H), −0.05 (s, 9 H) |
| BB-4-1B | 4-Nitro-1-(2-trimethylsilanyl-ethoxymethyl)-1H-pyrazole-3-carbaldehyde | BB-3-1B | A RT 24 | 0.79/0.99 (I) | no io | 10.25 (s, 1 H), 9.20 (s, 1 H), 5.57 (s, 2 H), 3.62 (m, 2 H), 0.88 (m, 2 H), −0.02 (m, 9 H) |
| BB-4-2 | 3-Nitro-1-(2-trimethylsilanyl-ethoxymethyl)-1H-pyrazole-4-carbaldehyde | BB-3-2 | A RT 18 | 1.00 (I) | no io | 10.14 (s, 1 H), 8.82 (s, 1 H), 5.58 (s, 2 H), 3.62 (m, 2 H), 0.88 (m, 2 H), −0.02 (m, 9 H) |
| BB-4-3 | 1-Methyl-4-nitro-1H-pyrazole-3-carbaldehyde | BB-3-3 | A 45 3.5 | 0.35 (III) | no io | 10.23 (s, 1 H), 8.98 (s, 1 H), 4.00 (s, 3 H) |
| BB-4-4 | 5-Nitro-3-(2-trimethylsilanyl-ethoxymethyl)-3H-imidazole-4-carbaldehyde | BB-11-1 | B RT 0.5 | 0.89 | 289.99 (hydrate) | 10.28 (s, 1 H), 8.39 (s, 1 H), 5.70 (s, 2 H), 3.58 (m, 2 H), 0.88 (m, 2 H), −0.03-0.02 (m, 9 H) |
| BB-4-5 | 1-Methyl-3-nitro-1H-pyrazole-4-carbaldehyde | | commercially available | | | |

Synthesis of Building Blocks BB-5

Synthesis of 5-aminomethyl-3-benzyl-3H-[1,2,3]triazol-4-ylamine (BB-5-2)

Step A: Cyclocondensation (see Table 5)

A suspension of benzyl azide (1 eq), malononitrile (1.4 eq) and K$_2$CO$_3$ (4 eq) in DMSO (1.4 mL/mmol) was stirred at RT for 18h. The rxn mixture was partitioned between EtOAc and H$_2$O. The org. phase was washed with H$_2$O and brine, dried over MgSO$_4$ and concentrated in vacuo. The crude was purified by CC using Hept/EtOAc.

TABLE 5

| BB-5A | Name | $t_R$ [min] (LC/MS method) | MS-data m/z [M + H]$^+$ |
|---|---|---|---|
| BB-5-2A | 5-Amino-1-benzyl-1H-[1,2,3]triazole-4-carbonitrile | 0.67 (II) | 200.19 |

TABLE 6

| BB-5 | Name | Reactant BB-5A | $t_R$ [min] (LC/MS method) | MS-data m/z [M + H]$^+$ |
|---|---|---|---|---|
| BB-5-1 | 4-Aminomethyl-1-methyl-1H-pyrazol-3-amine | commercially available | | |
| BB-5-2 | 5-Aminomethyl-3-benzyl-3H-[1,2,3]triazol-4-ylamine | BB-5-2A | 0.41 (II) | 204.20 |

Building Blocks BB-6

TABLE 7

| BB-6 | Name | |
|---|---|---|
| BB-6-1 | 3-Amino-1-methyl-1H-pyrazole-4-carbaldehyde | commercially available |

Synthesis of Building Blocks BB-7

Method A: Boc Cleavage from BB-30

To a soln. of intermediate BB-30 (1 eq) in DCM (4 mL/mmol) was added dropwise TFA (1 mL/mmol) and the rxn mixture was stirred for 1h to 18h at RT (see Table 8). It was basified with a 1M aq. soln. of NaOH until pH 12-13 and extracted with DCM. The combined org. phases were dried over MgSO₄ and concentrated in vacuo.

Method B: Reductive Amination from BB-8

To a soln. of ketone intermediate BB-8 (1 eq) in dioxane (9.1 mL/mmol) was added a 25% aq. soln. of NH₄OH (36 to 38 eq) and H₂O (0.35 mL/mmol). The flask was evacuated three times and refilled with nitrogen. Wet Pd/C (0.03 to 0.06 eq) was added and the flask was evacuated and refilled three times with hydrogen. The suspension was stirred under a hydrogen atmosphere for 24 to 48h (see Table 8) and filtered over a pad of Celite. The cake was washed with dioxane and MeOH and the filtrate was concentrated in vacuo. The crude was purified by CC using DCM/MeOH or Hept/EtOAc.

Method B2: Reductive Amination from BB-8

To a soln. of ketone intermediate BB-8 (1 eq) and ammonium acetate (10 eq) in MeOH (5 mL/mmol) was added AcOH (2 eq). The rxn mixture was stirred for 2h at RT, NaBH(OAc)₃ (2 eq) was added and the mixture was stirred at RT for 2h. MeOH was evaporated and the residue was partitioned between a 1M aq. soln. of NaOH and DCM. The org. phase was dried over MgSO₄ and concentrated in vacuo. The crude was purified by CC using Hept/EtOAc/MeOH.

TABLE 9

| BB-8 | Name | Reactant BB-29 | $t_R$ [min] (LC/MS method) | MS-data m/z [M + H]⁺ |
|---|---|---|---|---|
| BB-8-1 | 1-(2-Fluoro-6-methyl-phenyl)-piperidin-4-one | BB-29-1 | 0.94 (I) | 208.19 |
| BB-8-2 | 2'-Methoxy-4'-methyl-2,3,5,6-tetrahydro-[1,3']bipyridinyl-4-one | BB-29-2 | 0.78 (I) | 221.24 |
| BB-8-3 | 1-(2-Fluoro-6-methyl-phenyl)-azepan-4-one | BB-29-3 | 0.96 (I) | 222.25 |
| BB-8-4 | 1-(2-Fluoro-6-methyl-phenyl)-piperidin-3-one | BB-29-4 | 0.95 (I) | 208.26 |
| BB-8-6 | 2'-Methoxy-4'-trifluoromethyl-2,3,5,6-tetrahydro-[1,3']bipyridinyl-4-one | BB-29-5 | 0.96 (I) | 275.15 |
| BB-8-7 | 4'-Chloro-2'-methoxy-2,3,5,6-tetrahydro-[1,3']bipyridinyl-4-one | BB-29-6 | 0.87 (I) | 241.11 |

Synthesis of Building Blocks BB-9

Method A: Benzylic Bromination

A suspension of methyl-heteroarene (1 eq) in chlorobenzene (4 mL/mmol) was heated to 50° C. and NBS (1.3 eq)

TABLE 8

| BB-7 | Name | Reactant BB-30 or BB-8 | Method | $t_R$ [min] (LC/MS method) | MS-data m/z [M + H]⁺ |
|---|---|---|---|---|---|
| BB-7-1 | 1-(2-Fluoro-6-methyl-phenyl)-piperidin-4-ylamine | BB-30-1 | A | 0.62 (I) | 209.21 |
| BB-7-2 | 2'-Methoxy-4'-methyl-3,4,5,6-tetrahydro-2H-[1,3']bipyridinyl-4-ylamine | BB-8-2 | B | 0.51 (I) | 222.27 |
| BB-7-3 | 1-(2-Fluoro-6-methyl-phenyl)-4-methyl-piperidin-4-ylamine | BB-30-2 | A | 0.65 (I) | 223.19 |
| BB-7-4 | 1-(2-Fluoro-6-methyl-phenyl)-3-methyl-pyrrolidin-3-ylamine | BB-30-3 | A | 0.65 (I) | 209.28 |
| BB-7-5 | (R)-1-(2-Fluoro-6-methyl-phenyl)-pyrrolidin-3-ylamine | BB-30-4 | A | 0.60 (I) | 195.22 |
| BB-7-7 | 1-(2-Difluoromethyl-6-fluoro-phenyl)-piperidin-4-ylamine | BB-30-6 | A | 0.65 (I) | 245.39 |
| BB-7-8 | 1-(2-Chloro-6-fluoro-phenyl)-piperidin-4-ylamine | BB-30-7 | A | 0.61 (I) | 229.11 |
| BB-7-9 | 1-(2-Cyclopropyl-6-fluoro-phenyl)-piperidin-4-ylamine | BB-30-8 | A | 0.70 (I) | 235.18 |
| BB-7-10 | 4'-Difluoromethyl-2'-methoxy-3,4,5,6-tetrahydro-2H-[1,3']bipyridinyl-4-ylamine | BB-30-9 | A | 0.61 (I) | 258.01 |
| BB-7-11 | 1-(2-Bromo-6-fluoro-phenyl)-piperidin-4-ylamine | BB-30-6C | A | 0.65 (I) | 273.20 |
| BB-7-12 | 2'-Methoxy-4'-trifluoromethyl-3,4,5,6-tetrahydro-2H-[1,3']bipyridinyl-4-ylamine | BB-8-6 | B1 | 0.65 (I) | 276.21 |
| BB-7-13 | 4'-Chloro-2'-methoxy-3,4,5,6-tetrahydro-2H-[1,3']bipyridinyl-4-ylamine | BB-8-7 | B2 | 0.58 (I) | 241.92 |

Synthesis of Building Blocks BB-8

To a soln. of ketal intermediate BB-29 (1 eq) in anh. THF (3 mL/mmol) was added a 1 aq. soln. of HCl (2 to 2.5 mL/mmol) at RT (see Table 9). The rxn mixture was heated to 70° C. and stirred for 3 to 24h. It was quenched with a sat. aq. soln. of NaHCO₃ or a 1M aq. soln. of NaOH and extracted with EtOAc or DCM. The combined org. phases were washed with brine, dried over MgSO₄ and concentrated in vacuo. When necessary, the crude was purified by CC using Hept/EtOAc.

was added portionwise at 50° C. (see Table 13). The flask was purged with argon and AIBN (0.1 eq) was added in one portion. Then mixture was heated to 80° C. and stirred for 6h. After cooling to RT, the mixture was diluted with Et₂O and washed with a 1 M aq. soln. of HCl. The org. phase was washed with brine, dried over MgSO₄ and concentrated in vacuo. The crude was purified by CC using Hept/EtOAc.

Method B: Multi-Step

Step B1: O-Alkylation Via Mitsunobu (see Table 10)

To a soln. of methyl ester (1 eq) and 2-propanol (1.5 eq) in toluene (1.5 mL/mmol) was added a 1M soln. of (tributylphosphoranylidene)acetonitrile in toluene (2 eq)

under argon. The rxn mixture was heated to 11000 and stirred for 2h. It was quenched with water and extracted with DCM. The combined org. phases were washed with brine, dried over MgSO$_4$ and concentrated in vacuo. The crude was purified by CC using Hept/EtOAc.

TABLE 10

| BB-9A | Name | Carboxylic acid reactant | Method/ Step | $t_R$ [min] (LC/MS method) | MS-data m/z [M + H]$^+$ |
|---|---|---|---|---|---|
| BB-9-13A | 2,4-Difluoro-6-isopropoxy-benzoic acid methyl ester | 2,4-Difluoro-6-hydroxybenzoic acid methyl ester | B1 | 0.89 (II) | 231.10 |

Step B2: Methyl/Ethyl Ester Reduction Using CaCl$_2$/NaBH$_4$ (See Table 13)

To a soln. of methyl or ethyl ester (1 eq) in anh. EtOH (15 mL/mmol) was added CaCl$_2$ (0.3 eq) and the rxn mixture was cooled to −10° C. NaBH$_4$ (2.5 eq) was added portionwise and the mixture was stirred for 30 min at −10° C. and for 1.5 h at 70° C. It was quenched at 0° C. with water and EtOH was evaporated off. The residue was partitioned between EtOAc and water and the aq. phase was further extracted with EtOAc. The combined org. phases were washed with brine, dried over MgSO$_4$ and concentrated in vacuo. When necessary the crude was purified by CC using DCM/MeOH.

Step B3: Methyl/Ethyl Ester Reduction Using LiAlH$_4$ (See Table 13)

To a soln. of methyl or ethyl ester (1 eq) in anh. THF (4.5 to 7 mL/mmol) was added dropwise at 0° C. a 2.4 M soln. of LiAlH$_4$ in THF (1 eq). The rxn mixture was stirred for 1.5 h at 0° C., quenched with a sat. aq. soln. of NH$_4$C and extracted with EtOAc. The combined org. phases were dried over MgSO$_4$ and concentrated in vacuo. When necessary the crude was purified by CC using EtOAc.

Method C: Multi-Step

Step C1: Nucleophilic Aromatic Substitution (See Table 11)

To a soln. of halo-heteroarene (1 eq) in anh. THF (5 mL/mmol) was added dropwise at 0° C. a 2M soln. of lithium isopropoxide in THF (1.05 eq). The rxn mixture was stirred for 1h at 0° C. and poured into a 1M aq. soln. of HCl. The aq. soln. was neutralized with a sat. aq. soln. of NaHCO$_3$ and extracted with EtOAc. The combined org. phases were washed with brine, dried over MgSO$_4$ and concentrated in vacuo. The crude was purified by CC using Hept/EtOAc.

TABLE 11

| BB-9A | Name | Halo-heteroarene reactant | Method/ Step | $t_R$ [min] (LC/MS method) | MS-data m/z [M + H]$^+$ |
|---|---|---|---|---|---|
| BB-9-19A | 6-Chloro-4-isopropoxy-pyridazine-3-carboxylic acid isopropyl ester | 4,6-dichloropyridazine-3-carboxylic acid methyl ester | C1 | 0.88 (I) | 259.17 |

Step C2: Hydrogenation (see Table 12)

To a soln. of intermediate BB-9A (1 eq) in EtOH (4 mL/mmol) was added ammonium formate (2 eq) and the rxn mixture was flushed with nitrogen. Wet Pd/C (0.05 eq) was added and after inertising with nitrogen the rxn mixture was heated to 60° C. and stirred for 1h. It was filtered over a pad of Celite, the cake was washed with MeOH and the filtrate was concentrated in vacuo. The crude was purified by CC using Hept/EtOAc.

TABLE 12

| BB-9B | Name | Halo-heteroarene reactant | Method/ Step | $t_R$ [min] (LC/MS method) | MS-data m/z [M + H]$^+$ |
|---|---|---|---|---|---|
| BB-9-19B | 4-Isopropoxy-pyridazine-3-carboxylic acid isopropyl ester | BB-9-19A | C2 | 0.74 (I) | 225.05 |

Final Step C3: Ester Reduction (see Table 13)

To a soln. of ester intermediate BB-9B (1 eq) in anh. EtOH (15.8 mL/mmol) was added CaCl$_2$ (0.3 eq) and the rxn mixture was cooled to −10° C. NaBH$_4$ (2.5 eq) was added portionwise and the mixture was stirred for 30 min at −10° C. and for 3.5h at RT. It was quenched at 0° C. with water and EtOH was evaporated off. The residue was partitioned between EtOAc and water and the aq. phase was further extracted with EtOAc. The combined org. phases were washed with brine, dried over MgSO$_4$ and concentrated in vacuo.

water and extracted with DCM. The org. phase was washed with H$_2$O and brine, dried over MgSO$_4$ and concentrated in vacuo. The crude was purified by CC using DCM/MeOH.

Step B: Appel rxn (see Table 15)

To a soln. of intermediate BB-10A (1 eq) in DCM (5.2 mL/mmol) was added CBr$_4$ (1.5 eq) and diphenyl-2-pyridylphosphine (1.5 eq) at 0° C. The rxn mixture was stirred at 0° C. for 10 min and at RT for 1h. It was partitioned between DCM and a 5% aq. soln. of citric acid and the org.

TABLE 13

| BB-9 | Name | Reactant | Method/Step | $t_R$ [min] (LC/MS method) | MS-data m/z [M + H]$^+$ | $^1$H NMR (500 MHz, DMSO-d6) δ: |
|---|---|---|---|---|---|---|
| BB-9-1 | 2-(Trifluoromethyl) benzyl bromide | | commercially available | | | |
| BB-9-2 | 2-Bromomethyl-3-trifluoromethyl-pyrazine | 2-Methyl-3-trifluoromethyl pyrazine | A | 0.76 (II) | no io | 9.03 (d, J = 2.2 Hz, 1 H), 8.84 (d, J = 2.3 Hz, 1 H), 4.84 (d, J = 0.9 Hz, 2 H) |
| BB-9-3 | (4-Trifluoromethyl-pyridin-3-yl)-methanol | | commercially available | | | |
| BB-9-4 | [3-(Trifluoromethyl) pyridin-2-yl]methanol | | | | | |
| BB-9-5 | 1-(Bromomethyl)-2-cyclopropyloxybenzene | | | | | |
| BB-9-6 | 2-(Trifluoromethyl) benzyl alcohol | | | | | |
| BB-9-7 | 2-(Chloromethyl)-3-(trifluoromethyl)pyridine | | | | | |
| BB-9-8 | 2-Bromo-6-(trifluoromethyl) benzylbromide | | | | | |
| BB-9-9 | (2-Cyclopropylphenyl) methanol | | | | | |
| BB-9-10 | 1-(Bromomethyl)-2-isopropylbenzene | | | | | |
| BB-9-11 | 2-(Trifluoromethoxy) benzyl bromide | | | | | |
| BB-9-12 | 2-Chlorobenzyl bromide | | | | | |
| BB-9-13 | (2,4-Difluoro-6-isopropoxy-phenyl)-methanol | BB-9-13A | B3 | 0.78 (II) | no io | 6.41-6.47 (m, 2 H), 4.70 (d, J = 1.5 Hz, 2 H), 4.58 (m, 1 H), 1.40-1.45 (m, 6 H) |
| BB-9-14 | [2-Methyl-4-(trifluoromethyl)-1,3-thiazol-5-yl]methanol hydrochloride | | commercially available | | | |
| BB-9-15 | 1-(2-Trifluoromethyl-phenyl)-ethanol | | | | | |
| BB-9-16 | 2-(Bromomethyl)phenyl acetate | | | | | |
| BB-9-17 | (4-Isopropyl-pyrimidin-5-yl)-methanol | 4-Isopropyl pyrimidine-5-carboxylic acid ethyl ester | B2 | 0.47 (II) | 153.46 | |
| BB-9-18 | (2-Ethoxy phenyl)methanol | | commercially available | | | |
| BB-9-19 | (4-Isopropoxy-pyridazin-3-yl)-methanol | BB-9-19B | C3 | 0.34 (I) | 169.08 | |

Synthesis of Building Blocks BB-10

Method A

Step A: Carboxylic Acid Reduction (See Table 14)

To a soln. of carboxylic acid (1 eq) in anh. THF (10 mL/mmol) was added 4-methylmorpholine (2 eq) and ethyl chloroformate (2 eq) at −10° C. The mixture was stirred for 1h at −10° C. and NaBH$_4$ (3 eq) was added in one portion. It was allowed to warm to 0° C. over 1h, quenched with phase was washed with brine, dried over MgSO$_4$ and concentrated in vacuo. The crude was purified by CC using Hept/EtOAc.

Method B

Step A: Sulfonylation (see Table 14)

A soln. of amino alcohol (1 eq) and TEA (3 eq) in DCM (5 mL/mmol) was cooled to 0° C. and 2-nitro benzenesulfonyl chloride (1.2 eq) was added dropwise at 0° C. The rxn mixture was allowed to slowly reach RT and stirred for 1h.

It was diluted with DCM and washed with a sat. aq. soln. of NaHCO$_3$ and with brine. The org. phase was dried over MgSO$_4$ and concentrated in vacuo. The crude was purified by CC using Hept/EtOAc.

Step B: Aziridine Formation (see Table 15)

To a stirred soln. of amino alcohol derivative (1 eq) and TEA (2 eq) in DCM (mL/mmol) was added dropwise at 0° C. methanesulfonylchloride (1.05 eq). The rxn mixture was allowed to warm to RT and stirred for 45 min. It was partitioned between DCM and H$_2$O and the org. phase was dried over MgSO$_4$ and concentrated in vacuo. The crude was dissolved in THE (4.2 mL/mmol) and TEA (2 eq) was added. The rxn mixture was stirred at RT for 18h and at 500 for 30 min and partitioned between DCM and H$_2$. The org. phase was dried over MgSO$_4$ and concentrated in vacuo. The crude was purified by CC using Hept/EtOAc.

TABLE 14

| BB-10A | Name | Method Reactant | $t_R$ [min] (LC/MS method) | MS-data m/z [M + H]$^+$ | $^1$H NMR (500 MHz, DMSO-d6) δ: |
|---|---|---|---|---|---|
| BB-10-1A | (2,2,2-Trifluoro-1-hydroxymethyl-ethyl)-carbamic acid tert-butyl ester | A (step A) 2-{[(tert-Butoxy) carbonyl]amino}-3,3,3-trifluoro propanoic acid | | | 7.43 (d, J = 9.2 Hz, 1 H), 5.07 (t, J = 5.9 Hz, 1 H), 4.11-4.19 (m, 1 H), 3.64 (m, 1 H), 3.51 (m, 1 H), 1.41 (s, 9 H) |
| BB-10-2A | 4-Chloro-N-(2-hydroxy-1,1-dimethylethyl) benzene sulfonamide | commercially available | | | |
| BB-10-3A | N-(2-Hydroxy-1,1-dimethyl-ethyl)-2-nitro-benzene sulfonamide | B (step A) 2-Amino-2-methyl-1-propanol | 0.68 (II) | 275.04 | 8.11-8.13 (m, 1 H), 7.92-7.95 (m, 1 H), 7.81-7.87 (m, 2 H), 7.59 (s, 1 H), 4.94 (t, J = 5.7 Hz, 1 H), 3.24 (d, J = 5.7 Hz, 2 H), 1.06 (s, 6 H) |

TABLE 15

| BB-10 | Name | Method Reactant BB-10A | $t_R$ [min] (LC/MS method) | MS-data m/z [M + H]$^+$ | $^1$H NMR (500 MHz, DMSO-d6) δ: |
|---|---|---|---|---|---|
| BB-10-1 | (3-Bromo-1,1,1-trifluoropropan-2-yl)-carbamic acid tert-butyl ester | A (step B) BB-10-1A | | | 7.79 (d, J = 9.4 Hz, 1 H), 4.41-4.48 (m, 1 H), 3.78 (dd, J$_1$ = 10.6 Hz, J$_2$ = 3.5 Hz, 1 H), 3.46 (dd, J$_1$ = J$_2$ = 10.6 Hz, 1 H), 1.42 (s, 9 H) |
| BB-10-2 | 1-(4-Chloro-benzene sulfonyl)-2,2-dimethyl-aziridine | B (step B) BB-10-2A | 0.84 (II) | 246.11 | 7.90 (d, J = 8.8 Hz, 2 H), 7.71 (d, J = 8.6 Hz, 2 H), 2.53 (s, 2 H), 1.47 (s, 6 H) |
| BB-10-3 | 2,2-Dimethyl-1-(2-nitro-benzenesulfonyl)-aziridine | B (step B) BB-10-3A | 0.87 (I) | 257.07 | |
| BB-10-4 | (R)-3-Chloro-1-trityl-azetidin-2-one | Prepared according to J. Heterocyclic Chem., 2006, 43, 11-19. | 1.09 (I) | 348.06 | 7.12-7.40 (m, 15 H), 5.13 (dd, J$_1$ = 5.1 Hz, J$_2$ = 2.0 Hz, 1 H), 3.78 (dd, J$_1$ = 6.4 Hz, J$_2$ = 5.1 Hz, 1 H), 3.32 (m, 1 H) |

Building Blocks BB-11, BB-12, BB-13, BB-14, BB-15 and BB-16

TABLE 16

| | | Name | |
|---|---|---|---|
| BB-11 | BB-11-1 | 5-Nitro-1H-imidazole-4-carbaldehyde | commercially available |
| BB-12 | BB-12-1 | 3-Trifluoromethyl-2-formylpyridine | |
| | BB-12-2 | 6-Chloro-3-(trifluoromethyl)picolinaldehyde | |
| | BB-12-3 | 2-Fluoro-6-(trifluoromethyl)benzaldehyde | |
| | BB-12-4 | 2-(Trifluoromethyl)benzaldehyde | |
| | BB-12-5 | 2-Cyclopropylbenzaldehyde | |
| BB-13 | BB-13-1 | N-Boc-3-pyrrolidinone | |
| | BB-13-2 | N-Boc-4-piperidone | |

TABLE 16-continued

| | | Name |
|---|---|---|
| BB-14 | BB-14-1 | 3-Amino-1-methyl-1H-pyrazole-4-carbaldehyde |
| BB-15 | BB-15-1 | tert-Butyl-4-aminoazepane-1-carboxylate |
| | BB-15-2 | tert-Butyl 4-aminopiperidine-1-carboxylate |
| BB-16 | BB-16-1 | 2-Bromo-3-fluorotoluene |
| | BB-16-2 | 2-Bromo-1,3-dimethylbenzene |
| | BB-16-3 | 2-Bromo-1-methoxy-3-methylbenzene |
| | BB-16-4 | Isopropyl chloroformate |
| | BB-16-5 | 2,3-Difluorobenzonitrile |
| | BB-16-6 | 3-Bromo-2-fluoro-4-methylpyridine |
| | BB-16-7 | 3-Bromo-2-methoxy-4-methylpyridine |
| | BB-16-8 | 2-Bromo-3-fluoropyridine |
| | BB-16-9 | 2-Bromo-3-methylpyridine |
| | BB-16-10 | 2-Bromo-3-methoxypyridine |
| | BB-16-11 | 3-Bromo-4-methylpicolinonitrile |
| | BB-16-12 | 3-Bromo-4-fluoro-2-methylpyridine |
| | BB-16-13 | 3-Bromo-2,4-dimethoxypyridine |
| | BB-16-14 | 5-Bromo-4-methoxy-6-methylpyrimidine |
| | BB-16-15 | 5-Bromo-4,6-dimethoxypyrimidine |
| | BB-16-16 | 5-chloro-1,3-dimethyl-1H-pyrazole-4-carbonitrile |
| | BB-16-17 | 5-chloro-1,3-dimethyl-1H-pyrazole-4-carbaldehyde |
| | BB-16-18 | Cyclopropyl chloroformate |
| | BB-16-19 | 2-Bromo-3-fluorobenzotrifluoride |
| | BB-16-20 | 2-Bromo-1-fluoro-3-(trifluoromethoxy)benzene |
| | BB-16-21 | 2-Bromo-3-chlorotoluene |
| | BB-16-22 | 1-Bromo-2-isopropylbenzene |
| | BB-16-23 | 1-Bromo-2-cyclopropylbenzene |
| | BB-16-24 | 2-Bromo-1-chloro-3-fluorobenzene |
| | BB-16-25 | 1-Bromo-2,6-difluorobenzene |
| | BB-16-26 | 2-Bromo-1-ethyl-3-fluorobenzene |
| | BB-16-27 | 2-Bromo-1-(difluoromethyl)-3-fluorobenzene |
| | BB-16-28 | 2-Bromo-1-cyclopropyl-3-fluorobenzene |

Synthesis of Building Blocks BB-17

To a soln. of amines B (1 eq, see Table 17) and DIPEA (2.5 eq) in MeCN (5 mL/mmol) was added DMAP (0.2 eq) and methylchloroformate (2.5 eq) at 0° C. The rxn mixture was stirred for 5 min at 0° C. and for 3h at RT. MeOH (3 mL/mmol) was added followed by a 1 M aq. soln. of NaOH (1.7 eq). The rxn mixture was stirred for 1.5h at RT and the volatiles were evaporated. The residue was diluted with EtOAc and washed successively with a 10% aq. soln. of citric acid, a sat. aq. soln. of NaHCO$_3$ and brine. The org. phase was dried over MgSO$_4$ and concentrated in vacuo. The crude was purified by CC using Hept/EtOAc.

TABLE 17

| BB-17 | Name | Amino-(hetero)arene reactant B | $t_R$ [min] (LC/MS method) | MS-data m/z [M + H]$^+$ | $^1$H NMR (500 MHz, DMSO-d6) δ: |
|---|---|---|---|---|---|
| BB-17-1 | 5-Methoxycarbonylamino-2-methyl-oxazole-4-carboxylic acid ethyl ester | 5-Amino-2-methyl-1,3-oxazole-4-carboxylic acid ethyl ester | 0.56 (II) | 229.13 | 10.12 (s, 1 H), 4.20 (q, J = 7.1 Hz, 2 H), 3.67 (s, 3 H), 2.39 (s, 3 H), 1.24 (t, J = 7.1 Hz, 3 H) |

TABLE 18

| BB-20 | Name | Bromo-(hetero)arene reactant C | $t_R$ [min] (LC/MS method) | MS-data m/z [M + H]$^+$ |
|---|---|---|---|---|
| BB-20-1 | 5-Azido-2-methyl-thiazole-4-carbaldehyde | 5-Bromo-2-methylthiazole-4-carbaldehyde | 0.56 (II) | 169.04 |

Synthesis of Building Blocks BB-20

To a soln. of bromides C (1 eq) in DMSO (2.5 mL/mmol) was added NaN$_3$ (1.5 eq) at RT. The rxn mixture was stirred at RT for 5h (see Table 18) and quenched with H$_2$O. It was extracted with EtOAc and the combined org. phases were dried over MgSO$_4$ and concentrated in vacuo.

Synthesis of Building Blocks BB-18

A 2.4 M soln. of LiAlH$_4$ in THF (1 eq) was diluted with anh. THF (2 mL/mmol) and cooled to −10° C. A soln. of ethyl ester BB-17 (1 eq, see Table) in anh. THF (2 mL/mmol) was added dropwise at −10° C. The rxn mixture was allowed to warm from −10° C. to 5° C. over 1h and quenched successively at 0° C. with ice water, with a 2M aq.

soln. of NaOH and with ice water. The suspension was diluted with THF, stirred for 30 min at RT, filtered over a pad of celite and the filtrate was concentrated in vacuo. The crude was purified by CC using DCM/MeOH.

TABLE 19

| BB-18 | Name | Reactant BB-17 | $t_R$ [min] (LC/MS method) | MS-data m/z [M + H]$^+$ | $^1$H NMR (500 MHz, DMSO-d6) δ: |
|---|---|---|---|---|---|
| BB-18-1 | (4-Hydroxymethyl-2-methyl-oxazol-5-yl)-carbamic acid methyl ester | BB-17-1 | 0.37 (II) | 187.14 | 9.47 (s, 1 H), 4.92 (t, J = 5.6 Hz, 1 H), 4.16 (d, J = 5.7 Hz, 2 H), 3.65 (s, 3 H), 2.32 (s, 3 H) |

Synthesis of Building Blocks BB-19

To a soln. of alcohol BB-18 (1 eq, see Table) in anh. DCM (10 mL/mmol) was added portionwise MnO$_2$ (9 eq) at RT and the rxn mixture was stirred at 45° C. for 4h. It was filtered over a pad of celite and the filtrate was washed with a sat. aq. soln. of NaHCO$_3$ and brine, dried over MgSO$_4$ and concentrated in vacuo.

TABLE 20

| BB-19 | Name | Reactant BB-18 | $t_R$ [min] (LC/MS method) | MS-data m/z [M + H]$^+$ | $^1$H NMR (500 MHz, DMSO-d6) δ: |
|---|---|---|---|---|---|
| BB-19-1 | (4-Formyl-2-methyl-oxazol-5-yl)-carbamic acid methyl ester | BB-18-1 | 0.44 (II) | 185.17 | 11.10 (s, 1 H), 9.81 (s, 1 H), 3.74 (s, 3 H), 2.39 (s, 3 H) |

Synthesis of Building Blocks BB-21

To a soln. of amines D (1 eq, see Table 20) and TEA (3 eq) in THF (10 mL/mmol) was added Boc$_2$O (1.1 eq) at 0° C. The rxn mixture was stirred at 0° C. for 10 min and at RT for 18h. It was partitioned between DCM and H$_2$O and the aq. phase was extracted with DCM. The combined org. phases were washed with brine, dried over MgSO$_4$ and concentrated in vacuo.

TABLE 20

| BB-21 | Name | Amino-(hetero)arene reactant D | $t_R$ [min] (LC/MS method) | MS-data m/z [M + H]$^+$ | $^1$H NMR (500 MHz, DMSO-d6) δ: |
|---|---|---|---|---|---|
| BB-21-1 | (5-Carbamoyl-1H-[1,2,3]triazol-4-yl)-carbamic acid tert-butyl ester | 4-Amino-1H-1,2,3-triazole-5-carboxamide | 0.59 (II) | no | 14.70 (s br, 1 H), 9.03 (s, 1 H), 7.88 (s, 1 H), 7.56 (s, 1 H), 1.48 (s, 9 H) |

Synthesis of Building Blocks BB-22

NaH (3 eq, as a 60% dispersion in mineral oil) was added portionwise at 0° C. to a soln. or suspension of intermediate BB-21 (1 eq) in THF (10 mL/mmol). The suspension was stirred at RT for 20 min and MeI (1.1 eq) was added at 0° C. The rxn mixture was stirred at 0° C. for 10 min and at RT for 48h (see Table 21). When necessary to reach completion of the rxn, extra amounts of NaH (1 eq) and/or MeI (0.3 eq) were needed. The rxn mixture was quenched with half sat. aq. soln. of NaHCO$_3$ at 0° C. and extracted with EtOAc. The combined org. phases were washed with brine, dried over MgSO$_4$ and concentrated in vacuo. The crude was purified by precipitation of the impurities from a soln. of the crude in DCM/MeOH and addition of Et$_2$O.

TABLE 21

| BB-22 | Name | Reactant BB-21 | $t_R$ [min] (LC/MS method) | MS-data m/z [M + H]$^+$ | $^1$H NMR (500 MHz, DMSO-d6) δ: |
|---|---|---|---|---|---|
| BB-22-1 | (5-Carbamoyl-2-methyl-2H-[1,2,3]triazol-4-yl)-carbamic acid tert-butyl ester | BB-21-1 | 0.61 (II) | 242.19 | 8.89 (s, 1 H), 7.84 (s, 1 H), 7.60 (s, 1 H), 4.10 (s, 3 H), 1.44 (s, 9 H) |

Synthesis of Building Blocks BB-23

To a stirred soln. of amide intermediate BB-22 (1 eq) in DCM (10 mL/mmol) was added portionwise Burgess' reagent (3 eq) under argon. The rxn mixture was stirred at RT for 18h (see Table 22) and partitioned between DCM and H$_2$O. The org. phase was washed with brine, dried over MgSO$_4$ and concentrated in vacuo. The crude was purified by CC using Hept/EtOAc.

TABLE 22

| BB-23 | Name | Reactant BB-22 | $t_R$ [min] (LC/MS method) | MS-data m/z [M + H]$^+$ | $^1$H NMR (500 MHz, DMSO-d6) δ: |
|---|---|---|---|---|---|
| BB-23-1 | (5-Cyano-2-methyl-2H-[1,2,3]triazol-4-yl)-carbamic acid tert-butyl ester | BB-22-1 | 0.74 (II) | 224.12 | 10.38 (s, 1 H), 4.16 (s, 3 H), 1.48 (s, 9 H) |

Synthesis of Building Blocks BB-24

Nitrile BB-23 (1 eq) was dissolved in a 7M soln. of NH$_3$ in MeOH (7 mL/mmol). The flask was evacuated and refilled with nitrogen. Raney nickel (0.1 eq) was added at 0° C. and the temperature was allowed to reach RT. The flask was evacuated and refilled with hydrogen. The suspension was stirred under a hydrogen atmosphere at RT for 4h (see Table 23) and filtered over a pad of Celite. The cake was washed with MeOH and the filtrate was concentrated in vacuo.

TABLE 23

| BB-24 | Name | Reactant BB-23 | $t_R$ [min] (LC/MS method) | MS-data m/z [M + H]$^+$ | $^1$H NMR (500 MHz, DMSO-d6) δ: |
|---|---|---|---|---|---|
| BB-24-1 | (5-Aminomethyl-2-methyl-2H-[1,2,3]triazol-4-yl)-carbamic acid tert-butyl ester | BB-23-1 | 0.45 (II) | 228.17 | 9.07 (s br, 1 H), 3.99 (s, 3 H), 3.58 (s, 2 H), 1.43 (s, 9 H) |

Synthesis of Building Blocks BB-25

Method A (Pentafluorophenyl Ester)

A soln. of the appropriate alcohol (1 eq) and bis(pentafluorophenyl)carbonate (1.2 eq) in MeCN (0.55 mL/mmol) was cooled to 0° C. and Et$_3$N (3.2 eq) was added dropwise. The rxn mixture was allowed to reach RT and stirred for 18h (see Table 24). The mixture was concentrated in vacuo and the residue was purified by CC using DCM/MeOH and/or by prep. LC-MS using method 3.

Method B (Cyclisation)

A soln. of the appropriate hydrazide (1 eq) and CDI (1.5 eq) in anh. Dioxane (4.2 mL/mmol) was heated to 85° C. and stirred for 18h. The solvent was evaporated under reduced pressure and the residue was partitioned between EtOAc and H$_2$O. The org. phase was washed with brine, dried over MgSO$_4$ and concentrated in vacuo. The crude was purified by CC using Hept/EtOAc.

TABLE 24

| BB-25 | Name | Method Reactant alcohol/hydrazide | $t_R$ [min] (LC/MS method) | MS-data m/z $[M + H]^+$ | $^1$H NMR (500 MHz, DMSO-d6) δ: |
|---|---|---|---|---|---|
| BB-25-1 | Carbonic acid oxetan-3-yl ester pentafluorophenyl ester | A 3-Hydroxy oxetane | 0.86 (II) | no io | 5.65 (m, 1 H), 4.87 (m, 2 H), 4.65 (ddd, $J_1$ = 0.9 Hz, $J_2$ = 4.7 Hz, $J_3$ = 8.1 Hz, 2 H) |
| BB-25-2 | Carbonic acid pentafluorophenyl ester 3-trifluoromethyl-oxetan-3-yl ester | Prepared according to Med. Chem. Commun., 2013, 4, 95-100 | 0.95 (II) | no io | 5.18 (d, J = 8.7 Hz, 2 H), 4.87 (d, J = 9.6 Hz, 2 H) |
| BB-25-3 | Carbonic acid 3-methyl-oxetan-3-yl ester pentafluorophenyl ester | A 3-Methyloxetan-3-ol | 0.90 (II) | no io | 4.77 (d, J = 7.7 Hz, 2 H), 4.54 (d, J = 8.2 Hz, 2 H), 1.76 (s, 3 H) |
| BB-25-4 | 5-Isopropyl-3H-[1,3,4]oxadiazol-2-one | B Isobutyric acid hydrazide | 0.49 (II) | 130.49 | 12.05 (s br, 1 H), 2.81-2.91 (m, 1 H), 1.19 (d, J = 6.9 Hz, 6 H) |

Synthesis of Building Blocks BB-26

Method A (SEM Protection)

To a suspension of the appropriate ketone (1 eq) and SEM-Cl (1.3 eq) in DCM (3.5 mL/mmol) was added dropwise DIPEA (1.5 eq) at 0° C. The rxn mixture was stirred at 0° C. for 1.5 h and quenched with a sat. aq. soln. of NaHCO$_3$. It was extracted with DCM, the org. phase was washed with a sat. aq. sol. of NaHCO$_3$, dried over MgSO$_4$ and concentrated in vacuo. The crude was purified by CC using Hept/EtOAc.

Method B (THP Protection)

To a suspension of the appropriate ketone (1 eq) in DCM (1.6 mL/mmol) was added TsOH (0.1 eq) and 3,4-dihydro-2H-pyran (1.3 eq). The rxn mixture was stirred at RT for 1.5 h and quenched with a sat. aq. soln. of NaHCO$_3$. It was extracted with DCM, the org. phase was washed with a sat. aq. soln. of NaHCO$_3$ and brine, dried over MgSO$_4$ and concentrated in vacuo. The crude was purified by CC using Hept/EtOAc.

Building Blocks BB-28

TABLE 26

| BB-28 | Name | |
|---|---|---|
| BB-28-1 | 3-Amino-1-methyl-1H-pyrazole-4-carbonitrile | commercially available |

Synthesis of Building Blocks BB-29

To a mixture of the appropriate amine E (1 eq), the appropriate halide (1.05 to 1.2 eq) and sodium tert-butoxide (2 eq) in toluene (3 mL/mmol) under N$_2$, was added BINAP (0.2 eq) and Pd$_2$(dba)$_3$ (0.1 eq). The rxn mixture was flushed with N$_2$, heated to a given temperature in a sealed vial and stirred for a given time (see Table 27). It was partitioned between water and EtOAc and the org. phase was washed with brine, dried over MgSO$_4$ and concentrated in vacuo. The crude was purified by CC using Hept/EtOAc.

TABLE 25

| BB-26 | Name | Method Reactant ketone | $t_R$ [min] (LC/MS method) | MS-data m/z $[M + H]^+$ | $^1$H NMR (500 MHz, DMSO-d6) δ: |
|---|---|---|---|---|---|
| BB-26-1 | 1-(1-Methyl-4-nitro-1H-pyrazol-3-yl)-ethanone | commercially available | | | |
| BB-26-2 | 1-[4-Nitro-2-(2-trimethylsilanyl-ethoxymethyl)-2H-pyrazol-3-yl]-ethanone | A 1-(4-Nitro-1H-pyrazol-5-yl)ethanone | 1.05 (I) | no io | 8.41 (s, 1 H), 5.48 (s, 2 H), 3.55 (m, 2 H), 2.65 (s, 3 H), 0.85 (m, 2 H), −0.03 (m, 9 H) |
| BB-26-3 | 1-[4-Nitro-1-(2-trimethylsilanyl-ethoxymethyl)-1H-pyrazol-3-yl]-ethanone | | 1.01 (I) | 286.25 | |
| BB-26-4 | 1-[4-Nitro-1-(tetrahydro-pyran-2-yl)-1H-pyrazol-3-yl]-ethanone | B 1-(4-Nitro-1H-pyrazol-5-yl)ethanone | 0.80 (I) | 240.22 | |

TABLE 27

| BB-29 | Name | Reactant amine E | Reactant halide | T [° C.] time [h] | $t_R$ [min] (LC/MS method) | MS-data m/z [M + H]+ |
|---|---|---|---|---|---|---|
| BB-29-1 | 8-(2-Fluoro-6-methyl-phenyl)-1,4-dioxa-8-aza-spiro[4.5]decane | 1,4-Dioxa-8-azaspiro[4.5]decane | 2-Bromo-3-fluorotoluene | 100 18 | 1.01 (I) | 252.19 |
| BB-29-2 | 8-(2-Methoxy-4-methyl-pyridin-3-yl)-1,4-dioxa-8-aza-spiro[4.5]decane | 1,4-Dioxa-8-azaspiro[4.5]decane | 3-Bromo-2-methoxy-4-methylpyridine | 100 20 | 0.81 (I) | 265.19 |
| BB-29-3 | 8-(2-Fluoro-6-methyl-phenyl)-1,4-dioxa-8-aza-spiro[4.6]undecane | 1,4-Dioxa-8-azaspiro[4.6]undecane | 2-Bromo-3-fluorotoluene | 100 2.5 | 1.03 (I) | 266.30 |
| BB-29-4 | 7-(2-Fluoro-6-methyl-phenyl)-1,4-dioxa-7-aza-spiro[4.5]decane | 1,4-Dioxa-7-azaspiro[4.5]decane | 2-Bromo-3-fluorotoluene | 100 6 | 1.00 (I) | 252.29 |
| BB-29-5 | 8-(2-Methoxy-4-trifluoromethyl-pyridin-3-yl)-1,4-dioxa-8-aza-spiro[4.5]decane | 1,4-Dioxa-8-azaspiro[4.5]decane | 3-Bromo-2-methoxy-4-trifluoromethyl-pyridine | 100 18 | 1.03 (I) | 319.16 |
| BB-29-6 | 8-(4-Chloro-2-methoxy-pyridin-3-yl)-1,4-dioxa-8-aza-spiro[4.5]decane | 1,4-Dioxa-8-azaspiro[4.5]decane | 3-Bromo-4-chloro-2-methoxy-pyridine | 80 6 | 0.96 (I) | 285.12 |

Synthesis of Building Blocks BB-30

Step A: Aromatic Nucleophilic Substitution

To a soln. of the appropriate amine F (1 eq) and the appropriate halide (1.1 eq) in a given solvent (0.9 to 1.5 mL/mmol) was added $K_2CO_3$ (2 eq) and the mixture was heated to a given temperature and stirred for 18h (see Table 28). It was quenched with water and extracted with DCM or EtOAc. The org. phase was washed with water and brine, dried over $MgSO_4$ and concentrated in vacuo. The crude was purified by CC using Hept/EtOAc or DCM/MeOH.

Step B:
Method A: Reduction

A suspension of intermediate BB-30A (1 eq) in anh. MeOH (2 mL/mmol) was cooled to 0° C. and $NaBH_4$ (1.2 to 1.3 eq) was added portionwise at 0° C. (see Table 29). The rxn mixture was stirred for 1h at 0° C. to reach completion. It was carefully quenched by dropwise addition of water at 0° C. and extracted with EtOAc. The org. phase was washed with water and brine, dried over $MgSO_4$ and concentrated in vacuo.

TABLE 28

| BB-30A | Name | Reactant amine F | Reactant halide | Solvent T [° C.] | $t_R$ [min] (LC/MS method) | MS-data m/z [M + H]+ |
|---|---|---|---|---|---|---|
| BB-30-1A | [1-(2-Fluoro-6-formyl-phenyl)-piperidin-4-yl]-carbamic acid tert-butyl ester | 4-(Boc-amino)piperidine | 2,3-Difluoro-benzaldehyde | DMSO 100 | 0.93 (II) | 323.20 |
| BB-30-2A | [1-(2-Fluoro-6-formyl-phenyl)-4-methyl-piperidin-4-yl]-carbamic acid tert-butyl ester | 4-(Boc-amino)-4-methyl-piperidine | 2,3-Difluoro-benzaldehyde | DMA 120 | 1.05 (I) | 337.15 |
| BB-30-3A | [1-(2-Fluoro-6-formyl-phenyl)-3-methyl-pyrrolidin-3-yl]-carbamic acid tert-butyl ester | 3-(Boc-amino)-3-methyl-pyrrolidine | 2,3-Difluoro-benzaldehyde | DMA 120 | 1.03 (I) | 323.17 |
| BB-30-4A | [(R)-1-(2-Fluoro-6-formyl-phenyl)-pyrrolidin-3-yl]-carbamic acid tert-butyl ester | (R)-3-(Boc-amino)pyrrolidine | 2,3-Difluoro-benzaldehyde | DMSO 100 | 0.98 (I) | 309.19 |
| BB-30-6A | [1-(2-Fluoro-6-nitro-phenyl)-piperidin-4-yl]-carbamic acid tert-butyl ester | 4-(Boc-amino)piperidine | 2,3-Difluoro-nitrobenzene | DMA 80 | 1.05 (I) | 340.22 |
| BB-30-7A | (4'-Formyl-2'-methoxy-3,4,5,6-tetrahydro-2H-[1,3']bipyridinyl-4-yl)-carbamic acid tert-butyl ester | 4-(Boc-amino)piperidine | 3-fluoro-2-methoxypyridine-4-carbaldehyde | DMA 120 | 0.95 (I) | 336.21 |

Method B: Hydrogenation

Intermediate BB-30A (1 eq) was dissolved in EtOH (5 mL/mmol). The flask was evacuated three times and refilled with nitrogen. Wet Pd/C (0.05 eq) was added and the flask was evacuated three times and refilled with hydrogen. The suspension was stirred under an atmospheric pressure of hydrogen for 3h and filtered over a pad of Celite. The cake was washed with EtOAc and MeOH and the filtrate was concentrated in vacuo.

TABLE 29

| BB-30B | Name | Method Reactant BB-32A | $t_R$ [min] (LC/MS method) | MS-data m/z [M + H]$^+$ |
|---|---|---|---|---|
| BB-30-1B | [1-(2-Fluoro-6-hydroxymethyl-phenyl)-piperidin-4-yl]-carbamic acid tert-butyl ester | A BB-30-1A | 0.82 (II) | 325.24 |
| BB-30-2B | [1-(2-Fluoro-6-hydroxymethyl-phenyl)-4-methyl-piperidin-4-yl]-carbamic acid tert-butyl ester | A BB-30-2A | 0.86 (I) | 339.23 |
| BB-30-3B | [1-(2-Fluoro-6-hydroxymethyl-phenyl)-3-methyl-pyrrolidin-3-yl]-carbamic acid tert-butyl ester | A BB-30-3A | 0.82 (I) | 325.22 |
| BB-30-4B | [(R)-1-(2-Fluoro-6-hydroxymethyl-phenyl)-pyrrolidin-3-yl]-carbamic acid tert-butyl ester | A BB-30-4A | 0.82 (I) | 311.23 |
| BB-30-6B | [1-(2-Amino-6-fluoro-phenyl)-piperidin-4-yl]-carbamic acid tert-butyl ester | B BB-30-6A | 0.88 (I) | 310.28 |

Step C:

Method A: Acetylation

A soln. of intermediate BB-30B (1 eq) and TEA (1.5 eq) in DCM (0.5 to 5 mL/mmol) was cooled to 0° C. and AcCl (1.5 eq) was added dropwise at 0° C. (see Table 30). The rxn mixture was stirred for 1h at 0° C. to reach completion. It was diluted with DCM and washed with a 10% aq. soln. of citric acid, with a sat. aq. soln. of NaHCO$_3$ and with brine. The org. phase was dried over MgSO$_4$ and concentrated in vacuo. The crude was purified by CC using Hept/EtOAc.

Method B: Sandmeyer rxn (Bromination)

To a soln. of intermediate BB-30B (1 eq) in MeCN (5 mL/mmol) was added dropwise at 0° C. tetrafluoroboric acid as diethyl ether complex (1.2 eq). The soln. was stirred for 5 min at 0° C. and tert-butyl nitrite (1.2 eq) was added dropwise. The rxn mixture was added dropwise at 0° C. to a suspension of copper(I) bromide (1.5 eq) and copper(II) bromide (3 eq) in H$_2$O (3.1 mL/mmol). The resulting soln. was stirred for 18h allowing the temperature to reach RT. It was partitioned between EtOAc and a sat soln. of NH$_4$Cl. The org. phase was washed with a sat. soln. of NH$_4$Cl and brine, dried over MgSO$_4$ and concentrated in vacuo. The crude was purified by CC using Hept/EtOAc.

TABLE 30

| BB-30C | Name | Method Reactant BB-30B | $t_R$ [min] (LC/MS method) | MS-data m/z [M + H]$^+$ |
|---|---|---|---|---|
| BB-30-1C | Acetic acid 2-(4-tert-butoxycarbonylamino-piperidin-1-yl)-3-fluoro-benzyl ester | A BB-30-1B | 0.97 (II) | 367.25 |
| BB-30-2C | Acetic acid 2-(4-tert-butoxycarbonylamino-4-methyl-piperidin-1-yl)-3-fluoro-benzyl ester | A BB-30-2B | 1.09 (I) | 381.22 |
| BB-30-3C | Acetic acid 2-(3-tert-butoxycarbonylamino-3-methyl-pyrrolidin-1-yl)-3-fluoro-benzyl ester | A BB-30-3B | 1.06 (I) | 367.22 |
| BB-30-4C | Acetic acid 2-((R)-3-tert-butoxycarbonylamino-pyrrolidin-1-yl)-3-fluoro-benzyl ester | A BB-30-4B | 1.02 (I) | 353.14 |
| BB-30-6C | [1-(2-Bromo-6-fluoro-phenyl)-piperidin-4-yl]-carbamic acid tert-butyl ester | B BB-30-6B | 1.13 (I) | 373.15 |

Final Step:

Method A: hydrogenation (using BB-30C) Intermediate BB-30 (1 eq) was dissolved in a mixture of MeOH (6 mL/mmol) and EtOAc (2 mL/mmol) and the flask was evacuated three times and refilled with nitrogen (see Table 31). Wet Pd/C (0.08 eq) was added and the flask was evacuated three times and refilled with hydrogen. The suspension was hydrogenated under atmospheric pressure for 3h and filtered over a pad of Celite. The cake was washed with EtOAc and MeOH and the filtrate was concentrated in vacuo. The crude was purified by CC using Hept/EtOAc.

Method B: Fluorination (Using BB-30A)

To a soln. of intermediate BB-30A (1 eq) in DCM (6 to 58 mL/mmol) was added dropwise a 50% soln. of bis(2-methoxyethyl)aminosulfur trifluoride (2 to 2.75 eq). The soln. was stirred for 4 to 18h at RT (see Table 31), quenched at 0° C. with a sat. aq. soln. of NaHCO₃ and extracted with DCM. The org. phase was dried over MgSO₄ and concentrated in vacuo. The crude was purified by CC using Hept/EtOAc.

Method C: Sandmeyer Rxn (Chlorination Using BB-30B)

To a soln. of intermediate BB-30B (1 eq) in MeCN (5 mL/mmol) was added dropwise at 0° C. tetrafluoroboric acid as diethyl ether complex (1.2 eq). The soln. was stirred for 5 min at 0° C. and tert-butyl nitrite (1.2 eq) was added dropwise. The rxn mixture was added dropwise at 0° C. to a suspension of copper(I) chloride (1.5 eq) and copper(I) chloride (3 eq) in H₂O (3.1 mL/mmol). The resulting soln. was stirred for 18h allowing the temperature to reach RT. It was partitioned between EtOAc and a sat. soln. of NH₄Cl. The org. phase was washed with a sat. soln. of NH₄Cl and brine, dried over MgSO₄ and concentrated in vacuo. The crude was purified by CC using Hept/EtOAc.

Method D: Kumada Rxn (Using BB-30C)

To a mixture of intermediate BB-30(1 eq) and di-μ-iodobis(tri-t-butylphosphino)dipalladium(I) in toluene (3.8 mL/mmol) was added dropwise under argon a 1 M soln. of cyclopropylmagnesium bromide in 2-methyl tetrahydrofuran (4 eq). The rxn mixture was stirred at RT for a given time (see Table 31). When necessary, an extra amount of a 1M soln. of cyclopropylmagnesium bromide in 2-methyltetrahydrofuran (2 eq) was added. The rxn mixture was quenched with H₂O and extracted with EtOAc. The org. phase was washed with H₂O and brine, dried over MgSO₄ and concentrated in vacuo. The crude was purified by CC using Hept/EtOAc and when necessary, an additional purification by prep. LC-MS using method 1 was performed.

TABLE 31

| BB-30 | Name | Method Reactant BB-30C, BB-30-B or BB-30A | $t_R$ [min] (LC/MS method) | MS-data m/z [M + H]⁺ |
|---|---|---|---|---|
| BB-30-1 | [1-(2-Fluoro-6-methyl-phenyl)-piperidin-4-yl]-carbamic acid tert-butyl ester | A BB-30-1C | 1.00 (II) | 309.16 |
| BB-30-2 | [1-(2-Fluoro-6-methyl-phenyl)-4-methyl-piperidin-4-yl]-carbamic acid tert-butyl ester | A BB-30-2C | 1.12 (I) | 323.24 |
| BB-30-3 | [1-(2-Fluoro-6-methyl-phenyl)-3-methyl-pyrrolidin-3-yl]-carbamic acid tert-butyl ester | A BB-30-3C | 1.02 (I) | 309.24 |
| BB-30-4 | [(R)-1-(2-Fluoro-6-methyl-phenyl)-pyrrolidin-3-yl]-carbamic acid tert-butyl ester | A BB-30-4C | 0.99 (I) | 295.29 |
| BB-30-6 | [1-(2-Difluoromethyl-6-fluoro-phenyl)-piperidin-4-yl]-carbamic acid tert-butyl ester | B BB-30-1A | 1.09 (I) | 345.43 |
| BB-30-7 | [1-(2-Chloro-6-fluoro-phenyl)-piperidin-4-yl]-carbamic acid tert-butyl ester | C BB-30-6B | 1.10 (I) | 329.16 |
| BB-30-8 | [1-(2-Cyclopropyl-6-fluoro-phenyl)-piperidin-4-yl]-carbamic acid tert-butyl ester | D BB-30-6C | 1.14 (I) | 335.26 |
| BB-30-9 | (4'-Difluoromethyl-2'-methoxy-3,4,5,6-tetrahydro-2H-[1,3']bipyridinyl-4-yl)-carbamic acid tert-butyl ester | B BB-30-7A | 1.09 (I) | 358.21 |

Synthesis of Building Blocks BB-31

To a mixture of the appropriate amine G (1 eq), the appropriate halide (1.5 eq) and sodium tert-butoxide (2 eq) in toluene (3.5 mL/mmol) under N₂, was added BINAP (0.2 eq) and Pd₂(dba)₃ (0.1 eq) (see Table 32). The rxn mixture was flushed with N₂, heated to 110° C. in a sealed vial and stirred for 1h. It was partitioned between water and DCM and the org. phase was washed with brine, dried over MgSO₄ and concentrated in vacuo. The crude was purified by CC using Hept/EtOAc.

TABLE 32

| BB-31 | Name | Reactant amine G | Reactant halide | $t_R$ [min] (LC/MS method) | MS-data m/z [M + H]⁺ |
|---|---|---|---|---|---|
| BB-31-1 | 3-(tert-Butyl-dimethyl-silanyloxy)-1-(2-fluoro-6-methyl-phenyl)-azetidine | 3-[(tert-Butyl dimethylsilanyl)oxy] azetidine | 2-Bromo-3-fluorotoluene | 1.21 (I) | 296.28 |

Synthesis of Building Blocks BB-32

To a soln. of intermediate BB-31 (1 eq) in THF (3 mL/mmol) was added dropwise at 0° C. a 1M soln. of TBAF (2 eq) in THF. The rxn mixture was stirred for 30 min at 0° C. (see Table 33) and partitioned between DCM and water. The org. phase was washed with brine, dried over MgSO$_4$ and concentrated in vacuo. The crude was purified by CC using DCM/MeOH.

TABLE 33

| BB-32 | Name | Reactant BB-31 | $t_R$ [min] (LC/MS method) | MS-data m/z [M + H]$^+$ |
|---|---|---|---|---|
| BB-32-1 | 1-(2-Fluoro-6-methyl-phenyl)-azetidin-3-ol | BB-31-1 | 0.60 (I) | 182.35 |

Synthesis of Building Blocks BB-33

To a soln. of intermediate BB-32 (1 eq), TEA (2 eq) and catalytic amount of DMAP (0.25 eq) in DCM (5 mL/mmol) was added at 0° C. p-toluenesulfonyl chloride (1.3 eq). The rxn mixture was allowed to warm to RT and stirred for 2h (see Table 34). When necessary to reach completion of the rxn, an extra amount of p-toluenesulfonyl chloride (0.3 eq) was added. It was partitioned between water and DCM and the org. phase was washed with brine, dried over MgSO$_4$ and concentrated in vacuo. The crude was purified by CC using DCM.

TABLE 34

| BB-33 | Name | Reactant BB-32 | $t_R$ [min] (LC/MS method) | MS-data m/z [M + H]$^+$ |
|---|---|---|---|---|
| BB-33-1 | Toluene-4-sulfonic acid 1-(2-fluoro-6-methyl-phenyl)-azetidin-3-yl ester | BB-32-2 | 1.08 (I) | 336.15 |

Building Blocks BB-34

| BB-34 | Name | |
|---|---|---|
| BB-34-1 | 3-amino-4-bromopyrazole | commercially available |
| BB-34-2 | 4-Bromo-1-methyl-1H-pyrazol-3-ylamine | |

Synthesis of Intermediates of Formula A-1

Method A (NaBH(OAc)$_3$/THF)

To a soln. of aldehyde BB-4 (1 eq) and amine BB-7 (1 to 1.15 eq) in THF (4 to 8 mL/mmol) were added AcOH (1.5 eq) and the rxn mixture was stirred for 20 min at RT. NaBH(OAc)$_3$ (1.5 eq) was added portionwise and the rxn mixture was stirred at RT for a given time (see Table 35). When necessary to reach completion of the rxn, an extra portion of NaBH(OAc)$_3$ (1 eq) was added at RT. It was partitioned between EtOAc and a sat. aq. soln. of NaHCO$_3$. The org. phase was washed with brine, dried over MgSO$_4$ and concentrated in vacuo. The crude was purified by CC using Hept/EtOAc/MeOH.

Method B (NaBH$_4$/TFE)

A soln. of aldehyde BB-4 (1 eq) and amine BB-7 (1 to 1.1 eq) in TFE (2 mL/mmol) was stirred for 10 min at 40° C. and cooled to 0° C. NaBH$_4$ (1.2 eq) was added portionwise and the rxn mixture was stirred at 40° C. for a given time (see Table 35). It was quenched with a sat. aq. soln. of NaHCO$_3$ and extracted with EtOAc. The combined org. phases were washed with brine, dried over MgSO$_4$ and concentrated in vacuo. The crude was purified by CC using Hept/EtOAc.

TABLE 35

| A-1 | Name | Reactant BB-4 | Reactant BB-7 | Method time [h] | $t_R$ [min] (LC/MS method) | MS-data m/z [M + H]$^+$ |
|---|---|---|---|---|---|---|
| A-1-1A | [1-(2-Fluoro-6-methyl-phenyl)-piperidin-4-yl]-[4-nitro-2-(2-trimethylsilanyl-ethoxymethyl)-2H-pyrazol-3-ylmethyl]-amine | BB-4-1A | BB-7-1 | A 18 | 0.95 (I) | 464.26 |
| A-1-1B | [1-(2-Fluoro-6-methyl-phenyl)-piperidin-4-yl]-[4-nitro-1-(2-trimethylsilanyl-ethoxymethyl)-1H-pyrazol-3-ylmethyl]-amine | BB-4-1B | BB-7-1 | A 18 | 0.93 (I) | 464.29 |
| A-1-2 | [1-(2-Fluoro-6-methyl-phenyl)-piperidin-4-yl]-[3-nitro-1-(2-trimethylsilanyl-ethoxymethyl)-1H-pyrazol-4-ylmethyl]-amine | BB-4-2 | BB-7-1 | A 2 | 0.94 (I) | 464.25 |
| A-1-3 | [1-(2-Fluoro-6-methyl-phenyl)-piperidin-4-yl]-(1-methyl-4-nitro-1H-pyrazol-3-ylmethyl)-amine | BB-4-3 | BB-7-1 | A 1 | 0.69 (II) | 348.21 |
| A-1-4 | [1-(2-Fluoro-6-methyl-phenyl)-piperidin-4-yl]-[5-nitro-3-(2-trimethylsilanyl-ethoxymethyl)-3H-imidazol-4-ylmethyl]-amine | BB-4-4 | BB-7-1 | B 1 | 0.85 (II) | 464.22 |
| A-1-5 | (2'-Methoxy-4'-methyl-3,4,5,6-tetrahydro-2H-[1,3']bipyridinyl-4-yl)-[3-nitro-1-(2-trimethylsilanyl-ethoxymethyl)-1H-pyrazol-4-ylmethyl]-amine | BB-4-2 | BB-7-2 | A 24 | 0.93 (I) | 477.23 |

TABLE 35-continued

| A-1 | Name | Reactant BB-4 | Reactant BB-7 | Method time [h] | $t_R$ [min] (LC/MS method) | MS-data m/z $[M + H]^+$ |
|---|---|---|---|---|---|---|
| A-1-6 | (2'-Methoxy-4'-methyl-3,4,5,6-tetrahydro-2H-[1,3']bipyridinyl-4-yl)-[4-nitro-2-(2-trimethylsilanyl-ethoxymethyl)-2H-pyrazol-3-ylmethyl]-amine | BB-4-1A | BB-7-2 | A 24 | 0.93 (I) | 477.25 |
| A-1-7 | [1-(2-Fluoro-6-methyl-phenyl)-4-methyl-piperidin-4-yl]-(1-methyl-3-nitro-1H-pyrazol-4-ylmethyl)-amine | BB-4-5 | BB-7-3 | A 18 | 0.76 (I) | 362.21 |
| A-1-8 | [1-(2-Fluoro-6-methyl-phenyl)-3-methyl-pyrrolidin-3-yl]-(1-methyl-3-nitro-1H-pyrazol-4-ylmethyl)-amine | BB-4-5 | BB-7-4 | A 18 | 0.77 (I) | 348.21 |

Synthesis of Intermediates of Formula A-2

Method a (Nitro Reduction from A-1)

To a soln. of intermediate A-1 (1 eq) in EtOH (3.5 to 7.4 mL/mmol) was added 10% Pd/C moistened with ~50% water (0.02 eq) and the rxn mixture was hydrogenated under atmospheric pressure for a given time (see Table 36). It was filtered over a pad of celite and the filtrate was concentrated in vacuo. When necessary, the crude was purified by CC using Hept/EtOAc or DCM/MeOH.

Method B1 (Reductive Amination from BB-5 and BB-8 Using NaBH(OAc)$_3$)

To a soln. of amine BB-5 (1 eq) and ketone BB-8 (1.05 to 1.2 eq) in THF (4 mL/mmol) was added AcOH (1.5 eq) and the rxn mixture was stirred for 5 min at RT. NaBH(OAc)$_3$ (1.5 eq) was added portionwise and the rxn mixture was stirred at RT for a given time (see Table 36). It was acidified with a 1M aq. soln. of HCl until pH-3-4 and extracted with DCM. The aq. phase was basified with a sat. aq. soln. of NaHCO$_3$ and extracted with DCM. The combined org. phases were dried over MgSO$_4$ and concentrated in vacuo. When necessary, the crude was purified by CC using Hept/EtOAc/MeOH.

Method B2 (Reductive Amination from BB-5 and BB-8 Using NaBH$_4$)

A soln. of amine BB-5 (1 eq) and ketone BB-8 (1.05 eq) in MeOH (4 mL/mmol) was stirred for 18h at RT. NaBH$_4$ (1.6 eq) was added portionwise at 0° C. and the rxn mixture was stirred at RT for a given time (see Table 36). It was quenched with H$_2$O at 0° C., basified with a 1M aq. soln. of NaOH and extracted with DCM. The combined org. phases were dried over MgSO$_4$ and concentrated in vacuo. When necessary, the crude was purified by CC using EtOAc/MeOH.

Method C (Reductive Amination from BB-6 and BB-7)

To a soln. of aldehyde BB-6 (1 eq) and amine BB-7 (1.1 eq) in THF (4 mL/mmol) was added AcOH (1.5 eq) and the rxn mixture was stirred for 5 min at RT. NaBH(OAc)$_3$ (1.5 eq) was added portionwise and the rxn mixture was stirred at RT for a given time (see Table 36). It was acidified with a 10% aq. soln. of citric acid and extracted with DCM. The aq. phase was basified with a 1M aq. soln. of NaOH and extracted with DCM. The combined org. phases were dried over MgSO$_4$ and concentrated in vacuo. When necessary, the crude was purified by prep. LC-MS using method 7.

Method D (Reductive Amination from BB-7 and BB-20)

A soln. of aldehyde BB-20 (1 eq) in TFE (2 mL/mmol) was stirred at 35° C. for 5 min. Amine BB-7 (1 eq) was added and the rxn mixture stirred at 35° C. for 5 min. NaBH$_4$ (1.2 eq) was added portionwise and the rxn mixture was stirred at 3500 for a given time (see Table 36). It was quenched with H$_2$O, basified with a 1 M aq. sol. of NaOH and extracted with DCM. The combined org. phases were dried over MgSO$_4$ and concentrated in vacuo.

Method E (Boc Cleavage from A-4)

To a soln. of intermediate A-4 (1 eq) in DCM (5 mL/mmol) was added TEA (1.5 to 2 mL/mmol) at 0° C. and the rxn mixture was stirred at RT for a given time (see Table 36). It was cooled to 0°, quenched with a 1M aq. soln. of NaOH until pH reached 12 to 13 and extracted with DCM. The combined org. phases were washed with brine, dried over MgSO$_4$ and concentrated in vacuo.

Method F (Nucleophilic Substitution of BB-5 on BB-33)

A soln. of intermediate BB-33 (1 eq) and amine BB-5 (3 eq) in MeCN (5.7 mL/mmol) was heated at 110° C. under microwave irradiation for a given time (see Table 36) and filtered. The filtrate was purified by prep. LC-MS using method 12.

TABLE 36

| A-2 | Name | Reactant A-1, BB-5, BB-6, BB-20 or A-4 | Reactant BB-8, BB-7 or BB-33 | Method T [° C.] time [h] | $t_R$ [min] (LC/MS method) | MS-data m/z $[M + H]^+$ |
|---|---|---|---|---|---|---|
| A-2-1A | [4-Amino-2-(2-trimethylsilanyl-ethoxymethyl)-2H-pyrazol-3-ylmethyl]-[1-(2-fluoro-6-methyl-phenyl)-piperidin-4-yl]-amine | A-1-1A | — | A RT 3 | 0.85 (I) | 433.86 |
| A-2-1B | [4-Amino-1-(2-trimethylsilanyl-ethoxymethyl)-1H-pyrazol-3-ylmethyl]-[1-(2-fluoro-6-methyl-phenyl)-piperidin-4-yl]-amine | A-1-1B | — | A RT 2 | 0.81 (I) | 433.80 |

TABLE 36-continued

| A-2 | Name | Reactant A-1, BB-5, BB-6, BB-20 or A-4 | Reactant BB-8, BB-7 or BB-33 | Method T [° C.] time [h] | $t_R$ [min] (LC/MS method) | MS-data m/z $[M + H]^+$ |
|---|---|---|---|---|---|---|
| A-2-2 | [3-Amino-1-(2-trimethylsilanyl-ethoxymethyl)-1H-pyrazol-4-ylmethyl]-[1-(2-fluoro-6-methyl-phenyl)-piperidin-4-yl]-amine | A-1-2 | — | A RT 18 | 0.85 (I) | 434.10 |
| A-2-3 | (4-Amino-1-methyl-1H-pyrazol-3-ylmethyl)-[1-(2-fluoro-6-methyl-phenyl)-piperidin-4-yl]-amine | A-1-3 | — | A RT 2 | 0.56 (II) | 318.13 |
| A-2-4 | [5-Amino-3-(2-trimethylsilanyl-ethoxymethyl)-3H-imidazol-4-ylmethyl]-[1-(2-fluoro-6-methyl-phenyl)-piperidin-4-yl]-amine | A-1-4 | — | A (EtOAc replacing EtOH) RT 1.5 | 0.72 (II) | 434.23 |
| A-2-5 | (3-Amino-1-methyl-1H-pyrazol-4-ylmethyl)-[1-(2-fluoro-6-methyl-phenyl)-piperidin-4-yl]-amine | BB-5-1 | BB-8-1 | B RT 0.5 | 0.61 (II) | 318.13 |
| A-2-6 | 4-{[(R)-1-(2-Fluoro-6-methyl-phenyl)-pyrrolidin-3-ylamino]-methyl}-1-methyl-1H-pyrazol-3-ylamine | BB-6-1 | BB-7-5 | C RT 2.5 | 0.60 (II) | 304.12 |
| A-2-7 | (5-Amino-1-benzyl-1H-[1,2,3]triazol-4-ylmethyl)-[1-(2-fluoro-6-methyl-phenyl)-piperidin-4-yl]-amine | BB-5-2 | BB-8-1 | B RT 18 | 0.71 (II) | 395.21 |
| A-2-8 | (5-Amino-2-methyl-thiazol-4-ylmethyl)-[1-(2-fluoro-6-methyl-phenyl)-piperidin-4-yl]-amine | BB-20-1 | BB-7-1 | D 35 18 | 0.67 (II) | 335.11 |
| A-2-9 | (5-Amino-2-methyl-2H-[1,2,3]triazol-4-ylmethyl)-[1-(2-fluoro-6-methyl-phenyl)-piperidin-4-yl]-amine | A-4-1 | — | E RT 3 | 0.65 (II) | 319.17 |
| A-2-10 | (3-Amino-1-methyl-1H-pyrazol-4-ylmethyl)-(2'-methoxy-4'-methyl-3,4,5,6-tetrahydro-2H-[1,3']bipyridinyl-4-y1)-amine | BB-5-1 | BB-8-2 | B RT 1 | 0.53 (I) | 331.24 |
| A-2-11 | (5-Amino-2-methyl-2H-[1,2,3]triazol-4-ylmethyl)-(2'-methoxy-4'-methyl-3,4,5,6-tetrahydro-2H-[1,3']bipyridinyl-4-yl)-amine | A-4-2 | — | E RT 4 | 0.57 (I) | 332.17 |
| A-2-12 | [3-Amino-1-(2-trimethylsilanyl-ethoxymethyl)-1H-pyrazol-4-ylmethyl]-(2'-methoxy-4'-methyl-3,4,5,6-tetrahydro-2H-[1,3']bipyridinyl-4-yl)-amine | A-1-5 | — | A RT 5 | 0.79 (I) | 447.31 |
| A-2-13 | [4-Amino-2-(2-trimethylsilanyl-ethoxymethyl)-2H-pyrazol-3-ylmethyl]-(2'-methoxy-4'-methyl-3,4,5,6-tetrahydro-2H-[1,3']bipyridinyl-4-yl)-amine | A-1-6 | — | A RT 2.5 | 0.80 (I) | 447.30 |
| A-2-14 | (3-Amino-1-methyl-1H-pyrazol-4-ylmethyl)-[1-(2-fluoro-6-methyl-phenyl)-4-methyl-piperidin-4-yl]-amine | A-1-7 | — | A RT 4 | 0.67 (I) | 332.27 |
| A-2-15 | (3-Amino-1-methyl-1H-pyrazol-4-ylmethyl)-[1-(2-fluoro-6-methyl-phenyl)-azepan-4-yl]-amine | BB-5-1 | BB-8-3 | B RT 18 | 0.69 (I) | 332.25 |
| A-2-16 | 4-{[1-(2-Fluoro-6-methyl-phenyl)-3-methyl-pyrrolidin-3-ylamino]-methyl}-1-methyl-1H-pyrazol-3-ylamine | A-1-8 | — | A RT 2 | 0.66 (I) | 318.22 |
| A-2-17 | (3-Amino-1-methyl-1H-pyrazol-4-ylmethyl)-[1-(2-fluoro-6-methyl-phenyl)-piperidin-3-yl]-amine | BB-5-1 | BB-8-4 | B RT 20 | 0.64 (I) | 318.22 |
| A-2-18 | 4-{[1-(2-Fluoro-6-methyl-phenyl)-azetidin-3-ylamino]-methyl}-1-methyl-1H-pyrazol-3-ylamine | BB-5- | BB-33-1 | F 110 1 | 0.57 (I) | 290.04 |

Synthesis of Intermediates of Formula A-3

Method A1 (or A2, Respectively) (Cyclisation from A-2)

To a soln. of intermediate A-2 (1 eq) in MeCN (or DCM, respectively) (3.7 to 10 mL/mmol) was added CDI (or DSC, respectively) (0.2 to 2 eq) and the rxn mixture was stirred at a given temperature for a given time (see Table 37). When necessary to reach completion of the rxn an extra amount of CDI (0.5 to 1 eq) was added. The solvent was evaporated off and the residue was partitioned between EtOAc or DCM and water. The org. phase was washed with brine, dried over MgSO$_4$ and concentrated in vacuo. When necessary, the crude was purified by CC using Hept/EtOAc or DCM/MeOH, by precipitation from DCM/MeOH/Et$_2$O or MeCN or by prep. LC-MS using method 12.

Method B (Cyclisation from D-1)

A soln. of intermediate D-1 (1 eq) in DMF (8 mL/mmol) was heated at 1200 under microwave irradiation for a given time (see Table 37) and partitioned between EtOAc and H$_2$O. The org. phase was washed with H$_2$O and brine, dried over MgSO$_4$ and concentrated in vacuo. The crude was purified by CC using Hept/EtOAc.

TABLE 37

| A-3 | Name | Reactant A-2 or D-1 | Method T [° C.] time [h] | $t_R$ [min] (LC/MS method) | MS-data m/z [M + H]$^+$ |
|---|---|---|---|---|---|
| A-3-1A | 6-[1-(2-Fluoro-6-methyl-phenyl)-piperidin-4-yl]-1-(2-trimethylsilanyl-ethoxymethyl)-1,4,6,7-tetrahydro-pyrazolo[4,3-d]pyrimidin-5-one | A-2-1A | A1 RT 0.5 | 1.15 (I) | 460.16 |
| A-3-1B | 6-[1-(2-Fluoro-6-methyl-phenyl)-piperidin-4-yl]-2-(2-trimethylsilanyl-ethoxymethyl)-2,4,6,7-tetrahydro-pyrazolo[4,3-d]pyrimidin-5-one | A-2-1B | A1 RT 0.8 | 1.13 (I) | 460.28 |
| A-3-2 | 5-[1-(2-Fluoro-6-methyl-phenyl)-piperidin-4-yl]-2-(2-trimethylsilanyl-ethoxymethyl)-2,4,5,7-tetrahydro-pyrazolo[3,4-d]pyrimidin-6-one | A-2-2 | A1 RT 1.5 | 1.16 (I) | 460.26 |
| A-3-3 | 6-[1-(2-Fluoro-6-methyl-phenyl)-piperidin-4-yl]-2-methyl-2,4,6,7-tetrahydro-pyrazolo[4,3-d]pyrimidin-5-one | A-2-3 | A1 RT 18 | 0.85 (II) | 344.10 |
| A-3-4 | 1-[1-(2-Fluoro-6-methyl-phenyl)-piperidin-4-yl]-7-(2-trimethylsilanyl-ethoxymethyl)-1,3,6,7-tetrahydro-purin-2-one | A-2-4 | A1 RT 18 | 1.07 (II) | 460.24 |
| A-3-5 | 5-[1-(2-Fluoro-6-methyl-phenyl)-piperidin-4-yl]-2-methyl-2,4,5,7-tetrahydro-pyrazolo[3,4-d]pyrimidin-6-one | A-2-5 | A1 RT 1.5 | 0.93 (II) | 344.18 |
| A-3-6 | 5-[(R)-1-(2-Fluoro-6-methyl-phenyl)-pyrrolidin-3-yl]-2-methyl-2,4,5,7-tetrahydro-pyrazolo[3,4-d]pyrimidin-6-one | A-2-6 | A1 RT 2 | 0.70 (II) | 330.09 |
| A-3-7 | 3-Benzyl-6-[1-(2-fluoro-6-methyl-phenyl)-piperidin-4-yl]-3,4,6,7-tetrahydro-[1,2,3]triazolo[4,5-d]pyrimidin-5-one | A-2-7 | A1 (THF replacing MeCN) 80 24 | 0.93 (II) | 421.13 |
| A-3-8 | 6-[1-(2-Fluoro-6-methyl-phenyl)-piperidin-4-yl]-2-methyl-6,7-dihydro-4H-oxazolo[5,4-d]pyrimidin-5-one | D-1-1 | B 120 0.13 | 0.89 (II) | 345.19 |
| A-3-9 | 6-[1-(2-Fluoro-6-methyl-phenyl)-piperidin-4-yl]-2-methyl-6,7-dihydro-4H-thiazolo[5,4-d]pyrimidin-5-one | A-2-8 | A1 RT 24 | 0.90 (II) | 361.07 |
| A-3-10 | 6-[1-(2-Fluoro-6-methyl-phenyl)-piperidin-4-yl]-2-methyl-2,4,6,7-tetrahydro-[1,2,3]triazolo[4,5-d]pyrimidin-5-one | A-2-9 | A1 RT 3.5 | 0.89 (II) | 345.20 |
| A-3-11 | 5-(2'-Methoxy-4'-methyl-3,4,5,6-tetrahydro-2H-[1,3']bipyridinyl-4-yl)-2-methyl-2,4,5,7-tetrahydro-pyrazolo[3,4-d]pyrimidin-6-one | A-2-10 | A1 RT 0.25 | 0.83 (I) | 357.21 |
| A-3-12 | 6-(2'-Methoxy-4'-methyl-3,4,5,6-tetrahydro-2H-[1,3']bipyridinyl-4-yl)-2-methyl-2,4,6,7-tetrahydro-[1,2,3]triazolo[4,5-d]pyrimidin-5-one | A-2-11 | A1 RT 18 | 0.81 (I) | 358.21 |
| A-3-13 | 5-(2'-Methoxy-4'-methyl-3,4,5,6-tetrahydro-2H-[1,3']bipyridinyl-4-yl)-2-(2-trimethylsilanyl-ethoxymethyl)-2,4,5,7-tetrahydro-pyrazolo[3,4-d]pyrimidin-6-one | A-2-12 | A1 RT 2 | 1.06 (I) | 473.29 |
| A-3-14 | 6-(2'-Methoxy-4'-methyl-3,4,5,6-tetrahydro-2H-[1,3']bipyridinyl-4-yl)-1-(2-trimethylsilanyl-ethoxymethyl)-1,4,6,7-tetrahydro-pyrazolo[4,3-d]pyrimidin-5-one | A-2-13 | A1 RT 1 | 1.06 (I) | 473.27 |
| A-3-15 | 5-[1-(2-Fluoro-6-methyl-phenyl)-4-methyl-piperidin-4-yl]-2-methyl-2,4,5,7-tetrahydro-pyrazolo[3,4-d]pyrimidin-6-one | A-2-14 | A1 RT 18 | 1.02 (I) | 358.22 |
| A-3-16 | 5-[1-(2-Fluoro-6-methyl-phenyl)-azepan-4-yl]-2-methyl-2,4,5,7-tetrahydro-pyrazolo[3,4-d]pyrimidin-6-one | A-2-15 | A1 RT 2 | 1.03 (I) | 358.21 |

TABLE 37-continued

| A-3 | Name | Reactant A-2 or D-1 | Method T [° C.] time [h] | $t_R$ [min] (LC/MS method) | MS-data m/z [M + H]$^+$ |
|---|---|---|---|---|---|
| A-3-17 | 5-[1-(2-Fluoro-6-methyl-phenyl)-3-methyl-pyrrolidin-3-yl]-2-methyl-2,4,5,7-tetrahydro-pyrazolo[3,4-d]pyrimidin-6-one | A-2-16 | A1 RT 0.5 | 0.94 (I) | 344.18 |
| A-3-18 | 5-[1-(2-Fluoro-6-methyl-phenyl)-piperidin-3-yl]-2-methyl-2,4,5,7-tetrahydro-pyrazolo[3,4-d]pyrimidin-6-one | A-2-17 | A1 RT 1 | 0.99 (I) | 344.16 |
| A-3-19 | 5-[1-(2-Fluoro-6-methyl-phenyl)-azetidin-3-yl]-2-methyl-2,4,5,7-tetrahydro-pyrazolo[3,4-d]pyrimidin-6-one | A-2-18 | A2 45 18 | 0.61 (I) | 316.17 |

Synthesis of Intermediates of Formula A-4

To a soln. of amine BB-24 (1 eq) and ketone BB-8 (1.1 to 1.2 eq) in THF (10 mL/mmol) was added AcOH (1.5 eq) and the rxn mixture was stirred for 5 min at RT. NaBH(OAc)$_3$ (1.5 eq) was added portionwise and the rxn mixture was stirred at RT for a given time (see Table 38). It was quenched with a sat. aq. soln. of NaHCO$_3$ and extracted with DCM. The combined org. phases were washed with brine, dried over MgSO$_4$ and concentrated in vacuo. The crude was purified by CC using Hept/EtOAc/MeOH.

TABLE 38

| A-4 | Name | Reactant BB-24 | Reactant BB-8 | time [h] | $t_R$ [min] (LC/MS method) | MS-data m/z [M + H]$^+$ |
|---|---|---|---|---|---|---|
| A-4-1 | (5-{[1-(2-Fluoro-6-methyl-phenyl)-piperidin-4-ylamino]-methyl}-2-methyl-2H-[1,2,3]triazol-4-yl)-carbamic acid tert-butyl ester | BB-24-1 | BB-8-1 | 2 | 0.80 (II) | 419.19 |
| A-4-2 | {5-[(2'-Methoxy-4'-methyl-3,4,5,6-tetrahydro-2H-[1,3']bipyridinyl-4-ylamino)-methyl]-2-methyl-2H-[1,2,3]triazol-4-yl}-carbamic acid tert-butyl ester | BB-24-1 | BB-8-2 | 1.5 | 0.78 (I) | 432.29 |

Synthesis of Intermediates of Formula B-1

To a suspension of intermediate A-2 (1 eq) in anh. THF (3 mL/mmol) was added TEA (3 eq). The rxn mixture was cooled to 0° C. and Boc$_2$O (1.1 eq) was added. It was stirred for 10 min at 0° C. and at RT for a given time (see Table 39) and was partitioned between EtOAc and water. The org. phase was washed with brine, dried over MgSO$_4$ and concentrated in vacuo. When necessary, the crude was purified by CC using DCM/MeOH or Hept/EtOAc.

Synthesis of Intermediates of Formula B-2

Method A (NaBH(OAc)$_4$/AcOH/THF)

To a soln. of amine B-1 (1 eq) and aldehyde BB-12 (1.2 eq) in THF (4 to 5 mL/mmol) was added AcOH (1.5 eq) and the rxn mixture was stirred for 5 min at RT. NaBH(OAc)$_3$ (1.5 to 2 eq) was added portionwise and the rxn mixture was stirred at RT for a given time (see Table 40). When necessary to reach completion of the rxn an extra amount of NaBH(OAc)$_3$ (0.2 to 1 eq) was added. The rxn mixture was quenched with a sat. aq. soln. of NaHCO$_3$ and extracted with DCM. The combined org. phases were washed with brine, dried over MgSO$_4$ and concentrated in vacuo. When necessary, the crude was purified by CC using Hept/EtOAc/MeOH.

Method B (NaBH$_4$/TFE)

A soln. of amine B-1 (1 eq) and aldehyde BB-12 (1 eq) in TFE (2 mL/mmol) was stirred for 10 min at 35° C. and cooled to 0° C. NaBH$_4$ (1.2 eq) was added portionwise and the rxn mixture was stirred for a given time at a given temperature (see Table 40). When necessary to reach

TABLE 39

| B-1 | Name | Reactant A-2 | T [° C.] time [h] | $t_R$ [min] (LC/MS method) | MS-data m/z [M + H]$^+$ |
|---|---|---|---|---|---|
| B-1-1 | (3-Amino-1-methyl-1H-pyrazol-4-ylmethyl)-[1-(2-fluoro-6-methyl-phenyl)-piperidin-4-yl]-carbamic acid tert-butyl ester | A-2-5 | RT 18 | 0.91 (II) | 418.08 | completion of the rxn an extra amount of aldehyde BB-12 (1 eq) was added. It was quenched with a sat. aq. soln. of NaHCO₃ and extracted with DCM. The combined org. phases were washed with brine, dried over MgSO₄ and concentrated in vacuo. The crude was purified by CC using Hept/EtOAc.

Synthesis of Intermediates of Formula C-1

Method A (NaBH(OAc)₄/AcOH/THF)

To a soln. of amine BB-5 (1 eq) and ketone BB-13 (1.1 to 1.2 eq) in THF (4 mL/mmol) was added AcOH (1.5 eq) and

TABLE 40

| B-2 | Name | Reactant B-1 | Reactant BB-12 | Method T [° C.] time [h] | $t_R$ [min] (LC/MS method) | MS-data m/z $[M + H]^+$ |
|---|---|---|---|---|---|---|
| B-2-1 | [1-(2-Fluoro-6-methyl-phenyl)-piperidin-4-yl]-{1-methyl-3-[(3-trifluoromethyl-pyridin-2-ylmethyl)-amino]-1H-pyrazol-4-ylmethyl}-carbamic acid tert-butyl ester | B-1-1 | BB-12-1 | A RT 48 | 1.03 (II) | 577.03 |
| B-2-2 | {3-[(6-Chloro-3-trifluoromethyl-pyridin-2-ylmethyl)-amino]-1-methyl-1H-pyrazol-4-ylmethyl}-[1-(2-fluoro-6-methyl-phenyl)-piperidin-4-yl]-carbamic acid tert-butyl ester | B-1-1 | BB-12-2 | A RT 48 | 1.08 (II) | 611.06 |
| B-2-3 | [1-(2-Fluoro-6-methyl-phenyl)-piperidin-4-yl]-[3-(2-fluoro-6-trifluoromethyl-benzylamino)-1-methyl-1H-pyrazol-4-ylmethyl]-carbamic acid tert-butyl ester | B-1-1 | BB-12-3 | B 35 4 | 1.09 (II) | 594.02 |

Synthesis of Intermediates of Formula B-3

To a soln. of intermediate B-2 (1 eq) in DCM (4 to 16.5 mL/mmol) was added TEA (1 to 3.2 mL/mmol) and the rxn mixture was stirred at RT for a given time (see Table 41). It was quenched with a 2M aq. soln. of NaOH until pH 12-13 and extracted with DCM. The combined org. phases were washed with brine, dried over MgSO₄ and concentrated in vacuo. When necessary, the crude was purified by CC using DCM/MeOH.

the rxn mixture was stirred for 5 min at RT. NaBH(OAc)₃ (1.5 eq) was added portionwise and the rxn mixture was stirred at RT for a given time (see Table 42). It was quenched with a 1M aq. soln. of NaOH until pH 10 and extracted with DCM. The combined org. phases were dried over MgSO₄ and concentrated in vacuo. When necessary, the crude was purified by CC using EtOAc/MeOH.

Method B (NaBH₄/TFE)

A soln. of aldehyde BB-14 (1 eq) and amine BB-15 (1.1 eq) in TFE (2 mL/mmol) was stirred for 5 min at 40° C. and

TABLE 41

| B-3 | Name | Reactant B-2 | T [° C.] time [h] | $t_R$ [min] (LC/MS method) | MS-data m/z $[M + H]^+$ |
|---|---|---|---|---|---|
| B-3-1 | [1-(2-Fluoro-6-methyl-phenyl)-piperidin-4-yl]-{1-methyl-3-[(3-trifluoromethyl-pyridin-2-ylmethyl)-amino]-1H-pyrazol-4-ylmethyl}-amine | B-2-1 | RT 4 | 0.77 (II) | 477.10 |
| B-3-2 | {3-[(6-Chloro-3-trifluoromethyl-pyridin-2-ylmethyl)-amino]-1-methyl-1H-pyrazol-4-ylmethyl}-[1-(2-fluoro-6-methyl-phenyl)-piperidin-4-yl]-amine | B-2-2 | RT 3.5 | 0.82 (II) | 511.08 |
| B-3-3 | [1-(2-Fluoro-6-methyl-phenyl)-piperidin-4-yl]-[3-(2-fluoro-6-trifluoromethyl-benzylamino)-1-methyl-1H-pyrazol-4-ylmethyl]-amine | B-2-3 | RT 1 | 0.82 (II) | 494.10 | cooled to 0° C. NaBH₄ (1.2 eq) was added portionwise and the rxn mixture was stirred for a given time at a given temperature (see Table 42). It was quenched with a sat. aq. soln. of NaHCO₃ and extracted with DCM. The combined org. phases were washed with brine, dried over MgSO₄ and concentrated in vacuo. When necessary, the crude was purified by CC using Hept/EtOAc.

Method C (Nitro Reduction from C-4)

To a soln. of intermediate C-4 (1 eq) in EtOH (4.5 mL/mmol) was added 10% Pd/C moistened with ~50% water (0.02 eq) and the rxn mixture was hydrogenated under atmospheric pressure for a given time (see Table 42). It was filtered over a pad of celite and the filtrate was concentrated in vacuo.

TABLE 42

| C-1 | Name | Reactant BB-5 or BB-14 | Reactant BB-13 or BB-15 | Method T [° C.] time [h] | $t_R$ [min] (LC/MS method) | MS-data m/z $[M + H]^+$ |
|---|---|---|---|---|---|---|
| C-1-1 | 3-[(3-Amino-1-methyl-1H-pyrazol-4-ylmethyl)-amino]-pyrrolidine-1-carboxylic acid tert-butyl ester | BB-5-1 | BB-13-1 | A RT 18 | 0.49 (II) | 296.16 |
| C-1-2 | 4-[(3-Amino-1-methyl-1H-pyrazol-4-ylmethyl)-amino]-piperidine-1-carboxylic acid tert-butyl ester | BB-5-1 | BB-13-2 | A RT 1 | 0.51 (II) | 310.13 |
| C-1-3 | 4-[(3-Amino-1-methyl-1H-pyrazol-4-ylmethyl)-amino]-azepane-1-carboxylic acid tert-butyl ester | BB-14-1 | BB-15-1 | B 40 1 | 0.53 (II) | 324.19 |
| C-1-4 | 4-[(4-Amino-1-methyl-1H-pyrazol-3-ylmethyl)-amino]-piperidine-1-carboxylic acid tert-butyl ester | | C-4-1 | C RT 4.5 | 0.48 (I) | 310.28 |

Synthesis of Intermediates of Formula C-2

To a soln. of intermediate C-1 (1 eq) in MeCN (3.7 mL/mmol) was added CDI (1.2 to 2 eq) and the rxn mixture was stirred at a given temperature for a given time (see Table 43). The solvent was evaporated off and the residue was partitioned between DCM and water. The org. phase was washed with brine, dried over MgSO₄ and concentrated in vacuo. When necessary, the crude was purified by CC using Hept/EtOAc or triturated in MeCN and the solid was filtered.

TABLE 43

| C-2 | Name | Reactant C-1 | T [° C.] time [h] | $t_R$ [min] (LC/MS method) | MS-data m/z $[M + H]^+$ |
|---|---|---|---|---|---|
| C-2-1 | 3-(2-Methyl-6-oxo-2,4,6,7-tetrahydro-pyrazolo[3,4-d]pyrimidin-5-yl)-pyrrolidine-1-carboxylic acid tert-butyl ester | C-1-1 | RT 0.5 | 0.73 (II) | 321.98 |
| C-2-2 | 4-(2-Methyl-6-oxo-2,4,6,7-tetrahydro-pyrazolo[3,4-d]pyrimidin-5-yl)-piperidine-1-carboxylic acid tert-butyl ester | C-1-2 | RT 0.7 | 0.75 (II) | 336.14 |
| C-2-3 | 4-(2-Methyl-6-oxo-2,4,6,7-tetrahydro-pyrazolo[3,4-d]pyrimidin-5-yl)-azepane-1-carboxylic acid tert-butyl ester | C-1-3 | RT 18 | 0.77 (II) | 350.24 |
| C-2-4 | 4-(2-Methyl-5-oxo-2,4,5,7-tetrahydro-pyrazolo[4,3-d]pyrimidin-6-yl)-piperidine-1-carboxylic acid tert-butyl ester | C-1-4 | RT 0.5 | 0.75 (I) | 336.38 |

Synthesis of Intermediates of Formula C-3

To a soln. of intermediate Ii (1 eq) in DCM (4 to 10 mL/mmol) was added TEA (1 to 1.6 mL/mmol) at 0° C. and the rxn mixture was stirred at RT for a given time (see Table 44). It was cooled to 0° C., quenched with a 32% aq. soln. of NaOH until pH reached 12 to 13 and extracted with DCM. The combined org. phases were washed with brine, dried over $MgSO_4$ and concentrated in vacuo.

TABLE 44

| C-3 | Name | Reactant Ii | T [° C.] time [h] | $t_R$ [min] (LC/MS method) | MS-data m/z $[M + H]^+$ |
|---|---|---|---|---|---|
| C-3-1 | 2-Methyl-5-pyrrolidin-3-yl-7-(2-trifluoromethyl-benzyl)-2,4,5,7-tetrahydro-pyrazolo[3,4-d]pyrimidin-6-one | Ii-1 | RT 18 | 0.64 (II) | 380.17 |
| C-3-2 | 2-Methyl-5-piperidin-4-yl-7-(2-trifluoromethyl-benzyl)-2,4,5,7-tetrahydro-pyrazolo[3,4-d]pyrimidin-6-one | Ii-2 | RT 0.75 | 0.62 (II) | 394.08 |
| C-3-3 | 5-Azepan-4-yl-2-methyl-7-(2-trifluoromethyl-benzyl)-2,4,5,7-tetrahydro-pyrazolo[3,4-d]pyrimidin-6-one | Ii-3 | RT 0.5 | 0.64 (II) | 408.22 |
| C-3-4 | 2-Methyl-6-piperidin-4-yl-4-(2-trifluoromethyl-benzyl)-2,4,6,7-tetrahydro-pyrazolo[4,3-d]pyrimidin-5-one | Ii-4 | RT 1.5 | 0.67 (I) | 394.22 |
| C-3-5 | 2-Methyl-5-piperidin-4-yl-7-[1-(2-trifluoromethyl-phenyl)-ethyl]-2,4,5,7-tetrahydro-pyrazolo[3,4-d]pyrimidin-6-one | Ii-5 | RT 1 | 0.69 (I) | 408.29 |
| C-3-6 | 7-(2-Cyclopropyl-benzyl)-2-methyl-5-piperidin-4-yl-2,4,5,7-tetrahydro-pyrazolo[3,4-d]pyrimidin-6-one | Ii-6 | RT 1 | 0.67 (I) | 366.28 |

Synthesis of Intermediates of Formula C-4

A soln. of aldehyde BB-4 (1 eq) and amine BB-15 (1.1 eq) in MeOH (4 mL/mmol) was stirred for 1.5 h at RT and cooled to 0° C. $NaBH_4$ (1.6 eq) was added portionwise and the rxn mixture was stirred at RT for a given time (see Table 45). It was quenched with a 1M aq. soln. of NaOH and extracted with EtOAc. The combined org. phases were washed with brine, dried over $MgSO_4$ and concentrated in vacuo. The crude was purified by CC using Hept/EtOAc.

TABLE 45

| C-4 | Name | Reactant BB-4 | Reactant BB-15 | time [h] | $t_R$ [min] (LC/MS method) | MS-data m/z $[M + H]^+$ |
|---|---|---|---|---|---|---|
| C-4-1 | 4-[(1-Methyl-4-nitro-1H-pyrazol-3-ylmethyl)-amino]-piperidine-1-carboxylic acid tert-butyl ester | BB-4-3 | BB-15-2 | 0.5 | 0.61 (I) | 340.39 |

Synthesis of Intermediates of Formula D-1

To a soln. of aldehyde BB-19 (1 eq) and amine BB-7 (1.4 eq) in THF (10 mL/mmol) was added AcOH (1.5 eq) followed by $NaBH(OAc)_3$ (1.5 eq). The rxn mixture was stirred at RT for a given time (see Table). It was quenched with a sat. aq. soln. of $NaHCO_3$ and extracted with DCM. The combined org. phases were dried over $MgSO_4$ and concentrated in vacuo. The crude was purified by CC using DCM/MeOH.

TABLE 46

| D-1 | Name | Aldehyde BB-19 | Amine BB-7 | time [h] | $t_R$ [min] (LC/MS method) | MS-data m/z [M + H]$^+$ |
|---|---|---|---|---|---|---|
| D-1-1 | (4-{[1-(2-Fluoro-6-methyl-phenyl)-piperidin-4-ylamino]-methyl]-2-methyl-oxazol-5-yl)-carbamic acid methyl ester | BB-19-1 | BB-7-1 | 18 | 0.70 (II) | 377.27 |

Synthesis of Intermediates of Formula E-1

Method A (NaBH(OAc)$_3$/THF)

To a soln. of ketone BB-26 (1 eq) and amine BB-7 (1 eq) in THF (8 mL/mmol) were added AcOH (1.5 eq) and the rxn mixture was stirred for 20 min at RT. NaBH(OAc)$_3$ (1.5 eq) was added portionwise and the rxn mixture was stirred at RT for a given time (see Table). When necessary to reach completion of the rxn, an extra amount of NaBH(OAc)$_3$ (1 eq) was added at RT. It was partitioned between EtOAc and a sat. aq. soln. of NaHCO$_3$. The org. phase was washed with brine, dried over MgSO$_4$ and concentrated in vacuo. The crude was purified by CC using Hept/EtOAc.

Method B (Ti(OiPr)$_4$/NaBH$_4$)

A suspension of ketone BB-26 (1 eq) and amine BB-7 (1.05 eq) in titanium (IV) isopropoxide (3 eq) was stirred at RT for 18h. The rxn mixture was cooled to −10° C. and EtOH (1 mL/mmol), THF (1 mL/mmol) and NaBH$_4$ (3 eq) were sequentially added. The mixture was allowed to reach RT for 1 h and further stirred at RT for a given time (see Table). It was quenched with water at 0° C. and filtered. The filtrate was extracted with EtOAc and the combined org. phases were washed with brine, dried over MgSO$_4$ and concentrated in vacuo.

Method C (NaBH$_4$/TFE)

A soln. of ketone BB-26 (1 eq) and amine BB-7 (1.1 eq) in TFE (2 mL/mmol) was stirred for 1 to 2.5h at RT and cooled to 0° C. NaBH$_4$ (1.5 to 2 eq) was added portionwise and the rxn mixture was stirred for 20 min at 0° C. and for a given time at RT (see Table). It was quenched at 0° C. with a sat. aq. soln. of NaHCO$_3$ and extracted with DCM. The combined org. phases were washed with brine, dried over MgSO$_4$ and concentrated in vacuo. The crude was purified by CC using Hept/EtOAc.

TABLE 47

| E-1 | Name | Reactant BB-26 | Reactant BB-7 | Method time [h] | $t_R$ [min] (LC/MS method) | MS-data m/z [M + H]$^+$ |
|---|---|---|---|---|---|---|
| E-1-1 | [1-(2-Fluoro-6-methyl-phenyl)-piperidin-4-yl]-[1-(1-methyl-4-nitro-1H-pyrazol-3-yl)-ethyl]-amine | BB-26-1 | BB-7-1 | A 144 | 0.77 (I) | 362.23 |
| E-1-2 | [1-(2-Fluoro-6-methyl-phenyl)-piperidin-4-yl]-{1-[4-nitro-2-(2-trimethylsilanyl-ethoxymethyl)-2H-pyrazol-3-yl]-ethyl}-amine | BB-26-2 | BB-7-1 | B 2 | 1.01 (I) | 478.18 |
| E-1-3 | [1-(2-Fluoro-6-methyl-phenyl)-piperidin-4-yl]-{1-[4-nitro-1-(tetrahydro-pyran-2-yl)-1H-pyrazol-3-yl]-ethyl}-amine | BB-26-4 | BB-7-1 | C 0.5 | 0.87 (I) | 432.24 |
| E-1-4 | (2'-Methoxy-4'-methyl-3,4,5,6-tetrahydro-2H-[1,3']bipyridinyl-4-yl)-{1-[4-nitro-1-(tetrahydro-pyran-2-yl)-1H-pyrazol-3-yl]-ethyl}-amine | BB-26-4 | BB-7-2 | C 2.5 | 0.80 (I) | 445.23 |
| E-1-5 | [1-(2-Chloro-6-fluoro-phenyl)-piperidin-4-yl]-{1-[4-nitro-1-(tetrahydro-pyran-2-yl)-1H-pyrazol-3-yl]-ethyl}-amine | BB-26-4 | BB-7-8 | C 0 | 0.85 (I) | 452.22 |
| E-1-6 | [1-(2-Difluoromethyl-6-fluoro-phenyl)-piperidin-4-yl]-{1-[4-nitro-1-(tetrahydro-pyran-2-yl)-1H-pyrazol-3-yl]-ethyl}-amine | BB-26-4 | BB-7-7 | C 0 | 0.86 (I) | 468.25 |

Synthesis of Intermediates of Formula E-2

Method A: Hydrogenation

To a soln. of intermediate E-1 (1 eq) in EtOH (7 to 7.5 mL/mmol) was added 10% Pd/C moistened with ~50% water (0.02 eq) and the rxn mixture was hydrogenated under atmospheric pressure for a given time (see Table). It was filtered over a pad of celite and the filtrate was concentrated in vacuo. When necessary, the crude was purified by prep. LC-MS using method 5.

Method B: Reduction

To a soln. of intermediate E-1 (1 eq) in MeOH (9 mL/mmol) was added CoCl$_2$ (1.5 eq) and the rxn mixture was stirred for 5 min at RT and cooled to 0° C. NaBH$_4$ (5 eq) was added portionwise and the mixture was stirred for 15 min at 0° C. (see Table). It was quenched at 0° C. with water and MeOH was evaporated off. The residue was partitioned between EtOAc and water and the aq. phase was further extracted with EtOAc. The combined org. phases were washed with brine, dried over MgSO$_4$ and concentrated in vacuo.

TABLE 48

| E-2 | Name | Reactant E-1 | time [h] | $t_R$ [min] (LC/MS method) | MS-data m/z [M + H]⁺ |
|---|---|---|---|---|---|
| E-2-1 | [1-(4-Amino-1-methyl-1H-pyrazol-3-yl)-ethyl]-[1-(2-fluoro-6-methyl-phenyl)-piperidin-4-yl]-amine | E-1-1 | 4 | 0.59 (I) | 332.28 |
| E-2-2 | {1-[4-Amino-2-(2-trimethylsilanyl-ethoxymethyl)-2H-pyrazol-3-yl]-ethyl}-[1-(2-fluoro-6-methyl-phenyl)-piperidin-4-yl]-amine | E-1-2 | 24 | 0.92 (I) | 448.25 |
| E-2-3 | {1-[4-Amino-1-(tetrahydro-pyran-2-yl)-1H-pyrazol-3-yl]-ethyl}-[1-(2-fluoro-6-methyl-phenyl)-piperidin-4-yl]-amine | E-1-3 | A 2 | 0.71 (I) | 402.09 |
| E-2-4 | {1-[4-Amino-1-(tetrahydro-pyran-2-yl)-1H-pyrazol-3-yl]-ethyl}-(2'-methoxy-4'-methyl-3,4,5,6-tetrahydro-2H-[1,3']bipyridinyl-4-yl)-amine | E-1-4 | A 2 | 0.62 (I) | 415.32 |
| E-2-5 | {1-[4-Amino-1-(tetrahydro-pyran-2-yl)-1H-pyrazol-3-yl]-ethyl}-[1-(2-chloro-6-fluoro-phenyl)-piperidin-4-yl]-amine | E-1-5 | B 0.25 | 0.68 (I) | 422.24 |
| E-2-6 | {1-[4-Amino-1-(tetrahydro-pyran-2-yl)-1H-pyrazol-3-yl]-ethyl}-[1-(2-difluoromethyl-6-fluoro-phenyl)-piperidin-4-yl]-amine | E-1-6 | A 2 | 0.70 (I) | 438.30 |

Synthesis of Intermediates of Formula E-3

To a soln. of intermediate E-2 (1 eq) in MeCN (8.5 to 14.3 mL/mmol) was added CDI (1.2 to 1.5 eq) and the rxn mixture was stirred at a given temperature for a given time (see Table 50). The solvent was evaporated off and the residue was partitioned between DCM and water or a sat. aq. soln. of NaHCO₃. The org. phase was washed with brine, dried over MgSO₄ and concentrated in vacuo. When necessary the crude was purified by CC using Hept/EtOAc.

TABLE 50

| E-3 | Name | Reactant E-2 | T [° C.] time [h] | $t_R$ [min] (LC/MS method) | MS-data m/z [M + H]⁺ |
|---|---|---|---|---|---|
| E-3-1 | 6-[1-(2-Fluoro-6-methyl-phenyl)-piperidin-4-yl]-2,7-dimethyl-2,4,6,7-tetrahydro-pyrazolo[4,3-d]pyrimidin-5-one | E-2-1 | RT 18 | 0.94 (I) | 358.44 |
| E-3-2 | 6-[1-(2-Fluoro-6-methyl-phenyl)-piperidin-4-yl]-7-methyl-1-(2-trimethylsilanyl-ethoxymethyl)-1,4,6,7-tetrahydro-pyrazolo[4,3-d]pyrimidin-5-one | E-2-2 | RT 1.5 | 1.17 (I) | 474.19 |
| E-3-3 | 6-[1-(2-Fluoro-6-methyl-phenyl)-piperidin-4-yl]-7-methyl-2-(tetrahydro-pyran-2-yl)-2,4,6,7-tetrahydro-pyrazolo[4,3-d]pyrimidin-5-one | E-2-3 | RT 0.5 | 1.00 (I) | 428.25 |
| E-3-4 | 6-(2'-Methoxy-4'-methyl-3,4,5,6-tetrahydro-2H-[1,3']bipyridinyl-4-yl)-7-methyl-2-(tetrahydro-pyran-2-yl)-2,4,6,7-tetrahydro-pyrazolo[4,3-d]pyrimidin-5-one | E-2-4 | RT 0.5 | 0.84 (I) | 441.23 |
| E-3-5 | 6-[1-(2-Chloro-6-fluoro-phenyl)-piperidin-4-yl]-7-methyl-2-(tetrahydro-pyran-2-yl)-2,4,6,7-tetrahydro-pyrazolo[4,3-d]pyrimidin-5-one | E-2-5 | RT 1.5 | 1.02 (I) | 448.22 |
| E-3-6 | 6-[1-(2-Difluoromethyl-6-fluoro-phenyl)-piperidin-4-yl]-7-methyl-2-(tetrahydro-pyran-2-yl)-2,4,6,7-tetrahydro-pyrazolo[4,3-d]pyrimidin-5-one | E-2-6 | RT 1.5 | 1.02 (I) | 464.27 |

Synthesis of Intermediates of Formula E-4

To a soln. of amine BB-28 (1 eq) and aldehyde or ketone BB-12 (2 eq) in THF (2.6 mL/mmol) were added AcOH (1.5 eq) and the rxn mixture was stirred for 18h at RT. NaBH₄ (1.5 eq) was added portionwise and the rxn mixture was stirred at RT for a given time (see Table). It was partitioned between EtOAc and a sat. aq. soln. of NaHCO₃. The org. phase was washed with brine, dried over MgSO₄ and concentrated in vacuo. The crude was purified by CC using Hept/EtOAc.

TABLE 49

| E-4 | Name | Reactant BB-28 | Reactant BB-12 | time [h] | $t_R$ [min] (LC/MS method) | MS-data m/z [M + H]$^+$ |
|---|---|---|---|---|---|---|
| E-4-1 | 1-Methyl-3-(2-trifluoromethyl-benzylamino)-1H-pyrazole-4-carbonitrile | BB-28-1 | BB-12-4 | 2 | 0.90 (I) | 281.20 |

Synthesis of Intermediates of Formula E-5

Method a (Grignard Addition Using Nitriles E-4)

To a stirred soln. of nitrile E-4 (1 eq) in THF (6 mL/mmol) under argon was added dropwise at 0° C. a 3M soln. of R$^4$MgBr in Et$_2$O (6 eq). The rxn mixture was allowed to reach RT and stirred at a given temperature for a given time (see Table). When necessary to reach completion of the rxn, extra amounts of a 3M soln. of R$^4$MgBr in Et$_2$O (2 eq) were added. The mixture was cooled to 0° C., quenched with a sat. aq. soln. of NH$_4$Cl and extracted with DCM. The combined org. phases were washed with brine, dried over MgSO$_4$ and concentrated in vacuo. The crude was purified by CC using Hept/EtOAc.

Method B (Heck rxn Using Bromides E-7 or E-8)

A mixture of bromide E-7 or E-8 (1 eq), K$_2$CO$_3$ (1.2 eq), Pd(OAc)$_2$ (0.03 eq) and 1,3-bis(diphenylphosphino)propane (0.06 eq) in a mixture of DMF (2.5 mL/mmol) and H$_2$O (0.6 mL/mmol) was flushed with Ar and butyl vinyl ether (5 eq) was added dropwise at RT. The rxn mixture was heated at a given temperature for a given time (see Table). After cooling to RT, a 1M aq. solution of HCl (2 mL/mmol) was added and the mixture was stirred for 1h at RT. It was neutralised with a sat. aq. sol. of NaHCO$_3$ and extracted with EtOAc. The combined org. phases were washed with brine, dried over MgSO$_4$ and concentrated in vacuo. The crude was purified by CC using Hept/EtOAc.

Synthesis of Intermediates of Formula E-6

Method A

A suspension of ketone E-5 or E-10 (1 eq) and amine BB-7 (1.1 to 1.2 eq) in titanium (IV) isopropoxide (3 to 5 eq) was stirred at RT for 18h. The rxn mixture was cooled to 0° C. and EtOH (to 2.5 mL/mmol), THF (1 mL/mmol) and NaBH$_4$ (3 eq) were sequentially added. The mixture was stirred at RT for a given time (see Table), quenched with water at 0° C. and when necessary filtered over a pad of celite. It was extracted with EtOAc and the combined org. phases were washed with brine, dried over MgSO$_4$ and concentrated in vacuo. The crude was purified by CC using Hept/EtOAc.

Method B

To a mixture of ketone E-5 or E-10 (1 eq) and amine BB-7 (1.1 to 1.2 eq) in THF (3 mL/mmol) was added titanium (IV) isopropoxide (3 to 4.4 eq) and the soln. was stirred at RT for 18h. It was cooled to 0° C. and MeOH (6 mL/mmol) and NaBH$_4$ (1.3 to 2 eq) were sequentially added. After stirring for a given time at RT (see Table), it was quenched with water and a 1M soln. of NaOH and extracted with EtOAc. When necessary a filtration over a pad of celite was performed. The combined org. phases were washed with brine, dried over MgSO$_4$ and concentrated in vacuo. The crude was purified by CC using Hept/EtOAc or by prep. LC-MS using method 5 or 8.

TABLE 50

| E-5 | Name | Reactant E-4, E-7 or E-8 | Reactant R$^4$MgBr or vinyl ether | Method T [° C.] time [h] | $t_R$ [min] (LC/MS method) | MS-data m/z [M + H]$^+$ |
|---|---|---|---|---|---|---|
| E-5-1 | 1-[1-Methyl-3-(2-trifluoromethyl-benzylamino)-1H-pyrazol-4-yl]-ethanone | E-4-1 | MeMgBr, as a 3M soln. in Et$_2$O | A 80 3 | 0.91 (I) | 298.22 |
| E-5-2 | 1-[1-(Tetrahydro-pyran-2-yl)-3-(2-trifluoromethyl-benzylamino)-1H-pyrazol-4-yl]-ethanone | E-8-1 | Butyl vinyl ether | B 105 18 | 1.01 (I) | 368.24 |
| E-5-3 | 1-[3-(2-Cyclopropyl-benzylamino)-1-methyl-1H-pyrazol-4-yl]-ethanone | E-7-2 | Butyl vinyl ether | B 100 3 | 0.89 (I) | 270.35 |
| E-5-4 | 1-[3-(2-Cyclopropyl-benzylamino)-1-(tetrahydro-pyran-2-yl)-1H-pyrazol-4-yl]-ethanone | E-8-2 | Butyl vinyl ether | B 100 2 | 1.00 (I) | 340.24 |
| E-5-5 | 1-{1-Methyl-3-[(3-trifluoromethyl-pyridin-2-ylmethyl)-amino]-1H-pyrazol-4-yl}-ethanone | E-7-4 | Butyl vinyl ether | B 100 18 | 0.76 (I) | 299.22 |

TABLE 51

| E-6 | Name | Reactant E-5 or E-10 | Reactant BB-7 | Method time [h] | $t_R$ [min] (LC/MS method) | MS-data m/z $[M + H]^+$ |
|---|---|---|---|---|---|---|
| E-6-1 | [1-(2-Fluoro-6-methyl-phenyl)-piperidin-4-yl]-{1-[1-methyl-3-(2-trifluoromethyl-benzylamino)-1H-pyrazol-4-yl]-ethyl}-amine | E-5-1 | BB-7-1 | 1 | 0.89 (I) | 490.28 |
| E-6-2 | [1-(2-Fluoro-6-methyl-phenyl)-piperidin-4-yl]-{1-[1-(tetrahydro-pyran-2-yl)-3-(2-trifluoromethyl-benzylamino)-1H-pyrazol-4-yl]-ethyl}-amine | E-5-2 | BB-7-1 | A 18 | 0.96 (I) | 560.38 |
| E-6-3 | {1-[1-Cyclopropyl-3-(2-trifluoromethyl-benzylamino)-1H-pyrazol-4-yl]-ethyl}-[1-(2-fluoro-6-methyl-phenyl)-piperidin-4-yl]-amine | E-10-1 | BB-7-1 | A 1 | 0.98 (I) | 516.39 |
| E-6-4 | {1-[1-Cyclopropyl-3-(2-trifluoromethyl-benzylamino)-1H-pyrazol-4-yl]-ethyl}-[1-(2-difluoromethyl-6-fluoro-phenyl)-piperidin-4-yl]-amine | E-10-1 | BB-7-7 | A 0.5 | 0.93 (I) | 552.33 |
| E-6-5 | [1-(2-Difluoromethyl-6-fluoro-phenyl)-piperidin-4-yl]-{1-[1-methyl-3-(2-trifluoromethyl-benzylamino)-1H-pyrazol-4-yl]-ethyl}-amine | E-5-1 | BB-7-7 | A 0.5 | 0.92 (I) | 526.38 |
| E-6-6 | {1-[3-(2-Cyclopropyl-benzylamino)-1-methyl-1H-pyrazol-4-yl]-ethyl}-[1-(2-fluoro-6-methyl-phenyl)-piperidin-4-yl]-amine | E-5-3 | BB-7-1 | B 1 | 0.91 (I) | 462.36 |
| E-6-7 | [1-(2-Chloro-6-fluoro-phenyl)-piperidin-4-yl]-{1-[1-methyl-3-(2-trifluoromethyl-benzylamino)-1H-pyrazol-4-yl]-ethyl}-amine | E-5-1 | BB-7-8 | A 0.5 | 0.89 (I) | 510.26 |
| E-6-8 | [1-(2-Chloro-6-fluoro-phenyl)-piperidin-4-yl]-{1-[3-(2-cyclopropyl-benzylamino)-1-methyl-1H-pyrazol-4-yl]-ethyl}-amine | E-5-3 | BB-7-8 | B 18 | 0.91 (I) | 482.08 |
| E-6-9 | {1-[3-(2-Cyclopropyl-benzylamino)-1-methyl-1H-pyrazol-4-yl]-ethyl}-[1-(2-difluoromethyl-6-fluoro-phenyl)-piperidin-4-yl]-amine | E-5-3 | BB-7-7 | B 0.5 | 0.92 (I) | 498.15 |
| E-6-10 | {1-[3-(2-Cyclopropyl-benzylamino)-1-methyl-1H-pyrazol-4-yl]-ethyl}-[1-(2-cyclopropyl-6-fluoro-phenyl)-piperidin-4-yl]-amine | E-5-3 | BB-7-9 | B 0.5 | 0.92 (I) | 488.37 |
| E-6-11 | (2'-Methoxy-4'-methyl-3,4,5,6-tetrahydro-2H-[1,3']bipyridinyl-4-yl)-{1-[1-methyl-3-(2-trifluoromethyl-benzylamino)-1H-pyrazol-4-yl]-ethyl}-amine | E-5-1 | BB-7-2 | B 2 | 0.86 (I) | 503.33 |
| E-6-12 | [1-(2-Cyclopropyl-6-fluoro-phenyl)-piperidin-4-yl]-{1-[1-methyl-3-(2-trifluoromethyl-benzylamino)-1H-pyrazol-4-yl]-ethyl}-amine | E-5-1 | BB-7-9 | B 0.5 | 0.93 (I) | 516.24 |
| E-6-13 | [1-(2-Chloro-6-fluoro-phenyl)-piperidin-4-yl]-{1-[1-cyclopropyl-3-(2-trifluoromethyl-benzylamino)-1H-pyrazol-4-yl]-ethyl}-amine | E-10-1 | BB-7-8 | A 0.5 | 0.93 (I) | 536.22 |
| E-6-14 | {1-[1-Cyclopropyl-3-(2-cyclopropyl-benzylamino)-1H-pyrazol-4-yl]-ethyl}-[1-(2-fluoro-6-methyl-phenyl)-piperidin-4-yl]-amine | E-10-2 | BB-7-1 | B 3 | 0.95 (I) | 488.34 |
| E-6-15 | [1-(2-Chloro-6-fluoro-phenyl)-piperidin-4-yl]-{1-[1-cyclopropyl-3-(2-cyclopropyl-benzylamino)-1H-pyrazol-4-yl]-ethyl}-amine | E-10-2 | BB-7-8 | B 3 | 0.94 (I) | 508.32 |

TABLE 51-continued

| E-6 | Name | Reactant E-5 or E-10 | Reactant BB-7 | Method time [h] | $t_R$ [min] (LC/MS method) | MS-data m/z [M + H]+ |
|---|---|---|---|---|---|---|
| E-6-16 | {1-[1-Cyclopropyl-3-(2-trifluoromethyl-benzylamino)-1H-pyrazol-4-yl]-ethyl}-(2'-methoxy-4'-methyl-3,4,5,6-tetrahydro-2H-[1,3']bipyridinyl-4-yl)-amine | E-10-1 | BB-7-2 | A 0.5 | 0.91 (I) | 529.18 |
| E-6-17 | (4'-Difluoromethyl-2'-methoxy-3,4,5,6-tetrahydro-2H-[1,3']bipyridinyl-4-yl)-{1-[1-methyl-3-(2-trifluoromethyl-benzylamino)-1H-pyrazol-4-yl]-ethyl}-amine | E-5-1 | BB-7-10 | A 1 | 0.88 (I) | 539.26 |
| E-6-18 | [1-(2-Difluoromethyl-6-fluoro-phenyl)-piperidin-4-yl]-{1-[1-(tetrahydro-pyran-2-yl)-3-(2-trifluoromethyl-benzylamino)-1H-pyrazol-4-yl]-ethyl}-amine | E-5-2 | BB-7-7 | A 0.5 | 0.97 (I) | 596.33 |
| E-6-19 | [1-(2-Chloro-6-fluoro-phenyl)-piperidin-4-yl]-{1-[1-(tetrahydro-pyran-2-yl)-3-(2-trifluoromethyl-benzylamino)-1H-pyrazol-4-yl]-ethyl}-amine | E-5-2 | BB-7-8 | A 1 | 0.98 (I) | 580.31 |
| E-6-20 | (4'-Difluoromethyl-2'-methoxy-3,4,5,6-tetrahydro-2H-[1,3']bipyridinyl-4-yl)-{1-[1-(tetrahydro-pyran-2-yl)-3-(2-trifluoromethyl-benzylamino)-1H-pyrazol-4-yl]-ethyl}-amine | E-5-2 | BB-7-10 | A 0.5 | 0.98 (I) | 609.09 |
| E-6-21 | [1-(2-Fluoro-6-methyl-phenyl)-piperidin-4-yl]-(1-{1-methyl-3-[(3-trifluoromethyl-pyridin-2-ylmethyl)-amino]-1H-pyrazol-4-yl}-ethyl)-amine | E-5-5 | BB-7-1 | B 0.5 | 0.83 (I) | 491.26 |
| E-6-22 | (2'-Methoxy-4'-methyl-3,4,5,6-tetrahydro-2H-[1,3']bipyridinyl-4-yl)-(1-{1-methyl-3-[(3-trifluoromethyl-pyridin-2-ylmethyl)-amino]-1H-pyrazol-4-yl}-ethyl)-amine | E-5-5 | BB-7-2 | B 0.5 | 0.77 (I) | 504.26 |
| E-6-23 | {1-[1-Cyclopropyl-3-(2-trifluoromethyl-benzylamino)-1H-pyrazol-4-yl]-ethyl}-(4'-difluoromethyl-2'-methoxy-3,4,5,6-tetrahydro-2H-[1,3']bipyridinyl-4-yl)-amine | E-10-1 | BB-7-10 | B 1 | 0.92 (I) | 565.27 |
| E-6-24 | [1-(2-Bromo-6-fluoro-phenyl)-piperidin-4-yl]-{1-[1-cyclopropyl-3-(2-trifluoromethyl-benzylamino)-1H-pyrazol-4-yl]-ethyl}-amine | E-10-1 | BB-7-11 | B 1.5 | 0.93 (I) | 580.20 |
| E-6-25 | (2'-Methoxy-4'-trifluoromethyl-3,4,5,6-tetrahydro-2H-[1,3']bipyridinyl-4-yl)-{1-[1-methyl-3-(2-trifluoromethyl-benzylamino)-1H-pyrazol-4-yl]-ethyl}-amine | E-5-1 | BB-7-12 | A 1.5 | 0.93 (I) | 557.32 |
| E-6-26 | {1-[3-(2-Cyclopropyl-benzylamino)-1-methyl-1H-pyrazol-4-yl]-ethyl}-(2'-methoxy-4'-methyl-3,4,5,6-tetrahydro-2H-[1,3']bipyridinyl-4-yl)-amine | E-5-3 | BB-7-2 | B 1.5 | 0.86 (I) | 475.31 |
| E-6-27 | {1-[3-(2-Cyclopropyl-benzylamino)-1-methyl-1H-pyrazol-4-yl]-ethyl}-(4'-difluoromethyl-2'-methoxy-3,4,5,6-tetrahydro-2H-[1,3']bipyridinyl-4-yl)-amine | E-5-3 | BB-7-10 | B 1.5 | 0.91 (I) | 511.31 |
| E-6-28 | {1-[3-(2-Cyclopropyl-benzylamino)-1-(tetrahydro-pyran-2-yl)-1H-pyrazol-4-yl]-ethyl}-(4'-difluoromethyl-2'- | E-5-4 | BB-7-10 | B 1 | 0.98 (I) | 581.38 |

TABLE 51-continued

| E-6 | Name | Reactant E-5 or E-10 | Reactant BB-7 | Method time [h] | $t_R$ [min] (LC/MS method) | MS-data m/z [M + H]+ |
|---|---|---|---|---|---|---|
| | methoxy-3,4,5,6-tetrahydro-2H-[1,3']bipyridinyl-4-yl)-amine | | | | | |
| E-6-29 | [1-(2-Chloro-6-fluoro-phenyl)-piperidin-4-yl]-{1-[3-(2-cyclopropyl-benzylamino)-1-(tetrahydro-pyran-2-yl)-1H-pyrazol-4-yl]-ethyl}-amine | E-5-4 | BB-7-8 | B 1 | 0.98 (I) | 552.36 |
| E-6-30 | {1-[3-(2-Cyclopropyl-benzylamino)-1-methyl-1H-pyrazol-4-yl]-ethyl}-(2'-methoxy-4'-trifluoromethyl-3,4,5,6-tetrahydro-2H-[1,3']bipyridinyl-4-yl)-amine | E-5-3 | BB-7-12 | A 1 | 0.91 (I) | 529.14 |
| E-6-31 | (4'-Chloro-2'-methoxy-3,4,5,6-tetrahydro-2H-[1,3']bipyridinyl-4-yl)-{1-[1-methyl-3-(2-trifluoromethyl-benzylamino)-1H-pyrazol-4-yl]-ethyl}-amine | E-5-1 | BB-7-13 | A 0.5 | 0.87 (I) | 523.21 |
| E-6-32 | (4'-Chloro-2'-methoxy-3,4,5,6-tetrahydro-2H-[1,3']bipyridinyl-4-yl)-{1-[3-(2-cyclopropyl-benzylamino)-1-methyl-1H-pyrazol-4-yl]-ethyl}-amine | E-5-3 | BB-7-13 | A 0.5 | 0.87 (I) | 495.26 |
| E-6-33 | {1-[1-Cyclopropyl-3-(2-cyclopropyl-benzylamino)-1H-pyrazol-4-yl]-ethyl}-(2'-methoxy-4'-methyl-3,4,5,6-tetrahydro-2H-[1,3']bipyridinyl-4-yl)-amine | E-10-2 | BB-7-2 | B 0.5 | 0.90 (I) | 501.37 |
| E-6-34 | {1-[1-Cyclopropyl-3-(2-cyclopropyl-benzylamino)-1H-pyrazol-4-yl]-ethyl}-(4'-difluoromethyl-2'-methoxy-3,4,5,6-tetrahydro-2H-[1,3']bipyridinyl-4-yl)-amine | E-10-2 | BB-7-10 | B 0.5 | 0.95 (I) | 537.38 |
| E-6-35 | [1-(2-Bromo-6-fluoro-phenyl)-piperidin-4-yl]-{1-[3-(2-cyclopropyl-benzylamino)-1-methyl-1H-pyrazol-4-yl]-ethyl}-amine | E-5-3 | BB-7-11 | B 1 | 0.93 (I) | 526.28 |

Synthesis of Intermediates of Formula E-7

Method A

A soln. of amine BB-34(1 eq) and aldehyde or ketone BB-12 (1.05 to 1.1 eq) in MeOH (2 to 4 mL/mmol) was stirred for 1 h at RT. NaBH$_4$ (1.6 to 2 eq) was added portionwise at 0° C. and the rxn mixture was stirred at a given temperature for a given time (see Table 52). It was quenched with H$_2$O at 0° C. and extracted with EtOAc. The combined org. phases were washed with brine, dried over MgSO$_4$ and concentrated in vacuo. When necessary, the crude was purified by CC using EtOAc/MeOH.

Method B

A soln. of amine BB-34(1 eq), aldehyde or ketone BB-12 (1.1 eq) and AcOH (1.1 eq) in MeOH (1.5 mL/mmol) was stirred under Ar for 1h at RT. Molybdenum(VI) dichloride dioxide (0.05 eq) in MeOH (1.5 mL/mmol) was added at RT followed by phenylsilane (1.5 eq). The rxn mixture was stirred at a given temperature for a given time (see Table 52) and quenched with a sat. soln. of NaHCO$_3$. It was extracted with DCM and the combined org. phases were dried over MgSO$_4$ and concentrated in vacuo. The crude was purified by CC using EtOAc/MeOH.

TABLE 52

| E-7 | Name | Reactant BB-34 | Reactant BB-12 | Method T [° C.] time [h] | $t_R$ [min] (LC/MS method) | MS-data m/z [M + H]+ |
|---|---|---|---|---|---|---|
| E-7-1 | (4-Bromo-1H-pyrazol-3-yl)-(2-trifluoromethyl-benzyl)-amine | BB-34-1 | BB-12-4 | A 0 1.5 | 0.91 (I) | 320.02 |
| E-7-2 | (4-Bromo-1-methyl-1H-pyrazol-3-yl)-(2-cyclopropyl-benzyl)-amine | BB-34-2 | BB-12-5 | A RT 2.5 | 0.97 (I) | 305.85 |

TABLE 52-continued

| E-7 | Name | Reactant BB-34 | Reactant BB-12 | T [° C.] time [h] | Method (LC/MS method) | $t_R$ [min] | MS-data m/z $[M + H]^+$ |
|---|---|---|---|---|---|---|---|
| E-7-3 | (4-Bromo-1H-pyrazol-3-yl)-(2-cyclopropyl-benzyl)-amine | BB-34-1 | BB-12-5 | A RT 1 | | 0.89 (I) | 292.18 |
| E-7-4 | (4-Bromo-1-methyl-1H-pyrazol-3-yl)-(3-trifluoromethyl-pyridin-2-ylmethyl)-amine | BB-34-2 | BB-12-1 | B RT 18 | | 0.87 (I) | 335.08 |

Synthesis of Intermediates of Formula E-8

To a suspension or solution of the intermediate E-7 (1 eq) in DCM (2 to 4 mL/mmol) was added TsOH (0.1 eq) and 3,4-dihydro-2H-pyran (1.3 eq). The rxn mixture was stirred at a given temperature for a given time (see Table 53) and quenched with a sat. aq. soln. of $NaHCO_3$. It was extracted with DCM, the org. phase was washed with a sat. aq. soln. of $NaHCO_3$ and brine, dried over $MgSO_4$ and concentrated in vacuo. The crude was purified by CC using Hept/EtOAc.

TABLE 53

| E-8 | Name | Reactant E-7 | T [° C.] time [h] | $t_R$ [min] (LC/MS method) | MS-data m/z $[M + H]^+$ |
|---|---|---|---|---|---|
| E-8-1 | [4-Bromo-1-(tetrahydro-pyran-2-yl)-1H-pyrazol-3-yl]-(2-trifluoromethyl-benzyl)-amine | E-7-1 | 50 20 | 1.08 (I) | 404.09 |
| E-8-2 | [4-Bromo-1-(tetrahydro-pyran-2-yl)-1H-pyrazol-3-yl]-(2-cydopropyl-benzyl)-amine | E-7-3 | 45 18 | 1.06 (I) | 376.17 |

Synthesis of Intermediates of Formula E-9

To a sol. of THP-protected intermediate E-5 (1 eq) in DCM (2 mL/mmol) was added dropwise TA (1.5 mL/mmol). The soln. was stirred at RT for a given time (see Table 54), quenched at 0° C. with a 1 M aq. sol. of NaOH until pH 10-11 and extracted with DCM. The combined org. phases were dried over $MgSO_4$ and concentrated in vacuo. The crude was purified by CC using Hept/EtOAc.

TABLE 54

| E-9 | Name | Reactant E-5 | T [° C.] time [h] | $t_R$ [min] (LC/MS method) | MS-data m/z $[M + H]^+$ |
|---|---|---|---|---|---|
| E-9-1 | 1-[3-(2-Trifluoromethyl-benzylamino)-1H-pyrazol-4-yl]-ethanone | E-5-2 | RT 1 | 0.82 (I) | 284.16 |
| E-9-2 | 1-[3-(2-Cyclopropyl-benzylamino)-1H-pyrazol-4-yl]-ethanone | E-5-4 | RT 72 | 0.82 (I) | 256.33 |

Synthesis of Intermediates of Formula E-10

A mixture of intermediates E-9 (1 eq), boron species BB-10 (2 eq), $Na_2CO_3$ (2 eq), 2,2-bipyridyl (1 eq) and $Cu(OAc)_2$ (1 eq) in toluene (10 to 12 mL/mmol) was flushed with $N_2$ and heated at a given temperature for given time (see Table 55). It was partitioned between EtOAc or DCM and a sat. aq. soln. of $NaHCO_3$ and the org. phase was washed with brine, dried over $MgSO_4$ and concentrated in vacuo. The crude was purified by CC using Hept/EtOAc.

TABLE 55

| E-10 | Name | Reactant E-9 | Reactant BB-10 | T [° C.] time [h] | $t_R$ [min] (LC/MS- method) | MS-data m/z $[M + H]^+$ |
|---|---|---|---|---|---|---|
| E-10-1 | 1-[1-Cyclopropyl-3-(2-trifluoromethyl-benzylamino)-1H-pyrazol-4-yl]-ethanone | E-9-1 | Cyclopropyl boronic acid | 70 2.5 | 0.97 (I) | 324.22 |
| E-10-2 | 1-[1-Cyclopropyl-3-(2-cyclopropyl-benzylamino)-1H-pyrazol-4-yl]-ethanone | E-9-2 | Cyclopropyl boronic acid | 80 2 | 0.95 (I) | 296.33 |

Synthesis of Compounds of Formula Ia

Method A1 (Alkylation of A-3 or E-3: NaH/THF)

To a soln. of intermediate A-3 or E-3 (1 eq) in a mixture of anh. THE (3 to 7.3 mL/mmol) and anh. DMF (0 to 0.7 mL/mmol) was added NaH (1.5 to 10 eq, as a 60% dispersion in mineral oil) at 0° C. The suspension was stirred for 10 min and halide BB-9 (1.1 to 1.5 eq) was added at 0° C. The rxn mixture was stirred at a given temperature for a given time under possible microwave irradiation (see Table). When necessary to reach completion of the rxn an extra amount of NaH (0.5 eq, as a 60% dispersion in mineral oil) and/or halide BB-9 (0.5 eq) was added. The mixture was quenched with water or a sat. aq. soln. of NaHCO$_3$ and extracted with EtOAc. The combined org. phases were washed with brine, dried over MgSO$_4$ and concentrated in vacuo. The crude was purified by CC using Hept/EtOAc or by prep. LC-MS using method 1, 2 or 5.

Method A2 (Alkylation of A-3 or E-3 Using NaH/THF Followed by Saponification)

Similar to method A1 except that the rxn mixture was quenched with a 2M aq. soln. of NaOH and stirred ON at RT before the extraction with EtOAc.

Method B (Mitsunobu with A-3 or E-3)

To a soln. or suspension of intermediate A-3 or E-3 (1 eq) and alcohol BB-9 (1.1 to 6 eq) in toluene (3.4 to 24 mL/mmol) was added a 1M soln. of (tributylphosphoranylidene)acetonitrile in toluene (1.1 to 2 eq) under argon. The rxn mixture was heated to a given temperature and stirred for a given time (see Table). When necessary to reach completion of the rxn, extra amounts of a 1M soln. of (tributylphosphoranylidene)acetonitrile in toluene (0.2 eq) were sequentially added under argon. It was quenched with water or a sat. aq. soln. of NaHCO$_3$ and extracted with EtOAc or DCM. The combined org. phases were washed with brine, dried over MgSO$_4$ and concentrated in vacuo. The crude was purified by CC using Hept/EtOAc or DCM/MeOH. When necessary, an additional purification by prep. LC-MS using methods 2, 3, 4 or 5 was performed.

Method C (Cyclisation from B-3)

To a suspension of intermediate B-3 (1 eq) in MeCN (5.1 to 11.2 mL/mmol) was added CDI (5 to 7 eq) and the rxn mixture was stirred at a given temperature for a given time (see Table). The solvent was evaporated off and the residue was partitioned between EtOAc and water. The org. phase was washed with brine, dried over MgSO$_4$ and concentrated in vacuo. When necessary, the crude was purified by CC using Hept/EtOAc/MeOH.

Method D (Alkylation of A-3: K$_2$CO$_3$/DMF)

To a stirred soln. of intermediate A-3 (1 eq) in DMF (3.9 to 4.7 mL/mmol) was added K$_2$CO$_3$ (1.5 to 3 eq) followed by the appropriate halide BB-9 (1.3 to 1.5 eq). The rxn mixture was stirred at a given temperature for a given time (see Table). When necessary to reach completion of the rxn, extra amounts of halide BB-9 (1 eq) were added at RT. It was partitioned between EtOAc and H$_2$. The org. phase was washed with water and brine, dried over MgSO$_4$ and concentrated in vacuo. The crude was purified by CC using Hept/EtOAc and/or DCM/MeOH.

Method E (Cyclisation from E-6)

To a suspension of diamine E-6 (1 eq) in MeCN (or DCM, respectively) (8 to 12.7 mL/mmol) was added DSC (or CDT, respectively) (1.2 to 1.3 eq) and optionally Et$_3$N (3 eq) at RT. The rxn mixture was stirred at a given temperature for a given time (see Table) and partitioned between EtOAc or DCM and a 1 M soln. of NaOH or a sat. soln. of NaHCO$_3$. The org. phase was washed with water and brine, dried over MgSO$_4$ and concentrated in vacuo. The crude was purified by CC using Hept/EtOAc or by prep. LC-MS using method 4, 5, 8 or 10.

TABLE 56

| Ia | Name | Reactant A-3, B-3, E-3 or E-6 | Reactant BB-9 | Method T [° C.] time [h] | $t_R$ [min] (LC/MS- method) | MS-data m/z $[M + H]^+$ |
|---|---|---|---|---|---|---|
| Ia-1A | 6-[1-(2-Fluoro-6-methyl-phenyl)-piperidin-4-yl]-4-(2-trifluoromethyl-benzyl)-1-(2-trimethylsilanyl-ethoxymethyl)-1,4,6,7-tetrahydro-pyrazolo[4,3-d]pyrimidin-5-one (Example 1) | A-3-1A | BB-9-1 | A1 RT 66 | 1.30 (I) | 618.26 |
| Ia-1B | 6-[1-(2-Fluoro-6-methyl-phenyl)-piperidin-4-yl]-4-(2-trifluoromethyl-benzyl)-2-(2-trimethylsilanyl-ethoxymethyl)-2,4,6,7-tetrahydro-pyrazolo[4,3-d]pyrimidin-5-one (Example 195) | A-3-1B | BB-9-1 | A1 RT 2 | 1.29 (I) | 618.28 |
| Ia-2 | 5-[1-(2-Fluoro-6-methyl-phenyl)-piperidin-4-yl]-7-(2-trifluoromethyl-benzyl)-2-(2-trimethylsilanyl-ethoxymethyl)-2,4,5,7-tetrahydro-pyrazolo[3,4-d]pyrimidin-6-one (Example 5) | A-3-2 | BB-9-1 | A1 RT 24 | 1.31 (I) | 618.38 |

TABLE 56-continued

| Ia | Name | Reactant A-3, B-3, E-3 or E-6 | Reactant BB-9 | Method T [° C.] time [h] | $t_R$ [min] (LC/MS-method) | MS-data m/z $[M + H]^+$ |
|---|---|---|---|---|---|---|
| Ia-3 | 6-[1-(2-Fluoro-6-methyl-phenyl)-piperidin-4-yl]-2-methyl-4-(3-trifluoromethyl-pyrazin-2-ylmethyl)-2,4,6,7-tetrahydro-pyrazolo[4,3-d]pyrimidin-5-one (Example 11) | A-3-3 | BB-9-2 | A1 RT 18 | 1.00 (II) | 504.17 |
| Ia-4 | 6-[1-(2-Fluoro-6-methyl-phenyl)-piperidin-4-yl]-2-methyl-4-(4-trifluoromethyl-pyridin-3-ylmethyl)-2,4,6,7-tetrahydro-pyrazolo[4,3-d]pyrimidin-5-one (Example 12) | A-3-3 | BB-9-3 | B 110 3 | 1.04 (II) | 503.19 |
| Ia-5 | 1-[1-(2-Fluoro-6-methyl-phenyl)-piperidin-4-yl]-3-(2-trifluoromethyl-benzyl)-7-(2-trimethylsilanyl-ethoxymethyl)-1,3,6,7-tetrahydro-purin-2-one (Example 13) | A-3-4 | BB-9-1 | A1 RT 18 | 1.12 (II) | 618.17 |
| Ia-6 | 6-[1-(2-Fluoro-6-methyl-phenyl)-piperidin-4-yl]-2-methyl-4-(3-trifluoromethyl-pyridin-2-ylmethyl)-2,4,6,7-tetrahydro-pyrazolo[4,3-d]pyrimidin-5-one (Example 15) | A-3-3 | BB-9-4 | B 110 18 | 1.01 (II) | 503.16 |
| Ia-7 | 7-(2-Cyclopropoxy-benzyl)-5-[1-(2-fluoro-6-methyl-phenyl)-piperidin-4-yl]-2-methyl-2,4,5,7-tetrahydro-pyrazolo[3,4-d]pyrimidin-6-one (Example 21) | A-3-5 | BB-9-5 | A1 RT 18 | 1.06 (II) | 490.15 |
| Ia-8 | 5-[1-(2-Fluoro-6-methyl-phenyl)-piperidin-4-yl]-2-methyl-7-(3-trifluoromethyl-pyridin-2-ylmethyl)-2,4,5,7-tetrahydro-pyrazolo[3,4-d]pyrimidin-6-one (Example 22) | B-3-1 | — | C 80 2 | 1.00 (II) | 503.09 |
| Ia-9 | 7-(6-Chloro-3-trifluoromethyl-pyridin-2-ylmethyl)-5-[1-(2-fluoro-6-methyl-phenyl)-piperidin-4-yl]-2-methyl-2,4,5,7-tetrahydro-pyrazolo[3,4-d]pyrimidin-6-one (Example 35) | B-3-2 | — | C 80 2 | 1.05 (II) | 537.07 |
| Ia-10 | 5-[(R)-1-(2-Fluoro-6-methyl-phenyl)-pyrrolidin-3-yl]-2-methyl-7-(2-trifluoromethyl-benzyl)-2,4,5,7-tetrahydro-pyrazolo[3,4-d]pyrimidin-6-one (Example 55) | A-3-6 | BB-9-1 | A1 RT 18 | 0.91 (II) | 488.09 |
| Ia-11 | 5-[1-(2-Fluoro-6-methyl-phenyl)-piperidin-4-yl]-7-(2-fluoro-6-trifluoromethyl-benzyl)-2-methyl-2,4,5,7-tetrahydro-pyrazolo[3,4-d]pyrimidin-6-one (Example 61) | B-3-3 | — | C 80 72 | 1.06 (II) | 520.07 |
| Ia-12 | 3-Benzyl-6-[1-(2-fluoro-6-methyl-phenyl)-piperidin-4-yl]-4-(2-trifluoromethyl-benzyl)-3,4,6,7-tetrahydro-[1,2,3]triazolo[4,5-d]pyrimidin-5-one | A-3-7 | BB-9-1 | D 45 and 80 18 and 5 | 1.10 (II) | 579.16 |
| Ia-13 | 6-[1-(2-Fluoro-6-methyl-phenyl)-piperidin-4-yl]-2-methyl-4-(2-trifluoromethyl-benzyl)-6,7-dihydro-4H-oxazolo[5,4-d]pyrimidin-5-one (Example 89) | A-3-8 | BB-9-6 | B 110 0.25 | 1.12 (II) | 503.15 |
| Ia-14 | 6-[1-(2-Fluoro-6-methyl-phenyl)-piperidin-4-yl]-2-methyl-4-(2-trifluoromethyl-benzyl)-6,7-dihydro-4H-thiazolo[5,4-d]pyrimidin-5-one (Example 90) | A-3-9 | BB-9-6 | B 110 0.5 | 1.12 (II) | 519.04 |
| Ia-15 | 6-[1-(2-Fluoro-6-methyl-phenyl)-piperidin-4-yl]-2-methyl-4-(3-trifluoromethyl-pyridin-2-ylmethyl)-2,4,6,7-tetrahydro-[1,2,3]triazolo[4,5-d]pyrimidin-5-one (Example 128) | A-3-10 | BB-9-4 | B 110 2 | 1.17 (I) | 504.17 |
| Ia-16 | 5-(2'-Methoxy-4'-methyl-3,4,5,6-tetrahydro-2H-[1,3']bipyridinyl-4-yl)-2-methyl-7-(3-trifluoromethyl-pyridin-2-ylmethyl)-2,4,5,7-tetrahydro-pyrazolo[3,4-d]pyrimidin-6-one (Example 138) | A-3-11 | BB-9-7 | A1 microwave 100 0.75 | 1.01 (I) | 516.14 |
| Ia-17 | 6-(2'-Methoxy-4'-methyl-3,4,5,6-tetrahydro-2H-[1,3']bipyridinyl-4-yl)-2-methyl-4-(2-trifluoromethyl-benzyl)-2,4,6,7-tetrahydro-[1,2,3]triazolo[4,5-d]pyrimidin-5-one (Example 145) | A-3-12 | BB-9-6 | B 110 1 | 1.17 (I) | 516.02 |
| Ia-18 | 6-(2'-Methoxy-4'-methyl-3,4,5,6-tetrahydro-2H-[1,3']bipyridinyl-4-yl)-2-methyl-4-(3-trifluoromethyl-pyridin-2-ylmethyl)-2,4,6,7-tetrahydro-[1,2,3]triazolo[4,5-d]pyrimidin-5-one (Example 146) | A-3-12 | BB-9-4 | B 110 18 | 1.07 (I) | 517.11 |
| Ia-19 | 5-[1-(2-Fluoro-6-methyl-phenyl)-piperidin-4-yl]-7-(3-trifluoromethyl-pyridin-2-ylmethyl)-2-(2-trimethylsilanyl-ethoxymethyl)-2,4,5,7-tetrahydro-pyrazolo[3,4-d]pyrimidin-6-one | A-3-2 | BB-9-7 | D 140 4 microwave | 1.26 (I) | 619.39 |

TABLE 56-continued

| Ia | Name | Reactant A-3, B-3, E-3 or E-6 | Reactant BB-9 | Method T [° C.] time [h] | $t_R$ [min] (LC/MS-method) | MS-data m/z [M + H]$^+$ |
|---|---|---|---|---|---|---|
| Ia-20 | 5-(2'-Methoxy-4'-methyl-3,4,5,6-tetrahydro-2H-[1,3']bipyridinyl-4-yl)-7-(2-trifluoromethyl-benzyl)-2-(2-trimethylsilanyl-ethoxymethyl)-2,4,5,7-tetrahydro-pyrazolo[3,4-d]pyrimidin-6-one (Example 196) | A-3-13 | BB-9-1 | A1 RT 18 | 1.27 (I) | 631.22 |
| Ia-21 | 6-[1-(2-Fluoro-6-methyl-phenyl)-piperidin-4-yl]-4-(3-trifluoromethyl-pyridin-2-ylmethyl)-2-(2-trimethylsilanyl-ethoxymethyl)-2,4,6,7-tetrahydro-pyrazolo[4,3-d]pyrimidin-5-one (Example 199) | A-3-1B | BB-9-7 | A1 RT 18 | 1.24 (I) | 619.25 |
| Ia-22 | 6-[1-(2-Fluoro-6-methyl-phenyl)-piperidin-4-yl]-2,7-dimethyl-4-(2-trifluoromethyl-benzyl)-2,4,6,7-tetrahydro-pyrazolo[4,3-d]pyrimidin-5-one | E-3-1 | BB-9-1 | A1 RT 3 | 1.22 (I) | 516.07 |
| Ia-23 | 7-(2-Bromo-6-trifluoromethyl-benzyl)-5-[1-(2-fluoro-6-methyl-phenyl)-piperidin-4-yl]-2-(2-trimethylsilanyl-ethoxymethyl)-2,4,5,7-tetrahydro-pyrazolo[3,4-d]pyrimidin-6-one | A-3-2 | BB-9-8 | A1 RT 18 | 1.35 (I) | 696.27 |
| Ia-24 | 6-(2'-Methoxy-4'-methyl-3,4,5,6-tetrahydro-2H-[1,3']bipyridinyl-4-yl)-4-(2-trifluoromethyl-benzyl)-1-(2-trimethylsilanyl-ethoxymethyl)-1,4,6,7-tetrahydro-pyrazolo[4,3-d]pyrimidin-5-one (Example 216) | A-3-14 | BB-9-1 | A1 RT 18 | 1.25 (I) | 631.40 |
| Ia-25 | 5-[1-(2-Fluoro-6-methyl-phenyl)-4-methyl-piperidin-4-yl]-2-methyl-7-(2-trifluoromethyl-benzyl)-2,4,5,7-tetrahydro-pyrazolo[3,4-d]pyrimidin-6-one (Example 217) | A-3-15 | BB-9-1 | A1 RT 24 | 1.20 (I) | 516.26 |
| Ia-26 | 5-[1-(2-Fluoro-6-methyl-phenyl)-piperidin-4-yl]-2,4-dimethyl-7-(2-trifluoromethyl-benzyl)-2,4,5,7-tetrahydro-pyrazolo[3,4-d]pyrimidin-6-one | E-6-1 | — | E 40 3.5 | 1.21 (I) | 516.22 |
| Ia-27 | 5-[1-(2-Fluoro-6-methyl-phenyl)-azepan-4-yl]-2-methyl-7-(2-trifluoromethyl-benzyl)-2,4,5,7-tetrahydro-pyrazolo[3,4-d]pyrimidin-6-one | A-3-16 | BB-9-1 | A1 RT 5 | 1.22 (I) | 516.17 |
| Ia-28 | 7-(2-Cyclopropyl-benzyl)-5-[1-(2-fluoro-6-methyl-phenyl)-piperidin-4-yl]-2-methyl-2,4,5,7-tetrahydro-pyrazolo[3,4-d]pyrimidin-6-one (Example 228) | A-3-5 | BB-9-9 | B 110 1 | 1.19 (I) | 474.23 |
| Ia-29 | 6-[1-(2-Fluoro-6-methyl-phenyl)-piperidin-4-yl]-4-(3-trifluoromethyl-pyridin-2-ylmethyl)-1-(2-trimethylsilanyl-ethoxymethyl)-1,4,6,7-tetrahydro-pyrazolo[4,3-d]pyrimidin-5-one (Example 230) | A-3-1A | BB-9-7 | A1 RT 48 | 1.24 (I) | 619.22 |
| Ia-30 | 5-[1-(2-Fluoro-6-methyl-phenyl)-piperidin-4-yl]-7-(2-isopropyl-benzyl)-2-methyl-2,4,5,7-tetrahydro-pyrazolo[3,4-d]pyrimidin-6-one (Example 231) | A-3-5 | BB-9-10 | A1 RT 18 | 1.22 (I) | 476.21 |
| Ia-31 | 5-[1-(2-Fluoro-6-methyl-phenyl)-piperidin-4-yl]-2-methyl-7-(2-trifluoromethoxy-benzyl)-2,4,5,7-tetrahydro-pyrazolo[3,4-d]pyrimidin-6-one (Example 232) | A-3-5 | BB-9-11 | A1 RT 18 | 1.20 (I) | 518.19 |
| Ia-32 | 7-(2-Chloro-benzyl)-5-[1-(2-fluoro-6-methyl-phenyl)-piperidin-4-yl]-2-methyl-2,4,5,7-tetrahydro-pyrazolo[3,4-d]pyrimidin-6-one (Example 233) | A-3-5 | BB-9-12 | A1 RT 18 | 1.17 (I) | 468.13 |
| Ia-33 | 5-[1-(2-Fluoro-6-methyl-phenyl)-3-methyl-pyrrolidin-3-yl]-2-methyl-7-(2-trifluoromethyl-benzyl)-2,4,5,7-tetrahydro-pyrazolo[3,4-d]pyrimidin-6-one | A-3-17 | BB-9-1 | A1 RT 18 | 1.15 (I) | 502.16 |
| Ia-34 | 7-(2,4-Difluoro-6-isopropoxy-benzyl)-5-[1-(2-fluoro-6-methyl-phenyl)-piperidin-4-yl]-2-methyl-2,4,5,7-tetrahydro-pyrazolo[3,4-d]pyrimidin-6-one (Example 236) | A-3-5 | BB-9-13 | B 110 2 | 1.18 (I) | 528.23 |
| Ia-35 | 6-[1-(2-Fluoro-6-methyl-phenyl)-piperidin-4-yl]-7-methyl-4-(2-trifluoromethyl-benzyl)-1-(2-trimethylsilanyl-ethoxymethyl)-1,4,6,7-tetrahydro-pyrazolo[4,3-d]pyrimidin-5-one (Example 237) | E-3-2 | BB-9-1 | A1 RT 18 | 1.31 (I) | 632.19 |
| Ia-36 | 5-[1-(2-Fluoro-6-methyl-phenyl)-piperidin-4-yl]-2-methyl-7-(2-methyl-4-trifluoromethyl-thiazol-5-ylmethyl)-2,4,5,7-tetrahydro-pyrazolo[3,4-d]pyrimidin-6-one (Example 240) | A-3-5 | BB-9-14 | B 110 18 | 1.16 (I) | 523.16 |

TABLE 56-continued

| Ia | Name | Reactant A-3, B-3, E-3 or E-6 | Reactant BB-9 | Method T [° C.] time [h] | $t_R$ [min] (LC/MS-method) | MS-data m/z [M + H]$^+$ |
|---|---|---|---|---|---|---|
| Ia-37 | 5-[1-(2-Fluoro-6-methyl-phenyl)-piperidin-3-yl]-2-methyl-7-(2-trifluoromethyl-benzyl)-2,4,5,7-tetrahydro-pyrazolo[3,4-d]pyrimidin-6-one | A-3-18 | BB-9-1 | A1 RT 18 | 1.17 (I) | 502.18 |
| Ia-38 | 5-[1-(2-Fluoro-6-methyl-phenyl)-piperidin-4-yl]-2-methyl-7-[1-(2-trifluoromethyl-phenyl)-ethyl]-2,4,5,7-tetrahydropyrazolo[3,4-d]pyrimidin-6-one | A-3-5 | BB-9-15 | B 110 1 | 1.21 (I) | 516.21 |
| Ia-39 | 5-[1-(2-Fluoro-6-methyl-phenyl)-piperidin-4-yl]-7-(2-hydroxy-benzyl)-2-methyl-2,4,5,7-tetrahydro-pyrazolo[3,4-d]pyrimidin-6-one | A-3-5 | BB-9-16 | A2 RT 5 | 1.15 (I) | 449.95 |
| Ia-40 | 5-[1-(2-Fluoro-6-methyl-phenyl)-piperidin-4-yl]-7-(4-isopropyl-pyrimidin-5-ylmethyl)-2-methyl-2,4,5,7-tetrahydro-pyrazolo[3,4-d]pyrimidin-6-one (Example 249) | A-3-5 | BB-9-17 | B 110 5.5 | 1.19 (I) | 478.22 |
| Ia-41 | 7-(2-Ethoxy-benzyl)-5-[1-(2-fluoro-6-methyl-phenyl)-piperidin-4-yl]-2-methyl-2,4,5,7-tetrahydro-pyrazolo[3,4-d]pyrimidin-6-one (Example 252) | A-3-5 | BB-9-18 | B 110 1 | 1.16 (I) | 478.19 |
| Ia-42 | 4-(2-Cyclopropyl-benzyl)-6-[1-(2-fluoro-6-methyl-phenyl)-piperidin-4-yl]-2-methyl-2,4,6,7-tetrahydro-pyrazolo[4,3-d]pyrimidin-5-one (Example 259) | A-3-3 | BB-9-9 | B 110 1 | 1.20 (I) | 474.20 |
| Ia-43 | 6-[1-(2-Fluoro-6-methyl-phenyl)-piperidin-4-yl]-4-isopropyl-benzyl)-2-methyl-2,4,6,7-tetrahydro-pyrazolo[4,3-d]pyrimidin-5-one (Example 260) | A-3-3 | BB-9-10 | A1 RT 18 | 1.22 (I) | 476.20 |
| Ia-44 | 6-[1-(2-Fluoro-6-methyl-phenyl)-piperidin-4-yl]-2-methyl-4-[1-(2-trifluoromethyl-phenyl)-ethyl]-2,4,6,7-tetrahydro-pyrazolo[4,3-d]pyrimidin-5-one | A-3-3 | BB-9-15 | B 110 2 | 1.18 (I) | 516.21 |
| Ia-45 | 5-[1-(2-Fluoro-6-methyl-phenyl)-azetidin-3-yl]-2-methyl-7-(2-trifluoromethyl-benzyl)-2,4,5,7-tetrahydro-pyrazolo[3,4-d]pyrimidin-6-one (Example 264) | A-3-19 | BB-9-6 | B 100 1 | 1.17 (IV) | 474.01 |
| Ia-46 | 5-[1-(2-Fluoro-6-methyl-phenyl)-piperidin-4-yl]-7-(4-isopropoxy-pyridazin-3-ylmethyl)-2-methyl-2,4,5,7-tetrahydro-pyrazolo[3,4-d]pyrimidin-6-one (Example 267) | A-3-5 | BB-9-19 | B 100 18 | 0.89 (I) | 494.21 |
| Ia-47 | 4-(2-Cyclopropyl-benzyl)-6-[1-(2-fluoro-6-methyl-phenyl)-piperidin-4-yl]-7-methyl-2-(tetrahydro-pyran-2-yl)-2,4,6,7-tetrahydro-pyrazolo[4,3-d]pyrimidin-5-one (mixture of diastereoisomers) (Example 268) | E-3-3 | BB-9-9 | B 110 3.5 | 1.22 (I) | 558.34 |
| Ia-48 | 4-(2-Cyclopropyl-benzyl)-6-(2'-methoxy-4'-methyl-3,4,5,6-tetrahydro-2H-[1,3']bipyridinyl-4-yl)-methyl-2-(tetrahydro-pyran-2-yl)-2,4,6,7-tetrahydro-pyrazolo[4,3-d]pyrimidin-5-one (mixture of diastereoisomers) (Example 269) | E-3-4 | BB-9-9 | B 110 18 | 1.14 (I) | 571.34 |
| Ia-51 | 5-[1-(2-Fluoro-6-methyl-phenyl)-piperidin-4-yl]-4-methyl-2-(tetrahydro-pyran-2-yl)-7-(2-trifluoromethyl-benzyl)-2,4,5,7-tetrahydro-pyrazolo[3,4-d]pyrimidin-6-one (mixture of diastereoisomers) (Example 313) | E-6-2 | — | E RT 1.5 +50 0.25 | 1.25 (I) | 586.40 |
| Ia-53 | 6-(2'-Methoxy-4'-methyl-3,4,5,6-tetrahydro-2H-[1,3']bipyridinyl-4-yl)-7-methyl-2-(tetrahydro-pyran-2-yl)-4-(2-trifluoromethyl-benzyl)-2,4,6,7-tetrahydro-pyrazolo[4,3-d]pyrimidin-5-one (mixture of diastereoisomers) | E-3-4 | BB-9-6 | B 110 18 | 1.14 (I) | 599.35 |
| Ia-54 | 6-[1-(2-Fluoro-6-methyl-phenyl)-piperidin-4-yl]-7-methyl-2-(tetrahydro-pyran-2-yl)-4-(2-trifluoromethyl-benzyl)-2,4,6,7-tetrahydro-pyrazolo[4,3-d]pyrimidin-5-one (mixture of diastereoisomers) (Example 294) | E-3-3 | BB-9-1 | A1 RT 18 | 1.21 (I) | 586.35 |
| Ia-55 | 2-Cyclopropyl-5-[1-(2-fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one | E-6-3 | — | E RT 72 | 1.24 (I) | 542.28 |
| Ia-56 | 2-Cyclopropyl-5-[1-(2-difluoromethyl-6-fluoro-phenyl)-piperidin-4-yl]-4-methyl-7-(2-trifluoromethyl-benzyl)-2,4,5,7-tetrahydro-pyrazolo[3,4-d]pyrimidin-6-one | E-6-4 | — | E RT 5 | 1.24 (I) | 578.15 |

TABLE 56-continued

| Ia | Name | Reactant A-3, B-3, E-3 or E-6 | Reactant BB-9 | Method T [° C.] time [h] | $t_R$ [min] (LC/MS-method) | MS-data m/z [M + H]+ |
|---|---|---|---|---|---|---|
| Ia-57 | 5-[1-(2-Difluoromethyl-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one | E-6-5 | — | E RT 18 | 1.22 (I) | 552.30 |
| Ia-58 | 7-(2-Cyclopropyl-benzyl)-5-[1-(2-fluoro-6-methyl-phenyl)-piperidin-4-yl]-2,4-dimethyl-2,4,5,7-tetrahydro-pyrazolo[3,4-d]pyrimidin-6-one | E-6-6 | — | E RT 20 | 1.22 (I) | 488.34 |
| Ia-59 | 5-[1-(2-Chloro-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one | E-6-7 | — | E RT 20 | 1.23 (I) | 536.23 |
| Ia-60 | 5-[1-(2-Chloro-6-fluoro-phenyl)-piperidin-4-yl]-7-(2-cyclopropyl-benzyl)-2,4-dimethyl-2,4,5,7-tetrahydro-pyrazolo[3,4-d]pyrimidin-6-one | E-6-8 | — | E RT 5 | 1.20 (I) | 508.32 |
| Ia-61 | 7-(2-Cyclopropyl-benzyl)-5-[1-(2-difluoromethyl-6-fluoro-phenyl)-piperidin-4-yl]-2,4-dimethyl-2,4,5,7-tetrahydro-pyrazolo[3,4-d]pyrimidin-6-one | E-6-9 | — | E RT 4 | 1.18 (I) | 524.31 |
| Ia-62 | 7-(2-Cyclopropyl-benzyl)-5-[1-(2-cyclopropyl-6-fluoro-phenyl)-piperidin-4-yl]-2,4-dimethyl-2,4,5,7-tetrahydro-pyrazolo[3,4-d]pyrimidin-6-one | E-6-10 | — | E RT 3 | 1.22 (I) | 514.05 |
| Ia-63 | 6-[1-(2-Chloro-6-fluoro-phenyl)-piperidin-4-yl]-7-methyl-2-(tetrahydro-pyran-2-yl)-4-(2-trifluoromethyl-benzyl)-2,4,6,7-tetrahydro-pyrazolo[4,3-d]pyrimidin-5-one (mixture of diastereoisomers) | E-3-5 | BB-9-1 | A1 RT 18 | 1.25 (I) | 606.32 |
| Ia-64 | 6-[1-(2-Difluoromethyl-6-fluoro-phenyl)-piperidin-4-yl]-7-methyl-2-(tetrahydro-pyran-2-yl)-4-(2-trifluoromethyl-benzyl)-2,4,6,7-tetrahydro-pyrazolo[4,3-d]pyrimidin-5-one (mixture of diastereoisomers) | E-3-6 | BB-9-1 | A1 RT 18 | 1.24 (I) | 622.34 |
| Ia-65 | 5-(2'-Methoxy-4'-methyl-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one | E-6-11 | — | E RT 18 | 1.13 (I) | 529.13 |
| Ia-66 | 5-[1-(2-Cyclopropyl-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one | E-6-12 | — | E RT 2 | 1.22 (I) | 542.33 |
| Ia-67 | 5-[1-(2-Chloro-6-fluoro-phenyl)-piperidin-4-yl]-2-cyclopropyl-4-methyl-7-(2-trifluoromethyl-benzyl)-2,4,5,7-tetrahydro-pyrazolo[3,4-d]pyrimidin-6-one | E-6-13 | — | E RT 18 | 1.26 (I) | 562.05 |
| Ia-68 | 2-Cyclopropyl-7-(2-cyclopropyl-benzyl)-5-[1-(2-fluoro-6-methyl-phenyl)-piperidin-4-yl]-4-methyl-2,4,5,7-tetrahydro-pyrazolo[3,4-d]pyrimidin-6-one | E-6-14 | — | E RT 18 | 1.23 (I) | 514.16 |
| Ia-69 | 5-[1-(2-Chloro-6-fluoro-phenyl)-piperidin-4-yl]-2-cyclopropyl-7-(2-cyclopropyl-benzyl)-4-methyl-2,4,5,7-tetrahydro-pyrazolo[3,4-d]pyrimidin-6-one | E-6-15 | — | E RT 18 | 1.24 (I) | 534.32 |
| Ia-70 | 2-Cyclopropyl-5-(2'-methoxy-4'-methyl-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one | E-6-16 | — | E RT 18 | 1.16 (I) | 555.35 |
| Ia-71 | 5-(4'-Difluoromethyl-2'-methoxy-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one | E-6-17 | — | E RT 16 | 1.21 (I) | 565.26 |
| Ia-72 | 5-[1-(2-Difluoromethyl-6-fluoro-phenyl)-piperidin-4-yl]-4-methyl-2-(tetrahydro-pyran-2-yl)-7-(2-trifluoromethyl-benzyl)-2,4,5,7-tetrahydro-pyrazolo[3,4-d]pyrimidin-6-one (mixture of diastereoisomers) (Example 341) | E-6-18 | — | E RT 18 | 1.25 (I) | 622.35 |
| Ia-73 | 5-[1-(2-Chloro-6-fluoro-phenyl)-piperidin-4-yl]-4-methyl-2-(tetrahydro-pyran-2-yl)-7-(2-trifluoromethyl-benzyl)-2,4,5,7-tetrahydro-pyrazolo[3,4-d]pyrimidin-6-one (mixture of diastereoisomers) (Example 342) | E-6-19 | — | E RT 72 | 1.27 (I) | 606.26 |

TABLE 56-continued

| Ia | Name | Reactant A-3, B-3, E-3 or E-6 | Reactant BB-9 | Method T [° C.] time [h] | t_R [min] (LC/MS-method) | MS-data m/z [M + H]+ |
|---|---|---|---|---|---|---|
| Ia-74 | 5-(4'-Difluoromethyl-2'-methoxy-3,4,5,6-tetrahydro-2H-[1,3']bipyridinyl-4-yl)-4-methyl-2-(tetrahydro-pyran-2-yl)-7-(2-trifluoromethyl-benzyl)-2,4,5,7-tetrahydro-pyrazolo[3,4-d]pyrimidin-6-one (mixture of diastereoisomers) (Example 343) | E-6-20 | — | E RT 72 | 1.26 (I) | 635.34 |
| Ia-75 | 5-[1-(2-Fluoro-6-methyl-phenyl)-piperidin-4-yl]-2,4-dimethyl-7-(3-trifluoromethyl-pyridin-2-ylmethyl)-2,4,5,7-tetrahydro-pyrazolo[3,4-d]pyrimidin-6-one | E-6-21 | — | E RT 18 | 1.12 (I) | 517.27 |
| Ia-76 | 5-(2'-Methoxy-4'-methyl-3,4,5,6-tetrahydro-2H-[1,3']bipyridinyl-4-yl)-2,4-dimethyl-7-(3-trifluoromethyl-pyridin-2-ylmethyl)-2,4,5,7-tetrahydro-pyrazolo[3,4-d]pyrimidin-6-one | E-6-22 | — | E RT 18 | 1.01 (I) | 530.12 |
| Ia-77 | 2-Cyclopropyl-5-(4'-difluoromethyl-2'-methoxy-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one | E-6-23 | — | E RT 18 | 1.23 (I) | 591.28 |
| Ia-78 | 5-[1-(2-Bromo-6-fluoro-phenyl)-piperidin-4-yl]-2-cydopropyl-4-methyl-7-(2-trifluoromethyl-benzyl)-2,4,5,7-tetrahydro-pyrazolo[3,4-d]pyrimidin-6-one | E-6-24 | — | E RT 18 | 1.26 (I) | 606.19 |
| Ia-79 | 5-(2'-Methoxy-4'-trifluoromethyl-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one | E-6-25 | — | E RT 18 | 1.24 (I) | 583.25 |
| Ia-80 | 7-(2-Cyclopropyl-benzyl)-5-(2'-methoxy-4'-methyl-3,4,5,6-tetrahydro-2H-[1,3']bipyridinyl-4-yl)-2,4-dimethyl-2,4,5,7-tetrahydro-pyrazolo[3,4-d]pyrimidin-6-one | E-6-26 | — | E RT 18 | 1.11 (I) | 501.29 |
| Ia-81 | 7-(2-Cyclopropyl-benzyl)-5-(4'-difluoromethyl-2'-methoxy-3,4,5,6-tetrahydro-2H-[1,3']bipyridinyl-4-yl)-2,4-dimethyl-2,4,5,7-tetrahydro-pyrazolo[3,4-d]pyrimidin-6-one | E-6-27 | — | E RT 72 | 1.19 (I) | 537.25 |
| Ia-82 | 7-(2-Cydopropyl-benzyl)-5-(4'-difluoromethyl-2'-methoxy-3,4,5,6-tetrahydro-2H-[1,3']bipyridinyl-4-yl)-4-methyl-2-(tetrahydro-pyran-2-yl)-2,4,5,7-tetrahydro-pyrazolo[3,4-d]pyrimidin-6-one (mixture of diastereoisomers) (Example 364) | E-6-28 | — | E RT 18 | 1.24 (I) | 607.35 |
| Ia-83 | 5-[1-(2-Chloro-6-fluoro-phenyl)-piperidin-4-yl]-7-(2-cyclopropyl-benzyl)-4-methyl-2-(tetrahydro-pyran-2-yl)-2,4,5,7-tetrahydro-pyrazolo[3,4-d]pyrimidin-6-one (mixture of diastereoisomers) (Example 365) | E-6-29 | — | E RT 18 | 1.25 (I) | 578.16 |
| Ia-84 | 7-(2-Cyclopropyl-benzyl)-5-(2'-methoxy-4'-trifluoromethyl-3,4,5,6-tetrahydro-2H-[1,3']bipyridinyl-4-yl)-2,4-dimethyl-2,4,5,7-tetrahydro-pyrazolo[3,4-d]pyrimidin-6-one | E-6-30 | — | E RT 18 | 1.23 (I) | 555.33 |
| Ia-85 | 5-(4'-Chloro-2'-methoxy-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one | E-6-31 | — | E RT 18 | 1.19 (I) | 549.26 |
| Ia-86 | 5-(4'-Chloro-2'-methoxy-3,4,5,6-tetrahydro-2H-[1,3']bipyridinyl-4-yl)-7-(2-cyclopropyl-benzyl)-2,4-dimethyl-2,4,5,7-tetrahydro-pyrazolo[3,4-d]pyrimidin-6-one | E-6-32 | — | E RT 18 | 1.19 (I) | 521.29 |
| Ia-87 | 2-Cydopropyl-7-(2-cyclopropyl-benzyl)-5-(2'-methoxy-4'-methyl-3,4,5,6-tetrahydro-2H-[1,3']bipyridinyl-4-yl)-4-methyl-2,4,5,7-tetrahydro-pyrazolo[3,4-d]pyrimidin-6-one | E-6-33 | — | E RT 18 | 1.15 (I) | 527.37 |
| Ia-88 | 2-Cydopropyl-7-(2-cyclopropyl-benzyl)-5-(4'-difluoromethyl-2'-methoxy-3,4,5,6-tetrahydro-2H-[1,3']bipyridinyl-4-yl)-4-methyl-2,4,5,7-tetrahydro-pyrazolo[3,4-d]pyrimidin-6-one | E-6-34 | — | E RT 18 | 1.22 (I) | 563.37 |
| Ia-89 | 5-[1-(2-Bromo-6-fluoro-phenyl)-piperidin-4-yl]-7-(2-cyclopropyl-benzyl)-2,4-dimethyl-2,4,5,7-tetrahydro-pyrazolo[3,4-d]pyrimidin-6-one | E-6-35 | — | E RT 1.5 | 1.22 (I) | 552.28 |

Synthesis of Compounds of Formula Ib and Ic

Method A (Complete SEM Cleavage)

Step A (TFA Treatment):

To a soln. of SEM-protected intermediate Ia (1 eq) in DCM (2 to 4 mL/mmol) was added dropwise TFA (4 to 6 mL/mmol). The soln. was stirred at RT for a given time (see Table), quenched at 0° C. with a 32% or 1M aq. soln. of NaOH until pH 7-8 and extracted with DCM. The combined org. phases were dried over MgSO$_4$ and concentrated in vacuo.

Step B (Additional Treatment):

The crude was dissolved in THF (5 to 10 mL/mmol) and treated with ethylenediamine (3 eq) for 30 min to 1h at 60° C. The rxn mixture was partitioned between DCM and water and the org. phase was washed with brine, dried over MgSO$_4$ and concentrated in vacuo. When necessary, the crude was purified by CC using Hept/EtOAc.

Method B (Partial SEM Cleavage with O-Alkylation)

Step a (TFA Treatment):

To a soln. of SEM-protected intermediate Ia (1 eq) in DCM (2 mL/mmol) was added dropwise TFA (4 mL/mmol). The soln. was stirred at RT for a given time (see Table), quenched at 0° C. with a 32% aq. soln. of NaOH until pH 7-8 and extracted with DCM. The combined org. phases were dried over MgSO$_4$ and concentrated in vacuo.

Step B (Treatment with Alcohol):

The crude was dissolved in EtOH or MeOH (5 mL/mmol) and treated with a 4M soln. of HCl in dioxane (5 mL/mmol) for 30 min at 70° C. The rxn mixture was basified with a 1M aq. soln. of NaOH until pH 8-9 and extracted with DCM. The combined org. phases were washed with brine, dried over MgSO$_4$ and concentrated in vacuo. The crude was purified by CC using Hept/EtOAc.

Method C (Bn Cleavage)

To a soln. of Bn-protected intermediate Ia (1 eq) in EtOH (9.8 mL/mmol) was added ammonium formate (4 eq). The flask was evacuated three times and refilled with nitrogen. 10% Pd/C moistened with ~50% water (0.1 eq) was added and the flask was evacuated and refilled with hydrogen. The rxn mixture was hydrogenated under atmospheric pressure at a given temperature for a given time (see Table). When necessary to reach completion of the rxn, extra amounts of ammonium formate (4 eq) and/or 10% Pd/C moistened with ~50% water (0.1 eq) were added. The rxn mixture was filtered over a pad of celite and the filtrate was concentrated in vacuo. The crude was purified by CC using Hept/EtOAc.

Method D (THP Cleavage)

To soln. of THP-protected intermediate Ia (1 eq) in DM (4 to 5 mL/mmol) was added dropwise TA (2 to 4 mL/mmol). The soln. was stirred at RT for a given time (see Table), quenched at 0° C. with a 1M aq. soln. of NaOH until pH 10-11 and extracted with DCM. The combined org. phases were dried over MgSO$_4$ and concentrated in vacuo. The crude was purified by CC using Hept/EtOAc or by prep. LC-MS using method 2, 5 or 11.

TABLE 57

| Ib or Ic | Name | Reactant Ia | Method T [° C.] time [h] | t$_R$ [min] (LC/MS method) | MS-data m/z [M + H]$^+$ |
|---|---|---|---|---|---|
| Ib-1 | 6-[1-(2-Fluoro-6-methyl-phenyl)-piperidin-4-yl]-4-(2-trifluoromethyl-benzyl)-1,4,6,7-tetrahydro-pyrazolo[4,3-d]pyrimidin-5-one or 6-[1-(2-Fluoro-6-methyl-phenyl)-piperidin-4-yl]-4-(2-trifluoromethyl-benzyl)-2,4,6,7-tetrahydro-pyrazolo[4,3-d]pyrimidin-5-one (Example 2) | Ia-1A or Ia-1B | A RT 2 | 1.15 (I) | 488.22 |
| Ib-2 | 5-[1-(2-Fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 6) | Ia-2 | A RT 2.5 | 1.14 (I) | 488.24 |
| Ic-1 | 2-Ethoxymethyl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 7) | Ia-2 | B (EtOH) RT 1 | 1.08 (II) | 546.02 |
| Ib-3 | 1-[1-(2-Fluoro-6-methyl-phenyl)-piperidin-4-yl]-3-(2-trifluoromethyl-benzyl)-1,3,6,9-tetrahydro-purin-2-one (Example 14) | Ia-5 | A (only step A) RT 4.5 | 0.91 (II) | 488.11 |
| Ib-4 | 6-[1-(2-Fluoro-6-methyl-phenyl)-piperidin-4-yl]-4-(2-trifluoromethyl-benzyl)-3,4,6,7-tetrahydro-[1,2,3]triazolo[4,5-d]pyrimidin-5-one or 6-[1-(2-Fluoro-6-methyl-phenyl)-piperidin-4-yl]-4-(2-trifluoromethyl-benzyl)-2,4,6,7-tetrahydro-[1,2,3]triazolo[4,5-d]pyrimidin-5-one (Example 76) | Ia-12 | C 60 48 | 1.02 (II) | 489.10 |
| Ib-5 | 5-[1-(2-Fluoro-6-methyl-phenyl)-piperidin-4-yl]-7-(3-trifluoromethyl-pyridin-2-ylmethyl)-2,4,5,7-tetrahydro-pyrazolo[3,4-d]pyrimidin-6-one (Example 193) | Ia-19 | A RT 0.7 | 1.04 (I) | 489.22 |
| Ib-6 | 5-(2'-Methoxy-4'-methyl-3,4,5,6-tetrahydro-2H-[1,3']bipyridinyl-4-yl)-7-(2-trifluoromethyl-benzyl)-2,4,5,7-tetrahydro-pyrazolo[3,4-d]pyrimidin-6-one (Example 197) | Ia-20 | A RT 1 | 1.03 (I) | 501.24 |
| Ib-7 | 6-[1-(2-Fluoro-6-methyl-phenyl)-piperidin-4-yl]-4-(3-trifluoromethyl-pyridin-2-ylmethyl)-2,4,6,7-tetrahydro-pyrazolo[4,3-d]pyrimidin-5-one (Example 204) | Ia-21 | A RT 2 | 1.04 (I) | 489.22 |

TABLE 57-continued

| Ib or Ic | Name | Reactant Ia | Method T [° C.] time [h] | $t_R$ [min] (LC/MS method) | MS-data m/z $[M + H]^+$ |
|---|---|---|---|---|---|
| Ib-8 | 7-(2-Bromo-6-trifluoromethyl-benzyl)-5-[1-(2-fluoro-6-methyl-phenyl)-piperidin-4-yl]-2,4,5,7-tetrahydro-pyrazolo[3,4-d]pyrimidin-6-one (Example 211) | Ia-23 | A RT 0.5 | 1.16 (I) | 566.11 |
| Ib-9 | 6-(2'-Methoxy-4'-methyl-3,4,5,6-tetrahydro-2H-[1,3']bipyridinyl-4-yl)-4-(2-trifluoromethyl-benzyl)-2,4,6,7-tetrahydro-pyrazolo[4,3-d]pyrimidin-5-one (Example 218) | Ia-24 | A RT 2 | 1.03 (I) | 501.22 |
| Ic-92 | 2-Methoxymethyl-5-(2'-methoxy-4'-methyl-3,4,5,6-tetrahydro-2H-[1,3']bipyridinyl-4-yl)-7-(2-trifluoromethyl-benzyl)-2,4,5,7-tetrahydro-pyrazolo[3,4-d]pyrimidin-6-one (Example 227) | Ia-20 | B (MeOH) RT 1 | 1.21 (IV) | 544.80 |
| Ib-10 | 6-[1-(2-Fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one | Ia-35 | A RT 1 | 1.16 (I) | 502.18 |
| Ib-11 | 4-(2-Cyclopropyl-benzyl)-6-(2'-methoxy-4'-methyl-3,4,5,6-tetrahydro-2H-[1,3']bipyridinyl-4-yl)-7-methyl-2,4,6,7-tetrahydro-pyrazolo[4,3-d]pyrimidin-5-one | Ia-48 | D RT 20 | 1.02 (I) | 487.25 |
| Ib-12 | 4-(2-Cyclopropyl-benzyl)-6-[1-(2-fluoro-6-methyl-phenyl)-piperidin-4-yl]-7-methyl-2,4,6,7-tetrahydro-pyrazolo[4,3-d]pyrimidin-5-one | Ia-47 | D RT 20 | 1.13 (I) | 474.29 |
| Ib-13 | 5-[1-(2-Fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one | Ia-51 | D RT 20 | 1.14 (I) | 502.33 |
| Ib-14 | 6-(2'-Methoxy-4'-methyl-3,4,5,6-tetrahydro-2H-[1,3']bipyridinyl-4-yl)-7-methyl-4-(2-trifluoromethyl-benzyl)-2,4,6,7-tetrahydro-pyrazolo[4,3-d]pyrimidin-5-one | Ia-53 | D RT 2 | 1.03 (I) | 515.31 |
| Ib-15 | 6-[1-(2-Chloro-6-fluoro-phenyl)-piperidin-4-yl]-7-methyl-4-(2-trifluoromethyl-benzyl)-2,4,6,7-tetrahydro-pyrazolo[4,3-d]pyrimidin-5-one | Ia-63 | D RT 1.5 | 1.17 (I) | 522.19 |
| Ib-16 | 6-[1-(2-Difluoromethyl-6-fluoro-phenyl)-piperidin-4-yl]-7-methyl-4-(2-trifluoromethyl-benzyl)-2,4,6,7-tetrahydro-pyrazolo[4,3-d]pyrimidin-5-one | Ia-64 | D RT 1.5 | 1.16 (I) | 538.21 |
| Ib-17 | 5-[1-(2-Difluoromethyl-6-fluoro-phenyl)-piperidin-4-yl]-4-methyl-7-(2-trifluoromethyl-benzyl)-2,4,5,7-tetrahydro-pyrazolo[3,4-d]pyrimidin-6-one | Ia-72 | D RT 18 | 1.15 (I) | 538.19 |
| Ib-18 | 5-[1-(2-Chloro-6-fluoro-phenyl)-piperidin-4-yl]-4-methyl-7-(2-trifluoromethyl-benzyl)-2,4,5,7-tetrahydro-pyrazolo[3,4-d]pyrimidin-6-one | Ia-73 | D RT 18 | 1.16 (I) | 522.17 |
| Ib-19 | 5-(4'-Difluoromethyl-2'-methoxy-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one | Ia-74 | D RT 18 | 1.14 (I) | 551.23 |
| Ib-20 | 7-(2-Cyclopropyl-benzyl)-5-(4'-difluoromethyl-2'-methoxy-3,4,5,6-tetrahydro-2H-[1,3']bipyridinyl-4-yl)-4-methyl-2,4,5,7-tetrahydro-pyrazolo[3,4-d]pyrimidin-6-one | Ia-82 | D RT 3 | 1.12 (I) | 523.30 |
| Ib-21 | 5-[1-(2-Chloro-6-fluoro-phenyl)-piperidin-4-yl]-7-(2-cyclopropyl-benzyl)-4-methyl-2,4,5,7-tetrahydro-pyrazolo[3,4-d]pyrimidin-6-one | Ia-83 | D RT 6 | 1.15 (I) | 494.22 |

Synthesis of Compounds of Formula Ic, Id and Ie

Method a (Methylation Using Silver Carbonate)

To a suspension of intermediate Ib (1 eq) and silver carbonate (1.2 eq) in toluene (6 mL/mmol) was added MeI (5 eq) and the rxn mixture was stirred at 85° C. for a given time (see Table). It was filtered and the filtrate was concentrated in vacuo. The crude was purified by CC using DCM/MeOH. When necessary, an additional purification by prep. LC-MS using methods 1, 3 or 4 was performed.

Method B (Alkylation Using NaH and Halide or Aziridine)

Method B1: A soln. or suspension of intermediate Ib (1 eq) in anh. THF (6 to 10 mL/mmol) was added dropwise at 0° C. to a suspension of NaH (2.2 to 4 eq, as a 60% dispersion in mineral oil) in anh. THF (4 to 6 mL/mmol).

Method B2: NaH (4 eq, as a 60% dispersion in mineral oil) was added portionwise at 0° C. to a soln. or suspension of intermediate Ib (1 eq) in THF (10 to 13 mL/mmol).

Common following procedure: The suspension was stirred for 10 to 30 min at RT, cooled to 0° C. and halide or aziridine BB-10 (1.2 to 3 eq) was added. The rxn mixture was stirred at a given temperature for a given time (see Table). When necessary to reach completion of the rxn, extra amounts of NaH (1 to 2 eq) and/or halide or aziridine BB-10 (1 eq) were added. The rxn mixture was quenched with $H_2O$ at 0° C. and extracted with EtOAc or DCM. The combined org. phases were washed with brine, dried over $MgSO_4$ and concentrated in vacuo. The crude was purified by CC using Hept/EtOAc and/or DCM/MeOH.

Method C (Alkylation Using Mitsunobu Conditions)

To a soln. or suspension of intermediate Ib (1 eq) and alcohol BB-10 (1.5 to 2 eq) in toluene (6 to 12 mL/mmol)

was added a 1M soln. of (tributylphosphoranylidene)acetonitrile in toluene (2 eq) under argon. The rxn mixture was heated to a given temperature and stirred for a given time (see Table). It was quenched with water and extracted with EtOAc or DCM. The combined org. phases were washed with brine, dried over MgSO$_4$ and concentrated in vacuo. The crude was purified by CC using Hept/EtOAc or DCM/MeOH. When necessary, an additional purification by prep. LC-MS using methods 2, 4, 5, 8 or 10 was performed.

Method D (Methylation Using DBU)

To a soln. of intermediate Ib (1 eq) and DBU (1.2 eq) in anh. DMF (4 mL/mmol) was added MeI (1.3 eq). The rxn mixture was stirred at RT for a given time (see Table) and evaporated under reduced pressure. The residue was purified by prep. LC-MS using methods 2, 4 and/or 5.

Method E (Alkylation Using K$_2$CO$_3$ and Halide or Epoxide)

A mixture of compound Ib (1 eq), K$_2$CO$_3$ (1.5 to 5 eq) and epoxide or halide BB-10 (2 to 5 eq) in DMF (5 to 8.5 mL/mmol) was heated to a given temperature and stirred for a given time (see Table). When necessary to reach completion of the rxn an extra amount of epoxide or halide BB-10 (1 eq) was added and the rxn mixture was further stirred for 2h at 120° C. It was partitioned between EtOAc and H$_2$O and the org. phase was washed with H$_2$O and brine, dried over MgSO$_4$ and concentrated in vacuo. The crude was purified by CC using Hept/EtOAc.

Method F (1,4-Nucleophilic Addition Using K$_2$CO$_3$)

A mixture of compound Ib (1 eq), α,β-unsaturated carbonyl reagent BB-10 (2 eq), K$_2$CO$_3$ (1.5 eq) and TEA (3 eq) in THF (10 mL/mmol) was heated to 60° C. and stirred for a given time (see Table). It was partitioned between DCM and H$_2$O and the org. phase was washed with brine, dried over MgSO$_4$ and concentrated in vacuo. The crude was purified by CC using Hept/EtOAc.

Method G (1,4-Nucleophilic Addition Using CsF)

To a soln. of compound Ib (1 eq) in DMF (10 mL/mmol) was added nitroalkene BB-10 (1 eq) and CsF (1.2 eq) at 0° C. The rxn mixture was stirred for 30 min at 0° C. and at RT for a given time (see Table). Consecutive additions of BB-10 (1 eq) and CsF (1 eq) at 0° C. were necessary to allow the rxn to proceed. It was partitioned between EtOAc and H$_2$O and the org. phase was washed with H$_2$O and brine, dried over MgSO$_4$ and concentrated in vacuo. The crude was purified by prep LC-MS using method 4.

Method H (Alkoxycarbonylation/Alkylcarbamylation)

A soln. of compound Ib (1 eq) and TEA (3 eq) in DCM (8.1 mL/mmol) was cooled to 0° C. and chloroformate or isocyanate BB-10 (2 eq) was added dropwise at 0° C. The rxn mixture was allowed to slowly reach RT and stirred for a given time (see Table). It was diluted with DCM and washed with a sat. aq. soln. of NaHCO$_3$ and with brine. The org. phase was dried over MgSO$_4$ and concentrated in vacuo. The crude was purified by CC using Hept/EtOAc.

Method I (Urea Formation)

A soln. of compound Ib (1 eq) and TEA (3 eq) in THF (10 mL/mmol) was treated with CDI (1.2 eq) and the rxn mixture was stirred at RT for 15 min. Amine BB-10 (3 to 5 eq) was added at RT and the mixture was stirred at a given temperature for a given time (see Table). The rxn mixture was partitioned between DCM and a half sat. aq. soln. of NaHCO$_3$ and the org. phase was washed with brine, dried over MgSO$_4$ and concentrated in vacuo. The crude was purified by CC using Hept/EtOAc.

Method J1 (Chan-Lam rxn 1)

A mixture of compound Ib (1 eq), boron species BB-10 (2 eq), Na$_2$CO$_3$ (2 eq), 2,2'-bipyridyl (1 eq) and Cu(OAc)$_2$ (1 eq) in toluene (10 to 12 mL/mmol) was flushed with N$_2$ and heated at a given temperature for a given time (see Table). When necessary to reach completion of the rxn an extra amount of boron species BB-10 (2 eq) was added. It was partitioned between EtOAc or DCM and a sat. aq. soln. of NaHCO$_3$ and the org. phase was washed with brine, dried over MgSO$_4$ and concentrated in vacuo. The crude was purified by CC using Hept/EtOAc or DCM/MeOH and/or by prep. HPLC using method 3 or 5.

Method J2 (Chan-Lam rxn 2)

A suspension of 2,2-bipyridyl(1 eq) and Cu(OAc)$_2$(1 eq) in trifluorobenzene (3 mL/mmol) was heated to 70° C. and stirred for 30 min. It was added at RT to a mixture of compound Ib (1 eq), boron species BB-10 (2 eq) and Na$_2$CO$_3$ (2 eq) in trifluoromethylbenzene (1.5 mL/mmol). The rxn mixture was heated to 110° C. and stirred for a given time (see Table). It was diluted with EtOAc and washed with a 10% soln. of citric acid. The org. phase was washed with brine dried over MgSO$_4$ and concentrated in vacuo. The crude was purified by prep. LC-MS using method 4.

Method K (Alkylation Using Cs$_2$CO$_3$ and Tosylate)

A mixture of compound Ib (1 eq), tosylate BB-10 (1.05 to 1.5 eq) and Cs$_2$CO$_3$ (2 to 2.3 eq) in DMA (5 to 7 mL/mmol) was heated at a given temperature for a given time (see Table). It was partitioned between EtOAc and water and the org. phase was washed with brine, dried over MgSO$_4$ and concentrated in vacuo. The crude was purified by CC using Hept/EtOAc or/and by prep. LC-MS using method 4 or 5.

TABLE 60

| Ic/Id/Ie | Name | Reactant Ib | Reactant BB-10 | Method T [° C.] time [h] | $t_R$ [min] (LC/MS-method) | MS-data m/z $[M + H]^+$ |
|---|---|---|---|---|---|---|
| Ic-2 | 6-[1-(2-Fluoro-6-methyl-phenyl)-piperidin-4-yl]-2-methyl-4-(2-trifluoromethyl-benzyl)-2,4,6,7-tetrahydro-pyrazolo[4,3-d]pyrimidin-5-one (Example 3) | Ib-1 | MeI | A 85 0.25 | 1.08 (II) | 502.27 |
| Id-1 | 6-[1-(2-Fluoro-6-methyl-phenyl)-piperidin-4-yl]-1-methyl-4-(2-trifluoromethyl-benzyl)-1,4,6,7-tetrahydro-pyrazolo[4,3-d]pyrimidin-5-one (Example 4) | | | | 1.07 (II) | 502.70 |
| Ic-3 | 5-[1-(2-Fluoro-6-methyl-phenyl)-piperidin-4-yl]-2-methyl-7-(2-trifluoromethyl-benzyl)-2,4,5,7-tetrahydro-pyrazolo[3,4-d]pyrimidin-6-one (Example 8) | Ib-2 | MeI | B1 RT 1.5 | 1.22 (I) | 502.16 |

TABLE 60-continued

| Ic/Id/Ie | Name | Reactant Ib | Reactant BB-10 | Method T [° C.] time [h] | $t_R$ [min] (LC/MS-method) | MS-data m/z $[M + H]^+$ |
|---|---|---|---|---|---|---|
| Ic-4 | 5-[1-(2-Fluoro-6-methyl-phenyl)-piperidin-4-yl]-2-[$^2$H$_3$]methyl-7-(2-trifluoromethyl-benzyl)-2,4,5,7-tetrahydro-pyrazolo[3,4-d]pyrimidin-6-one (Example 9) | Ib-2 | CD$_3$OD | C 110 1 | 1.20 (I) | 505.27 |
| Ie-1 | 5-[1-(2-Fluoro-6-methyl-phenyl)-piperidin-4-yl]-1-methyl-7-(2-trifluoromethyl-benzyl)-1,4,5,7-tetrahydro-pyrazolo[3,4-d]pyrimidin-6-one (Example 10) | Ib-2 | MeI | A 85 3 | 1.11 (II) | 502.10 |
| Id-2 | 1-[1-(2-Fluoro-6-methyl-phenyl)-piperidin-4-yl]-7-methyl-3-(2-trifluoromethyl-benzyl)-1,3,6,7-tetrahydro-purin-2-one (Example 16) | Ib-3 | MeI | D RT 18 | 0.99 (II) | 502.11 |
| Ic-5 | [5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-acetic acid methyl ester (Example 17) | Ib-2 | Bromoacetic acid methyl ester | B1 RT 1.5 | 1.05 (II) | 560.09 |
| Ic-6 | [6-[1-(2-Fluoro-6-methyl-phenyl)-piperidin-4-yl]-5-oxo-4-(2-trifluoromethyl-benzyl)-4,5,6,7-tetrahydro-pyrazolo[4,3-d]pyrimidin-2-yl]-acetic acid methyl ester (Example 18) | Ib-1 | Bromoacetic acid methyl ester | B1 RT 4 | 1.04 (II) | 560.19 |
| Id-3 | [6-[1-(2-Fluoro-6-methyl-phenyl)-piperidin-4-yl]-5-oxo-4-(2-trifluoromethyl-benzyl)-4,5,6,7-tetrahydro-pyrazolo[4,3-d]pyrimidin-1-yl]-acetic acid methyl ester (Example 19) | | | | 1.04 (II) | 560.19 |
| Ic-8 | [5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-acetonitrile (Example 24) | Ib-2 | Bromo acetonitrile | B1 RT 0.25 | 1.04 (II) | 527.12 |
| Ic-9 | 5-[1-(2-Fluoro-6-methyl-phenyl)-piperidin-4-yl]-2-(2-hydroxy-2-methyl-propyl)-7-(2-trifluoromethyl-benzyl)-2,4,5,7-tetrahydro-pyrazolo[3,4-d]pyrimidin-6-one (Example 25) | Ib-2 | 2,2-Dimethyl oxirane | E 100 18 | 1.18 (I) | 560.16 |
| Ic-10 | 2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-2-methyl-propionic acid methyl ester (Example 27) | Ib-2 | 2-Bromo-2-methyl propanoic acid methyl ester | B1 60 18 | 1.10 (II) | 588.08 |
| Ic-11 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-2-methyl-propionic acid methyl ester (Example 31) | | | | 1.09 (II) | 588.12 |
| Ic-12 | 2-(2,2-Diethoxy-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 28) | Ib-2 | Bromo acetaldehyde diethyl acetal | B1 70 192 | 1.11 (II) | 604.06 |
| Ic-13 | 2-(2,3-Dihydroxy-propyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 40) | Ib-2 | Oxiran-2-yl methanol | E 100 1 | 0.95 (II) | 561.98 |
| Ic-14 | 5-[1-(2-Fluoro-6-methyl-phenyl)-piperidin-4-yl]-2-((R)-2-hydroxy-3-methoxy-propyl)-7-(2-trifluoromethyl-benzyl)-2,4,5,7-tetrahydro-pyrazolo[3,4-d]pyrimidin-6-one (Example 41) | Ib-2 | (S)-2-(Methoxy methyl)oxirane | E 100 5 | 1.02 (II) | 576.10 |

TABLE 60-continued

| Ic/Id/Ie | Name | Reactant Ib | Reactant BB-10 | Method T [° C.] time [h] | $t_R$ [min] (LC/MS-method) | MS-data m/z [M + H]+ |
|---|---|---|---|---|---|---|
| Ic-15 | 2-Chloro-3-[5-[1-(2-fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-propionic acid methyl ester (Example 42) | Ib-2 | 2-Chloro acrylic acid methyl ester | F 60 24 | 1.09 (II) | 608.01 |
| Ic-16 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-2-methyl-propionitrile (Example 43) | Ib-2 | 2-Chloro-2-methyl propanenitrile | E 100 18 | 1.07 (II) | 555.12 |
| Ic-17 | 5-[1-(2-Fluoro-6-methyl-phenyl)-piperidin-4-yl]-2-((S)-2-hydroxy-3-methoxy-propyl)-7-(2-trifluoromethyl-benzyl)-2,4,5,7-tetrahydro-pyrazolo[3,4-d]pyrimidin-6-one (Example 46) | Ib-2 | (R)-2-(methoxy methyl)oxirane | E 100 4 | 1.02 (II) | 576.11 |
| Ic-18 | 2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-propionamide (Example 75) | Ib-2 | 2-Bromo propionamide | B1 RT 2 | 1.01 (II) | 559.19 |
| Ic-19 | 5-[1-(2-Fluoro-6-methyl-phenyl)-piperidin-4-yl]-2-oxetan-3-yl-7-(2-trifluoromethyl-benzyl)-2,4,5,7-tetrahydro-pyrazolo[3,4-d]pyrimidin-6-one (Example 77) | Ib-2 | Oxetan-3-ol | C 110 1.5 | 1.08 (II) | 544.18 |
| Ic-20 | 6-[1-(2-Fluoro-6-methyl-phenyl)-piperidin-4-yl]-2-methyl-4-(2-trifluoromethyl-benzyl)-2,4,6,7-tetrahydro-[1,2,3]triazolo[4,5-d]pyrimidin-5-one (Example 81) | Ib-4 | MeI | B2 RT 2 | 1.10 (II) | 503.15 |
| Ic-21 | 5-[1-(2-Fluoro-6-methyl-phenyl)-piperidin-4-yl]-2-(2-nitro-cyclohexyl)-7-(2-trifluoromethyl-benzyl)-2,4,5,7-tetrahydro-pyrazolo[3,4-d]pyrimidin-6-one (Example 82) | Ib-2 | 1-Nitro-1-cyclohexane | G RT 72 | 1.12 (II) | 615.13 |
| Ic-22 | {2,2,2-Trifluoro-1-[5-[1-(2-fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-1-methyl-ethyl}-carbamic acid tert-butyl ester (Example 83) | Ib-2 | BB-10-1 | E 80 24 | 1.14 (II) | 699.20 |
| Ic-23 | 2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-isobutyramide (Example 84) | Ib-2 | 2-Bromo-2-methyl propanamide | B2 RT 168 | 1.04 (II) | 573.09 |
| Ic-24 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid tert-butyl ester (Example 91) | Ib-2 | 3-Hydroxy azetidine-1-carboxylic acid tert-butyl ester | C 100 18 | 1.12 (II) | 643.17 |
| Ic-25 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-pyrrolidine-1-carboxylic acid tert-butyl ester (Example 93) | Ib-2 | 3-Hydroxy-pyrrolidine-1-carboxylic acid tert-butyl ester | C 110 1 | 1.13 (II) | 657.20 |
| Ic-26 | 2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid tert-butyl ester | Ib-2 | 2-Hydroxy methyl-azetidine-1-carboxylic acid tert-butyl ester | C 100 0.5 | 1.13 (II) | 657.18 |
| Ic-27 | 2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-pyrrolidine-1-carboxylic acid tert-butyl ester (Example 97) | Ib-2 | 2-Hydroxy methyl-pyrrolidine-1-carboxylic acid tert-butyl ester | C 110 1 | 1.14 (II) | 671.17 |

TABLE 60-continued

| Ic/Id/Ie | Name | Reactant Ib | Reactant BB-10 | Method T [° C.] time [h] | $t_R$ [min] (LC/MS-method) | MS-data m/z $[M + H]^+$ |
|---|---|---|---|---|---|---|
| Ic-28 | {2-[5-[1-(2-Fluoro-6-methyl-phenyl)-piperidin-4-yl]-6-oxo-7-(2-trifluoromethyl-benzyl-)-4,5,6,7-tetrahydro-pyrazolo[3,4-d]pyrimidin-2-yl]-cyclopentyl}-carbamic acid tert-butyl ester (Example 98) | Ib-2 | (2-Hydroxy-cyclopentyl)-carbamic acid tert-butyl ester | C 110 18 | 1.14 (II) | 671.21 |
| Ic-29 | 4-Chloro-N-{2-[5-[1-(2-fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-1,1-dimethyl-ethyl}-benzenesulfonamide (Example 101) | Ib-2 | BB-10-2 | B2 70 3.5 | 1.13 (II) | 733.18 |
| Ic-30 | (R)-4,4-Difluoro-2-[5-[1-(2-fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-pyrrolidine-1-carboxylic acid tert-butyl ester (Example 108) | Ib-2 | (R)-4,4-Difluoro-2-hydroxy methyl-pyrrolidine-1-carboxylic acid tert-butyl ester | C 110 1 | 1.30 (I) | 707.14 |
| Ic-31 | (S)-4,4-Difluoro-2-[5-[1-(2-fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-pyrrolidine-1-carboxylic acid tert-butyl ester (Example 109) | Ib-2 | (S)-4,4-Difluoro-2-hydroxy methyl-pyrrolidine-1-carboxylic acid tert-butyl ester | C 110 1 | 1.30 (I) | 707.16 |
| Ic-32 | N-{2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-1,1-dimethyl-ethyl}-2-nitro-benzenesulfonamide (Example 110) | Ib-2 | BB-10-3 | B2 RT 24 | 1.26 (I) | 744.23 |
| Ic-33 | (S)-2-[5-(1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid tert-butyl ester (Example 121) | Ib-2 | (S)-2-Hydroxy-methyl-azetidine-1-carboxylic acid tert-butyl ester | C 110 1.25 | 1.28 (I) | 657.21 |
| Ic-34 | (R)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid tert-butyl ester (Example 129) | Ib-2 | (R)-2-Hydroxy methyl-azetidine-1-carboxylic acid tert-butyl ester | C 110 1.5 | 1.30 (I) | 657.22 |
| Ic-35 | 5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidine-2-carboxylic acid isopropyl ester (Example 147) | Ib-2 | Isopropyl chloroformate (1M soln. In toluene) | H RT 1 | 1.27 (I) | 574.10 |
| Ic-36 | 5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidine-2-carboxylic acid isobutyl ester (Example 148) | Ib-2 | Isobutyl chloroformate | H RT 1.5 | 1.30 (I) | 588.12 |
| Ic-37 | 5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidine-2-carboxylic acid dimethylamide (Example 149) | Ib-2 | Dimethylamine (2M soln. in THF) | I RT 18 | 1.25 (I) | 559.11 |
| Ic-38 | 5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidine-2-carboxylic acid isobutyl-methyl-amide (Example 150) | Ib-2 | Isobutyl-methyl-amine | I RT | 1.32 (I) | 601.11 |
| Ic-39 | 5-[1-(2-Fluoro-6-methyl-phenyl)-piperidin-4-yl]-2-(1-methyl-2-oxo-pyrrolidin-3-yl)-7-(2-trifluoromethyl-benzyl)-2,4,5,7-tetrahydro-pyrazolo[3,4-d]pyrimidin-6-one (Example 151) | Ib-2 | 3-Bromo-1-methylpyrrolidin-2-one | B2 RT 0.5 | 1.17 (I) | 585.20 |

TABLE 60-continued

| Ic/Id/Ie | Name | Reactant Ib | Reactant BB-10 | Method T [° C.] time [h] | $t_R$ [min] (LC/MS-method) | MS-data m/z $[M + H]^+$ |
|---|---|---|---|---|---|---|
| Ic-40 | 5-[1-(2-Fluoro-6-methyl-phenyl)-piperidin-4-yl]-2-(1-isopropyl-2-oxo-pyrrolidin-3-yl)-7-(2-trifluoromethyl-benzyl)-2,4,5,7-tetrahydro-pyrazolo[3,4-d]pyrimidin-6-one (Example 152) | Ib-2 | 3-Bromo-1-(propan-2-yl)pyrrolidin-2-one | B2 RT 0.5 | 1.22 (I) | 613.24 |
| Ic-41 | 5-[1-(2-Fluoro-6-methyl-phenyl)-piperidin-4-yl]-2-[2-([²H₃]methyl)[1,1,2,3,3,3-²H₆]propyl]-7-(2-trifluoromethyl-benzyl)-2,4,5,7-tetrahydro-pyrazolo[3,4-d]pyrimidin-6-one (Example 156) | Ib-2 | 2-([²H₃]methyl)[1,1,2,3,3,3-²H₆]propan-1-ol | C 110 2.5 | 1.27 (I) | 553.24 |
| Ic-42 | 5-[1-(2-Fluoro-6-methyl-phenyl)-piperidin-4-yl]-2-(2-oxo-1-trityl-azetidin-3-yl)-7-(2-trifluoromethyl-benzyl)-2,4,5,7-tetrahydro-pyrazolo[3,4-d]pyrimidin-6-one | Ib-2 | BB-10-4 | E 150 1.5 (microwave) | 1.35 (I) | 799.16 |
| Ic-43 | 5-[1-(2-Fluoro-6-methyl-phenyl)-piperidin-4-yl]-2-(1-methyl-cyclopropylmethyl)-7-(2-trifluoromethyl-benzyl)-2,4,5,7-tetrahydro-pyrazolo[3,4-d]pyrimidin-6-one (Example 158) | Ib-2 | (1-Methyl-cyclopropyl)-methanol | C 110 1 | 1.28 (I) | 556.14 |
| Ic-44 | 2-(2,2-Difluoro-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 159) | Ib-2 | 2,2-Difluoroethanol | C 110 18 | 1.21 (I) | 552.07 |
| Ic-45 | 2-(1,1-Dimethyl-prop-2-ynyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 160) | Ib-2 | 2-Methyl-3-butyn-2-ol | C 110 18 | 1.28 (I) | 554.13 |
| Ic-46 | 5-[1-(2-Fluoro-6-methyl-phenyl)-piperidin-4-yl]-2-isopropyl-7-(2-trifluoromethyl-benzyl)-2,4,5,7-tetrahydro-pyrazolo[3,4-d]pyrimidin-6-one (Example 161) | Ib-2 | 2-Propanol | C 110 1 | 1.26 (I) | 530.12 |
| Ic-47 | 5-[1-(2-Fluoro-6-methyl-phenyl)-piperidin-4-yl]-2-([1,1,1,2,3,3,3-²H₇]propan-2-yl)-7-(2-trifluoromethyl-benzyl)-2,4,5,7-tetrahydro-pyrazolo[3,4-d]pyrimidin-6-one (Example 162) | Ib-2 | 2-[1,1,1,2,3,3,3-²H₇]Propan[²H]ol | C 110 1.5 | 1.26 (I) | 537.31 |
| Ic-48 | 5-[1-(2-Fluoro-6-methyl-phenyl)-piperidin-4-yl]-2-([1,1,1,3,3,3-²H₆]propan-2-yl)-7-(2-trifluoromethyl-benzyl)-2,4,5,7-tetrahydro-pyrazolo[3,4-d]pyrimidin-6-one (Example 163) | Ib-2 | 2-[1,1,1,3,3,3-²H₆]Propanol | C 110 1.5 | 1.26 (I) | 536.30 |
| Ic-49 | 5-[1-(2-Fluoro-6-methyl-phenyl)-piperidin-4-yl]-2-(3-fluoro-oxetan-3-ylmethyl)-7-(2-trifluoromethyl-benzyl)-2,4,5,7-tetrahydro-pyrazolo[3,4-d]pyrimidin-6-one (Example 164) | Ib-2 | (3-Fluoro-oxetan-3-yl)-methanol | C 110 1.5 | 1.20 (I) | 576.12 |
| Ic-50 | 2-Cyclopropylmethyl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 165) | Ib-2 | Cyclopropyl-methanol | C 110 1 | 1.26 (I) | 542.09 |
| Ie-2 | 1-Cyclopropylmethyl-5-[1-(2-fluoro-6-methyl-phenyl)-piperidin-4-yl]-7-(2-trifluoromethyl-benzyl)-1,4,5,7-tetrahydro-pyrazolo[3,4-d]pyrimidin-6-one (Example 210) | | | | 1.24 (I) | 542.30 |

TABLE 60-continued

| Ic/Id/Ie | Name | Reactant Ib | Reactant BB-10 | Method T [° C.] time [h] | $t_R$ [min] (LC/MS-method) | MS-data m/z $[M + H]^+$ |
|---|---|---|---|---|---|---|
| Ic-52 | 5-[1-(2-Fluoro-6-methyl-phenyl)-piperidin-4-yl]-2-(3-methyl-oxetan-3-ylmethyl)-7-(2-trifluoromethyl-benzyl)-2,4,5,7-tetrahydro-pyrazolo[3,4-d]pyrimidin-6-one (Example 166) | Ib-2 | (3-Methyl-oxetan-3-yl)-methanol | C 110 1 | 1.23 (I) | 572.12 |
| Ic-53 | 2-(1-Fluoro-cyclopropylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 167) | Ib-2 | (1-Fluoro-cyclopropyl)-methanol | C 110 2 | 1.25 (I) | 560.22 |
| Ic-54 | 5-[1-(2-Fluoro-6-methyl-phenyl)-piperidin-4-yl]-2-(2-fluoro-2-methyl-propyl)-7-(2-trifluoromethyl-benzyl)-2,4,5,7-tetrahydro-pyrazolo[3,4-d]pyrimidin-6-one (Example 168) | Ib-2 | 2-Fluoro-2-methylpropan-1-ol | C 110 2 | 1.27 (I) | 562.23 |
| Ic-55 | 2-Ethyl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 169) | Ib-2 | Ethanol | C 110 1 | 1.23 (I) | 516.03 |
| Ic-56 | 2-[1,1,2,2,2-$^2H_5$]Ethyl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 170) | Ib-2 | [1,1,2,2,2-$^2H_5$]Ethan-[$^2$H]ol 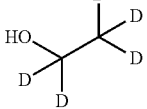 | C 110 2 | 1.24 (I) | 521.27 |
| Ic-57 | 5-[1-(2-Fluoro-6-methyl-phenyl)-piperidin-4-yl]-2-(3-hydroxy-oxetan-3-ylmethyl)-7-(2-trifluoromethyl-benzyl)-2,4,5,7-tetrahydro-pyrazolo[3,4-d]pyrimidin-6-one (Example 171) | Ib-2 | 3-Hydroxy methyl-oxetan-3-ol | C 110 1 | 1.12 (I) | 574.22 |
| Ic-58 | 2-(2,2-Difluoro-propyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 172) | Ib-2 | 2,2-Difluoro propanol | C 110 5 | 1.24 (I) | 566.14 |
| Ic-59 | 2-tert-Butyl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 173) | Ib-2 | tert-Butanol | C 110 18 | 1.30 (I) | 544.29 |
| Ic-60 | 2-Cyclopropyl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 174) | Ib-2 | Cyclopropyl boronic acid | J 70 18 | 1.22 (I) | 528.26 |
| Ic-61 | 2-Cyclopropyl-6-[1-(2-fluoro-6-methyl-phenyl)-piperidin-4-yl]-4-(2-trifluoromethyl-benzyl)-2,4,6,7-tetrahydro-pyrazolo[4,3-d]pyrimidin-5-one (Example 175) | Ib-1 | Cyclopropyl boronic acid | J 90 18 | 1.22 (I) | 528.17 |
| Ic-62 | 6-[1-(2-Fluoro-6-methyl-phenyl)-piperidin-4-yl]-2-(2-fluoro-2-methyl-propyl)-4-(2-trifluoromethyl-benzyl)-2,4,6,7-tetrahydro-pyrazolo[4,3-d]pyrimidin-5-one (Example 176) | Ib-1 | 2-Fluoro-2-methylpropan-1-ol | C 100 2 | 1.22 (I) | 562.14 |
| Id-4 | 6-[1-(2-Fluoro-6-methyl-phenyl)-piperidin-4-yl]-1-(2-fluoro-2-methyl-propyl)-4-(2-trifluoromethyl-benzyl)-1,4,6,7-tetrahydro-pyrazolo[4,3-d]pyrimidin-5-one (Example 177) | | | | 1.22 (I) | 562.13 |
| Ic-64 | 2-Cyclopropylmethyl-6-[1-(2-fluoro-6-methyl-phenyl)-piperidin-4-yl]-4-(2-trifluoromethyl-benzyl)-2,4,6,7-tetrahydro-pyrazolo[4,3-d]pyrimidin-5-one (Example 178) | Ib-1 | Cyclopropyl methanol | C 100 1 | 1.24 (I) | 542.28 |

TABLE 60-continued

| Ic/Id/Ie | Name | Reactant Ib | Reactant BB-10 | Method T [° C.] time [h] | $t_R$ [min] (LC/MS-method) | MS-data m/z $[M + H]^+$ |
|---|---|---|---|---|---|---|
| Id-5 | 1-Cyclopropylmethyl-6-[1-(2-fluoro-6-methyl-phenyl)-piperidin-4-yl]-4-(2-trifluoromethyl-benzyl)-1,4,6,7-tetrahydro-pyrazolo[4,3-d]pyrimidin-5-one (Example 179) | | | | 1.23 (I) | 542.27 |
| Ic-66 | 6-[1-(2-Fluoro-6-methyl-phenyl)-piperidin-4-yl]-2-(1-methyl-cyclopropylmethyl)-4-(2-trifluoromethyl-benzyl)-2,4,6,7-tetrahydro-pyrazolo[4,3-d]pyrimidin-5-one (Example 180) | Ib-1 | (1-Methyl-cyclopropyl)-methanol | C 100 1 | 1.25 (I) | 556.20 |
| Id-6 | 6-[1-(2-Fluoro-6-methyl-phenyl)-piperidin-4-yl]-1-(1-methyl-cyclopropylmethyl)-4-(2-trifluoromethyl-benzyl)-1,4,6,7-tetrahydro-pyrazolo[4,3-d]pyrimidin-5-one (Example 181) | | | | 1.24 (I) | 556.20 |
| Ic-68 | 2-Ethyl-6-[1-(2-fluoro-6-methyl-phenyl)-piperidin-4-yl]-4-(2-trifluoromethyl-benzyl)-2,4,6,7-tetrahydro-pyrazolo[4,3-d]pyrimidin-5-one (Example 182) | Ib-1 | Ethanol | C 100 1 | 1.22 (I) | 516.26 |
| Ic-69 | 2-tert-Butyl-6-[1-(2-fluoro-6-methyl-phenyl)-piperidin-4-yl]-4-(2-trifluoromethyl-benzyl)-2,4,6,7-tetrahydro-pyrazolo[4,3-d]pyrimidin-5-one (Example 183) | Ib-1 | tert-Butanol | C 100 48 | 1.26 (I) | 544.30 |
| Ic-70 | 2-(1-Fluoro-cyclopropylmethyl)-6-[1-(2-fluoro-6-methyl-phenyl)-piperidin-4-yl]-4-(2-trifluoromethyl-benzyl)-2,4,6,7-tetrahydro-pyrazolo[4,3-d]pyrimidin-5-one (Example 184) | Ib-1 | (1-Fluoro-cyclopropyl)-methanol | C 100 1 | 1.21 (I) | 560.26 |
| Ic-71 | 5-[1-(2-Fluoro-6-methyl-phenyl)-piperidin-4-yl]-2-(2-fluoro-propyl)-7-(2-trifluoromethyl-benzyl)-2,4,5,7-tetrahydro-pyrazolo[3,4-d]pyrimidin-6-one | Ib-2 | 2-Fluoro propan-1-ol | C 100 2.5 | 1.22 (I) | 548.15 |
| Ic-72 | 2-(2,2-Difluoro-1-methyl-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one | Ib-2 | 1,1-Difluoro propan-2-ol | C 100 18 | 1.23 (I) | 566.13 |
| Ic-73 | 2-(2,2-Difluoro-cyclopropylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one | Ib-2 | (2,2-Difluoro-cyclopropyl)-methanol | C 100 2.5 | 1.24 (I) | 578.23 |
| Ic-74 | 6-[1-(2-Fluoro-6-methyl-phenyl)-piperidin-4-yl]-2-isopropenyl-4-(2-trifluoromethyl-benzyl)-2,4,6,7-tetrahydro-pyrazolo[4,3-d]pyrimidin-5-one (Example 192) | Ib-1 | 2-Isopropenyl-4,4,5,5-tetramethyl-[1,3,2]dioxaborolane | J 70 18 | 1.26 (I) | 528.23 |
| Ic-75 | 2-(2,2-Difluoro-propyl)-5-[1-(2-fluoro-6-methyl-phenyl)-piperidin-4-yl]-7-(3-trifluoromethyl-pyridin-2-ylmethyl)-2,4,5,7-tetrahydro-pyrazolo[3,4-d]pyrimidin-6-one (Example 194) | Ib-5 | 2,2-Difluoro propanol | C 110 4 | 1.17 (I) | 567.25 |
| Ic-76 | 2-(2,2-Difluoro-propyl)-6-[1-(2-fluoro-6-methyl-phenyl)-piperidin-4-yl]-4-(2-trifluoromethyl-benzyl)-2,4,6,7-tetrahydro-pyrazolo[4,3-d]pyrimidin-5-one (Example 198) | Ib-1 | 2,2-Difluoro propanol | C 110 20 | 1.20 (I) | 566.02 |
| Ic-77 | 2-(1-Fluoro-cyclopropylmethyl)-5-[1-(2-fluoro-6-methyl-phenyl)-piperidin-4-yl]-7-(3-trifluoromethyl-pyridin-2-ylmethyl)-2,4,5,7-tetrahydro-pyrazolo[3,4-d]pyrimidin-6-one (Example 200) | Ib-5 | (1-Fluoro-cyclopropyl)-methanol | C 110 2 | 1.16 (I) | 561.12 |
| Ic-78 | 2-(1-Fluoro-cyclopropylmethyl)-5-(2'-methoxy-4'-methyl-3,4,5,6-tetrahydro-2H-[1,3']bipyridinyl-4-yl)-7-(2-trifluoromethyl-benzyl)-2,4,5,7-tetrahydro-pyrazolo[3,4-d]pyrimidin-6-one (Example 201) | Ib-6 | (1-Fluoro-cyclopropyl)-methanol | C 110 2.5 | 1.16 (I) | 573.27 |

TABLE 60-continued

| Ic/Id/Ie | Name | Reactant Ib | Reactant BB-10 | Method T [° C.] time [h] | $t_R$ [min] (LC/MS-method) | MS-data m/z [M + H]$^+$ |
|---|---|---|---|---|---|---|
| Ic-79 | 2-(2,2-Difluoro-propyl)-5-(2'-methoxy-4'-methyl-3,4,5,6-tetrahydro-2H-[1,3']bipyridinyl-4-yl)-7-(2-trifluoromethyl-benzyl)-2,4,5,7-tetrahydro-pyrazolo[3,4-d]pyrimidin-6-one (Example 205) | Ib-6 | 2,2-Difluoro propanol | C 110 18 | 1.17 (I) | 579.29 |
| Ic-80 | 2-Cyclopropyl-5-[1-(2-fluoro-6-methyl-phenyl)-piperidin-4-yl]-7-(3-trifluoromethyl-pyridin-2-ylmethyl)-2,4,5,7-tetrahydro-pyrazolo[3,4-d]pyrimidin-5-one (Example 206) | Ib-5 | Cyclopropyl boronic acid | J 70 18 | 1.17 (I) | 529.17 |
| Ic-81 | 2-(2,2-Difluoro-propyl)-6-[1-(2-fluoro-6-methyl-phenyl)-piperidin-4-yl]-4-(3-trifluoromethyl-pyridin-2-ylmethyl)-2,4,6,7-tetrahydro-pyrazolo[4,3-d]pyrimidin-5-one (Example 207) | Ib-7 | 2,2-Difluoro propanol | C 100 18 | 1.13 (I) | 567.23 |
| Ic-82 | 2-(1-Fluoro-cyclopropylmethyl)-6-[1-(2-fluoro-6-methyl-phenyl)-piperidin-4-yl]-4-(3-trifluoromethyl-pyridin-2-ylmethyl)-2,4,6,7-tetrahydro-pyrazolo[4,3-d]pyrimidin-5-one (Example 208) | Ib-7 | (1-Fluoro-cyclopropyl)-methanol | C 100 1 | 1.14 (I) | 561.21 |
| Ic-83 | 2-Cyclopropyl-5-(2'-methoxy-4'-methyl-3,4,5,6-tetrahydro-2H-[1,3']bipyridinyl-4-yl)-7-(2-trifluoromethyl-benzyl)-2,4,5,7-tetrahydro-pyrazolo[3,4-d]pyrimidin-6-one (Example 209) | Ib-6 | Cyclopropyl boronic acid | J 70 18 | 1.17 (I) | 541.22 |
| Ic-84 | 2-Cyclopropyl-6-[1-(2-fluoro-6-methyl-phenyl)-piperidin-4-yl]-4-(3-trifluoromethyl-pyridin-2-ylmethyl)-2,4,6,7-tetrahydro-pyrazolo[4,3-d]pyrimidin-5-one (Example 212) | Ib-7 | Cyclopropyl boronic acid | J 70 3.5 | 1.13 (I) | 529.13 |
| Id-7 | 1-Cyclopropyl-6-[1-(2-fluoro-6-methyl-phenyl)-piperidin-4-yl]-4-(3-trifluoromethyl-pyridin-2-ylmethyl)-1,4,6,7-tetrahydro-pyrazolo[4,3-d]pyrimidin-5-one (Example 215) | | | | 1.13 (I) | 529.08 |
| Ic-86 | 7-(2-Bromo-6-trifluoromethyl-benzyl)-2-cyclopropyl-5-[1-(2-fluoro-6-methyl-phenyl)-piperidin-4-yl]-2,4,5,7-tetrahydro-pyrazolo[3,4-d]pyrimidin-6-one (Example 213) | Ib-8 | Cyclopropyl boronic acid | J 70 2 | 1.24 (I) | 606.10 |
| Ic-87 | 7-(2-Bromo-6-trifluoromethyl-benzyl)-2-(2,2-difluoro-propyl)-5-[1-(2-fluoro-6-methyl-phenyl)-piperidin-4-yl]-2,4,5,7-tetrahydro-pyrazolo[3,4-d]pyrimidin-6-one (Example 214) | Ib-8 | 2,2-Difluoro propanol | C 100 3 | 1.23 (I) | 643.87 |
| Ic-88 | 2-(2,2-Difluoro-propyl)-6-(2'-methoxy-4'-methyl-3,4,5,6-tetrahydro-2H-[1,3']bipyridinyl-4-yl)-4-(2-trifluoromethyl-benzyl)-2,4,6,7-tetrahydro-pyrazolo[4,3-d]pyrimidin-5-one (Example 219) | Ib-9 | 2,2-Difluoro propanol | C 100 48 | 1.13 (I) | 579.24 |
| Ic-89 | 2-(1-Fluoro-cyclopropylmethyl)-6-(2'-methoxy-4'-methyl-3,4,5,6-tetrahydro-2H-[1,3']bipyridinyl-4-yl)-4-(2-trifluoromethyl-benzyl)-2,4,6,7-tetrahydro-pyrazolo[4,3-d]pyrimidin-5-one (Example 222) | Ib-9 | (1-Fluoro-cyclopropyl)-methanol | C 110 2.5 | 1.13 (I) | 573.27 |
| Ic-90 | 2-Cyclopropyl-6-(2'-methoxy-4'-methyl-3,4,5,6-tetrahydro-2H-[1,3']bipyridinyl-4-yl)-4-(2-trifluoromethyl-benzyl)-2,4,6,7-tetrahydro-pyrazolo[4,3-d]pyrimidin-5-one (Example 223) | Ib-9 | Cyclopropyl boronic acid | J 70 4 | 1.14 (I) | 541.28 |

TABLE 60-continued

| Ic/Id/Ie | Name | Reactant Ib | Reactant BB-10 | Method T [° C.] time [h] | $t_R$ [min] (LC/MS-method) | MS-data m/z $[M + H]^+$ |
|---|---|---|---|---|---|---|
| Ic-91 | 6-(2'-Methoxy-4'-methyl-3,4,5,6-tetrahydro-2H-[1,3']bipyridinyl-4-yl)-2-methyl-4-(2-trifluoromethyl-benzyl)-2,4,6,7-tetrahydro-pyrazolo[4,3-d]pyrimidin-5-one (Example 224) | Ib-9 | Methyl 4-toluenesulfonate | K 100 3 | 1.11 (I) | 515.26 |
| Id-8 | 2-(2,2-Difluoro-propyl)-6-[1-(2-fluoro-6-methyl-phenyl)-piperidin-4-yl]-4-(3-trifluoromethyl-pyridin-2-ylmethyl)-2,4,6,7-tetrahydro-pyrazolo[4,3-d]pyrimidin-5-one (Example 239) | Ib-7 | 2,2-Difluoropropyl 4-methyl benzene sulfonate | K 60 18 | 1.14 (I) | 567.20 |
| Ic-93 | 2-(2,2-Difluoro-propyl)-6-[1-(2-fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one | Ib-10 | 2,2-Difluoropropyl 4-methyl benzene sulfonate | K 100 2 | 1.21 (I) | 580.23 |
| Id-9 | 1-(2,2-Difluoro-propyl)-6-[1-(2-fluoro-6-methyl-phenyl)-piperidin-4-yl]-7-methyl-4-(2-trifluoromethyl-benzyl)-1,4,6,7-tetrahydro-pyrazolo[4,3-d]pyrimidin-5-one | | | | 1.20 (I) | 580.22 |
| Ic-94 | 2-Cyclopropyl-6-[1-(2-fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one | Ib-10 | Cyclopropyl boronic acid | J 70 72 | 1.22 (I) | 542.26 |
| Ic-95 | 4-(2-Cyclopropyl-benzyl)-2-(2,2-difluoro-propyl)-6-[1-(2-fluoro-6-methyl-phenyl)-piperidin-4-yl]-7-methyl-2,4,6,7-tetrahydro-pyrazolo[4,3-d]pyrimidin-5-one | Ib-12 | 2,2-Difluoropropyl 4-methyl benzene sulfonate | K 100 72 | 1.20 (I) | 552.31 |
| Id-10 | 4-(2-Cyclopropyl-benzyl)-1-(2,2-difluoro-propyl)-6-[1-(2-fluoro-6-methyl-phenyl)-piperidin-4-yl]-7-methyl-1,4,6,7-tetrahydro-pyrazolo[4,3-d]pyrimidin-5-one | | | | 1.19 (I) | 552.34 |
| Ic-96 | 2-Cyclopropyl-4-(2-cyclopropyl-benzyl)-6-[1-(2-fluoro-6-methyl-phenyl)-piperidin-4-yl]-7-methyl-2,4,6,7-tetrahydro-pyrazolo[4,3-d]pyrimidin-5-one | Ib-12 | Cyclopropyl boronic acid | J1 70 48 | 1.21 (I) | 514.09 |
| Id-11 | 1-Cyclopropyl-4-(2-cyclopropyl-benzyl)-6-[1-(2-fluoro-6-methyl-phenyl)-piperidin-4-yl]-7-methyl-1,4,6,7-tetrahydro-pyrazolo[4,3-d]pyrimidin-5-one | | | | 1.21 (I) | 514.12 |
| Ic-97 | 2-Cyclopropyl-4-(2-cyclopropyl-benzyl)-6-(2'-methoxy-4'-methyl-3,4,5,6-tetrahydro-2H-[1,3']bipyridinyl-4-yl)-7-methyl-2,4,6,7-tetrahydro-pyrazolo[4,3-d]pyrimidin-5-one | Ib-11 | Cyclopropyl boronic acid | J1 100 5 | 1.11 (I) | 527.40 |
| Id-12 | 1-Cyclopropyl-4-(2-cyclopropyl-benzyl)-6-(2'-methoxy-4'-methyl-3,4,5,6-tetrahydro-2H-[1,3']bipyridinyl-4-yl)-7-methyl-1,4,6,7-tetrahydro-pyrazolo[4,3-d]pyrimidin-5-one | | | | 1.13 (I) | 527.40 |
| Ic-98 | 2-Cyclopropyl-6-(2'-methoxy-4'-methyl-3,4,5,6-tetrahydro-2H-[1,3']bipyridinyl-4-yl)-7-methyl-4-(2-trifluoromethyl-benzyl)-2,4,6,7-tetrahydro-pyrazolo[4,3-d]pyrimidin-5-one | Ib-14 | Cyclopropyl boronic acid | J1 100 18 | 1.15 (I) | 555.37 |
| Id-13 | 1-Cyclopropyl-6-(2'-methoxy-4'-methyl-3,4,5,6-tetrahydro-2H-[1,3']bipyridinyl-4-yl)-7-methyl-4-(2-trifluoromethyl-benzyl)-1,4,6,7-tetrahydro-pyrazolo[4,3-d]pyrimidin-5-one | | | | 1.16 (I) | 555.36 |
| Ic-99 | 6-(2'-Methoxy-4'-methyl-3,4,5,6-tetrahydro-2H-[1,3']bipyridinyl-4-yl)-2,7-dimethyl-4-(2-trifluoromethyl-benzyl)-2,4,6,7-tetrahydro-pyrazolo[4,3-d]pyrimidin-5-one | Ib-14 | Methyl 4-methyl benzene sulfonate | K 100 1 | 1.13 (I) | 529.22 |

TABLE 60-continued

| Ic/Id/Ie | Name | Reactant Ib | Reactant BB-10 | Method T [° C.] time [h] | $t_R$ [min] (LC/MS-method) | MS-data m/z [M + H]$^+$ |
|---|---|---|---|---|---|---|
| Id-14 | 6-(2'-Methoxy-4'-methyl-3,4,5,6-tetrahydro-2H-[1,3']bipyridinyl-4-yl)-1,7-dimethyl-4-(2-trifluoromethyl-benzyl)-1,4,6,7-tetrahydro-pyrazolo[4,3-d]pyrimidin-5-one | | | | 1.14 (I) | 529.19 |
| Ic-100 | 2-(2,2-Difluoro-propyl)-5-[1-(2-fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one | Ib-13 | 2,2-Difluoropropyl 4-methyl benzene sulfonate | K 80 18 | 1.24 (I) | 580.34 |
| Ic-101 | 6-[1-(2-Chloro-6-fluoro-phenyl)-piperidin-4-yl]-2-cyclopropyl-7-methyl-4-(2-trifluoromethyl-benzyl)-2,4,6,7-tetrahydro-pyrazolo[4,3-d]pyrimidin-5-one | Ib-15 | Potassium cyclopropyl trifluoroborate | J2 110 18 | 1.36 (I) | 562.06 |
| Ic-102 | 2-Cyclopropyl-6-[1-(2-difluoromethyl-6-fluoro-phenyl)-piperidin-4-yl]-7-methyl-4-(2-trifluoromethyl-benzyl)-2,4,6,7-tetrahydro-pyrazolo[4,3-d]pyrimidin-5-one | Ib-16 | Potassium cyclopropyl trifluoroborate | J2 110 18 | 1.23 (I) | 578.15 |

Synthesis of Compounds of Formula if

Method a (Carboxylic Ester Reduction)

To a soln. of methyl ester Ic (1 eq) in anh. EtOH (12 to 22 mL/mmol) was added CaCl$_2$ (0.3 eq) and the rxn mixture was cooled to −10° C. NaBH$_4$ (2.5 eq) was added portionwise and the mixture was stirred for 30 min at −10° C. and at a given temperature for a given time (see Table 61). It was quenched at 0° C. with water and EtOH was evaporated off. The residue was partitioned between EtOAc (or DCM respectively) and water and the aq. phase was further extracted with EtOAc (or DCM respectively). The combined org. phases were washed with brine, dried over MgSO$_4$ and concentrated in vacuo. When necessary, the crude was purified by CC using Hept/EtOAc.

Method B (Nitrile Reduction)

To a suspension of nitrile Ic (1 eq) in anh. MeOH (28 mL/mmol) was added CoCl$_2$ (1.5 eq). The rxn mixture was stirred for 5 min at RT, cooled to 0° C. and NaBH$_4$ (5 eq) was added portionwise. The rxn mixture was stirred for 5 min at 0° C. and at RT for a given time (see Table 61). It was quenched with a 10% aq. soln. of citric acid, stirred for 30 min at RT and extracted with DCM. The combined org. phases were washed with brine, dried over MgSO$_4$ and concentrated in vacuo. The crude was purified by CC using DCM/MeOH or EtOAc/MeOH.

Method C (Saponification/Amide Coupling)

Step A: Saponification

To a soln. of carboxylic ester Ic (1 eq) in THE (8 mL/mmol) was added a 2M aq. soln. of NaOH (7 eq) and the rxn mixture was stirred for 1h at RT. It was acidified with a 1M aq. soln. of HCl until pH-3-4 and extracted with EtOAc. The combined org. phases were washed with brine, dried over MgSO$_4$ and concentrated in vacuo.

Step B: Amide Coupling

To a soln. of the crude carboxylic acid (1 eq) in DCM (10 to 23 mL/mmol) were sequentially added DIPEA (3 eq), HOBt (1.5 eq) and EDC.HCl (1.5 eq). The rxn mixture was stirred for 5 min at RT and the appropriate amine (1.2 to 1.5 eq) pure or as soln. was added. The rxn mixture was further stirred at a given temperature for a given time and partitioned between DCM and a sat. aq. soln. of NaHCO$_3$. The org. phase was washed with water and brine, dried over MgSO$_4$ and concentrated in vacuo. The crude was purified by CC using Hept/EtOAc/MeOH.

Method D (Grignard Addition)

Step A: Acetal Cleavage

To a soln. of acetal Ic (1 eq) in THE (7.2 mL/mmol) was added a 1M aq. soln. of HCl (2 eq) and the rxn mixture was stirred for 3h30 at 70° C. It was quenched with a sat. aq. soln. of NaHCO$_3$ and extracted with EtOAc. The org. phase was washed with brine, dried over MgSO$_4$ and concentrated in vacuo.

Step B: Grignard Addition

To a soln. of the crude aldehyde (1 eq) in anh. THE (10.6 mL/mmol) was added dropwise at 0° C. a 3M soln. of methylmagnesium bromide in Et$_2$O (2 eq). The rxn mixture was stirred at a given temperature for a given time (see Table 61), quenched at 0° C. with a sat. aq. soln. of NH$_4$Cl and extracted with EtOAc. The combined org. phases were washed with brine, dried over MgSO$_4$ and concentrated in vacuo. The crude was purified by CC using Hept/EtOAc/MeOH.

Method E (Reductive Amination)

Step A: Acetal Cleavage

To a soln. of acetal Ic (1 eq) in THE (7.2 mL/mmol) was added a 1M aq. soln. of HCl (2 eq) and the rxn mixture was stirred for 3h30 at 70° C. It was quenched with a sat. aq. soln. of NaHCO$_3$ and extracted with EtOAc. The org. phase was washed with brine, dried over MgSO$_4$ and concentrated in vacuo.

Step B: Reductive Amination

To a mixture of aldehyde Ic (1 eq) and the appropriate amine (1.2 to 2 eq) (when the amine was used as HCl salt, TEA (1.2 eq) was additionally added) in THE (12 to 16 mL/mmol) was added AcOH (1.5 eq) and the rxn mixture was stirred for 5 min at RT. NaBH(OAc)$_3$ (1.5 eq) was added portionwise and the rxn mixture was stirred at RT for a given time (see Table 61). It was quenched with a sat. aq. soln. of NaHCO$_3$ and extracted with DCM. The combined org. phases were washed with brine, dried over MgSO$_4$ and concentrated in vacuo. The crude was purified by CC using DCM/MeOH or Hept/EtOAc/MeOH and/or by prep. LC-MS using method 3.

Method F (Nucleophilic Substitution)

To a soln. of Ic (1 eq) in DMF (10 mL/mmol) was added the appropriate amine (10 eq pure or as soln.). The rxn mixture was heated to a given temperature and stirred for a given time (see Table 61). It was partitioned between DCM and H$_2$O and the org. phase was washed brine, dried over MgSO$_4$ and concentrated in vacuo. The crude was purified by CC using Hept/EtOAc.

Method G (Dehydration of Primary Amide)

To a stirred soln. of amide intermediate Ic (1 eq) in DCM (11 mL/mmol) was added portionwise Burgess' reagent (3 eq) under argon. The rxn mixture was stirred at RT for a given time (see Table 61) and partitioned between DCM and H$_2$O. The org. phase was washed with brine, dried over MgSO$_4$ and concentrated in vacuo. The crude was purified by CC using Hept/EtOAc.

Method H (Boc Cleavage)

To a soln. of intermediate Ic (1 eq) in DCM (10 mL/mmol) was added TFA (2 mL/mmol) at 0° C. and the rxn mixture was stirred at RT for a given time (see Table 61). It was cooled to 0° C., quenched with a 32% or 1M aq. soln. of NaOH until pH reached 12 to 13 and extracted with DCM. The combined org. phases were washed with brine, dried over MgSO$_4$ and concentrated in vacuo. The crude was purified by CC using Hept/EtOAc/MeOH or DCM/MeOH.

Method I (Sulfonamide Cleavage)

A soln. of intermediate Ic (1 eq) in THF (37 mL/mmol) was treated with Cs$_2$CO$_3$ (3.25 eq) and QuadraPure® MPA (3 eq). The rxn mixture was heated at 130° C. under microwave irradiation for a given time (see Table 61). It was diluted with EtOAc and filtered. The filtrate was washed with a 0.5M aq. soln. of NaOH and with brine and the org. phase was dried over MgSO$_4$ and concentrated in vacuo. The crude was purified by CC using Hept/EtOAc and/or by prep. LC-MS using method 5.

Method J (Dehydration of Tertiary Alcohol)

POCl$_3$ (2 eq) was added dropwise at 0° C. to a soln. of compound Ic (1 eq) in pyridine (8 mL/mmol). The rxn mixture was heated to 50° C. and stirred for a given time (see Table 61). The rxn mixture was diluted with EtOAc and washed with a 1M aq. soln. of HCl and brine. The org. phase was dried over MgSO$_4$ and concentrated in vacuo. The crude was purified by CC using DCM/MeOH.

Method K (Trityl Cleavage)

Compound Ic (1 eq) was treated with TFA (9 mL/mmol) and H$_2$O (1 mL/mmol) at 0° C. The rxn mixture was stirred at 0° C. for a given time (see Table 61), poured into a 1M aq. soln. of NaOH and extracted with DCM. The combined org. phases were washed with brine, dried over MgSO$_4$ and concentrated in vacuo. The crude was purified by prep. LC-MS using method 9.

Method L (Hydrogenation)

Compound of formula Ic (1 eq) was dissolved in EtOAc (27 mL/mmol). The flask was evacuated three times and refilled with nitrogen. Wet Pd/C (0.05 eq) was added and the flask was evacuated three times and refilled with hydrogen. The suspension was stirred under an atmospheric pressure of hydrogen for a given time (see Table 61) and filtered over a pad of Celite. The cake was washed with MeOH and the filtrate was concentrated in vacuo. The crude was purified by CC using Hept/EtOAc.

TABLE 61

| If | Name | Reactant Ic | Amine | Method T [° C.] time [h] | $t_R$ [min] (LC/MS method) | MS-data m/z [M + H]$^+$ |
|---|---|---|---|---|---|---|
| If-1 | 5-[1-(2-Fluoro-6-methyl-phenyl)-piperidin-4-yl]-2-(2-hydroxy-ethyl)-7-(2-trifluoromethyl-benzyl)-2,4,5,7-tetrahydro-pyrazolo[3,4-d]pyrimidin-6-one (Example 20) | Ic-5 | — | A 0 1 | 1.01 (II) | 532.26 |
| If-2 | 2-(2-Amino-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 26) | Ic-8 | — | B RT 2 | 0.83 (II) | 531.12 |
| If-3 | 2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-acetamide (Example 29) | Ic-5 | 25% aq. soln. of NH$_4$OH | C 40 24 | 0.97 (II) | 545.15 |
| If-4 | 2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-N,N-dimethyl-acetamide (Example 30) | Ic-5 | 2M soln. of dimethylamine in THF | C 40 5 | 1.02 (II) | 573.24 |
| If-5 | 5-[1-(2-Fluoro-6-methyl-phenyl)-piperidin-4-yl]-2-(2-hydroxy-1,1-dimethyl-ethyl)-7-(2-trifluoromethyl-benzyl)-2,4,5,7-tetrahydro-pyrazolo[3,4-d]pyrimidin-6-one (Example 32) | Ic-10 | — | A RT 3 | 1.07 (II) | 560.05 |
| If-6 | 5-[1-(2-Fluoro-6-methyl-phenyl)-piperidin-4-yl]-2-(2-hydroxy-propyl)-7-(2-trifluoromethyl-benzyl)-2,4,5,7-tetrahydro-pyrazolo[3,4-d]pyrimidin-6-one (Example 33) | Ic-12 | — | D RT 3 | 1.02 (II) | 546.18 |
| If-7 | 5-[1-(2-Fluoro-6-methyl-phenyl)-piperidin-4-yl]-2-[2-(3-methoxy-azetidin-1-yl)-ethyl]-7-(2-trifluoromethyl-benzyl)-2,4,5,7-tetrahydro-pyrazolo[3,4-d]pyrimidin-6-one (Example 34) | Ic-12 | 3-Methoxyazetidine hydrochloride | E RT 4.5 | 0.85 (II) | 601.11 |
| If-8 | 5-[1-(2-Fluoro-6-methyl-phenyl)-piperidin-4-yl]-2-(3-hydroxy-2-methyl-propyl)-7-(2-trifluoromethyl-benzyl)-2,4,5,7-tetrahydro-pyrazolo[3,4-d]pyrimidin-6-one (Example 39) | Ic-11 | — | A RT 1.5 | 1.04 (II) | 560.13 |

TABLE 61-continued

| If | Name | Reactant Ic | Amine | Method T [° C.] time [h] | $t_R$ [min] (LC/MS method) | MS-data m/z [M + H]$^+$ |
|---|---|---|---|---|---|---|
| If-9 | 2-(3-Amino-2-methyl-propyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 45) | Ic-16 | — | B RT 0.25 | 0.84 (II) | 559.15 |
| If-10 | 2-Dimethylamino-3-[5-[1-(2-fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-propionic acid methyl ester (Example 53) | Ic-15 | 2M soln. of dimethylamine in THF | F 70 3 | 0.88 (II) | 617.09 |
| If-11 | 5-[1-(2-Fluoro-6-methyl-phenyl)-piperidin-4-yl]-2-(2-methylamino-ethyl)-7-(2-trifluoromethyl-benzyl)-2,4,5,7-tetrahydro-pyrazolo[3,4-d]pyrimidin-6-one (Example 59) | Ic-12 | 2M soln. of methylamine in THF | E RT 18 | 0.85 (II) | 545.08 |
| If-12 | 2-(2-Dimethylamino-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 60) | Ic-12 | 2M soln. of dimethylamine in THF | E RT 18 | 0.86 (II) | 559.17 |
| If-13 | 5-[1-(2-Fluoro-6-methyl-phenyl)-piperidin-4-yl]-2-(2-pyrrolidin-1-yl-ethyl)-7-(2-trifluoromethyl-benzyl)-2,4,5,7-tetrahydro-pyrazolo[3,4-d]pyrimidin-6-one (Example 62) | Ic-12 | Pyrrolidine | E RT 18 | 0.88 (II) | 585.14 |
| If-14 | 5-[1-(2-Fluoro-6-methyl-phenyl)-piperidin-4-yl]-2-(2-piperidin-1-yl-ethyl)-7-(2-trifluoromethyl-benzyl)-2,4,5,7-tetrahydro-pyrazolo[3,4-d]pyrimidin-6-one (Example 63) | Ic-12 | Piperidine | E RT 18 | 0.90 (II) | 599.14 |
| If-15 | 5-[1-(2-Fluoro-6-methyl-phenyl)-piperidin-4-yl]-2-(2-morpholin-4-yl-ethyl)-7-(2-trifluoromethyl-benzyl)-2,4,5,7-tetrahydro-pyrazolo[3,4-d]pyrimidin-6-one (Example 64) | Ic-12 | Morpholine | E RT 18 | 0.86 (II) | 601.14 |
| If-16 | 5-[1-(2-Fluoro-6-methyl-phenyl)-piperidin-4-yl]-2-[2-(4-methyl-piperazin-1-yl)-ethyl]-7-(2-trifluoromethyl-benzyl)-2,4,5,7-tetrahydro-pyrazolo[3,4-d]pyrimidin-6-one (Example 65) | Ic-12 | 1-Methyl-piperazine | E RT 18 | 0.84 (II) | 614.15 |
| If-17 | 2-(2-Cyclopropylamino-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 71) | Ic-12 | Cyclopropylamine | E RT 18 | 0.86 (II) | 571.20 |
| If-18 | 5-[1-(2-Fluoro-6-methyl-phenyl)-piperidin-4-yl]-2-[2-(isopropyl-methyl-amino)-ethyl]-7-(2-trifluoromethyl-benzyl)-2,4,5,7-tetrahydro-pyrazolo[3,4-d]pyrimidin-6-one (Example 72) | Ic-12 | N-Iso-propylmethylamine | E RT 18 | 0.88 (II) | 587.21 |
| If-19 | 2-[2-(Cyclopropyl-methyl-amino)-ethyl]-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 73) | Ic-12 | N-methyl-cyclopropanamine | E RT 18 | 0.87 (II) | 585.20 |
| If-20 | 5-[1-(2-Fluoro-6-methyl-phenyl)-piperidin-4-yl]-2-{2-[(2-methoxy-ethyl)-methyl-amino]-ethyl}-7-(2-trifluoromethyl-benzyl)-2,4,5,7-tetrahydro-pyrazolo[3,4-d]pyrimidin-6-one (Example 74) | Ic-12 | N-(2-Methoxyethyl)methylamine | E RT 18 | 0.87 (II) | 603.19 |
| If-21 | 2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-propionitrile (Example 78) | Ic-18 | — | G RT 18 | 1.07 (II) | 541.10 |
| If-22 | 2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-2-methyl-propionitrile (Example 87) | Ic-23 | — | G RT 18 | 1.09 (II) | 555.07 |
| If-23 | 2-Azetidin-3-yl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 92) | Ic-24 | — | H RT 0.4 | 0.89 (I) | 543.16 |
| If-24 | 5-[1-(2-Fluoro-6-methyl-phenyl)-piperidin-4-yl]-2-pyrrolidin-3-yl-7-(2-trifluoromethyl-benzyl)-2,4,5,7-tetrahydro-pyrazolo[3,4-d]pyrimidin-6-one (Example 94) | Ic-25 | — | H RT 1 | 0.86 (II) | 557.20 |
| If-25 | 2-Azetidin-2-ylmethyl-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one | Ic-26 | — | H RT 18 | 0.86 (II) | 557.21 |

TABLE 61-continued

| If | Name | Reactant Ic | Amine | Method T [° C.] time [h] | $t_R$ [min] (LC/MS method) | MS-data m/z $[M + H]^+$ |
|---|---|---|---|---|---|---|
| If-26 | 5-[1-(2-Fluoro-6-methyl-phenyl)-piperidin-4-yl]-2-pyrrolidin-2-ylmethyl-7-(2-trifluoromethyl-benzyl)-2,4,5,7-tetrahydro-pyrazolo[3,4-d]pyrimidin-6-one (Example 89) | Ic-27 | — | H RT 1.5 | 0.87 (II) | 571.21 |
| If-27 | 2-((R)-4,4-Difluoro-pyrrolidin-2-ylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 111) | Ic-30 | — | H RT 1.5 | 0.94 (I) | 607.19 |
| If-28 | 2-((S)-4,4-Difluoro-pyrrolidin-2-ylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 112) | Ic-31 | — | H RT 1.5 | 0.94 (I) | 607.16 |
| If-29 | 2-(2-Amino-2-methyl-propyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 118) | Ic-32 | — | I 130 0.5 | 0.93 (I) | 559.29 |
| If-30 | (S)-2-(Azetidin-2-ylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 122) | Ic-33 | — | H RT 5 | 0.91 (I) | 557.19 |
| If-31 | (R)-2-(Azetidin-2-ylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 130) | Ic-34 | — | H RT 4 | 0.91 (I) | 557.14 |
| If-32 | 5-[1-(2-Fluoro-6-methyl-phenyl)-piperidin-4-yl]-2-(2-methyl-propenyl)-7-(2-trifluoromethyl-benzyl)-2,4,5,7-tetrahydro-pyrazolo[3,4-d]pyrimidin-6-one (Example 153) | Ic-9 | — | J 50 0.5 | 1.32 (I) | 542.18 |
| If-33 | 5-[1-(2-Fluoro-6-methyl-phenyl)-piperidin-4-yl]-2-(2-methyl-allyl)-7-(2-trifluoromethyl-benzyl)-2,4,5,7-tetrahydro-pyrazolo[3,4-d]pyrimidin-6-one (Example 154) | | | | 1.28 (I) | 542.17 |
| If-34 | 5-[1-(2-Fluoro-6-methyl-phenyl)-piperidin-4-yl]-2-(2-oxo-azetidin-3-yl)-7-(2-trifluoromethyl-benzyl)-2,4,5,7-tetrahydro-pyrazolo[3,4-d]pyrimidin-6-one (Example 157) | Ic-42 | — | K 0 72 | 1.11 (I) | 557.13 |
| If-35 | 6-[1-(2-Fluoro-6-methyl-phenyl)-piperidin-4-yl]-2-isopropyl-4-(2-trifluoromethyl-benzyl)-2,4,6,7-tetrahydro-pyrazolo[4,3-d]pyrimidin-5-one (Example 191) | Ic-74 | — | L RT 18 | 1.22 (I) | 530.05 |

Synthesis of Compounds of Formula Ig

Method a (Carboxylic Ester Reduction)

To a soln. of methyl ester If (1 eq) in anh. EtOH (23 mL/mmol) was added $CaCl_2$ (0.3 eq) and the rxn mixture was cooled to −10° C. $NaBH_4$ (4 eq) was added portionwise and the mixture was stirred for 15 min at −10° C. and at a given temperature for a given time (see Table). When necessary to reach completion of the rxn, a further amount of $NaBH_4$ (4 eq) was added. It was quenched at 0° C. with water and EtOH was evaporated off. The residue was partitioned between DCM and water and the aq. phase was further extracted with DCM. The combined org. phases were washed with brine, dried over $MgSO_4$ and concentrated in vacuo. The crude was purified by CC using Hept/EtOAc.

Method B (Acylation/Alkoxycarbonylation/Dialkylcarbamylation/Alkylsulfonylation/Dialkylsulfamylation)

A soln. of amine If (1 eq) and TEA (1.5 to 6 eq) in DCM (0.5 to 36 mL/mmol) (or DMF, respectively) was cooled to 0° C. and halide BB-25 (1.1 to 2 eq) (or pentafluorophenylcarbonate BB-25, respectively) was added dropwise at 0° C. (or at RT, respectively). The rxn mixture was allowed to slowly reach RT and stirred for a given time (or stirred at a given temperature for a given time, respectively) (see Table). It was diluted with DCM and washed with a 10% aq. soln. of citric acid when suitable, with a sat. aq. soln. of $NaHCO_3$ and with brine. The org. phase was dried over $MgSO_4$ and concentrated in vacuo. The crude was purified by CC using Hept/EtOAc or DCM/MeOH and/or by prep. LC-MS using methods 3 or 8.

Method C (Boc Protection)

To a soln. of amine If (1 eq) in anh. THF (2 mL/mmol) was added TEA (3 eq). The rxn mixture was cooled to 0° C. and $Boc_2O$ (1.5 eq) was added. It was stirred for 5 min at 0° C. and at RT for a given time (see Table) and was partitioned between DCM and water. The org. phase was washed with brine, dried over $MgSO_4$ and concentrated in vacuo. When necessary, the crude was purified by CC using Hept/EtOAc.

Method D (Nitrile Reduction)

Nitrile If (1 eq) was suspended in a 7M soln. of $NH_3$ in MeOH (40 mL/mmol). The flask was evacuated and refilled with nitrogen. Raney nickel (0.1 eq) was added at 0° C. and the temperature was allowed to reach RT. The flask was evacuated and refilled with hydrogen. The suspension was stirred under a hydrogen atmosphere at RT for a given time (see Table) and filtered over a pad of Celite. The cake was washed with MeOH and the filtrate was concentrated in vacuo.

Method E

Step A: Mitsunobu

To a suspension of alcohol If (1 eq) and phtalimide (1.5 eq) in toluene (16 mL/mmol) was added a 1M soln. of (tributylphosphoranylidene)acetonitrile in toluene (2 eq) under argon. The rxn mixture was heated to 110° C. and stirred for 18h. It was quenched with water and extracted with DCM. The combined org. phases were washed with brine, dried over MgSO$_4$ and concentrated in vacuo. The crude was purified by CC using Hept/EtOAc and/or DCM/MeOH.

Step B: Phtalimide Cleavage

A soln. of the crude from previous step (1 eq) was dissolved in EtOH (35 mL/mmol) and treated with hydrazine hydrate (20 eq). The rxn mixture was heated to 80° C. and stirred for a given time (see Table). It was basified with a 1M aq. soln. of NaOH and partitioned between DCM and H$_2$O. The org. phase was dried over MgSO$_4$ and concentrated in vacuo. The crude was purified by CC using DCM/MeOH.

Method F (Reductive Amination)

To a stirred soln. of amine If (1 eq) in a mixture of DCM (10 mL/mmol) and MeOH (15 mL/mmol) or in THF (7 to 8.5 mL/mmol) was added successively AcOH (1.2 to 1.5 eq), the appropriate aldehyde BB-25 (1.3 to 2 eq) and NaBH(OAc)$_3$ (1.5 to 2 eq). The rxn mixture was stirred at RT for a given time (see Table) and the volatiles were evaporated in vacuo. The residue was partitioned between DCM and a sat. aq. soln. of NaHCO$_3$. The org. phase was dried over MgSO$_4$ and concentrated in vacuo. The crude was purified by CC using Hept/EtOAc.

Method G (Alkylation)

To a soln. of amine If (1 eq) in DMF (10 mL/mmol) was added the appropriate halide BB-25 (3 eq), DIPEA (2 eq) and KI (0.05 eq). The rxn mixture was heated at 150° C. under microwave irradiation for a given time (see Table) and partitioned between EtOAc and H$_2$O. The org. phase was washed with H$_2$O and brine, dried over MgSO$_4$ and concentrated in vacuo. The crude was purified by CC using Hept/EtOAc.

Method H (Urea Formation)

A soln. of amine If (1 eq) and TEA (4 eq) in THF (12 mL/mmol) was treated with CDI (1.5 eq) and the rxn mixture was stirred at RT for 15 min. Amine BB-25 (1.5 eq) was added at RT and the mixture was stirred at a given temperature for a given time (see Table). When necessary to reach completion of the rxn, extra amounts of amine (1 to 10 eq) were added. The rxn mixture was partitioned between DCM and H$_2$O and the org. phase was washed with brine, dried over MgSO$_4$ and concentrated in vacuo. The crude was purified by CC using DCM/MeOH and/or by prep. LC-MS using method 4.

Method I (PyBOP Activated SNAr)

Compound If (1 eq), heteroarene BB-25 (1.5 eq) and DIPEA (2 eq) were dissolved in anh. DMF (5 mL/mmol) and the mixture was stirred for 5 min at RT. PyBOP (1.6 eq) was added portionwise and the rxn mixture was further stirred at RT for a given time (see Table). It was partitioned between EtOAc and a 5% aq. soln. of KHSO$_4$ and the org. phase was washed with a sat. aq. soln. of NaHCO$_3$ and brine, dried over MgSO$_4$ and concentrated in vacuo. The crude was purified by CC using Hept/EtOAc.

Method J (SNAr)

To a soln. of compound If (1 eq) in DMSO (5 mL/mmol) was added DIPEA (3 eq) and halo-heteroarene BB-25 (1.2 eq). The rxn mixture was stirred at RT for a given time (see Table) and partitioned between EtOAc and a 5% aq. soln. of KHSO$_4$. The org. phase was washed with a 5% aq. soln. of KHSO$_4$ and brine, dried over MgSO$_4$ and concentrated in vacuo. The crude was purified by CC using Hept/EtOAc.

Method K (Hydrogenation)

Compound of formula If (1 eq) was dissolved in EtOH (10 mL/mmol). The flask was evacuated three times and refilled with nitrogen. Wet Pd/C (0.02 eq) was added and the flask was evacuated three times and refilled with hydrogen. The suspension was stirred under an atmospheric pressure of hydrogen for a given time (see Table) and filtered over a pad of Celite. The cake was washed with MeOH and the filtrate was concentrated in vacuo.

TABLE 62

| Ig | Name | Reactant If | Reactant BB-25 | Method T [° C.] time [h] | t$_R$ [min] (LC/MS method) | MS-data m/z [M + H]$^+$ |
|---|---|---|---|---|---|---|
| Ig-1 | 2-(2-Dimethylamino-3-hydroxy-propyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 56) | If-10 | — | A RT 18 | 0.85 (II) | 589.12 |
| Ig-2 | N-{2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-ethyl}-acetamide (Example 66) | If-2 | Acetyl chloride | B RT 2 | 1.02 (II) | 573.15 |
| Ig-3 | {2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-ethyl}-carbamic acid tert-butyl ester (Example 67) | If-2 | — | C RT 18 | 1.09 (II) | 631.15 |
| Ig-4 | 2-(2-Amino-1-methyl-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 79) | If-21 | — | D RT 2 | 0.86 (II) | 545.23 |
| Ig-5 | 2-(2-Amino-propyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 80) | If-6 | — | E 80 2 | 0.81 (II) | 545.13 |

TABLE 62-continued

| Ig | Name | Reactant If | Reactant BB-25 | Method T [° C.] time [h] | $t_R$ [min] (LC/MS method) | MS-data m/z [M + H]$^+$ |
|---|---|---|---|---|---|---|
| Ig-6 | 2-(2-Amino-1,1-dimethyl-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 88) | If-22 | — | D RT 3.5 | 0.88 (II) | 559.25 |
| Ig-7 | 5-[1-(2-Fluoro-6-methyl-phenyl)-piperidin-4-yl]-2-(1-methyl-azetidin-3-yl)-7-(2-trifluoromethyl-benzyl)-2,4,5,7-tetrahydro-pyrazolo[3,4-d]pyrimidin-6-one (Example 102) | If-23 | Formaldehyde (as a 37% soln. in H$_2$O) | F RT 1.5 | 0.91 (I) | 557.16 |
| Ig-8 | 2-(1-Ethyl-azetidin-3-yl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 103) | If-23 | Acetaldehyde | F RT 1.5 | 0.93 (I) | 571.19 |
| Ig-9 | 5-[1-(2-Fluoro-6-methyl-phenyl)-piperidin-4-yl]-2-(1-isobutyl-azetidin-3-yl)-7-(2-trifluoromethyl-benzyl)-2,4,5,7-tetrahydro-pyrazolo[3,4-d]pyrimidin-6-one (Example 104) | If-23 | Isobutyraldehyde | F RT 1.5 | 0.98 (I) | 599.23 |
| Ig-10 | 5-[1-(2-Fluoro-6-methyl-phenyl)-piperidin-4-yl]-2-(1-isopropyl-azetidin-3-yl)-7-(2-trifluoromethyl-benzyl)-2,4,5,7-tetrahydro-pyrazolo[3,4-d]pyrimidin-6-one (Example 105) | If-23 | Acetone | F RT 0.5 | 0.95 (I) | 585.18 |
| Ig-11 | 2-[1-(2,2-Difluoro-ethyl)-azetidin-3-yl]-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 106) | If-23 | 2-Bromo-1,1-difluoroethane | G 150 0.25 | 0.95 (I) | 607.18 |
| Ig-12 | 2-[1-(2-Fluoro-ethyl)-azetidin-3-yl]-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 107) | If-23 | 1-Chloro-2-fluoroethane | G 150 0.25 | 0.93 (I) | 589.20 |
| Ig-13 | 2-(1-Acetyl-pyrrolidin-3-yl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 113) | If-24 | Acetyl chloride | B RT 0.5 | 1.24 (I) | 599.21 |
| Ig-14 | 2-(1-Acetyl-azetidin-2-ylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 114) | If-25 | Acetyl chloride | B RT 0.5 | 1.20 (I) | 599.26 |
| Ig-15 | 2-(1-Acetyl-pyrrolidin-2-ylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 115) | If-26 | Acetyl chloride | B RT 0.5 | 1.21 (I) | 613.25 |
| Ig-16 | 2-(1-Acetyl-azetidin-3-yl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Example 116) | If-23 | Acetyl chloride | B RT 1 | 1.22 (I) | 585.21 |
| Ig-17 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid methyl ester (Example 117) | If-23 | Methyl chloroformate | B RT 1 | 1.21 (I) | 601.18 |
| Ig-18 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid dimethylamide (Example 119) | If-23 | Dimethylamine (as 2M soln. in THF) | H 45 18 | 1.24 (I) | 614.25 |
| Ig-19 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid methylamide (Example 120) | If-23 | Methylamine (as 2M soln. in THF) | H 45 18 | 1.17 (I) | 600.19 |
| Ig-20 | (S)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid methyl ester (Example 123) | If-30 | Methyl chloroformate | B RT 0.25 | 1.21 (I) | 615.16 |

TABLE 62-continued

| Ig | Name | Reactant If | Reactant BB-25 | Method T [° C.] time [h] | $t_R$ [min] (LC/MS method) | MS-data m/z $[M + H]^+$ |
|---|---|---|---|---|---|---|
| Ig-21 | (S)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid ethyl ester (Example 124) | If-30 | Ethyl chloroformate | B RT 0.25 | 1.23 (I) | 629.18 |
| Ig-22 | (S)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid isopropyl ester (Example 125) | If-30 | Isopropyl chloroformate | B RT 0.25 | 1.26 (I) | 643.11 |
| Ig-23 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid ethyl ester (Example 126) | If-23 | Ethyl chloroformate | B RT 2 | 1.25 (I) | 615.21 |
| Ig-24 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid isopropyl ester (Example 127) | If-23 | Isopropyl chloroformate | B RT 2 | 1.27 (I) | 629.21 |
| Ig-25 | 5-[1-(2-Fluoro-6-methyl-phenyl)-piperidin-4-yl]-2-(1-isobutyryl-azetidin-3-yl)-7-(2-trifluoromethyl-benzyl)-2,4,5,7-tetrahydro-pyrazolo[3,4-d]pyrimidin-6-one (Example 131) | If-23 | Isobutyryl chloride | B RT 1.5 | 1.24 (I) | 613.29 |
| Ig-26 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid isobutyl ester (Example 132) | If-23 | Isobutyl chloroformate | B RT 1.5 | 1.29 (I) | 643.23 |
| Ig-27 | (R)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid methyl ester (Example 133) | If-31 | Methyl chloroformate | B RT 0.5 | 1.22 (I) | 615.15 |
| Ig-28 | (R)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid ethyl ester (Example 134) | If-31 | Ethyl chloroformate | B RT 0.5 | 1.24 (I) | 629.16 |
| Ig-29 | (R)-2-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-ylmethyl]-azetidine-1-carboxylic acid isopropyl ester (Example 135) | If-31 | Isopropyl chloroformate | B RT 0.5 | 1.26 (I) | 643.11 |
| Ig-30 | 5-[1-(2-Fluoro-6-methyl-phenyl)-piperidin-4-yl]-2-(1-methanesulfonyl-azetidin-3-yl)-7-(2-trifluoromethyl-benzyl)-2,4,5,7-tetrahydro-pyrazolo[3,4-d]pyrimidin-6-one (Example 136) | If-23 | Methanesulfonyl chloride | B RT 3 | 1.20 (I) | 621.21 |
| Ig-31 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-sulfonic acid dimethylamide (Example 137) | If-23 | N,N-Dimethylsulfamoyl chloride | B RT 3 | 1.23 (I) | 650.14 |
| Ig-32 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid oxetan-3-yl ester (Example 139) | If-23 | BB-25-1 | B 110 1 | 1.19 (I) | 643.12 |
| Ig-33 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid 3-trifluoromethyl-oxetan-3-yl ester (Example 140) | If-23 | BB-25-2 | B 110 1 | 1.27 (I) | 711.15 |
| Ig-34 | 3-[5-[1-(2-Fluoro-6-methyl-phenyl)-piperidin-4-yl]-6-oxo-7-(2-trifluoromethyl-benzyl)-4,5,6,7-tetrahydro-pyrazolo[3,4-d]pyrimidin-2-yl]-azetidine-1-carboxylic acid 3-methyl-oxetan-3-yl ester (Example 141) | If-23 | BB-25-3 | B 110 1 | 1.24 (I) | 657.11 |

TABLE 62-continued

| Ig | Name | Reactant If | Reactant BB-25 | Method T [° C.] time [h] | $t_R$ [min] (LC/MS method) | MS-data m/z [M + H]$^+$ |
|---|---|---|---|---|---|---|
| Ig-35 | 5-[1-(2-Fluoro-6-methyl-phenyl)-piperidin-4-yl]-2-[1-(5-methyl-[1,3,4]oxadiazol-2-yl)-azetidin-3-yl]-7-(2-trifluoromethyl-benzyl)-2,4,5,7-tetrahydro-pyrazolo[3,4-d]pyrimidin-6-one (Example 142) | If-23 | 5-Methyl-3H-[1,3,4]oxadiazol-2-one | I RT 1.5 | 1.24 (I) | 625.04 |
| Ig-36 | 5-[1-(2-Fluoro-6-methyl-phenyl)-piperidin-4-yl]-2-[1-(5-isopropyl-[1,3,4]oxadiazol-2-yl)-azetidin-3-yl]-7-(2-trifluoromethyl-benzyl)-2,4,5,7-tetrahydro-pyrazolo[3,4-d]pyrimidin-6-one (Example 143) | If-23 | BB-25-4 | I RT 1.5 | 1.28 (I) | 653.15 |
| Ig-37 | 5-[1-(2-Fluoro-6-methyl-phenyl)-piperidin-4-yl]-7-(2-trifluoromethyl-benzyl)-2-[1-(5-trifluoromethyl-[1,3,4]oxadiazol-2-yl)-azetidin-3-yl]-2,4,5,7-tetrahydro-pyrazolo[3,4-d]pyrimidin-6-one (Example 144) | If-23 | 2-Iodo-5-(trifluoromethyl)-1,3,4-oxadiazole | J RT 1 | 1.26 (I) | 679.11 |
| Ig-38 | 5-[1-(2-Fluoro-6-methyl-phenyl)-piperidin-4-yl]-2-isobutyl-7-(2-trifluoromethyl-benzyl)-2,4,5,7-tetrahydro-pyrazolo[3,4-d]pyrimidin-6-one (Example 155) | If-33 | — | K RT 5 | 1.28 (I) | 544.11 |

Synthesis of Compounds of Formula Ih

Method a (Deuteration)

Compound of formula Ia (1 eq) was dissolved in a mixture of CD$_3$OD (12 mL/mmol) and EtOAc (4 mL/mmol). The flask was evacuated three times and refilled with nitrogen. Wet Pd/C (0.1 eq) was added and the flask was evacuated three times and refilled with deuterium. The suspension was stirred under an atmospheric pressure of deuterium for a given time (see Table) and filtered over a pad of Celite. The cake was washed with EtOAc and the filtrate was concentrated in vacuo. The crude was purified by prep. LC-MS using method 4.

Method B (Substitution with F)

A suspension of compound Ia (1 eq) and dry CsF (6 eq) in anh. DMSO (5.4 mL/mmol) was heated to a given temperature under argon and stirred for a given time (see Table). The rxn mixture was partitioned between EtOAc and H$_2$O and the org. phase was washed with brine, dried over MgSO$_4$ and concentrated in vacuo. The crude was purified by CC using Hept/EtOAc.

Method C (Suzuki Coupling)

A mixture of compound Ia (1 eq), boron species (1.1 eq), Pd(dppf)Cl$_2$.CH$_2$Cl$_2$ (0.03 eq) and K$_2$CO$_3$ (2 eq) in dioxane (13.6 mL/mmol) was flushed with N$_2$ and heated at a given temperature for a given time (see Table). It was partitioned between EtOAc and a sat. aq. soln. of NaHCO$_3$ and the org. phase was washed with brine, dried over MgSO$_4$ and concentrated in vacuo. The crude was purified by CC using Hept/EtOAc/MeOH.

Method D (Substitution with OMe)

A suspension of compound Ia (1 eq) in MeOH (6 mL) was treated with a 25% soln. of NaOMe in MeOH (6 eq). The rxn mixture was heated to a given temperature for a given time (see Table) and partitioned between DCM and water. The org. phase was washed with brine, dried over MgSO$_4$ and concentrated in vacuo. The crude was purified by CC using Hept/EtOAc.

Method E (Substitution with Amine)

A soln. of compound Ia (1 eq) in MeOH (9 mL/mmol) was treated with the appropriate amine (21 eq, pure or as soln.). The rxn mixture was heated at 150° C. under microwave irradiation for a given time (see Table) and partitioned between DCM and H$_2$O. The org. phase was washed with brine, dried over MgSO$_4$ and concentrated in vacuo. The crude was purified by CC using Hept/EtOAc.

Method F (Phenol Alkylation Using NaH as Base)

To a soln. of compound Ia (1 eq) in anh. THE (9.7 mL/mmol) was added NaH (5 eq, as a 60% dispersion in mineral oil) at 0° C. The suspension was stirred for 10 min and the appropriate halide (1.1 to 1.5 eq) was added at 0° C. The rxn mixture was stirred at a given temperature for a given time (see Table). When necessary to reach completion of the rxn, extra amounts of NaH (5 eq, as a 60% dispersion in mineral oil) and/or halide BB-9 (3 eq) were added. The mixture was quenched with water at 0° C. and extracted with EtOAc. The combined org. phases were washed with brine, dried over MgSO$_4$ and concentrated in vacuo. The crude was purified by CC using Hept/EtOAc or by prep. LC-MS using method 11.

Method G (Phenol Alkylation Using K$_2$CO$_3$ as Base)

To a stirred suspension of compound Ia (1 eq) in DMF (8.5 mL/mmol) was added K$_2$CO$_3$ (3 eq) followed by the appropriate halide (5 eq). The rxn mixture was stirred at a given temperature under microwave irradiation for a given time (see Table). It was partitioned between EtOAc and H$_2$O and the org. phase was washed with water and brine, dried over MgSO$_4$ and concentrated in vacuo. The crude was purified by CC using Hept/EtOAc.

Method H (Phenol Alkylation Using Mitsunobu Conditions)

To a soln. of compound Ia (1 eq) and alcohol (3 eq) in toluene (8 mL/mmol) was added 1M soln. of (tributylphosphoranylidene)acetonitrile in toluene (1.5 eq) under argon. The rxn mixture was heated to 110° C. and stirred for a given time (see Table). It was quenched with water and extracted with DCM. The combined org. phases were washed with brine, dried over MgSO$_4$ and concentrated in vacuo. The crude was purified by CC using Hept/EtOAc and/or by prep. LC-MS using method 11.

TABLE 63

| Ih | Name | Reactant Ia | Amine/ halide/ alcohol/ boron reagent | Method T [° C.] time [h] | $t_R$ [min] (LC/MS method) | MS-data m/z $[M + H]^+$ |
|---|---|---|---|---|---|---|
| Ih-1 | 5-(1-(2-fluoro-6-methylphenyl)piperidin-4-yl)-2-methyl-7-(3-trifluoromethyl-[6-$^2$H]pyridine-2-yl-methyl)-2,4,5,7-tetrahydro-6H-pyrazolo[3,4-d]pyrimidin-6-one (Example 23) | Ia-9 | — | A RT 48 | 1.00 (II) | 504.12 |
| Ih-2 | 5-[1-(2-Fluoro-6-methyl-phenyl)-piperidin-4-yl]-7-(6-fluoro-3-trifluoromethyl-pyridin-2-ylmethyl)-2-methyl-2,4,5,7-tetrahydro-pyrazolo[3,4-d]pyrimidin-6-one (Example 36) | Ia-9 | — | B 100 3 | 1.03 | 521.11 |
| Ih-3 | 5-[1-(2-Fluoro-6-methyl-phenyl)-piperidin-4-yl]-2-methyl-7-(6-methyl-3-trifluoromethyl-pyridin-2-ylmethyl)-2,4,5,7-tetrahydro-pyrazolo[3,4-d]pyrimidin-6-one (Example 37) | Ia-9 | Trimethyl boroxine | C 100 2 | 1.03 (I) | 517.13 |
| Ih-4 | 5-[1-(2-Fluoro-6-methyl-phenyl)-piperidin-4-yl]-7-(6-methoxy-3-trifluoromethyl-pyridin-2-ylmethyl)-2-methyl-2,4,5,7-tetrahydro-pyrazolo[3,4-d]pyrimidin-6-one (Example 38) | Ia-9 | 25% soln. of NaOMe in MeOH | D 70 2 | 1.05 (II) | 533.13 |
| Ih-5 | 7-(6-Dimethylamino-3-trifluoromethyl-pyridin-2-ylmethyl)-5-[1-(2-fluoro-6-methyl-phenyl)-piperidin-4-yl]-2-methyl-2,4,5,7-tetrahydro-pyrazolo[3,4-d]pyrimidin-6-one (Example 50) | Ia-9 | 2M soln. of dimethylamine in THF | E 150 1 | 1.05 (II) | 546.06 |
| Ih-6 | 5-[1-(2-Fluoro-6-methyl-phenyl)-piperidin-4-yl]-2-methyl-7-(6-methylamino-3-trifluoromethyl-pyridin-2-ylmethyl)-2,4,5,7-tetrahydro-pyrazolo[3,4-d]pyrimidin-6-one (Example 51) | Ia-9 | 2M soln. of methylamine in THF | E 150 4 | 0.99 (II) | 532.13 |
| Ih-7 | 7-(2-Cyclopropylmethoxy-benzyl)-5-[1-(2-fluoro-6-methyl-phenyl)-piperidin-4-yl]-2-methyl-2,4,5,7-tetrahydro-pyrazolo[3,4-d]pyrimidin-6-one (Example 248) | Ia-39 | (Bromomethyl) cyclopropane | F RT to 70 120 | 1.20 (I) | 504.25 |
| Ih-8 | 5-[1-(2-Fluoro-6-methyl-phenyl)-piperidin-4-yl]-2-methyl-7-[2-(oxetan-3-yloxy)-benzyl]-2,4,5,7-tetrahydro-pyrazolo[3,4-d]pyrimidin-6-one (Example 250) | Ia-39 | 3-Bromooxetane | G 150 7 | 1.10 (I) | 506.20 |
| Ih-9 | 5-[1-(2-Fluoro-6-methyl-phenyl)-piperidin-4-yl]-7-(2-isopropoxy-benzyl)-2-methyl-2,4,5,7-tetrahydro-pyrazolo[3,4-d]pyrimidin-6-one (Example 251) | Ia-39 | 2-Propanol | H 110 18 | 1.19 (I) | 492.20 |

Synthesis of Compounds of Formula Ii

Method A (Alkylation Using NaH)

To suspension or soln. of intermediate C-2 (1 eq) in mixture of anh. THF (3 to 3.6 mL/mmol) and anh. DMF (0.1 to 0.25 mL/mmol) was added NaH (2 eq, as a 60% dispersion in mineral oil) at 0° C. The suspension was stirred for 10 min at 0° C. and BB-9 (1.2 to 1.5 eq) was added at 0° C. The rxn mixture was stirred at a given temperature for a given time (see Table), quenched at 0° C. with a sat. aq. soln. of NaHCO$_3$ and extracted with EtOAc or DCM. The combined org. phases were washed with brine, dried over MgSO$_4$ and concentrated in vacuo. The crude was purified by CC using Hept/EtOAc.

Method B (Mitsunobu)

To a soln. or suspension of intermediate-2(1 eq) and alcohol B-9(1 to 1.3 eq) in toluene (7 mL/mmol) was added a 1M soln. of (tributylphosphoranylidene)acetonitrile in toluene (2 eq) under argon. The rxn mixture was heated to a given temperature and stirred for a given time (see Table). When necessary to reach completion of the rxn, extra amounts of a 1M soln. of (tributylphosphoranylidene)acetonitrile in toluene (0.2 eq) were sequentially added under argon. It was quenched with water or a sat. aq. soln. of NaHCO$_3$ and extracted with EtOAc or DCM. The combined org. phases were washed with brine, dried over MgSO$_4$ and concentrated in vacuo. The crude was purified by CC using Hept/EtOAc or DCM/MeOH. When necessary, an additional purification by prep. LC-MS using methods 2,3,4 or 5 was performed.

TABLE 64

| Ii | Name | Reactant C-2 | Reactant BB-9 | Method T [° C.] time [h] | $t_R$ [min] (LC/MS-method) | MS-data m/z [M + H]$^+$ |
|---|---|---|---|---|---|---|
| Ii-1 | 3-[2-Methyl-6-oxo-7-(2-trifluoromethyl-benzyl)-2,4,6,7-tetrahydro-pyrazolo[3,4-d]pyrimidin-5-yl]-pyrrolidine-1-carboxylic acid tert-butyl ester | C-2-1 | BB-9-1 | A RT 18 | 0.94 (II) | 480.08 |
| Ii-2 | 4-[2-Methyl-6-oxo-7-(2-trifluoromethyl-benzyl)-2,4,6,7-tetrahydro-pyrazolo[3,4-d]pyrimidin-5-yl]-piperidine-1-carboxylic acid tert-butyl ester | C-2-2 | BB-9-1 | A RT 18 | 0.97 (II) | 494.09 |
| Ii-3 | 4-[2-Methyl-6-oxo-7-(2-trifluoromethyl-benzyl)-2,4,6,7-tetrahydro-pyrazolo[3,4-d]pyrimidin-5-yl]-azepane-1-carboxylic acid tert-butyl ester | C-2-3 | BB-9-1 | A RT 18 | 0.98 (II) | 508.19 |
| Ii-4 | 4-[2-Methyl-5-oxo-4-(2-trifluoromethyl-benzyl)-2,4,5,7-tetrahydro-pyrazolo[4,3-d]pyrimidin-6-yl]-piperidine-1-carboxylic acid tert-butyl ester | C-2-4 | BB-9-1 | A RT 2 | 1.07 (I) | 494.21 |
| Ii-5 | 4-{2-Methyl-6-oxo-7-[1-(2-trifluoromethyl-phenyl)-ethyl]-2,4,6,7-tetrahydro-pyrazolo[3,4-d]pyrimidin-5-yl}-piperidine-1-carboxylic acid tert-butyl ester | C-2-2 | BB-9-15 | B 110 24 | 1.07 (I) | 508.26 |
| Ii-6 | 4-[7-(2-Cyclopropyl-benzyl)-2-methyl-6-oxo-2,4,6,7-tetrahydro-pyrazolo[3,4-d]pyrimidin-5-yl]-piperidine-1-carboxylic acid tert-butyl ester | C-2-2 | BB-9-9 | B 110 1.5 | 1.05 (I) | 466.03 |

Synthesis of Compounds of Formula Ij

Method A (Buchwald Coupling)

To mixture of intermediate C-3 (1 eq), halo-(hetero)arene BB-16(1.1 to 2 eq) and sodium tert-butoxide (2 to 2.3 eq) in toluene (3 to 7.8 mL/mmol) under $N_2$, was added BINAP (0.2 to 0.3 eq) and $Pd_2(dba)_3$(0.1 to 0.15 eq). The rxn mixture was flushed with $N_2$, heated under stirring at a given temperature for a given time (see Table). It was partitioned between water and EtOAc or DCM and the org. phase was washed with brine, dried over $MgSO_4$ and concentrated in vacuo. The crude was purified by CC using Hept/EtOAc or DCM/MeOH. When necessary, an additional purification by prep. LC-MS using methods 1, 3, 4, 5, 6 or 10 was performed.

Method B (Aromatic Nucleophilic Substitution)

To a soln. of intermediate C-3(1 eq) and halo-(hetero) arene BB-16 (1.2 to 2 eq) in DMSO (1.5 to 4.5 mL/mmol) was added $K_2CO_3$ or CsF (2 eq) and the mixture was heated to a given temperature and stirred for a given time under possible microwave irradiation (see Table). It was partitioned between EtOAc and $H_2$. The org. phase was washed with $H_2O$ and brine, dried over $MgSO_4$ and concentrated in vacuo. The crude was purified by CC using Hept/EtOAc. When necessary, an additional purification by prep. LC-MS using method 1 was performed.

TABLE 58

| Ij | Name | Reactant C-3 | Reactant BB-16 | Method T [° C.] time [h] | $t_R$ [min] (LC/MS-method) | MS-data m/z [M + H]$^+$ |
|---|---|---|---|---|---|---|
| Ij-1 | 5-[1-(2-Fluoro-6-methyl-phenyl)-pyrrolidin-3-yl]-2-methyl-7-(2-trifluoromethyl-benzyl)-2,4,5,7-tetrahydro-pyrazolo[3,4-d]pyrimidin-6-one (Example 44) | C-3-1 | BB-16-1 | A 110 2.5 | 0.92 (II) | 488.06 |
| Ij-2 | 5-[1-(2,6-Dimethyl-phenyl)-piperidin-4-yl]-2-methyl-7-(2-trifluoromethyl-benzyl)-2,4,5,7-tetrahydro-pyrazolo[3,4-d]pyrimidin-6-one (Example 47) | C-3-2 | BB-16-2 | A 110 18 | 1.08 (II) | 498.01 |
| Ij-3 | 5-[1-(2-Methoxy-6-methyl-phenyl)-piperidin-4-yl]-2-methyl-7-(2-trifluoromethyl-benzyl)-2,4,5,7-tetrahydro-pyrazolo[3,4-d]pyrimidin-6-one (Example 48) | C-3-2 | BB-16-3 | A 110 18 | 0.91 (II) | 514.01 |
| Ij-4 | 3-Fluoro-2-{4-[2-methyl-6-oxo-7-(2-trifluoromethyl-benzyl)-2,4,6,7-tetrahydro-pyrazolo[3,4-d]pyrimidin-5-yl]-piperidin-1-yl}-benzonitrile (Example 49) | C-3-2 | BB-16-5 | B 100 3.5 | 1.02 (II) | 513.00 |

TABLE 58-continued

| Ij | Name | Reactant C-3 | Reactant BB-16 | Method T [° C.] time [h] | $t_R$ [min] (LC/MS-method) | MS-data m/z [M + H]$^+$ |
|---|---|---|---|---|---|---|
| Ij-5 | 5-[1-(2,6-Dimethyl-phenyl)-pyrrolidin-3-yl]-2-methyl-7-(2-trifluoromethyl-benzyl)-2,4,5,7-tetrahydro-pyrazolo[3,4-d]pyrimidin-6-one | C-3-1 | BB-16-2 | A 110 18 | 0.95 (II) | 484.10 |
| Ij-6 | 5-(2'-Fluoro-4'-methyl-3,4,5,6-tetrahydro-2H-[1,3']bipyridinyl-4-yl)-2-methyl-7-(2-trifluoromethyl-benzyl)-2,4,5,7-tetrahydro-pyrazolo[3,4-d]pyrimidin-6-one (Example 52) | C-3-2 | BB-16-6 | A 110 18 | 1.01 (II) | 503.10 |
| Ij-7 | 5-(2'-Methoxy-4'-methyl-3,4,5,6-tetrahydro-2H-[1,3']bipyridinyl-4-yl)-2-methyl-7-(2-trifluoromethyl-benzyl)-2,4,5,7-tetrahydro-pyrazolo[3,4-d]pyrimidin-6-one (Example 54) | C-3-2 | BB-16-7 | A 110 18 | 1.01 (II) | 515.11 |
| Ij-8 | 5-(3'-Fluoro-3,4,5,6-tetrahydro-2H-[1,2']bipyridinyl-4-yl)-2-methyl-7-(2-trifluoromethyl-benzyl)-2,4,5,7-tetrahydro-pyrazolo[3,4-d]pyrimidin-6-one (Example 68) | C-3-2 | BB-16-8 | A 110 18 | 0.90 (II) | 489.12 |
| Ij-9 | 2-Methyl-5-(3'-methyl-3,4,5,6-tetrahydro-2H-[1,2']bipyridinyl-4-yl)-7-(2-trifluoromethyl-benzyl)-2,4,5,7-tetrahydro-pyrazolo[3,4-d]pyrimidin-6-one (Example 69) | C-3-2 | BB-16-9 | A 110 18 | 0.73 (II) | 485.12 |
| Ij-10 | 5-(3'-Methoxy-3,4,5,6-tetrahydro-2H-[1,2']bipyridinyl-4-yl)-2-methyl-7-(2-trifluoromethyl-benzyl)-2,4,5,7-tetrahydro-pyrazolo[3,4-d]pyrimidin-6-one (Example 70) | C-3-2 | BB-16-10 | A 110 18 | 0.74 (II) | 501.11 |
| Ij-11 | 4'-Methyl-4-[2-methyl-6-oxo-7-(2-trifluoromethyl-benzyl)-2,4,6,7-tetrahydro-pyrazolo[3,4-d]pyrimidin-5-yl]-3,4,5,6-tetrahydro-2H-[1,3']bipyridinyl-2'-carbonitrile (Example 85) | C-3-2 | BB-16-11 | A 110 18 | 0.98 (II) | 510.11 |
| Ij-12 | 5-(4'-Fluoro-2'-methyl-3,4,5,6-tetrahydro-2H-[1,3']bipyridinyl-4-yl)-2-methyl-7-(2-trifluoromethyl-benzyl)-2,4,5,7-tetrahydro-pyrazolo[3,4-d]pyrimidin-6-one (Example 86) | C-3-2 | BB-16-12 | A 110 18 | 0.74 (II) | 503.10 |
| Ij-13 | 5-(2',4'-Dimethoxy-3,4,5,6-tetrahydro-2H-[1,3']bipyridinyl-4-yl)-2-methyl-7-(2-trifluoromethyl-benzyl)-2,4,5,7-tetrahydro-pyrazolo[3,4-d]pyrimidin-6-one (Example 95) | C-3-2 | BB-16-13 | A 110 18 | 0.76 (II) | 531.09 |
| Ij-14 | 5-[1-(4-Methoxy-6-methyl-pyrimidin-5-yl)-piperidin-4-yl]-2-methyl-7-(2-trifluoromethyl-benzyl)-2,4,5,7-tetrahydro-pyrazolo[3,4-d]pyrimidin-6-one (Example 96) | C-3-2 | BB-16-14 | A 110 18 | 0.84 (II) | 516.11 |
| Ij-15 | 5-[1-(4,6-Dimethoxy-pyrimidin-5-yl)-piperidin-4-yl]-2-methyl-7-(2-trifluoromethyl-benzyl)-2,4,5,7-tetrahydro-pyrazolo[3,4-d]pyrimidin-6-one (Example 100) | C-3-2 | BB-16-15 | A 110 18 | 0.93 (II) | 532.09 |
| Ij-16 | 1,3-Dimethyl-5-{4-[2-methyl-6-oxo-7-(2-trifluoromethyl-benzyl)-2,4,6,7-tetrahydro-pyrazolo[3,4-d]pyrimidin-5-yl]-piperidin-1-yl}-1H-pyrazole-4-carbonitrile (Example 229) | C-3-2 | BB-16-16 | B 130 2.5 microwave | 1.04 (I) | 513.01 |
| Ij-18 | 5-[1-(2-Fluoro-6-trifluoromethyl-phenyl)-piperidin-4-yl]-2-methyl-7-(2-trifluoromethyl-benzyl)-2,4,5,7-tetrahydro-pyrazolo[3,4-d]pyrimidin-6-one (Example 243) | C-3-2 | BB-16-19 | A 110 2.5 | 1.22 (I) | 556.19 |
| Ij-19 | 5-[1-(2-Fluoro-6-trifluoromethoxy-phenyl)-piperidin-4-yl]-2-methyl-7-(2-trifluoromethyl-benzyl)-2,4,5,7-tetrahydro-pyrazolo[3,4-d]pyrimidin-6-one (Example 244) | C-3-2 | BB-16-20 | A 110 2.5 | 1.22 (I) | 572.17 |

TABLE 58-continued

| Ij | Name | Reactant C-3 | Reactant BB-16 | Method T [° C.] time [h] | $t_R$ [min] (LC/MS-method) | MS-data m/z $[M + H]^+$ |
|---|---|---|---|---|---|---|
| Ij-20 | 5-[1-(2-Chloro-6-methyl-phenyl)-piperidin-4-yl]-2-methyl-7-(2-trifluoromethyl-benzyl)-2,4,5,7-tetrahydro-pyrazolo[3,4-d]pyrimidin-6-one (Example 245) | C-3-2 | BB-16-21 | A 110 2.5 | 1.22 (I) | 518.17 |
| Ij-21 | 5-[1-(2-Isopropyl-phenyl)-piperidin-4-yl]-2-methyl-7-(2-trifluoromethyl-benzyl)-2,4,5,7-tetrahydro-pyrazolo[3,4-d]pyrimidin-6-one (Example 257) | C-3-2 | BB-16-22 | A 110 2 | 1.06 (I) | 512.24 |
| Ij-22 | 5-[1-(2-Cyclopropyl-phenyl)-piperidin-4-yl]-2-methyl-7-(2-trifluoromethyl-benzyl)-2,4,5,7-tetrahydro-pyrazolo[3,4-d]pyrimidin-6-one (Example 258) | C-3-2 | BB-16-23 | A 110 2 | 1.02 (I) | 510.24 |
| Ij-23 | 6-[1-(2-Fluoro-6-trifluoromethoxy-phenyl)-piperidin-4-yl]-2-methyl-4-(2-trifluoromethyl-benzyl)-2,4,6,7-tetrahydro-pyrazolo[4,3-d]pyrimidin-5-one (Example 270) | C-3-4 | BB-16-20 | A 110 18 | 1.25 (I) | 572.23 |
| Ij-24 | 6-[1-(2-Fluoro-6-trifluoromethyl-phenyl)-piperidin-4-yl]-2-methyl-4-(2-trifluoromethyl-benzyl)-2,4,6,7-tetrahydro-pyrazolo[4,3-d]pyrimidin-5-one (Example 271) | C-3-4 | BB-16-19 | A 100 18 | 1.24 (I) | 556.23 |
| Ij-25 | 5-[1-(2-Chloro-6-fluoro-phenyl)-piperidin-4-yl]-2-methyl-7-(2-trifluoromethyl-benzyl)-2,4,5,7-tetrahydro-pyrazolo[3,4-d]pyrimidin-6-one (Example 272) | C-3-2 | BB-16-24 | A 100 2.5 | 1.19 (I) | 522.18 |
| Ij-26 | 5-[1-(2,6-Difluoro-phenyl)-piperidin-4-yl]-2-methyl-7-(2-trifluoromethyl-benzyl)-2,4,5,7-tetrahydro-pyrazolo[3,4-d]pyrimidin-6-one (Example 273) | C-3-2 | BB-16-25 | A 100 2.5 | 1.15 (I) | 506.18 |
| Ij-27 | 5-(2'-Methoxy-4'-methyl-3,4,5,6-tetrahydro-2H-[1,3']bipyridinyl-4-yl)-2-methyl-7-[1-(2-trifluoromethyl-phenyl)-ethyl]-2,4,5,7-tetrahydro-pyrazolo[3,4-d]pyrimidin-6-one | C-3-5 | BB-16-7 | A 100 2 | 1.11 (I) | 529.16 |
| Ij-28 | 3-Fluoro-2-(4-{2-methyl-6-oxo-7-[1-(2-trifluoromethyl-phenyl)-ethyl]-2,4,6,7-tetrahydro-pyrazolo[3,4-d]pyrimidin-5-yl}-piperidin-1-yl)-benzonitrile | C-3-5 | BB-16-5 | B 100 5 | 1.13 (I) | 527.27 |
| Ij-29 | 5-[1-(2,6-Difluoro-phenyl)-piperidin-4-yl]-2-methyl-7-[1-(2-trifluoromethyl-phenyl)-ethyl]-2,4,5,7-tetrahydro-pyrazolo[3,4-d]pyrimidin-6-one | C-3-5 | BB-16-25 | A 100 2 | 1.16 (I) | 520.27 |
| Ij-30 | 7-(2-Cyclopropyl-benzyl)-5-[1-(2-fluoro-6-trifluoromethyl-phenyl)-piperidin-4-yl]-2-methyl-2,4,5,7-tetrahydro-pyrazolo[3,4-d]pyrimidin-6-one (Example 280) | C-3-6 | BB-16-19 | A 100 4 | 1.22 (I) | 528.31 |
| Ij-31 | 7-(2-Cyclopropyl-benzyl)-5-[1-(2-fluoro-6-trifluoromethoxy-phenyl)-piperidin-4-yl]-2-methyl-2,4,5,7-tetrahydro-pyrazolo[3,4-d]pyrimidin-6-one (Example 281) | C-3-6 | BB-16-20 | A 100 1.5 | 1.22 (I) | 544.31 |
| Ij-32 | 2-{4-[7-(2-Cydopropyl-benzyl)-2-methyl-6-oxo-2,4,6,7-tetrahydro-pyrazolo[3,4-d]pyrimidin-5-yl]-piperidin-1-yl}-3-fluoro-benzonitrile (Example 282) | C-3-6 | BB-16-5 | B 100 4 | 1.13 (I) | 485.25 |
| Ij-33 | 7-(2-Cyclopropyl-benzyl)-5-(2'-methoxy-4'-methyl-3,4,5,6-tetrahydro-2H-[1,3']bipyridinyl-4-yl)-2-methyl-2,4,5,7-tetrahydro-pyrazolo[3,4-d]pyrimidin-6-one (Example 283) | C-3-6 | BB-16-7 | A 100 2 | 1.10 (I) | 487.28 |
| Ij-34 | 5-[1-(2-Chloro-6-fluoro-phenyl)-piperidin-4-yl]-7-(2-cyclopropyl-benzyl)-2-methyl-2,4,5,7-tetrahydro-pyrazolo[3,4-d]pyrimidin-6-one (Example 284) | C-3-6 | BB-16-24 | A 100 2 | 1.19 (I) | 494.27 |

TABLE 58-continued

| Ij | Name | Reactant C-3 | Reactant BB-16 | Method T [° C.] time [h] | $t_R$ [min] (LC/MS-method) | MS-data m/z [M + H]$^+$ |
|---|---|---|---|---|---|---|
| Ij-35 | 7-(2-Cyclopropyl-benzyl)-5-[1-(2,6-difluoro-phenyl)-piperidin-4-yl]-2-methyl-2,4,5,7-tetrahydro-pyrazolo[3,4-d]pyrimidin-6-one (Example 285) | C-3-6 | BB-16-25 | A 100 5 | 1.14 (I) | 478.31 |
| Ij-36 | 5-[1-(2-Ethyl-6-fluoro-phenyl)-piperidin-4-yl]-2-methyl-7-(2-trifluoromethyl-benzyl)-2,4,5,7-tetrahydro-pyrazolo[3,4-d]pyrimidin-6-one (Example 299) | C-3-2 | BB-16-26 | A 100 1 | 1.12 (I) | 516.35 |
| Ij-37 | 5-[1-(2-Difluoromethyl-6-fluoro-phenyl)-piperidin-4-yl]-2-methyl-7-(2-trifluoromethyl-benzyl)-2,4,5,7-tetrahydro-pyrazolo[3,4-d]pyrimidin-6-one (Example 300) | C-3-2 | BB-16-27 | A 100 1 | 1.18 (I) | 538.35 |
| Ij-38 | 6-[1-(2-Difluoromethyl-6-fluoro-phenyl)-piperidin-4-yl]-2-methyl-4-(2-trifluoromethyl-benzyl)-2,4,6,7-tetrahydro-pyrazolo[4,3-d]pyrimidin-5-one (Example 301) | C-3-4 | BB-16-27 | A 100 4 | 1.18 (I) | 538.29 |
| Ij-40 | 6-[1-(2-Chloro-6-fluoro-phenyl)-piperidin-4-yl]-2-methyl-4-(2-trifluoromethyl-benzyl)-2,4,6,7-tetrahydro-pyrazolo[4,3-d]pyrimidin-5-one (Example 302) | C-3-4 | BB-16-24 | A 100 4 | 1.21 (I) | 522.27 |
| Ij-41 | 5-[1-(2-Cyclopropyl-6-fluoro-phenyl)-piperidin-4-yl]-2-methyl-7-(2-trifluoromethyl-benzyl)-2,4,5,7-tetrahydro-pyrazolo[3,4-d]pyrimidin-6-one (Example 303) | C-3-2 | BB-16-28 | A 100 4 | 1.21 (I) | 528.35 |
| Ij-42 | 6-[1-(2-Cyclopropyl-6-fluoro-phenyl)-piperidin-4-yl]-2-methyl-4-(2-trifluoromethyl-benzyl)-2,4,6,7-tetrahydro-pyrazolo[4,3-d]pyrimidin-5-one (Example 304) | C-3-4 | BB-16-28 | A 100 2.5 | 1.22 (I) | 528.32 |
| Ij-43 | 7-(2-Cyclopropyl-benzyl)-5-[1-(2-cyclopropyl-6-fluoro-phenyl)-piperidin-4-yl]-2-methyl-2,4,5,7-tetrahydro-pyrazolo[3,4-d]pyrimidin-6-one (Example 307) | C-3-6 | BB-16-28 | A 100 3 | 1.21 (I) | 500.36 |
| Ij-44 | 7-(2-Cyclopropyl-benzyl)-5-[1-(2-difluoromethyl-6-fluoro-phenyl)-piperidin-4-yl]-2-methyl-2,4,5,7-tetrahydro-pyrazolo[3,4-d]pyrimidin-6-one (Example 308) | C-3-6 | BB-16-27 | A 100 3 | 1.17 (I) | 510.36 |

Method D (Multistep)

Step A: Aromatic Nucleophilic Substitution

To a soln. of amine C-3 (1 eq) and halide BB-16 (2 eq) in DMSO (3.4 mL/mmol) was added CsF (2 eq). The rxn mixture was heated at a given temperature for a given time under possible microwave irradiation (see Table) and was partitioned between EtOAc and water. The org. phase was washed with water and brine, dried over MgSO$_4$ and concentrated in vacuo. The crude was purified by CC using Hept/EtOAc.

Step B: Decarbonylation

To a soln. of Ij-A (1 eq) in MeOH (8 mL/mmol) was added toluene-4-sulfonic acid monohydrate (0.25 eq) and the rxn mixture was heated at 120° C. under microwave condition for a given time (see Table). It was concentrated in vacuo and partitioned between EtOAc and a sat. aq. soln. of NaHCO$_3$. The org. phase was washed with brine, dried over MgSO$_4$ and concentrated in vacuo. The crude was purified by CC using Hept/EtOAc/MeOH.

TABLE 59

| Ij-A | Name | Reactant C-3 | Reactant BB-16 | T [° C.] time [h] | $t_R$ [min] (LC/MS method) | MS-data m/z [M + H]$^+$ |
|---|---|---|---|---|---|---|
| Ij-17A | 1,3-Dimethyl-5-{4-[2-methyl-6-oxo-7-(2-trifluoromethyl-benzyl)-2,4,6,7-tetrahydro-pyrazolo[3,4-d]pyrimidin-5-yl]-piperidin-1-yl}-1H-pyrazole-4-carbaldehyde | C-3-2 | BB-16-17 | 150 3 microwave | 1.01 (I) | 516.21 |

TABLE 60

| Ij-B | Name | Reactant Ij-A | time [h] | $t_R$ [min] (LC/MS-method) | MS-data m/z [M + H]+ |
|---|---|---|---|---|---|
| Ij-17B | 5-[1-(2,5-Dimethyl-2H-pyrazol-3-yl)-piperidin-4-yl]-2-methyl-7-(2-trifluoromethyl-benzyl)-2,4,5,7-tetrahydro-pyrazolo[3,4-d]pyrimidin-6-one | Ij-17A | 9 | 0.86 (I) | 488.21 |

Step C: Chlorination

To a soln. of Ij-B (1 eq) in THF (5 mL/mmol) was added NCS (1.4 eq) and the rxn mixture was stirred at RT for a given time (see Table). It was partitioned between EtOAc and water and the org. phase was washed with brine, dried over MgSO$_4$ and concentrated in vacuo. The crude was purified by CC using Hept/EtOAc. When necessary an additional purification by prep. LC-MS using method 5 was performed.

TABLE 61

| Ij | Name | Reactant Ij-B | time [h] | $t_R$ [min] (LC/MS method) | MS-data m/z [M + H]+ |
|---|---|---|---|---|---|
| Ij-17 | 5-[1-(4-Chloro-2,5-dimethyl-2H-pyrazol-3-yl)-piperidin-4-yl]-2-methyl-7-(2-trifluoromethyl-benzyl)-2,4,5,7-tetrahydro-pyrazolo[3,4-d]pyrimidin-6-one (Example 238) | Ij-17B | 0.5 | 1.11 (I) | 522.17 |

Chiral Separation of Compounds of Formula Ia, Ic or Ii

Racemates of formula Ia, Ic or Ij were separated into the respective enantiomers using preparative chiral HPLC or SFC (equipped with a given column and eluting with given parameters (see Table), detection: UV 210 nm).

Both enantiomers were characterized by analytical chiral HPLC or SFC (equipped with a given Daicel column and eluting with given parameters (see Table), detection: UV 210 to 280 nm).

The absolute configuration for the molecule Ik-70 (Example 324, enantiomer B) was assessed by single crystal X-ray diffraction (suitable crystal obtained from iPrOH) and proved to be in absolute (R)-configuration. Consequently, the absolute configuration for the molecule Ik-69 (Example 323, enantiomer A) was assigned (S). In analogy, for all example compounds wherein R$^4$ represents methyl listed in Table 69 below, the enantiomer showing higher activity in the in vitro biological assay disclosed below may be assumed to have the absolute (S)-configuration.

TABLE 62

| Ik | Name | Racemate Ia, Ic or Ij | Column Eluent Flow (preparative) | Column Eluent Flow (analytical) | $t_R$ [min] chiral HPLC |
|---|---|---|---|---|---|
| Ik-1 | 5-[(R)- or (S)-1-(2,6-Dimethyl-phenyl)-pyrrolidin-3-yl]-2-methyl-7-(2-trifluoromethyl-benzyl)-2,4,5,7-tetrahydro-pyrazolo[3,4-d]pyrimidin-6-one (Enantiomer A) (Example 57) | Ij-5 | ChiralCel OD-H 20 × 250 mm, 5 µm Hept/(EtOH + 0.1% DEA) 70/30 16 mL/min | ChiralCel OD-H 4.6 × 250 mm, 5 µm (Hept + 0.05% DEA)/(EtOH + 0.05% DEA) 70/30 0.8 mL/min | 5.97 |
| Ik-2 | 5-[(S)- or (R)-1-(2,6-Dimethyl-phenyl)-pyrrolidin-3-yl]-2-methyl-7-(2-trifluoromethyl-benzyl)-2,4,5,7-tetrahydro-pyrazolo[3,4-d]pyrimidin-6-one (Enantiomer B) (Example 58) | | | | 8.36 |
| Ik-3 | 5-[1-(2-Fluoro-6-methyl-phenyl)-piperidin-4-yl]-2-((S)- or (R)-2-fluoro-propyl)-7-(2-trifluoromethyl-benzyl)-2,4,5,7-tetrahydro-pyrazolo[3,4-d]pyrimidin-6-one (Enantiomer B) (Example 185) | Ic-71 | ChiralPak ID 20 × 250 mm, 5 µm Hept/(EtOH + 0.1% DEA) 90/10 16 mL/min | ChiralPak ID 4.6 × 250 mm, 5 µm (Hept + 0.02% DEA)/(EtOH + 0.02% DEA) 90/10 | 12.8 |
| Ik-4 | 5-[1-(2-Fluoro-6-methyl-phenyl)-piperidin-4-yl]-2-((R)- or (S)-2-fluoro-propyl)-7-(2-trifluoromethyl-benzyl)-2,4,5,7-tetrahydro-pyrazolo[3,4-d]pyrimidin-6-one (Enantiomer A) (Example 186) | | | 0.8 mL/min | 10.0 |

TABLE 62-continued

| Ik | Name | Racemate Ia, Ic or Ij | Column Eluent Flow (preparative) | Column Eluent Flow (analytical) | $t_R$ [min] chiral HPLC |
|---|---|---|---|---|---|
| Ik-5 | 2-((S)-or (R)-2,2-Difluoro-1-methyl-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Enantiomer B) (Example 187) | Ic-72 | ChiralPak IC 30 × 250 mm, 5 µm Hept/(EtOH + 0.1% DEA) 90/10 34 mL/min | ChiralPak IC 4.6 × 250 mm, 5 µm (Hept + 0.02% DEA)/(EtOH + 0.02% DEA) 90/10 0.8 mL/min | 10.29 |
| Ik-6 | 2-((R)- or (S)-2,2-Difluoro-1-methyl-ethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Enantiomer A) (Example 188) | | | | 8.49 |
| Ik-7 | 2-((R)- or (S)-2,2-Difluoro-cyclopropylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Enantiomer A) (Example 189) | Ic-73 | ChiralPak IG 20 × 250 mm, 5 µm Hept/(EtOH + 0.1% DEA) 70/30 16 mL/min | ChiralPak IG 4.6 × 250 mm, 5 µm (Hept + 0.02% DEA)/(EtOH + 0.02% DEA) 70/30 0.8 mL/min | 8.12 |
| Ik-8 | 2-((S)- or (R)-2,2-Difluoro-cyclopropylmethyl)-5-[1-(2-fluoro-6-methyl-phenyl)-piperidin-4-yl]-7-(2-trifluoromethyl-benzyl)-2,4,5,7-tetrahydro-pyrazolo[3,4-d]pyrimidin-6-one (Enantiomer B) (Example 190) | | | | 9.87 |
| Ik-9 | (R)- or (S)-6-[1-(2-Fluoro-6-methyl-phenyl)-piperidin-4-yl]-2,7-dimethyl-4-(2-trifluoromethyl-benzyl)-2,4,6,7-tetrahydro-pyrazolo[4,3-d]pyrimidin-5-one (Enantiomer A) (Example 202) | Ia-22 | Chiralpak IA 30 × 250 mm, 5 µm $CO_2$/(2-propanol + 0.1% DEA) 90/10 160 mL/min 100 bars, 40° C. | Chiralpak IA 4.6 × 250 mm, 5 µm $CO_2$/EtOH 85/15 4 mL/min 150 bars, 40° C. | 1.73 |
| Ik-10 | (S)- or (R)-6-[1-(2-Fluoro-6-methyl-phenyl)-piperidin-4-yl]-2,7-dimethyl-4-(2-trifluoromethyl-benzyl)-2,4,6,7-tetrahydro-pyrazolo[4,3-d]pyrimidin-5-one (Enantiomer B) (Example 203) | | | | 2.02 |
| Ik-11 | (R)- or (S)-5-[1-(2-Fluoro-6-methyl-phenyl)-piperidin-4-yl]-2,4-dimethyl-7-(2-trifluoromethyl-benzyl)-2,4,5,7-tetrahydro-pyrazolo[3,4-d]pyrimidin-6-one (Enantiomer A) (Example 220) | Ia-26 | Chiralpak IC 30 × 250 mm, 5 µm $CO_2$/EtOH 80/20 160 mL/min 100 bars, 40° C. | Chiralpak IC 4.6 × 250 mm, 5 µm $CO_2$/EtOH 80/20 4 mL/min 150 bars, 40° C. | 1.81 |
| Ik-12 | (S)- or (R)-5-[1-(2-Fluoro-6-methyl-phenyl)-piperidin-4-yl]-2,4-dimethyl-7-(2-trifluoromethyl-benzyl)-2,4,5,7-tetrahydro-pyrazolo[3,4-d]pyrimidin-6-one (Enantiomer B) (Example 221) | | | | 2.82 |
| Ik-13 | 5-[(S)- or (R)-1-(2-Fluoro-6-methyl-phenyl)-azepan-4-yl]-2-methyl-7-(2-trifluoromethyl-benzyl)-2,4,5,7-tetrahydro-pyrazolo[3,4-d]pyrimidin-6-one (Enantiomer A) (Example 225) | Ia-27 | Chiralpak AD-H 30 × 250 mm, 5 µm $CO_2$/EtOH 85/15 160 mL/min 100 bars, 40° C. | Chiralpak AD-H 4.6 × 250 mm, 5 µm $CO_2$/EtOH 85/15 4 mL/min 150 bars, 40° C. | 3.69 |
| Ik-14 | 5-[(R)- or (S)-1-(2-Fluoro-6-methyl-phenyl)-azepan-4-yl]-2-methyl-7-(2-trifluoromethyl-benzyl)-2,4,5,7-tetrahydro-pyrazolo[3,4-d]pyrimidin-6-one (Enantiomer B) (Example 226) | | | | 2.77 |
| Ik-15 | 5-[(R)- or (S)-1-(2-Fluoro-6-methyl-phenyl)-3-methyl-pyrrolidin-3-yl]-2-methyl-7-(2-trifluoromethyl-benzyl)-2,4,5,7-tetrahydro-pyrazolo[3,4-d]pyrimidin-6-one (Enantiomer A) (Example 234) | Ia-33 | Chiralpak AD-H 30 × 250 mm, 5 µm $CO_2$/EtOH 80/20 160 mL/min 100 bars, 40° C. | Chiralpak AD-H 4.6 × 250 mm, 5 µm $CO_2$/(EtOH + 1% DEA) 85/15 4 mL/min 150 bars, 40° C. | 1.40 |

TABLE 62-continued

| Ik | Name | Racemate Ia, Ic or Ij | Column Eluent Flow (preparative) | Column Eluent Flow (analytical) | $t_R$ [min] chiral HPLC |
|---|---|---|---|---|---|
| Ik-16 | 5-[(S)- or (R)-1-(2-Fluoro-6-methyl-phenyl)-3-methyl-pyrrolidin-3-yl]-2-methyl-7-(2-trifluoromethyl-benzyl)-2,4,5,7-tetrahydro-pyrazolo[3,4-d]pyrimidin-6-one (Enantiomer B) (Example 235) | | | | 1.82 |
| Ik-17 | 5-[(R)- or (S)-1-(2-Fluoro-6-methyl-phenyl)-piperidin-3-yl]-2-methyl-7-(2-trifluoromethyl-benzyl)-2,4,5,7-tetrahydro-pyrazolo[3,4-d]pyrimidin-6-one (Enantiomer A) (Example 241) | Ia-37 | Chiralpak IF 30 × 250 mm, 5 μm $CO_2$/EtOH 75/25 160 mL/min 100 bars, 40° C. | Chiralpak IF 4.6 × 250 mm, 5 μm $CO_2$/EtOH 75/25 4 mL/min 150 bars, 40° C. | 2.07 |
| Ik-18 | 5-[(S)- or (R)-1-(2-Fluoro-6-methyl-phenyl)-piperidin-3-yl]-2-methyl-7-(2-trifluoromethyl-benzyl)-2,4,5,7-tetrahydro-pyrazolo[3,4-d]pyrimidin-6-one (Enantiomer B) (Example 242) | | | | 2.70 |
| Ik-19 | 5-[1-(2-Fluoro-6-methyl-phenyl)-piperidin-4-yl]-2-methyl-7-[(R)- or (S)-1-(2-trifluoromethyl-phenyl)-ethyl]-2,4,5,7-tetrahydro-pyrazolo[3,4-d]pyrimidin-6-one (Enantiomer A) (Example 246) | Ia-38 | Chiralpak AZ-H 30 × 250 mm, 5 μm $CO_2$/EtOH 75/25 160 mL/min 100 bars, 40° C. | Chiralpak AZ-H 4.6 × 250 mm, 5 μm $CO_2$/EtOH 75/25 4 mL/min 150 bars, 40° C. | 1.88 |
| Ik-20 | 5-[1-(2-Fluoro-6-methyl-phenyl)-piperidin-4-yl]-2-methyl-7-[(S)- or (R)-1-(2-trifluoromethyl-phenyl)-ethyl]-2,4,5,7-tetrahydro-pyrazolo[3,4-d]pyrimidin-6-one (Enantiomer B) (Example 247) | | | | 2.63 |
| Ik-21 | (R)- or (S)-2-(2,2-Difluoro-propyl)-6-[1-(2-fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one (Enantiomer A) (Example 253) | Ic-93 | Regis (R,R) Whelk-O1 30 × 250 mm, 5 μm $CO_2$/(MeCN/EtOH 1/1) 70/30 160 mL/min 100 bars, 40° C. | Regis (R,R) Whelk-O1 4.6 × 250 mm, 5 μm $CO_2$/(MeCN/EtOH 1/1) 70/30 4 mL/min 150 bars, 40° C. | 1.57 |
| Ik-22 | (S)- or (R)-2-(2,2-Difluoro-propyl)-6-[1-(2-fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one (Enantiomer B) (Example 254) | | | | 2.09 |
| Ik-23 | (R)- or (S)-1-(2,2-Difluoro-propyl)-6-[1-(2-fluoro-6-methyl-phenyl)-piperidin-4-yl]-7-methyl-4-(2-trifluoromethyl-benzyl)-1,4,6,7-tetrahydro-pyrazolo[4,3-d]pyrimidin-5-one (Enantiomer A) (Example 255) | Id-9 | Regis (R,R) Whelk-O1 30 × 250 mm, 5 μm $CO_2$/(MeCN/EtOH 1/1) 70/30 160 mL/min 100 bars, 40° C. | Regis (R,R) Whelk-O1 4.6 × 250 mm, 5 μm $CO_2$/(MeCN/EtOH 1/1) 70/30 4 mL/min 150 bars, 40° C. | 1.69 |
| Ik-24 | (S)- or (R)-1-(2,2-Difluoro-propyl)-6-[1-(2-fluoro-6-methyl-phenyl)-piperidin-4-yl]-7-methyl-4-(2-trifluoromethyl-benzyl)-1,4,6,7-tetrahydro-pyrazolo[4,3-d]pyrimidin-5-one (Enantiomer B) (Example 256) | | | | 2.21 |
| Ik-25 | 6-[1-(2-Fluoro-6-methyl-phenyl)-piperidin-4-yl]-2-methyl-4-[(R)- or (S)-1-(2-trifluoromethyl-phenyl)-ethyl]-2,4,6,7-tetrahydro-pyrazolo[4,3-d]pyrimidin-5-one (Enantiomer A) (Example 261) | Ia-44 | Chiralpak IG 30 × 250 mm, 5 μm $CO_2$/EtOH 70/30 160 mL/min 100 bars, 40° C. | Chiralpak IG 4.6 × 250 mm, 5 μm $CO_2$/EtOH 70/30 4 mL/min 150 bars, 40° C. | 1.88 |
| Ik-26 | 6-[1-(2-Fluoro-6-methyl-phenyl)-piperidin-4-yl]-2-methyl-4-[(S)- or (R)-1-(2-trifluoromethyl-phenyl)-ethyl]-2,4,6,7-tetrahydro-pyrazolo[4,3-d]pyrimidin-5-one (Enantiomer B) (Example 262) | | | | 2.42 |

TABLE 62-continued

| Ik | Name | Racemate Ia, Ic or Ij | Column Eluent Flow (preparative) | Column Eluent Flow (analytical) | $t_R$ [min] chiral HPLC |
|---|---|---|---|---|---|
| Ik-27 | (R)- or (S)-6-[1-(2-Fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one (Enantiomer A) (Example 263) | Ib-10 | Regis (R,R) Whelk-O1 30 × 250 mm, 5 μm $CO_2$/EtOH 60/40 160 mL/min 100 bars, 40° C. | Regis (R,R) Whelk-O1 4.6 × 250 mm, 5 μm $CO_2$/EtOH 60/40 4 mL/min 150 bars, 40° C. | 1.74 |
| Ik-28 | (S)- or (R)-6-[1-(2-Fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one (Enantiomer B) | | | | 2.30 |
| Ik-29 | (R)- or (S)-2-Cyclopropyl-6-[1-(2-fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one (Enantiomer A) (Example 265) | Ic-94 | Regis (R,R) Whelk-O1 30 × 250 mm, 5 μm $CO_2$/(MeCN/EtOH 1/1) 70/30 160 mL/min 100 bars, 40° C. | Regis (R,R) Whelk-O1 4.6 × 250 mm, 5 μm $CO_2$/(MeCN/EtOH 1/1) 70/30 4 mL/min 150 bars, 40° C. | 1.90 |
| Ik-30 | (S)- or (R)-2-Cyclopropyl-6-[1-(2-fluoro-6-methyl-phenyl)-piperidin-4-yl]-7-methyl-4-(2-trifluoromethyl-benzyl)-2,4,6,7-tetrahydro-pyrazolo[4,3-d]pyrimidin-5-one (Enantiomer B) (Example 266) | | | | 2.48 |
| Ik-31 | (R)- or (S)-4-(2-Cyclopropyl-benzyl)-6-(2'-methoxy-4'-methyl-3,4,5,6-tetrahydro-2H-[1,3']bipyridinyl-4-yl)-7-methyl-2,4,6,7-tetrahydro-pyrazolo[4,3-d]pyrimidin-5-one (Enantiomer A) | Ib-11 | Chiralpak IB 30 × 250 mm, 5 μm $CO_2$/EtOH 75/25 160 mL/min 100 bars, 40° C. | Chiralpak IB 4.6 × 250 mm, 5 μm $CO_2$/EtOH 75/25 4 mL/min 150 bars, 40° C. | 2.16 |
| Ik-32 | (S)- or (R)-4-(2-Cyclopropyl-benzyl)-6-(2'-methoxy-4'-methyl-3,4,5,6-tetrahydro-2H-[1,3']bipyridinyl-4-yl)-7-methyl-2,4,6,7-tetrahydro-pyrazolo[4,3-d]pyrimidin-5-one (Enantiomer B) (Example 274) | | | | 2.80 |
| Ik-33 | (R)- or (S)-4-(2-Cyclopropyl-benzyl)-6-[1-(2-fluoro-6-methyl-phenyl)-piperidin-4-yl]-7-methyl-2,4,6,7-tetrahydro-pyrazolo[4,3-d]pyrimidin-5-one (Enantiomer A) | Ib-12 | Chiralpak IB 30 × 250 mm, 5 μm $CO_2$/EtOH 70/30 160 mL/min 100 bars, 40° C. | Chiralpak IB 4.6 × 250 mm, 5 μm $CO_2$/EtOH 75/25 4 mL/min 150 bars, 40° C. | 2.16 |
| Ik-34 | (S)- or (R)-4-(2-Cyclopropyl-benzyl)-6-[1-(2-fluoro-6-methyl-phenyl)-piperidin-4-yl]-7-methyl-2,4,6,7-tetrahydro-pyrazolo[4,3-d]pyrimidin-5-one (Enantiomer B) (Example 275) | | | | 3.06 |
| Ik-35 | (R)- or (S)-4-(2-Cyclopropyl-benzyl)-2-(2,2-difluoro-propyl)-6-[1-(2-fluoro-6-methyl-phenyl)-piperidin-4-yl]-7-methyl-2,4,6,7-tetrahydro-pyrazolo[4,3-d]pyrimidin-5-one (Enantiomer A) (Example 276) | Ic-95 | Chiralpak IB 30 × 250 mm, 5 μm $CO_2$/EtOH 80/20 160 mL/min 100 bars, 40° C. | Chiralpak IB 4.6 × 250 mm, 5 μm $CO_2$/EtOH 80/20 4 mL/min 150 bars, 40° C. | 1.56 |
| Ik-36 | (S)- or (R)-4-(2-Cyclopropyl-benzyl)-2-(2,2-difluoro-propyl)-6-[1-(2-fluoro-6-methyl-phenyl)-piperidin-4-yl]-7-methyl-2,4,6,7-tetrahydro-pyrazolo[4,3-d]pyrimidin-5-one (Enantiomer B) (Example 277) | | | | 2.32 |
| Ik-37 | (R)- or (S)-2-Cyclopropyl-4-(2-cyclopropyl-benzyl)-6-[1-(2-fluoro-6-methyl-phenyl)-piperidin-4-yl]-7-methyl-2,4,6,7-tetrahydro-pyrazolo[4,3-d]pyrimidin-5-one (Enantiomer A) (Example 278) | Ic-96 | Chiralpak IB 30 × 250 mm, 5 μm $CO_2$/EtOH 75/25 160 mL/min 100 bars, 40° C. | Chiralpak IB 4.6 × 250 mm, 5 μm $CO_2$/EtOH 75/25 4 mL/min 150 bars, 40° C. | 1.74 |
| Ik-38 | (S)- or (R)-2-Cyclopropyl-4-(2-cyclopropyl-benzyl)-6-[1-(2-fluoro-6-methyl-phenyl)-piperidin-4-yl]-7-methyl-2,4,6,7-tetrahydro-pyrazolo[4,3-d]pyrimidin-5-one (Enantiomer B) (Example 279) | | | | 2.42 |

TABLE 62-continued

| Ik | Name | Racemate Ia, Ic or Ij | Column Eluent Flow (preparative) | Column Eluent Flow (analytical) | $t_R$ [min] chiral HPLC |
|---|---|---|---|---|---|
| Ik-39 | 5-(2'-Methoxy-4'-methyl-3,4,5,6-tetrahydro-2H-[1,3']bipyridinyl-4-yl)-2-methyl-7-[(R)- or (S)-1-(2-trifluoromethyl-phenyl)-ethyl]-2,4,5,7-tetrahydro-pyrazolo[3,4-d]pyrimidin-6-one (Enantiomer A) (Example 286) | Ij-27 | Regis (R,R) Whelk-O1 30 × 250 mm, 5 μm $CO_2$/EtOH 70/30 160 mL/min 100 bars, 40° C. | Regis (R,R) Whelk-O1 4.6 × 250 mm, 5 μm $CO_2$/EtOH 70/30 4 mL/min 150 bars, 40° C. | 2.12 |
| Ik-40 | 5-(2'-Methoxy-4'-methyl-3,4,5,6-tetrahydro-2H-[1,3']bipyridinyl-4-yl)-2-methyl-7-[(S)- or (R)-1-(2-trifluoromethyl-phenyl)-ethyl]-2,4,5,7-tetrahydro-pyrazolo[3,4-d]pyrimidin-6-one (Enantiomer B) (Example 287) | | | | 2.66 |
| Ik-41 | 3-Fluoro-2-(4-{2-methyl-6-oxo-7-[(R)- or (S)-1-(2-trifluoromethyl-phenyl)-ethyl]-2,4,6,7-tetrahydro-pyrazolo[3,4-d]pyrimidin-5-yl}-piperidin-1-yl)-benzonitrile (Enantiomer A) (Example 288) | Ij-28 | Regis (R,R) Whelk-O1 30 × 250 mm, 5 μm $CO_2$/EtOH 75/25 160 mL/min 100 bars, 40° C. | Regis (R,R) Whelk-O1 4.6 × 250 mm, 5 μm $CO_2$/EtOH 75/25 4 mL/min 150 bars, 40° C. | 2.81 |
| Ik-42 | 3-Fluoro-2-(4-{2-methyl-6-oxo-7-[(S)- or (R)-1-(2-trifluoromethyl-phenyl)-ethyl]-2,4,6,7-tetrahydro-pyrazolo[3,4-d]pyrimidin-5-yl}-piperidin-1-yl)-benzonitrile (Enantiomer B) (Example 289) | | | | 3.32 |
| Ik-43 | 5-[1-(2,6-Difluoro-phenyl)-piperidin-4-yl]-2-methyl-7-[(R)- or (S)-1-(2-trifluoromethyl-phenyl)-ethyl]-2,4,5,7-tetrahydro-pyrazolo[3,4-d]pyrimidin-6-one (Enantiomer A) (Example 290) | Ij-29 | Regis (R,R) Whelk-O1 30 × 250 mm, 5 μm $CO_2$/EtOH 80/20 160 mL/min 100 bars, 40° C. | Regis (R,R) Whelk-O1 4.6 × 250 mm, 5 μm $CO_2$/EtOH 80/20 4 mL/min 150 bars, 40° C. | 2.61 |
| Ik-44 | 5-[1-(2,6-Difluoro-phenyl)-piperidin-4-yl]-2-methyl-7-[(S)- or (R)-1-(2-trifluoromethyl-phenyl)-ethyl]-2,4,5,7-tetrahydro-pyrazolo[3,4-d]pyrimidin-6-one (Enantiomer B) (Example 291) | | | | 3.11 |
| Ik-45 | (R)- or (S)-2-Cyclopropyl-4-(2-cyclopropyl-benzyl)-6-(2'-methoxy-4'-methyl-3,4,5,6-tetrahydro-2H-[1,3']bipyridinyl-4-yl)-7-methyl-2,4,6,7-tetrahydro-pyrazolo[4,3-d]pyrimidin-5-one (Enantiomer A) (Example 293) | Ic-97 | Chiralpak AD-H 30 × 250 mm, 5 μm $CO_2$/EtOH 70/30 160 mL/min 100 bars, 40° C. | Chiralpak AD-H 4.6 × 250 mm, 5 μm $CO_2$/EtOH 70/30 4 mL/min 150 bars, 40° C. | 1.42 |
| Ik-46 | (S)- or (R)-2-Cyclopropyl-4-(2-cyclopropyl-benzyl)-6-(2'-methoxy-4'-methyl-3,4,5,6-tetrahydro-2H-[1,3']bipyridinyl-4-yl)-7-methyl-2,4,6,7-tetrahydro-pyrazolo[4,3-d]pyrimidin-5-one (Enantiomer B) (Example 292) | | | | 1.97 |
| Ik-47 | (R)- or (S)-6-(2'-Methoxy-4'-methyl-3,4,5,6-tetrahydro-2H-[1,3']bipyridinyl-4-yl)-7-methyl-4-(2-trifluoromethyl-benzyl)-2,4,6,7-tetrahydro-pyrazolo[4,3-d]pyrimidin-5-one (Enantiomer A) (Example 295) | Ib-14 | Regis (R,R) Whelk-O1 30 × 250 mm, 5 μm $CO_2$/(MeCN/EtOH 1/1) 65/35 160 mL/min 100 bars, 40° C. | Regis (R,R) Whelk-O1 4.6 × 250 mm, 5 μm $CO_2$/(MeCN/EtOH 1/1) 65/35 4 mL/min 150 bars, 40° C. | 1.80 |
| Ik-48 | (S)- or (R)-6-(2'-Methoxy-4'-methyl-3,4,5,6-tetrahydro-2H-[1,3']bipyridinyl-4-yl)-7-methyl-4-(2-trifluoromethyl-benzyl)-2,4,6,7-tetrahydro-pyrazolo[4,3-d]pyrimidin-5-one (Enantiomer B) | | | | 2.50 |
| Ik-49 | (R)- or (S)-2-Cyclopropyl-6-(2'-methoxy-4'-methyl-3,4,5,6-tetrahydro-2H-[1,3']bipyridinyl-4-yl)-7-methyl-4-(2-trifluoromethyl-benzyl)-2,4,6,7-tetrahydro-pyrazolo[4,3-d]pyrimidin-5-one (Enantiomer A) (Example 296) | Ic-98 | Chiralpak IE 30 × 250 mm, 5 μm $CO_2$/EtOH 65/35 160 mL/min 100 bars, 40° C. | Chiralpak IE 4.6 × 250 mm, 5 μm $CO_2$/EtOH 65/35 4 mL/min 150 bars, 40° C. | 1.89 |

TABLE 62-continued

| Ik | Name | Racemate Ia, Ic or Ij | Column Eluent Flow (preparative) | Column Eluent Flow (analytical) | $t_R$ [min] chiral HPLC |
|---|---|---|---|---|---|
| Ik-50 | (S)- or (R)-2-Cyclopropyl-6-(2'-methoxy-4'-methyl-3,4,5,6-tetrahydro-2H-[1,3']bipyridinyl-4-yl)-7-methyl-4-(2-trifluoromethyl-benzyl)-2,4,6,7-tetrahydro-pyrazolo[4,3-d]pyrimidin-5-one (Enantiomer B) (Example 297) | | | | 2.39 |
| Ik-51 | (R)- or (S)-6-(2'-Methoxy-4'-methyl-3,4,5,6-tetrahydro-2H-[1,3']bipyridinyl-4-yl)-2,7-dimethyl-4-(2-trifluoromethyl-benzyl)-2,4,6,7-tetrahydro-pyrazolo[4,3-d]pyrimidin-5-one (Enantiomer A) (Example 298) | Ic-99 | Chiralpak IE 30 × 250 mm, 5 μm $CO_2$/EtOH 75/25 160 mL/min 100 bars, 40° C. | Chiralpak IE 4.6 × 250 mm, 5 μm $CO_2$/EtOH 75/25 4 mL/min 150 bars, 40° C. | 2.56 |
| Ik-52 | (S)- or (R)-6-(2'-Methoxy-4'-methyl-3,4,5,6-tetrahydro-2H-[1,3']bipyridinyl-4-yl)-2,7-dimethyl-4-(2-trifluoromethyl-benzyl)-2,4,6,7-tetrahydro-pyrazolo[4,3-d]pyrimidin-5-one (Enantiomer B) | | | | 3.19 |
| Ik-53 | (R)- or (S)-2-(2,2-Difluoro-propyl)-5-[1-(2-fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one (Enantiomer A) (Example 305) | Ic-100 | Regis (R,R) Whelk-O1 30 × 250 mm, 5 μm $CO_2$/EtOH 70/30 160 mL/min 100 bars, 40° C. | Regis (R,R) Whelk-O1 4.6 × 250 mm, 5 μm $CO_2$/EtOH 70/30 4 mL/min 150 bars, 40° C. | 2.24 |
| Ik-54 | (S)- or (R)-2-(2,2-Difluoro-propyl)-5-[1-(2-fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one (Enantiomer B) (Example 306) | | | | 2.76 |
| Ik-55 | (R)- or (S)-2-Cyclopropyl-5-[1-(2-fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one (Enantiomer A) (Example 309) | Ia-55 | Chiralpak IC 30 × 250 mm, 5 μm $CO_2$/EtOH 65/35 160 mL/min 100 bars, 40° C. | Chiralpak IC 4.6 × 250 mm, 5 μm $CO_2$/EtOH 65/35 4 mL/min 150 bars, 40° C. | 1.19 |
| Ik-56 | (S)- or (R)-2-Cyclopropyl-5-[1-(2-fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one (Enantiomer B) (Example 310) | | | | 1.59 |
| Ik-57 | (R)- or (S)-2-Cyclopropyl-5-[1-(2-difluoromethyl-6-fluoro-phenyl)-piperidin-4-yl]-4-methyl-7-(2-trifluoromethyl-benzyl)-2,4,5,7-tetrahydro-pyrazolo[3,4-d]pyrimidin-6-one (Enantiomer A) (Example 311) | Ia-56 | Chiralpak IC 30 × 250 mm, 5 μm $CO_2$/EtOH 75/25 160 mL/min 100 bars, 40° C. | Chiralpak IC 4.6 × 250 mm, 5 μm $CO_2$/EtOH 75/25 4 mL/min 150 bars, 40° C. | 1.22 |
| Ik-58 | (S)- or (R)-2-Cyclopropyl-5-[1-(2-difluoromethyl-6-fluoro-phenyl)-piperidin-4-yl]-4-methyl-7-(2-trifluoromethyl-benzyl)-2,4,5,7-tetrahydro-pyrazolo[3,4-d]pyrimidin-6-one (Enantiomer B) (Example 312) | | | | 1.62 |
| Ik-59 | (R)- or (S)-5-[1-(2-Difluoromethyl-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one (Enantiomer A) (Example 314) | Ia-57 | Chiralpak IC 30 × 250 mm, 5 μm $CO_2$/EtOH 80/20 160 mL/min 100 bars, 40° C. | Chiralpak IC 4.6 × 250 mm, 5 μm $CO_2$/EtOH 80/20 4 mL/min 150 bars, 40° C. | 1.33 |
| Ik-60 | (S)- or (R)-5-[1-(2-Difluoromethyl-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one (Enantiomer B) (Example 315) | | | | 1.80 |

TABLE 62-continued

| Ik | Name | Racemate Ia, Ic or Ij | Column Eluent Flow (preparative) | Column Eluent Flow (analytical) | $t_R$ [min] chiral HPLC |
|---|---|---|---|---|---|
| Ik-61 | (R)- or (S)-5-[1-(2-Fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one (Enantiomer A) | Ib-13 | Chiralpak AD-H 30 × 250 mm, 5 μm $CO_2$/EtOH 55/45 160 mL/min 100 bars, 40° C. | Chiralpak AD-H 4.6 × 250 mm, 5 μm $CO_2$/EtOH 55/45 4 mL/min 150 bars, 40° C. | 0.86 |
| Ik-62 | (S)- or (R)-5-[1-(2-Fluoro-6-methyl-phenyl)-piperidin-4-yl]-4-methyl-7-(2-trifluoromethyl-benzyl)-2,4,5,7-tetrahydro-pyrazolo[3,4-d]pyrimidin-6-one (Enantiomer B) (Example 316) | | | | 1.20 |
| Ik-63 | (R)- or (S)-7-(2-Cyclopropyl-benzyl)-5-[1-(2-fluoro-6-methyl-phenyl)-piperidin-4-yl]-2,4-dimethyl-2,4,5,7-tetrahydro-pyrazolo[3,4-d]pyrimidin-6-one (Enantiomer A) (Example 317) | Ia-58 | Chiralpak AD-H 30 × 250 mm, 5 μm $CO_2$/EtOH 70/30 160 mL/min 100 bars, 40° C. | Chiralpak AD-H 4.6 × 250 mm, 5 μm $CO_2$/EtOH 70/30 4 mL/min 150 bars, 40° C. | 1.75 |
| Ik-64 | (S)- or (R)-7-(2-Cyclopropyl-benzyl)-5-[1-(2-fluoro-6-methyl-phenyl)-piperidin-4-yl]-2,4-dimethyl-2,4,5,7-tetrahydro-pyrazolo[3,4-d]pyrimidin-6-one (Enantiomer B) (Example 318) | | | | 2.32 |
| Ik-65 | (R)- or (S)-5-[1-(2-Chloro-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one (Enantiomer A) (Example 319) | Ia-59 | Chiralpak IC 30 × 250 mm, 5 μm $CO_2$/EtOH 70/30 160 mL/min 100 bars, 40° C. | Chiralpak IC 4.6 × 250 mm, 5 μm $CO_2$/EtOH 70/30 4 mL/min 150 bars, 40° C. | 1.32 |
| Ik-66 | (S)- or (R)-5-[1-(2-Chloro-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one (Enantiomer B) (Example 320) | | | | 1.78 |
| Ik-67 | (R)- or (S)-5-[1-(2-Chloro-6-fluoro-phenyl)-piperidin-4-yl]-7-(2-cyclopropyl-benzyl)-2,4-dimethyl-2,4,5,7-tetrahydro-pyrazolo[3,4-d]pyrimidin-6-one (Enantiomer A) (Example 321) | Ia-60 | Chiralpak IB 30 × 250 mm, 5 μm $CO_2$/EtOH 70/30 160 mL/min 100 bars, 40° C. | Chiralpak IB 4.6 × 250 mm, 5 μm $CO_2$/EtOH 70/30 4 mL/min 150 bars, 40° C. | 1.97 |
| Ik-68 | (S)- or (R)-5-[1-(2-Chloro-6-fluoro-phenyl)-piperidin-4-yl]-7-(2-cyclopropyl-benzyl)-2,4-dimethyl-2,4,5,7-tetrahydro-pyrazolo[3,4-d]pyrimidin-6-one (Enantiomer B) (Example 322) | | | | 2.46 |
| Ik-69 | (S)-7-(2-Cyclopropyl-benzyl)-5-[1-(2-difluoromethyl-6-fluoro-phenyl)-piperidin-4-yl]-2,4-dimethyl-2,4,5,7-tetrahydro-pyrazolo[3,4-d]pyrimidin-6-one (Enantiomer A) (Example 323) | Ia-61 | Chiralpak AD-H 30 × 250 mm, 5 μm $CO_2$/EtOH 75/25 160 mL/min 100 bars, 40° C. | Chiralpak AD-H 4.6 × 250 mm, 5 μm $CO_2$/EtOH 75/25 4 mL/min 150 bars, 40° C. | 1.34 |
| Ik-70 | (R)-7-(2-Cyclopropyl-benzyl)-5-[1-(2-difluoromethyl-6-fluoro-phenyl)-piperidin-4-yl]-2,4-dimethyl-2,4,5,7-tetrahydro-pyrazolo[3,4-d]pyrimidin-6-one (Enantiomer B) (Example 324) | | | | 1.70 |
| Ik-71 | (R)- or (S)-7-(2-Cyclopropyl-benzyl)-5-[1-(2-cyclopropyl-6-fluoro-phenyl)-piperidin-4-yl]-2,4-dimethyl-2,4,5,7-tetrahydro-pyrazolo[3,4-d]pyrimidin-6-one (Enantiomer A) (Example 325) | Ia-62 | Chiralpak AD-H 30 × 250 mm, 5 μm $CO_2$/EtOH 70/30 160 mL/min 100 bars, 40° C. | Chiralpak AD-H 4.6 × 250 mm, 5 μm $CO_2$/EtOH 70/30 4 mL/min 150 bars, 40° C. | 1.59 |
| Ik-72 | (S)- or (R)-7-(2-Cyclopropyl-benzyl)-5-[1-(2-cyclopropyl-6-fluoro-phenyl)-piperidin-4-yl]-2,4-dimethyl-2,4,5,7-tetrahydro-pyrazolo[3,4-d]pyrimidin-6-one (Enantiomer B) (Example 326) | | | | 2.16 |

TABLE 62-continued

| Ik | Name | Racemate Ia, Ic or Ij | Column Eluent Flow (preparative) | Column Eluent Flow (analytical) | $t_R$ [min] chiral HPLC |
|---|---|---|---|---|---|
| Ik-73 | (R)- or (S)-6-[1-(2-Chloro-6-fluoro-phenyl)-piperidin-4-yl]-2-cyclopropyl-7-methyl-4-(2-trifluoromethyl-benzyl)-2,4,6,7-tetrahydro-pyrazolo[4,3-d]pyrimidin-5-one (Enantiomer A) (Example 327) | Ic-101 | Chiralpak AD-H 30 × 250 mm, 5 μm $CO_2$/EtOH 85/15 160 mL/min 100 bars, 40° C. | Chiralpak AD-H 4.6 × 250 mm, 5 μm $CO_2$/EtOH 85/15 4 mL/min 150 bars, 40° C. | 1.93 |
| Ik-74 | (S)- or (R)-6-[1-(2-Chloro-6-fluoro-phenyl)-piperidin-4-yl]-2-cyclopropyl-7-methyl-4-(2-trifluoromethyl-benzyl)-2,4,6,7-tetrahydro-pyrazolo[4,3-d]pyrimidin-5-one (Enantiomer B) (Example 328) | | | | 2.51 |
| Ik-75 | (R)- or (S)-2-Cyclopropyl-6-[1-(2-difluoromethyl-6-fluoro-phenyl)-piperidin-4-yl]-7-methyl-4-(2-trifluoromethyl-benzyl)-2,4,6,7-tetrahydro-pyrazolo[4,3-d]pyrimidin-5-one (Enantiomer A) (Example 329) | Ic-102 | Regis (R,R) Whelk-O1 30 × 250 mm, 5 μm $CO_2$/EtOH 65/35 160 mL/min 100 bars, 40° C. | Regis (R,R) Whelk-O1 4.6 × 250 mm, 5 μm $CO_2$/EtOH 65/35 4 mL/min 150 bars, 40° C. | 1.82 |
| Ik-76 | (S)- or (R)-2-Cyclopropyl-6-[1-(2-difluoromethyl-6-fluoro-phenyl)-piperidin-4-yl]-7-methyl-4-(2-trifluoromethyl-benzyl)-2,4,6,7-tetrahydro-pyrazolo[4,3-d]pyrimidin-5-one (Enantiomer B) (Example 330) | | | | 2.47 |
| Ik-77 | (R)- or (S)-5-(2'-Methoxy-4'-methyl-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one (Enantiomer A) (Example 331) | Ia-65 | Chiralpak IC 30 × 250 mm, 5 μm $CO_2$/EtOH 60/40 160 mL/min 100 bars, 40° C. | Chiralpak IC 4.6 × 250 mm, 5 μm $CO_2$/EtOH 60/40 4 mL/min 150 bars, 40° C. | 1.22 |
| Ik-78 | (S)- or (R)-5-(2'-Methoxy-4'-methyl-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one (Enantiomer B) (Example 332) | | | | 1.78 |
| Ik-79 | (R)- or (S)-5-[1-(2-Cydopropyl-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one (Enantiomer A) (Example 333) | Ia-66 | Chiralpak IC 30 × 250 mm, 5 μm $CO_2$/EtOH 75/25 160 mL/min 100 bars, 40° C. | Chiralpak IC 4.6 × 250 mm, 5 μm $CO_2$/EtOH 75/25 4 mL/min 150 bars, 40° C. | 1.55 |
| Ik-80 | (S)- or (R)-5-[1-(2-Cyclopropyl-6-fluoro-phenyl)-piperidin-4-yl]-2,4-dimethyl-7-(2-trifluoromethyl-benzyl)-2,4,5,7-tetrahydro-pyrazolo[3,4-d]pyrimidin-6-one (Enantiomer B) (Example 334) | | | | 2.18 |
| Ik-81 | (R)- or (S)-5-[1-(2-Chloro-6-fluoro-phenyl)-piperidin-4-yl]-2-cyclopropyl-4-methyl-7-(2-trifluoromethyl-benzyl)-2,4,5,7-tetrahydro-pyrazolo[3,4-d]pyrimidin-6-one (Enantiomer A) (Example 335) | Ia-67 | Chiralpak IC 30 × 250 mm, 5 μm $CO_2$/EtOH 70/30 160 mL/min 100 bars, 40° C. | Chiralpak IC 4.6 × 250 mm, 5 μm $CO_2$/EtOH 70/30 4 mL/min 150 bars, 40° C. | 1.41 |
| Ik-82 | (S)- or (R)-5-[1-(2-Chloro-6-fluoro-phenyl)-piperidin-4-yl]-2-cyclopropyl-4-methyl-7-(2-trifluoromethyl-benzyl)-2,4,5,7-tetrahydro-pyrazolo[3,4-d]pyrimidin-6-one (Enantiomer B) (Example 336) | | | | 2.01 |
| Ik-83 | (R)- or (S)-5-[1-(2-Chloro-6-fluoro-phenyl)-piperidin-4-yl]-2-cydopropyl-7-(2-cyclopropyl-benzyl)-4-methyl-2,4,5,7-tetrahydro-pyrazolo[3,4-d]pyrimidin-6-one (Enantiomer A) (Example 337) | Ia-69 | Chiralpak AD-H 30 × 250 mm, 5 μm $CO_2$/EtOH 50/50 160 mL/min 100 bars, 40° C. | Chiralpak AD-H 4.6 × 250 mm, 5 μm $CO_2$/EtOH 50/50 4 mL/min 150 bars, 40° C. | 1.24 |

TABLE 62-continued

| Ik | Name | Racemate Ia, Ic or Ij | Column Eluent Flow (preparative) | Column Eluent Flow (analytical) | $t_R$ [min] chiral HPLC |
|---|---|---|---|---|---|
| Ik-84 | (S)- or (R)-5-[1-(2-Chloro-6-fluoro-phenyl)-piperidin-4-yl]-2-cyclopropyl-7-(2-cyclopropyl-benzyl)-4-methyl-2,4,5,7-tetrahydro-pyrazolo[3,4-d]pyrimidin-6-one (Enantiomer B) (Example 338) | | | | 1.81 |
| Ik-85 | (R)- or (S)-2-Cyclopropyl-7-(2-cyclopropyl-benzyl)-5-[1-(2-fluoro-6-methyl-phenyl)-piperidin-4-yl]-4-methyl-2,4,5,7-tetrahydro-pyrazolo[3,4-d]pyrimidin-6-one (Enantiomer A) (Example 339) | Ia-68 | Chiralpak AD-H 30 × 250 mm, 5 μm $CO_2$/EtOH 50/50 160 mL/min 100 bars, 40° C. | Chiralpak AD-H 4.6 × 250 mm, 5 μm $CO_2$/EtOH 50/50 4 mL/min 150 bars, 40° C. | 1.07 |
| Ik-86 | (S)- or (R)-2-Cyclopropyl-7-(2-cyclopropyl-benzyl)-5-[1-(2-fluoro-6-methyl-phenyl)-piperidin-4-yl]-4-methyl-2,4,5,7-tetrahydro-pyrazolo[3,4-d]pyrimidin-6-one (Enantiomer B) (Example 340) | | | | 1.55 |
| Ik-87 | (R)- or (S)-2-Cyclopropyl-5-(2'-methoxy-4'-methyl-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one (Enantiomer A) (Example 344) | Ia-70 | Chiralpak IC 30 × 250 mm, 5 μm $CO_2$/EtOH 65/35 160 mL/min 100 bars, 40° C. | Chiralpak IC 4.6 × 250 mm, 5 μm $CO_2$/EtOH 65/35 4 mL/min 150 bars, 40° C. | 1.47 |
| Ik-88 | (S)- or (R)-2-Cyclopropyl-5-(2'-methoxy-4'-methyl-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one (Enantiomer B) (Example 345) | | | | 2.42 |
| Ik-89 | (R)- or (S)-5-(4'-Difluoromethyl-2'-methoxy-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one (Enantiomer A) (Example 346) | Ia-71 | Chiralpak IC 30 × 250 mm, 5 μm $CO_2$/EtOH 80/20 160 mL/min 100 bars, 40° C. | Chiralpak IC 4.6 × 250 mm, 5 μm $CO_2$/EtOH 80/20 4 mL/min 150 bars, 40° C. | 1.45 |
| Ik-90 | (S)- or (R)-5-(4'-Difluoromethyl-2'-methoxy-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one (Enantiomer B) (Example 347) | | | | 2.28 |
| Ik-91 | (R)- or (S)-5-[1-(2-Difluoromethyl-6-fluoro-phenyl)-piperidin-4-yl]-4-methyl-7-(2-trifluoromethyl-benzyl)-2,4,5,7-tetrahydro-pyrazolo[3,4-d]pyrimidin-6-one (Enantiomer A) (Example 348) | Ib-17 | ChiralCel OZ-H 30 × 250 mm, 5 μm $CO_2$/EtOH 60/40 160 mL/min 100 bars, 40° C. | ChiralCel OZ-H 4.6 × 250 mm, 5 μm $CO_2$/EtOH 60/40 4 mL/min 150 bars, 40° C. | 0.91 |
| Ik-92 | (S)- or (R)-5-[1-(2-Difluoromethyl-6-fluoro-phenyl)-piperidin-4-yl]-4-methyl-7-(2-trifluoromethyl-benzyl)-2,4,5,7-tetrahydro-pyrazolo[3,4-d]pyrimidin-6-one (Enantiomer B) (Example 349) | | | | 1.37 |
| Ik-93 | (R)- or (S)-5-[1-(2-Chloro-6-fluoro-phenyl)-piperidin-4-yl]-4-methyl-7-(2-trifluoromethyl-benzyl)-2,4,5,7-tetrahydro-pyrazolo[3,4-d]pyrimidin-6-one (Enantiomer A) (Example 350) | Ib-18 | ChiralCel OZ-H 30 × 250 mm, 5 μm $CO_2$/EtOH 50/50 160 mL/min 100 bars, 40° C. | ChiralCel OZ-H 4.6 × 250 mm, 5 μm $CO_2$/EtOH 50/50 4 mL/min 150 bars, 40° C. | 0.93 |
| Ik-94 | (S)- or (R)-5-[1-(2-Chloro-6-fluoro-phenyl)-piperidin-4-yl]-4-methyl-7-(2-trifluoromethyl-benzyl)-2,4,5,7-tetrahydro-pyrazolo[3,4-d]pyrimidin-6-one (Enantiomer B) (Example 351) | | | | 1.53 |

TABLE 62-continued

| Ik | Name | Racemate Ia, Ic or Ij | Column Eluent Flow (preparative) | Column Eluent Flow (analytical) | $t_R$ [min] chiral HPLC |
|---|---|---|---|---|---|
| Ik-95 | (R)- or (S)-5-(4'-Difluoromethyl-2'-methoxy-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one (Enantiomer A) (Example 352) | Ib-19 | ChiralCel OZ-H 30 × 250 mm, 5 µm $CO_2$/EtOH 60/40 160 mL/min 100 bars, 40° C. | ChiralCel OZ-H 4.6 × 250 mm, 5 µm $CO_2$/EtOH 60/40 4 mL/min 150 bars, 40° C. | 0.93 |
| Ik-96 | (S)- or (R)-5-(4'-Difluoromethyl-2'-methoxy-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one (Enantiomer B) (Example 353) | | | | 1.42 |
| Ik-97 | (R)- or (S)-5-[1-(2-Fluoro-6-methyl-phenyl)-piperidin-4-yl]-2,4-dimethyl-7-(3-trifluoromethyl-pyridin-2-ylmethyl)-2,4,5,7-tetrahydro-pyrazolo[3,4-d]pyrimidin-6-one (Enantiomer A) (Example 354) | Ia-75 | Chiralpak IC 30 × 250 mm, 5 µm $CO_2$/EtOH 50/50 160 mL/min 100 bars, 40° C. | Chiralpak IC 4.6 × 250 mm, 5 µm $CO_2$/EtOH 50/50 4 mL/min 150 bars, 40° C. | 0.98 |
| Ik-98 | (S)-or (R)-5-[1-(2-Fluoro-6-methyl-phenyl)-piperidin-4-yl]-2,4-dimethyl-7-(3-trifluoromethyl-pyridin-2-ylmethyl)-2,4,5,7-tetrahydro-pyrazolo[3,4-d]pyrimidin-6-one (Enantiomer B) (Example 355) | | | | 1.37 |
| Ik-99 | (R)- or (S)-5-(2'-Methoxy-4'-methyl-3,4,5,6-tetrahydro-2H-[1,3']bipyridinyl-4-yl)-2,4-dimethyl-7-(3-trifluoromethyl-pyridin-2-ylmethyl)-2,4,5,7-tetrahydro-pyrazolo[3,4-d]pyrimidin-6-one (Enantiomer A) (Example 356) | Ia-76 | Chiralpak IC 30 × 250 mm, 5 µm $CO_2$/EtOH 50/50 160 mL/min 100 bars, 40° C. | Chiralpak IC 4.6 × 250 mm, 5 µm $CO_2$/EtOH 50/50 4 mL/min 150 bars, 40° C. | 1.11 |
| Ik-100 | (S)- or (R)-5-(2'-Methoxy-4'-methyl-3,4,5,6-tetrahydro-2H-[1,3']bipyridinyl-4-yl)-2,4-dimethyl-7-(3-trifluoromethyl-pyridin-2-ylmethyl)-2,4,5,7-tetrahydro-pyrazolo[3,4-d]pyrimidin-6-one (Enantiomer B) (Example 357) | | | | 2.02 |
| Ik-101 | (R)- or (S)-2-Cyclopropyl-5-(4'-difluoromethyl-2'-methoxy-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one (Enantiomer A) (Example 358) | Ia-77 | Chiralpak IC 30 × 250 mm, 5 µm $CO_2$/EtOH 70/30 160 mL/min 100 bars, 40° C. | Chiralpak IC 4.6 × 250 mm, 5 µm $CO_2$/EtOH 70/30 4 mL/min 150 bars, 40° C. | 1.19 |
| Ik-102 | (S)- or (R)-2-Cyclopropyl-5-(4'-difluoromethyl-2'-methoxy-3,4,5,6-tetrahydro-2H-[1,3']bipyridinyl-4-yl)-4-methyl-7-(2-trifluoromethyl-benzyl)-2,4,5,7-tetrahydro-pyrazolo[3,4-d]pyrimidin-6-one (Enantiomer B) (Example 359) | | | | 1.66 |
| Ik-103 | (R)- or (S)-5-[1-(2-Bromo-6-fluoro-phenyl)-piperidin-4-yl]-2-cyclopropyl-4-methyl-7-(2-trifluoromethyl-benzyl)-2,4,5,7-tetrahydro-pyrazolo[3,4-d]pyrimidin-6-one (Enantiomer A) (Example 360) | Ia-78 | Chiralpak IC 30 × 250 mm, 5 µm $CO_2$/EtOH 65/35 160 mL/min 100 bars, 40° C. | Chiralpak IC 4.6 × 250 mm, 5 µm $CO_2$/EtOH 65/35 4 mL/min 150 bars, 40° C. | 1.34 |
| Ik-104 | (S)- or (R)-5-[1-(2-Bromo-6-fluoro-phenyl)-piperidin-4-yl]-2-cyclopropyl-4-methyl-7-(2-trifluoromethyl-benzyl)-2,4,5,7-tetrahydro-pyrazolo[3,4-d]pyrimidin-6-one (Enantiomer B) (Example 361) | | | | 1.86 |

TABLE 62-continued

| Ik | Name | Racemate Ia, Ic or Ij | Column Eluent Flow (preparative) | Column Eluent Flow (analytical) | $t_R$ [min] chiral HPLC |
|---|---|---|---|---|---|
| Ik-105 | (R)- or (S)-5-(2'-Methoxy-4'-trifluoromethyl-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one (Enantiomer A) (Example 362) | Ia-79 | Chiralpak IC 30 × 250 mm, 5 μm $CO_2$/EtOH 70/30 160 mL/min 100 bars, 40° C. | Chiralpak IC 4.6 × 250 mm, 5 μm $CO_2$/EtOH 70/30 4 mL/min 150 bars, 40° C. | 1.03 |
| Ik-106 | (S)- or (R)-5-(2'-Methoxy-4'-trifluoromethyl-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one (Enantiomer B) (Example 363) | | | | 1.37 |
| Ik-107 | (R)- or (S)-7-(2-Cydopropyl-benzyl)-5-(4'-difluoromethyl-2'-methoxy-3,4,5,6-tetrahydro-2H-[1,3']bipyridinyl-4-yl)-2,4-dimethyl-2,4,5,7-tetrahydro-pyrazolo[3,4-d]pyrimidin-6-one (Enantiomer A) (Example 366) | Ia-81 | Chiralpak AD-H 30 × 250 mm, 5 μm $CO_2$/EtOH 60/40 160 mL/min 100 bars, 40° C. | Chiralpak AD-H 4.6 × 250 mm, 5 μm $CO_2$/EtOH 60/40 4 mL/min 150 bars, 40° C. | 0.99 |
| Ik-108 | (S)- or (R)-7-(2-Cyclopropyl-benzyl)-5-(4'-difluoromethyl-2'-methoxy-3,4,5,6-tetrahydro-2H-[1,3']bipyridinyl-4-yl)-2,4-dimethyl-2,4,5,7-tetrahydro-pyrazolo[3,4-d]pyrimidin-6-one (Enantiomer B) (Example 367) | | | | 1.33 |
| Ik-109 | (R)- or (S)-7-(2-Cydopropyl-benzyl)-5-(2'-methoxy-4'-methyl-3,4,5,6-tetrahydro-2H-[1,3']bipyridinyl-4-yl)-2,4-dimethyl-2,4,5,7-tetrahydro-pyrazolo[3,4-d]pyrimidin-6-one (Enantiomer A) (Example 368) | Ia-80 | Chiralpak AD-H 30 × 250 mm, 5 μm $CO_2$/EtOH 50/50 160 mL/min 100 bars, 40° C. | Chiralpak AD-H 4.6 × 250 mm, 5 μm $CO_2$/EtOH 50/50 4 mL/min 150 bars, 40° C. | 0.99 |
| Ik-110 | (S)- or (R)-7-(2-Cyclopropyl-benzyl)-5-(2'-methoxy-4'-methyl-3,4,5,6-tetrahydro-2H-[1,3']bipyridinyl-4-yl)-2,4-dimethyl-2,4,5,7-tetrahydro-pyrazolo[3,4-d]pyrimidin-6-one (Enantiomer B) (Example 369) | | | | 1.39 |
| Ik-111 | (R)- or (S)-7-(2-Cyclopropyl-benzyl)-5-(4'-difluoromethyl-2'-methoxy-3,4,5,6-tetrahydro-2H-[1,3']bipyridinyl-4-yl)-4-methyl-2,4,5,7-tetrahydro-pyrazolo[3,4-d]pyrimidin-6-one (Enantiomer A) (Example 370) | Ib-20 | Chiralpak IF 30 × 250 mm, 5 μm $CO_2$/EtOH 65/35 160 mL/min 100 bars, 40° C. | Chiralpak IF 4.6 × 250 mm, 5 μm $CO_2$/EtOH 65/35 4 mL/min 150 bars, 40° C. | 1.52 |
| Ik-112 | (S)- or (R)-7-(2-Cyclopropyl-benzyl)-5-(4'-difluoromethyl-2'-methoxy-3,4,5,6-tetrahydro-2H-[1,3']bipyridinyl-4-yl)-4-methyl-2,4,5,7-tetrahydro-pyrazolo[3,4-d]pyrimidin-6-one (Enantiomer B) (Example 371) | | | | 1.94 |
| Ik-113 | (R)- or (S)-5-[1-(2-Chloro-6-fluoro-phenyl)-piperidin-4-yl]-7-(2-cyclopropyl-benzyl)-4-methyl-2,4,5,7-tetrahydro-pyrazolo[3,4-d]pyrimidin-6-one (Enantiomer A) (Example 372) | Ib-21 | Chiralpak IF 30 × 250 mm, 5 μm $CO_2$/EtOH 55/45 160 mL/min 100 bars, 40° C. | Chiralpak IF 4.6 × 250 mm, 5 μm $CO_2$/EtOH 55/45 4 mL/min 150 bars, 40° C. | 1.54 |
| Ik-114 | (S)- or (R)-5-[1-(2-Chloro-6-fluoro-phenyl)-piperidin-4-yl]-7-(2-cyclopropyl-benzyl)-4-methyl-2,4,5,7-tetrahydro-pyrazolo[3,4-d]pyrimidin-6-one (Enantiomer B) (Example 373) | | | | 2.05 |
| Ik-115 | (R)- or (S)-7-(2-Cyclopropyl-benzyl)-5-(2'-methoxy-4'-trifluoromethyl-3,4,5,6-tetrahydro-2H-[1,3']bipyridinyl-4-yl)-2,4-dimethyl-2,4,5,7-tetrahydro-pyrazolo[3,4-d]pyrimidin-6-one (Enantiomer A) (Example 374) | Ia-84 | Chiralpak AD-H 30 × 250 mm, 5 μm $CO_2$/EtOH 60/40 160 mL/min 100 bars, 40° C. | Chiralpak AD-H 4.6 × 250 mm, 5 μm $CO_2$/EtOH 60/40 4 mL/min 150 bars, 40° C. | 0.90 |

TABLE 62-continued

| Ik | Name | Racemate Ia, Ic or Ij | Column Eluent Flow (preparative) | Column Eluent Flow (analytical) | $t_R$ [min] chiral HPLC |
|---|---|---|---|---|---|
| Ik-116 | (S)- or (R)-7-(2-Cyclopropyl-benzyl)-5-(2'-methoxy-4'-trifluoromethyl-3,4,5,6-tetrahydro-2H-[1,3']bipyridinyl-4-yl)-2,4-dimethyl-2,4,5,7-tetrahydro-pyrazolo[3,4-d]pyrimidin-6-one (Enantiomer B) (Example 375) | | | | 1.26 |
| Ik-117 | (R)- or (S)-5-(4'-Chloro-2'-methoxy-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one (Enantiomer A) (Example 376) | Ia-85 | Chiralpak IC 30 × 250 mm, 5 μm $CO_2$/EtOH 55/45 160 mL/min 100 bars, 40° C. | Chiralpak IC 4.6 × 250 mm, 5 μm $CO_2$/EtOH 55/45 4 mL/min 150 bars, 40° C. | 1.10 |
| Ik-118 | (S)- or (R)-5-(4'-Chloro-2'-methoxy-3,4,5,6-tetrahydro-2H-[1,3']bipyridinyl-4-yl)-2,4-dimethyl-7-(2-trifluoromethyl-benzyl)-2,4,5,7-tetrahydro-pyrazolo[3,4-d]pyrimidin-6-one (Enantiomer B) (Example 377) | | | | 1.48 |
| Ik-119 | (R)- or (S)-5-(4'-Chloro-2'-methoxy-3,4,5,6-tetrahydro-2H-[1,3']bipyridinyl-4-yl)-7-(2-cyclopropyl-benzyl)-2,4-dimethyl-2,4,5,7-tetrahydro-pyrazolo[3,4-d]pyrimidin-6-one (Enantiomer A) (Example 378) | Ia-86 | Chiralpak AD-H 30 × 250 mm, 5 μm $CO_2$/EtOH 55/45 150 mL/min 100 bars, 40° C. | Chiralpak AD-H 4.6 × 250 mm, 5 μm $CO_2$/EtOH 55/45 4 mL/min 150 bars, 40° C. | 1.23 |
| Ik-120 | (S)- or (R)-5-(4'-Chloro-2'-methoxy-3,4,5,6-tetrahydro-2H-[1,3']bipyridinyl-4-yl)-7-(2-cyclopropyl-benzyl)-2,4-dimethyl-2,4,5,7-tetrahydro-pyrazolo[3,4-d]pyrimidin-6-one (Enantiomer B) (Example 379) | | | | 1.71 |
| Ik-121 | (R)- or (S)-2-Cyclopropyl-7-(2-cyclopropyl-benzyl)-5-(2'-methoxy-4'-methyl-3,4,5,6-tetrahydro-2H-[1,3']bipyridinyl-4-yl)-4-methyl-2,4,5,7-tetrahydro-pyrazolo[3,4-d]pyrimidin-6-one (Enantiomer A) (Example 380) | Ia-87 | Chiralpak AD-H 30 × 250 mm, 5 μm $CO_2$/EtOH 50/50 160 mL/min 100 bars, 40° C. | Chiralpak AD-H 4.6 × 250 mm, 5 μm $CO_2$/EtOH 50/50 4 mL/min 150 bars, 40° C. | 1.00 |
| Ik-122 | (S)- or (R)-2-Cyclopropyl-7-(2-cyclopropyl-benzyl)-5-(2'-methoxy-4'-methyl-3,4,5,6-tetrahydro-2H-[1,3']bipyridinyl-4-yl)-4-methyl-2,4,5,7-tetrahydro-pyrazolo[3,4-d]pyrimidin-6-one (Enantiomer B) (Example 381) | | | | 1.57 |
| Ik-123 | (R)- or (S)-2-Cyclopropyl-7-(2-cyclopropyl-benzyl)-5-(4'-difluoromethyl-2'-methoxy-3,4,5,6-tetrahydro-2H-[1,3']bipyridinyl-4-yl)-4-methyl-2,4,5,7-tetrahydro-pyrazolo[3,4-d]pyrimidin-6-one (Enantiomer A) (Example 382) | Ia-88 | Chiralpak AD-H 30 × 250 mm, 5 μm $CO_2$/EtOH 55/45 160 mL/min 100 bars, 40° C. | Chiralpak AD-H 4.6 × 250 mm, 5 μm $CO_2$/EtOH 55/45 4 mL/min 150 bars, 40° C. | 0.94 |
| Ik-124 | (S)- or (R)-2-Cyclopropyl-7-(2-cyclopropyl-benzyl)-5-(4'-difluoromethyl-2'-methoxy-3,4,5,6-tetrahydro-2H-[1,3']bipyridinyl-4-yl)-4-methyl-2,4,5,7-tetrahydro-pyrazolo[3,4-d]pyrimidin-6-one (Enantiomer B) (Example 383) | | | | 1.33 |
| Ik-125 | (R)- or (S)-5-[1-(2-Bromo-6-fluoro-phenyl)-piperidin-4-yl]-7-(2-cyclopropyl-benzyl)-2,4-dimethyl-2,4,5,7-tetrahydro-pyrazolo[3,4-d]pyrimidin-6-one (Enantiomer A) (Example 384) | Ia-89 | Chiralpak IF 30 × 250 mm, 5 μm $CO_2$/EtOH 50/50 160 mL/min 100 bars, 40° C. | Chiralpak IF 4.6 × 250 mm, 5 μm $CO_2$/EtOH 55/45 4 mL/min 150 bars, 40° C. | 1.96 |
| Ik-126 | (S)- or (R)-5-[1-(2-Bromo-6-fluoro-phenyl)-piperidin-4-yl]-7-(2-cyclopropyl-benzyl)-2,4-dimethyl-2,4,5,7-tetrahydro-pyrazolo[3,4-d]pyrimidin-6-one (Enantiomer B) (Example 385) | | | | 2.77 |

II. Biological Assays

In Vitro Assay

Adherent cells (CHO-K1 C5AR1 beta-arrestin cell line, DiscoverX, CA USA) are washed with PBS, detached by incubation with Dissociation Buffer (Gibco Cat #13151-014, 2 ml per 165 cm2 dish) for 3 minutes, then washed with 10 ml PBS (without Mg++ and Ca++) and counted. 7500 cells/384-well are seeded out in 384-well plates (Cell culture plate MTP384 white Polystyrene, Corning, Cat #3570) in 20 μl/well Cell plating medium (F12 HAMs/10% FCS/1% P/S) and incubated at 37° C./5% CO2/24h.

5 μl Antagonist at 6-fold end concentration or DMSO control is added to assay medium and subsequently 5 μl 1-10 nM C5a agonist at 6 fold end concentration. Cells are centrifuged for 1 min at 1000 rpm and incubated for 1.5 hour in at 37° C. Plates are equilibrated at room temperature for several minutes before adding 12 μl/well Detection Reagent (PathHunter Detection Kit, DiscoverX, Cat #93-0001). Plates are centrifuged for 1 min at 1000 rpm and incubated for 45 minutes at RT before being measured on a Fluostar Optima, BMG Labtech. $IC_{50}$ values are calculated from a serial dilution range of antagonist using inhouse software and given in nmol/l.

The calculated $IC_{50}$ values may fluctuate depending on the daily cellular assay performance. Fluctuations of this kind are known to those skilled in the art. Average $IC_{50}$ values from several measurements are given as geometric mean values.

Antagonistic activities of exemplified compounds are displayed in Table.

TABLE 70 list of examples and their antagonistic activities

| Example Number | Compound No | C5aR $IC_{50}$ (nM) |
|---|---|---|
| 1 | Ia-1A | 85 |
| 2 | Ib-1 | 10 |
| 3 | Ic-2 | 36 |
| 4 | Id-1 | 293 |
| 5 | Ia-2 | 16 |
| 6 | Ib-2 | 9 |
| 7 | Ic-1 | 16 |
| 8 | Ic-3 | 14 |
| 9 | Ic-4 | 8 |
| 10 | Ie-1 | 341 |
| 11 | Ia-3 | 603 |
| 12 | Ia-4 | 226 |
| 13 | Ia-5 | 28 |
| 14 | Ib-3 | 466 |
| 15 | Ia-6 | 45 |
| 16 | Id-2 | 74 |
| 17 | Ic-5 | 13 |
| 18 | Ic-6 | 132 |
| 19 | Ic-7 | 637 |
| 20 | If-1 | 12 |
| 21 | Ia-7 | 13 |
| 22 | Ia-8 | 10 |
| 23 | Ih-1 | 16 |
| 24 | Ic-8 | 15 |
| 25 | Ic-9 | 18 |
| 26 | If-2 | 173 |
| 27 | Ic-10 | 17 |
| 28 | Ic-12 | 83 |
| 29 | If-3 | 103 |
| 30 | If-4 | 95 |
| 31 | Ic-11 | 13 |
| 32 | If-5 | 14 |
| 33 | If-6 | 12 |
| 34 | If-7 | 22 |
| 35 | Ia-9 | 9 |
| 36 | Ih-2 | 7 |
| 37 | Ih-3 | 53 |
| 38 | Ih-4 | 12 |
| 39 | If-8 | 16 |
| 40 | Ic-13 | 27 |
| 41 | Ic-14 | 17 |
| 42 | Ic-15 | 24 |
| 43 | Ic-16 | 18 |
| 44 | Ij-1 | 35 |
| 45 | If-9 | 203 |
| 46 | Ic-17 | 21 |
| 47 | Ij-2 | 19 |
| 48 | Ij-3 | 18 |
| 49 | Ij-4 | 12 |
| 50 | Ih-5 | 85 |
| 51 | Ih-6 | 46 |
| 52 | Ij-6 | 72 |
| 53 | If-10 | 46 |
| 54 | Ij-7 | 14 |
| 55 | Ia-10 | 11 |
| 56 | Ig-1 | 91 |
| 57 | Ik-1 | 19 |
| 58 | Ik-2 | 238 |
| 59 | If-11 | 196 |
| 60 | If-12 | 56 |
| 61 | Ia-11 | 16 |
| 62 | If-13 | 105 |
| 63 | If-14 | 91 |
| 64 | If-15 | 21 |
| 65 | If-16 | 120 |
| 66 | Ig-2 | 152 |
| 67 | Ig-3 | 15 |
| 68 | Ij-8 | 318 |
| 69 | Ij-9 | 38 |
| 70 | Ij-10 | 512 |
| 71 | If-17 | 24 |
| 72 | If-18 | 43 |
| 73 | If-19 | 17 |
| 74 | If-20 | 26 |
| 75 | Ic-18 | 171 |
| 76 | Ib-4 | 20 |
| 77 | Ic-19 | 10 |
| 78 | If-21 | 14 |
| 79 | Ig-4 | 676 |
| 80 | Ig-5 | 350 |
| 81 | Ic-20 | 21 |
| 82 | Ic-21 | 119 |
| 83 | Ic-22 | 75 |
| 84 | Ic-23 | 74 |
| 85 | Ij-11 | 34 |
| 86 | Ij-12 | 230 |
| 87 | If-22 | 12 |
| 88 | Ig-6 | 156 |
| 89 | Ia-13 | 54 |
| 90 | Ia-14 | 153 |
| 91 | Ic-24 | 26 |
| 92 | If-23 | 428 |
| 93 | Ic-25 | 17 |
| 94 | If-24 | 727 |
| 95 | Ij-13 | 125 |
| 96 | Ij-14 | 492 |
| 97 | Ic-27 | 30 |
| 98 | Ic-28 | 24 |
| 99 | If-26 | 354 |
| 100 | Ij-15 | 339 |
| 101 | Ic-29 | 22 |
| 102 | Ig-7 | 278 |
| 103 | Ig-8 | 351 |
| 104 | Ig-9 | 146 |
| 105 | Ig-10 | 330 |
| 106 | Ig-11 | 24 |
| 107 | Ig-12 | 52 |
| 108 | Ic-30 | 21 |
| 109 | Ic-31 | 27 |

TABLE 70-continued list of examples and their antagonistic activities

| Example Number | Compound No | C5aR IC$_{50}$ (nM) |
|---|---|---|
| 110 | Ic-32 | 28 |
| 111 | If-27 | 29 |
| 112 | If-28 | 18 |
| 113 | Ig-13 | 110 |
| 114 | Ig-14 | 107 |
| 115 | Ig-15 | 137 |
| 116 | Ig-16 | 844 |
| 117 | Ig-17 | 33 |
| 118 | If-29 | 578 |
| 119 | Ig-18 | 296 |
| 120 | Ig-19 | 1354 |
| 121 | Ic-33 | 17 |
| 122 | If-30 | 342 |
| 123 | Ig-20 | 19 |
| 124 | Ig-21 | 13 |
| 125 | Ig-22 | 14 |
| 126 | Ig-23 | 15 |
| 127 | Ig-24 | 14 |
| 128 | Ia-15 | 15 |
| 129 | Ic-34 | 20 |
| 130 | If-31 | 390 |
| 131 | Ig-25 | 100 |
| 132 | Ig-26 | 8 |
| 133 | Ig-27 | 22 |
| 134 | Ig-28 | 13 |
| 135 | Ig-29 | 17 |
| 136 | Ig-30 | 163 |
| 137 | Ig-31 | 81 |
| 138 | Ia-16 | 11 |
| 139 | Ig-32 | 18 |
| 140 | Ig-33 | 18 |
| 141 | Ig-34 | 21 |
| 142 | Ig-35 | 32 |
| 143 | Ig-36 | 17 |
| 144 | Ig-37 | 14 |
| 145 | Ia-17 | 13 |
| 146 | Ia-18 | 32 |
| 147 | Ic-35 | 152 |
| 148 | Ic-36 | 341 |
| 149 | Ic-37 | 70 |
| 150 | Ic-38 | 767 |
| 151 | Ic-39 | 517 |
| 152 | Ic-40 | 322 |
| 153 | If-32 | 40 |
| 154 | If-33 | 26 |
| 155 | Ig-38 | 25 |
| 156 | Ic-41 | 10 |
| 157 | If-34 | 17 |
| 158 | Ic-43 | 11 |
| 159 | Ic-44 | 8 |
| 160 | Ic-45 | 147 |
| 161 | Ic-46 | 7 |
| 162 | Ic-47 | 9 |
| 163 | Ic-48 | 10 |
| 164 | Ic-49 | 13 |
| 165 | Ic-50 | 8 |
| 166 | Ic-52 | 12 |
| 167 | Ic-53 | 10 |
| 168 | Ic-54 | 6 |
| 169 | Ic-55 | 8 |
| 170 | Ic-56 | 6 |
| 171 | Ic-57 | 17 |
| 172 | Ic-58 | 11 |
| 173 | Ic-59 | 15 |
| 174 | Ic-60 | 7 |
| 175 | Ic-61 | 14 |
| 176 | Ic-62 | 16 |
| 177 | Id-4 | 48 |
| 178 | Ic-64 | 16 |
| 179 | Id-5 | 152 |
| 180 | Ic-66 | 11 |
| 181 | Id-6 | 50 |
| 182 | Ic-68 | 30 |
| 183 | Ic-69 | 22 |
| 184 | Ic-70 | 9 |
| 185 | Ik-3 | 10 |
| 186 | Ik-4 | 8 |
| 187 | Ik-5 | 13 |
| 188 | Ik-6 | 10 |
| 189 | Ik-7 | 10 |
| 190 | Ik-8 | 11 |
| 191 | If-35 | 4 |
| 192 | Ic-74 | 4 |
| 193 | Ib-5 | 14 |
| 194 | Ic-75 | 5 |
| 195 | Ia-1B | 45 |
| 196 | Ia-20 | 11 |
| 197 | Ib-6 | 17 |
| 198 | Ic-76 | 13 |
| 199 | Ia-21 | 32 |
| 200 | Ic-77 | 4 |
| 201 | Ic-78 | 6 |
| 202 | Ik-9 | 919 |
| 203 | Ik-10 | 74 |
| 204 | Ib-7 | 23 |
| 205 | Ic-79 | 8 |
| 206 | Ic-80 | 3 |
| 207 | Ic-81 | 15 |
| 208 | Ic-82 | 3 |
| 209 | Ic-83 | 5 |
| 210 | Ie-2 | 46 |
| 211 | Ib-8 | 275 |
| 212 | Ic-84 | 10 |
| 213 | Ic-86 | 53 |
| 214 | Ic-87 | 87 |
| 215 | Id-7 | 146 |
| 216 | Ia-24 | 41 |
| 217 | Ia-25 | 11 |
| 218 | Ib-9 | 12 |
| 219 | Ic-88 | 38 |
| 220 | Ik-11 | 8 |
| 221 | Ik-12 | 77 |
| 222 | Ic-89 | 19 |
| 223 | Ic-90 | 32 |
| 224 | Ic-91 | 76 |
| 225 | Ik-13 | 34 |
| 226 | Ik-14 | 24 |
| 227 | Ic-92 | 10 |
| 228 | Ia-28 | 10 |
| 229 | Ij-16 | 550 |
| 230 | Ia-29 | 37 |
| 231 | Ia-30 | 17 |
| 232 | Ia-31 | 16 |
| 233 | Ia-32 | 10 |
| 234 | Ik-15 | 109 |
| 235 | Ik-16 | 169 |
| 236 | Ia-34 | 312 |
| 237 | Ia-35 | 80 |
| 238 | Ij-17 | 166 |
| 239 | Id-8 | 59 |
| 240 | Ia-36 | 630 |
| 241 | Ik-17 | 112 |
| 242 | Ik-18 | 628 |
| 243 | Ij-18 | 28 |
| 244 | Ij-19 | 16 |
| 245 | Ij-20 | 16 |
| 246 | Ik-19 | 21 |
| 247 | Ik-20 | 21 |
| 248 | Ih-7 | 16 |
| 249 | Ia-40 | 69 |
| 250 | Ih-8 | 10 |
| 251 | Ih-9 | 9 |
| 252 | Ia-41 | 9 |
| 253 | Ik-21 | 16 |
| 254 | Ik-22 | 192 |
| 255 | Ik-23 | 87 |
| 256 | Ik-24 | 570 |
| 257 | Ij-21 | 9 |

TABLE 70-continued list of examples and their antagonistic activities

| Example Number | Compound No | C5aR IC$_{50}$ (nM) |
|---|---|---|
| 258 | Ij-22 | 14 |
| 259 | Ia-42 | 49 |
| 260 | Ia-43 | 40 |
| 261 | Ik-25 | 580 |
| 262 | Ik-26 | 472 |
| 263 | Ik-27 | 21 |
| 264 | Ia-45 | 216 |
| 265 | Ik-29 | 12 |
| 266 | Ik-30 | 356 |
| 267 | Ia-46 | 201 |
| 268 | Ia-47 | 72 |
| 269 | Ia-48 | 193 |
| 270 | Ij-23 | 54 |
| 271 | Ij-24 | 51 |
| 272 | Ij-25 | 18 |
| 273 | Ij-26 | 13 |
| 274 | Ik-32 | 37 |
| 275 | Ik-34 | 20 |
| 276 | Ik-35 | 491 |
| 277 | Ik-36 | 56 |
| 278 | Ik-37 | 492 |
| 279 | Ik-38 | 28 |
| 280 | Ij-30 | 12 |
| 281 | Ij-31 | 17 |
| 282 | Ij-32 | 18 |
| 283 | Ij-33 | 8 |
| 284 | Ij-34 | 9 |
| 285 | Ij-35 | 9 |
| 286 | Ik-39 | 33 |
| 287 | Ik-40 | 37 |
| 288 | Ik-41 | 75 |
| 289 | Ik-42 | 55 |
| 290 | Ik-43 | 351 |
| 291 | Ik-44 | 116 |
| 292 | Ik-46 | 515 |
| 293 | Ik-45 | 20 |
| 294 | Ia-54 | 56 |
| 295 | Ik-47 | 25 |
| 296 | Ik-49 | 15 |
| 297 | Ik-50 | 326 |
| 298 | Ik-51 | 29 |
| 299 | Ij-36 | 402 |
| 300 | Ij-37 | 29 |
| 301 | Ij-38 | 69 |
| 302 | Ij-40 | 48 |
| 303 | Ij-41 | 10 |
| 304 | Ij-42 | 35 |
| 305 | Ik-53 | 16 |
| 306 | Ik-54 | 285 |
| 307 | Ij-43 | 30 |
| 308 | Ij-44 | 22 |
| 309 | Ik-55 | 11 |
| 310 | Ik-56 | 30 |
| 311 | Ik-57 | 13 |
| 312 | Ik-58 | 72 |
| 313 | Ia-51 | 13 |
| 314 | Ik-59 | 8 |
| 315 | Ik-60 | 362 |
| 316 | Ik-62 | 9 |
| 317 | Ik-63 | 11 |
| 318 | Ik-64 | 131 |
| 319 | Ik-65 | 2 |
| 320 | Ik-66 | 325 |
| 321 | Ik-67 | 196 |
| 322 | Ik-68 | 3 |
| 323 | Ik-69 | 9 |
| 324 | Ik-70 | 182 |
| 325 | Ik-71 | 14 |
| 326 | Ik-72 | 355 |
| 327 | Ik-73 | 520 |
| 328 | Ik-74 | 10 |
| 329 | Ik-75 | 18 |
| 330 | Ik-76 | 1424 |
| 331 | Ik-77 | 6 |
| 332 | Ik-78 | 184 |
| 333 | Ik-79 | 14 |
| 334 | Ik-80 | 210 |
| 335 | Ik-81 | 12 |
| 336 | Ik-82 | 89 |
| 337 | Ik-83 | 15 |
| 338 | Ik-84 | 110 |
| 339 | Ik-85 | 12 |
| 340 | Ik-86 | 67 |
| 341 | Ia-72 | 31 |
| 342 | Ia-73 | 24 |
| 343 | Ia-74 | 57 |
| 344 | Ik-87 | 8 |
| 345 | Ik-88 | 35 |
| 346 | Ik-89 | 7 |
| 347 | Ik-90 | 201 |
| 348 | Ik-91 | 11 |
| 349 | Ik-92 | 918 |
| 350 | Ik-93 | 4 |
| 351 | Ik-94 | 784 |
| 352 | Ik-95 | 11 |
| 353 | Ik-96 | 997 |
| 354 | Ik-97 | 5 |
| 355 | Ik-98 | 298 |
| 356 | Ik-99 | 5 |
| 357 | Ik-100 | 572 |
| 358 | Ik-101 | 12 |
| 359 | Ik-102 | 185 |
| 360 | Ik-103 | 3 |
| 361 | Ik-104 | 13 |
| 362 | Ik-105 | 9 |
| 363 | Ik-106 | 97 |
| 364 | Ia-82 | 84 |
| 365 | Ia-83 | 45 |
| 366 | Ik-107 | 10 |
| 367 | Ik-108 | 286 |
| 368 | Ik-109 | 8 |
| 369 | Ik-110 | 256 |
| 370 | Ik-111 | 19 |
| 371 | Ik-112 | 1332 |
| 372 | Ik-113 | 11 |
| 373 | Ik-114 | 1006 |
| 374 | Ik-115 | 8 |
| 375 | Ik-116 | 146 |
| 376 | Ik-117 | 5 |
| 377 | Ik-118 | 552 |
| 378 | Ik-119 | 6 |
| 379 | Ik-120 | 412 |
| 380 | Ik-121 | 21 |
| 381 | Ik-122 | 190 |
| 382 | Ik-123 | 21 |
| 383 | Ik-124 | 204 |
| 384 | Ik-125 | 12 |
| 385 | Ik-126 | 491 |

The invention claimed is:

1. A compound of Formula (I):

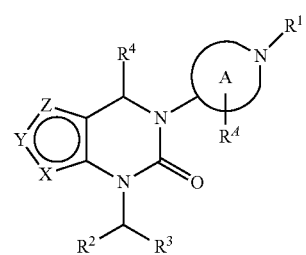

Formula (I)

or a pharmaceutically acceptable salt or deuterium labelled form thereof,
wherein:
(i) X represents N;
Y represents NR⁵; and
Z represents CH; or
(ii) X represents CH;
Y represents NR⁵; and
Z represents N;
ring A represents piperidin-1,4-diyl, wherein ring A is optionally substituted in position 4 with one R⁴ substituent;
R⁴ represents CH₃;
R¹ represents phenyl;
wherein the phenyl is substituted with one or two substituents;
wherein the phenyl is substituted in the ortho position with one substituent selected from the group consisting of F, CH₃, CHF₂, and OCH₃; and
wherein the phenyl is optionally substituted in the other ortho position with one substituent selected from the group consisting of F, CH₃, and OCH₃;
R² represents phenyl, wherein the phenyl is substituted in the ortho position with one substituent selected from the group consisting of F, Cl, CH(CH₃)₂, CF₃, OCH₂CH₃, OCH(CH₃)₂, OCF₃, OCH₂-cyclopropyl, O(cyclopropyl), and O(oxetan-3-yl);
R³ represents hydrogen;
R⁴ represents hydrogen; and
R⁵ represents CH₂CHF₂, CH(CH₃)CHF₂, CH₂CH(F)CH₃, CH₂CF₂CH₃, or CH₂C(F)(CH₃)CH₃.

2. A pharmaceutical composition comprising at least one pharmaceutically acceptable excipient and a compound according to claim 1, or a pharmaceutically acceptable salt or deuterium labelled form thereof.

3. A method for modulating C5a receptor activity in a patient, wherein the method comprises administering to the patient in need thereof a therapeutically effective amount of a compound according to claim 1, or a pharmaceutically acceptable salt or deuterium labelled form thereof.

4. The method of claim 3, wherein the patient has a disease or disorder selected from the group consisting of cancer, an autoimmune disease or disorder, a bullous disease or disorder, an immune complex disease or disorder, an inflammatory bowel disease or disorder, a complement related inflammatory disease or disorder, an inflammatory disease or disorder involving intravascular microvesicle release, an ischemia related disease or disorder, an ischemic reperfusion injury related disease or disorder, a neurodegenerative disease or disorder, and a vasculitic disease or disorder.

5. The method of claim 3, wherein the patient has a disease or disorder selected from the group consisting of coronary endothelial dysfunction induced by cardioplegia, coronary endothelial dysfunction induced by cardiopulmonary bypass, edema, increased capillary permeability, myocardial infarction, thrombosis, a deleterious consequence of contact sensitivity and inflammation caused by contact with an artificial surface, an increase in leukocyte and platelet activation, a pathologic sequelae associated with insulin-dependent diabetes mellitus, a pathologic sequelae associated with an injury, and a pathologic sequelae associated with intoxication.

6. The method of claim 5, wherein the pathologic sequelae associated with an injury or the pathologic sequelae associated with intoxication is selected from the group consisting of a hemorrhage, a shock, a surgery, and a trauma.

7. The method of claim 6, wherein the surgery is a surgery including transplantation.

8. The compound:

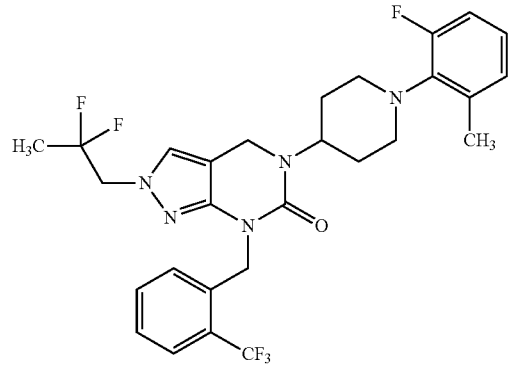

or a pharmaceutically acceptable salt thereof.

9. A pharmaceutical composition comprising at least one pharmaceutically acceptable excipient and the compound according to claim 8, or a pharmaceutically acceptable salt thereof.

10. A method for modulating C5a receptor activity in a patient, wherein the method comprises administering to the patient in need thereof a therapeutically effective amount of a compound according to claim 8, or a pharmaceutically acceptable salt thereof.

11. The method of claim 10, wherein the patient has a disease or disorder selected from the group consisting of cancer, an autoimmune disease or disorder, a bullous disease or disorder, an immune complex disease or disorder, an inflammatory bowel disease or disorder, a complement related inflammatory disease or disorder, an inflammatory disease or disorder involving intravascular microvesicle release, an ischemia related disease or disorder, an ischemic reperfusion injury related disease or disorder, a neurodegenerative disease or disorder, and a vasculitic disease or disorder.

12. The method of claim 10, wherein the patient has a disease or disorder selected from the group consisting of coronary endothelial dysfunction induced by cardioplegia, coronary endothelial dysfunction induced by cardiopulmonary bypass, edema, increased capillary permeability, myocardial infarction, thrombosis, a deleterious consequence of contact sensitivity and inflammation caused by contact with an artificial surface, an increase in leukocyte and platelet activation, a pathologic sequelae associated with insulin-dependent diabetes mellitus, a pathologic sequelae associated with an injury, and a pathologic sequelae associated with intoxication.

13. The method of claim 12, wherein the pathologic sequelae associated with an injury or the pathologic sequelae associated with intoxication is selected from the group consisting of a hemorrhage, a shock, a surgery, and a trauma.

14. The method of claim 13, wherein the surgery is a surgery including transplantation.

15. The compound:

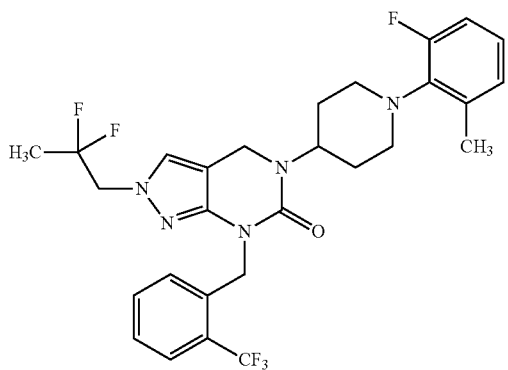 [SMILES: Cc1cccc(F)c1N1CCC(N2Cc3cn(CC(C)(F)F)nc3N(Cc3ccccc3C(F)(F)F)C2=O)CC1]

or a deuterium labelled form thereof.

16. The compound:

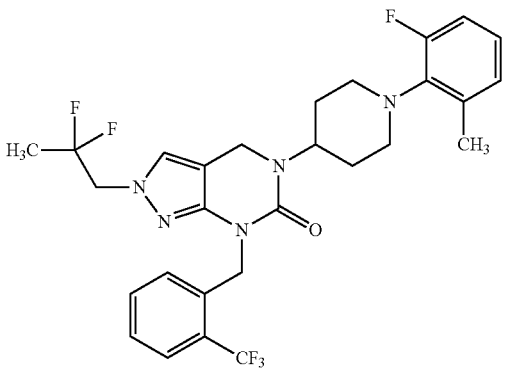

17. A pharmaceutical composition comprising at least one pharmaceutically acceptable excipient and the compound according to claim 16.

18. A method for modulating C5a receptor activity in a patient, wherein the method comprises administering to the patient in need thereof a therapeutically effective amount of a compound according to claim 16.

19. The method of claim 18, wherein the patient has a disease or disorder selected from the group consisting of cancer, an autoimmune disease or disorder, a bullous disease or disorder, an immune complex disease or disorder, an inflammatory bowel disease or disorder, a complement related inflammatory disease or disorder, an inflammatory disease or disorder involving intravascular microvesicle release, an ischemia related disease or disorder, an ischemic reperfusion injury related disease or disorder, a neurodegenerative disease or disorder, and a vasculitic disease or disorder.

20. The method of claim 18, wherein the patient has a disease or disorder selected from the group consisting of coronary endothelial dysfunction induced by cardioplegia, coronary endothelial dysfunction induced by cardiopulmonary bypass, edema, increased capillary permeability, myocardial infarction, thrombosis, a deleterious consequence of contact sensitivity and inflammation caused by contact with an artificial surface, an increase in leukocyte and platelet activation, a pathologic sequelae associated with insulin-dependent diabetes mellitus, a pathologic sequelae associated with an injury, and a pathologic sequelae associated with intoxication.

21. The method of claim 20, wherein the pathologic sequelae associated with an injury or the pathologic sequelae associated with intoxication is selected from the group consisting of a hemorrhage, a shock, a surgery, and a trauma.

22. The method of claim 21, wherein the surgery is a surgery including transplantation.

\* \* \* \* \*

UNITED STATES PATENT AND TRADEMARK OFFICE
CERTIFICATE OF CORRECTION

Page 1 of 1

PATENT NO. : 11,608,341 B2
APPLICATION NO. : 16/961600
DATED : March 21, 2023
INVENTOR(S) : Froidevaux et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 8 days.

Signed and Sealed this
Seventh Day of January, 2025

Derrick Brent
*Acting Director of the United States Patent and Trademark Office*